(12) United States Patent
Mjalli et al.

(10) Patent No.: US 8,404,731 B2
(45) Date of Patent: Mar. 26, 2013

(54) SUBSTITUTED IMIDAZOLE DERIVATIVES, COMPOSITIONS, AND METHODS OF USE AS PTPASE INHIBITORS

(75) Inventors: Adnan M. M. Mjalli, Oak Ridge, NC (US); Dharma R. Polisetti, High Point, NC (US); Govindan Subramanian, Bellemeade, NJ (US); James C. Quada, High Point, NC (US); Ravindra R. Yarragunta, Greensboro, NC (US); Robert C. Andrews, Jamestown, NC (US); Rongyuan Xie, Greensboro, NC (US)

(73) Assignee: TransTech Pharma, Inc., High Point, NC (US)

( * ) Notice: Subject to any disclaimer, the term of this patent is extended or adjusted under 35 U.S.C. 154(b) by 138 days.

(21) Appl. No.: 12/685,178

(22) Filed: Jan. 11, 2010

(65) Prior Publication Data

US 2010/0113331 A1    May 6, 2010

Related U.S. Application Data

(62) Division of application No. 11/699,780, filed on Jan. 30, 2007, now Pat. No. 7,723,369.

(60) Provisional application No. 60/763,256, filed on Jan. 30, 2006.

(51) Int. Cl.
A61K 31/4178 (2006.01)
C07D 233/64 (2006.01)

(52) U.S. Cl. ..................... 514/397; 548/311.1
(58) Field of Classification Search ............ 514/397
See application file for complete search history.

(56) References Cited

U.S. PATENT DOCUMENTS

| | | | |
|---|---|---|---|
| 5,106,732 A | 4/1992 | Kondo et al. |
| 5,348,969 A | 9/1994 | Romine et al. |
| 5,510,362 A | 4/1996 | Matassa et al. |
| 5,616,601 A | 4/1997 | Khanna et al. |
| 5,700,816 A | 12/1997 | Isakson et al. |
| 5,753,687 A | 5/1998 | Mjalli et al. |
| 5,840,721 A | 11/1998 | Mjalli et al. |
| 5,958,957 A | 9/1999 | Andersen et al. |
| 5,972,978 A | 10/1999 | Andersen et al. |
| 5,972,986 A | 10/1999 | Seibert et al. |
| 5,990,148 A | 11/1999 | Isakson et al. |
| 6,136,839 A | 10/2000 | Isakson et al. |
| 6,159,994 A | 12/2000 | McDonald et al. |
| 6,169,087 B1 | 1/2001 | Andersen et al. |
| 6,174,874 B1 | 1/2001 | Wang et al. |
| 6,214,564 B1 | 4/2001 | Rodan et al. |
| 6,238,902 B1 | 5/2001 | Cheng et al. |
| 6,265,426 B1 | 7/2001 | Alanine et al. |
| 6,358,634 B1 | 3/2002 | Igarashi et al. |
| 6,365,592 B1 | 4/2002 | Leblanc et al. |
| 6,388,076 B1 | 5/2002 | Mjalli et al. |
| 6,410,556 B1 | 6/2002 | Andersen et al. |
| 6,448,429 B1 | 9/2002 | Leblanc et al. |
| 6,465,444 B2 | 10/2002 | Bayly et al. |
| 6,472,545 B2 | 10/2002 | Liu et al. |
| 6,486,141 B2 | 11/2002 | Lau et al. |
| 6,486,142 B2 | 11/2002 | Leblanc et al. |
| 6,498,151 B2 | 12/2002 | Li et al. |
| 6,534,056 B1 | 3/2003 | Tromblay et al. |
| 6,583,126 B2 | 6/2003 | Leblanc et al. |
| 6,586,467 B2 | 7/2003 | Burgess et al. |
| 6,589,953 B2 | 7/2003 | Perez et al. |
| 6,596,772 B1 | 7/2003 | Huang et al. |
| 6,605,753 B1 | 8/2003 | Kennedy et al. |
| 6,613,903 B2 | 9/2003 | Andersen et al. |
| 6,624,182 B1 | 9/2003 | Haap et al. |
| 6,627,647 B1 | 9/2003 | Betageri |
| 6,627,767 B2 | 9/2003 | Liu et al. |
| 6,699,896 B1 | 3/2004 | Malamas et al. |
| 6,765,021 B2 | 7/2004 | Butera et al. |
| 6,770,466 B2 | 8/2004 | Shi et al. |
| 6,777,433 B2 | 8/2004 | Leblanc et al. |
| 6,784,205 B2 | 8/2004 | Barr et al. |
| 7,163,952 B2 | 1/2007 | Inaba et al. |
| 2002/0002199 A1 | 1/2002 | Jeppesen et al. |
| 2002/0009762 A1 | 1/2002 | Flint et al. |
| 2002/0035137 A1 | 3/2002 | Liu et al. |
| 2002/0072516 A1 | 6/2002 | Liu et al. |
| 2002/0099073 A1 | 7/2002 | Andersen et al. |
| 2002/0138862 A1 | 9/2002 | Kennedy et al. |
| 2002/0169157 A1 | 11/2002 | Liu et al. |
| 2002/0183518 A1 | 12/2002 | Mjalli et al. |
| 2003/0064979 A1 | 4/2003 | Hansen et al. |
| 2003/0069267 A1 | 4/2003 | Moller et al. |
| 2003/0108883 A1 | 6/2003 | Rondinone et al. |
| 2003/0114703 A1 | 6/2003 | Leblanc et al. |

(Continued)

FOREIGN PATENT DOCUMENTS

EP    1 227 084    7/2002
EP    1 253 142    10/2002

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Liu et al., "Acylsulfonamide-containing PTP1B inhibitors designed to mimic an enzyme-bound water of hydration," Bioorganic & Medicinal Chemistry Letters, vol. 13, pp. 3005-3007 (2003).
Wiesmann et al., "Allosteric inhibition of protein tyrosine phosphatase 1B," Nature Structural & Molecular Biology, vol. 11, pp. 730-737 (2004).

(Continued)

*Primary Examiner* — Shawquia Young
(74) *Attorney, Agent, or Firm* — Samuel B. Rollins

(57) ABSTRACT

The present invention provides imidazole derivatives of Formula (I-IV), methods of their preparation, pharmaceutical compositions comprising the compounds of Formula (I-IV), and their use in treating human or animal disorders. The compounds of the invention inhibit protein tyrosine phosphatase 1B and thus can be useful for the management, treatment, control, or the adjunct treatment of diseases mediated by PTPase activity. Such diseases include Type I diabetes and Type II diabetes.

18 Claims, No Drawings

U.S. PATENT DOCUMENTS

| | | |
|---|---|---|
| 2003/0120073 A1 | 6/2003 | Seto et al. |
| 2003/0130335 A1 | 7/2003 | Mjalli et al. |
| 2003/0144338 A1 | 7/2003 | Matsumoto et al. |
| 2003/0153756 A1 | 8/2003 | Guertin et al. |
| 2003/0170660 A1 | 9/2003 | Sondergaard et al. |
| 2003/0180827 A1 | 9/2003 | Welte et al. |
| 2003/0194745 A1 | 10/2003 | McDowell et al. |
| 2003/0215899 A1 | 11/2003 | Meng et al. |
| 2003/0217379 A1 | 11/2003 | Kennedy et al. |
| 2003/0220372 A1 | 11/2003 | Hirano et al. |
| 2004/0009946 A1 | 1/2004 | Lewis et al. |
| 2004/0009956 A1 | 1/2004 | Pei et al. |
| 2004/0014778 A1 | 1/2004 | Mjalli et al. |
| 2004/0023974 A1 | 2/2004 | Coppola et al. |
| 2004/0082542 A1 | 4/2004 | Mjalli et al. |
| 2004/0121353 A1 | 6/2004 | Lewis et al. |
| 2004/0127570 A1 | 7/2004 | Mayer et al. |
| 2004/0138218 A1 | 7/2004 | Pallen et al. |
| 2004/0147596 A1 | 7/2004 | Barr et al. |
| 2004/0147755 A1 | 7/2004 | Malamas et al. |
| 2004/0167187 A1 | 8/2004 | Saunders et al. |
| 2004/0167188 A1 | 8/2004 | Xin et al. |
| 2004/0176330 A1 | 9/2004 | Dufresne et al. |
| 2004/0176395 A1 | 9/2004 | Flynn et al. |
| 2004/0180906 A1 | 9/2004 | Flynn et al. |
| 2004/0186151 A1 | 9/2004 | Mjalli et al. |
| 2004/0192743 A1 | 9/2004 | Mjalli et al. |
| 2005/0014805 A1 | 1/2005 | Zhang et al. |
| 2005/0272778 A1 | 12/2005 | Combs et al. |

FOREIGN PATENT DOCUMENTS

| | | |
|---|---|---|
| EP | 1 402 888 | 3/2004 |
| EP | 1 019 364 | 6/2004 |
| EP | 1 452 530 | 9/2004 |
| EP | 1 553 091 | 7/2005 |
| JP | 63276054 | 11/1988 |
| JP | 05261293 | 10/1993 |
| JP | 09040651 | 2/1997 |
| JP | 2002 114768 | 4/2002 |
| JP | 2002-114768 | 4/2002 |
| JP | 2003-231679 | 8/2003 |
| JP | 2003313170 | 11/2003 |
| JP | 2003313172 | 11/2003 |
| WO | WO 94-08982 | 4/1994 |
| WO | WO 94-17059 | 8/1994 |
| WO | WO 96-41626 | 12/1996 |
| WO | WO 97-39748 | 10/1997 |
| WO | WO 98-16227 | 4/1998 |
| WO | WO 98-27065 | 6/1998 |
| WO | WO 98-51673 | 11/1998 |
| WO | WO 99-46244 | 9/1999 |
| WO | WO 00-27826 | 5/2000 |
| WO | WO 00-71120 | 11/2000 |
| WO | WO 02-04412 | 1/2002 |
| WO | WO 02-04459 | 1/2002 |
| WO | WO 02-32897 | 4/2002 |
| WO | WO 03-020688 | 3/2003 |
| WO | WO 03-033496 | 4/2003 |
| WO | WO 03-041729 | 5/2003 |
| WO | WO 03-064376 | 8/2003 |
| WO | WO 03-072537 | 9/2003 |
| WO | WO 03-073987 | 9/2003 |
| WO | WO 03-075921 | 9/2003 |
| WO | WO 03-082841 | 10/2003 |
| WO | WO 03-092679 | 11/2003 |
| WO | WO 03-093263 | 11/2003 |
| WO | WO 03-093498 | 11/2003 |
| WO | WO 2004-013141 | 2/2004 |
| WO | WO 2004-020466 | 3/2004 |
| WO | WO 2004-041799 | 5/2004 |
| WO | WO 2004-050646 | 6/2004 |
| WO | WO 2004-063169 | 7/2004 |
| WO | WO 2004-069394 | 8/2004 |
| WO | WO 2004-071447 | 8/2004 |
| WO | WO 2004-071448 | 8/2004 |
| WO | WO 2004-074238 | 9/2004 |
| WO | WO 2004-074256 | 9/2004 |
| WO | WO 2004-089918 | 10/2004 |
| WO | WO 2004-094395 | 11/2004 |
| WO | WO 2005-035551 | 4/2005 |
| WO | WO 2005-080346 | 9/2005 |

OTHER PUBLICATIONS

Li, X. et al., "Alpha,alpha-difluoro-beta-ketophosphonates as potent inhibitors of protein tyrosine phosphatase 1B," Bioorganic & Medicinal Chemistry Letters, vol. 14, pp. 4301-4306 (2004).

Arabaci et al., "Alpha-bromoacetophenone derivatives as neutral protein tyrosine phosphatase inhibitors: structure—Activity relationship," Bioorganic & Medicinal Chemistry Letters, vol. 12, pp. 3047-3050 (2002).

Cho et al., "Alpha-Lipoic acid decreases thiol reactivity of the insulin receptor and protein tyrosine phosphatase 1B in 3T3-L1 adipocytes," Biochemical Pharmacology, vol. 66, pp. 849-858 (2003).

Ahmad et al., "Alterations in skeletal muscle protein-tyrosine phosphatase activity and expression in insulin-resistant human obesity and diabetes," Journal of Clinical Investigation, vol. 100, pp. 449-458 (1997).

Wang et al., "An overview of the protein tyrosine phosphatase superfamily," Current Topics in Medicinal Chemistry, vol. 3, pp. 739-748 (2003).

Gum et al., "Antisense Protein Tyrosine Phosphatase 1B Reverses Activation of p38 Mitogen-Activated Protein Kinase in Liver of ob/ob Mice," Molecular Endocrinology, vol. 17, pp. 1131-1143 (2003).

Vetter et al., "Assessment of protein-tyrosine phosphatase 1B substrate specificity using "inverse alanine scanning"," The Journal of Biological Chemistry, vol. 275, pp. 2265-2268 (2000).

Patani et al., "Bioisosterism: A Rational Approach in Drug Design," Chemical Review, vol. 96, pp. 3147-3176 (1996).

Lee et al., "CD45 protein-tyrosine phosphatase inhibitor development," Current Topics in Medicinal Chemistry, vol. 3, pp. 797-807 (2003).

Irie-Sasaki et al., "CD45 regulated signaling pathways," Current Topics in Medicinal Chemistry, vol. 3, pp. 783-996 (2003).

Chu et al., "Cell-free Synthesis of Preparative Amounts of Enzymatically Active Human PtP1B," Biochemica, vol. 2, pp. 28-29 (2001).

Xie et al., "Cellular effects of small molecular PTP1B inhibitors on insulin signaling," Biochemistry, vol. 42, pp. 12792-12804 (2003).

Taylor et al., "Charged with meaning: the structure and mechanism of phosphoprotein phosphatases," Chemistry & Biology, vol. 2, pp. 713-718 (1995).

Patankar et al., "Classification of Inhibitors of Protein Tyrosine Phosphatase 1B Using Molecular Structure Based Descriptors," Journal of Chemical Information and Computer Sciences, vol. 43, pp. 885-899 (2003).

Sun et al., "Crystal structure of PTP1B complexed with a potent and selective bidentate inhibitor," The Journal of Biological Chemistry, vol. 278, pp. 12406-12414 (2003).

Database Caplus 'Online! Chemical Abstracts Service, Columbus, Ohio, US; retrieved from STN accession No. 62:29663 Database accession No. 1965:29663 RNs 805-66-3 and 810-22-0 abstract & PYL T ET AL: ANN., 1964, p. 679.

Yan Z., "Design and synthesis of phosphotyrosine mimetics," Bioorganic & Medicinal Chemistry Letters, 13:2083-2085 (2003).

Andersen et al., "Discovery and SAR of a novel selective and orally bioavailable nonpeptide classical competitive inhibitor class of protein-tyrosine phosphatase 1B," Journal of Medicinal Chemistry, vol. 45, pp. 4443-4459 (2002).

Pei et al., "Discovery and SAR of novel, potent and selective protein tyrosine phosphatase 1B inhibitors," Bioorganic & Medicinal Chemistry Letters, vol. 13, pp. 3129-3132 (2003).

Liu et al., "Discovery and structure—activity relationship of oxalylarylaminobenzoic acids as inhibitors of protein tyrosine phosphatase 1B," Journal of Medicinal Chemistry, vol. 46, pp. 2093-2103 (2003).

Erlanson et al., "Discovery of a New Phosphotyrosine Mimetic for PTP1B Using Breakaway Tethering," Journal of the American Chemical Society, vol. 125, pp. 5602-5603 (2003).

Cheon et al., "Discovery of a novel protein tyrosine phosphatase-1B inhibitor, KR61639: potential development as an antihyperglycemic agent," European Journal of Pharmacology, vol. 485, pp. 333-339 (2004).

Ockey et al., "Discovery of novel PTP1B inhibitors," Bioorganic & Medicinal Chemistry Letters, vol. 14, pp. 389-391 (2004).

Chen et al., "Divalent and trivalent alpha-ketocarboxylic acids as inhibitors of protein tyrosine phosphatases," Journal of Medicinal Chemistry, vol. 45, pp. 3946-3952 (2002).

Boute et al., "Dynamics of the interaction between the insulin receptor and protein tyrosine-phosphatase 1B in living cells," EMBO Reports, vol. 4, pp. 313-319 (2003).

Petrone A., "Emerging issues in receptor protein tyrosine phosphatase function: lifting fog or simply shifting?" Journal of Cell Science, vol. 113, pp. 2345-2354 (2000).

Peters et al., "Enzyme kinetic characterization of protein tyrosine phosphatases," Biochimie, vol. 85, pp. 527-534 (2003).

Shrestha et al., "Evans Blue and other dyes as protein tyrosine phosphatase inhibitors," Bioorganic & Medicinal Chemistry Letters, vol. 14, pp. 1923-1926 (2004).

Cross et al., "Finding discriminating structural features by reassembling common building blocks," Journal of Medicinal Chemistry, vol. 46, pp. 4770-4775 (2003).

Wang et al., "Flourescein monophosphates as fluorogenic substrates for protein tyrosine phosphatases," Biochimica Et Biophysica Acta, vol. 1431, pp. 14-23 (1999).

Shim et al., "Formylchromone derivatives as a novel class of protein tyrosine phosphatase 1B inhibitors," Bioorganic & Medicinal Chemistry Letters, vol. 13, pp. 2561-2563 (2003).

Liu et al., "Fragment screening and assembly: a highly efficient approach to a selective and cell active protein tyrosine phosphatase 1B inhibitor," Journal of Medicinal Chemistry, vol. 46, pp. 4232-4235 (2003).

Romsicki et al., "Functional characterization and crystal structure of the C215D mutant of protein-tyrosine phosphatase-1B," The Journal of Biological Chemistry, vol. 278, pp. 29009-29015 (2003).

Phan et al., "High-Resolution Structure of the Yersinia pestis Protein Tyrosine Phosphatase YopH in Complex with a Phosphotyrosyl Mimetic-Containing Hexapeptide," Biochemistry, vol. 42, pp. 13113-13121 (2003).

Xin et al., "Identification of a monoacid-Based, cell permeable, selective inhibitor of protein tyrosine phosphatase 1B," Bioorganic & Medicinal Chemistry Letters, vol. 13, pp. 3947-3950 (2003).

Puius et al., "Identification of a second aryl phosphate-binding site in protein-tyrosine phosphatase 1B: a paradigm for inhibitor design," Proceedings of the National Academy of Sciences, vol. 94, pp. 13420-13425 (1997).

Fukada et al., "Identification of YB-1 as a regulator of PTP1B expression: implications for regulation of insulin and cytokine signaling," The EMBO Journal, vol. 22, pp. 479-493 (2003).

Elchebly et al., "Increased insulin sensitivity and obesity resistance in mice lacking the protein tyrosine phosphatase-1B gene," Science, vol. 283, pp. 1544-1548 (1999).

Zabell et al., "Inhibition studies with rationally designed inhibitors of the human low molecular weight protein tyrosine phosphatase," Bioorganic & Medicinal Chemistry, vol. 12, pp. 1867-1880 (2004).

Taylor et al., "Inhibitors of protein tyrosine phosphatase 1B (PTP1B)," Current Topics in Medicinal Chemistry, vol. 3, pp. 759-782 (2003).

Tao et al., "Insulin stimulates tyrosine phosphorylation and inactivation of protein-tyrosine phosphatase 1B in vivo," The Journal of Biological Chemistry, vol. 276, pp. 29520-29525 (2001).

Dadke et al., "Interaction of protein tyrosine phosphatase (PTP) 1B with its substrates is influenced by two distinct binding domains," Biochemical Journal, vol. 364, pp. 377-383 (2002).

Blanchetot et al., "Intra- and intermolecular interactions between intracellular domains of receptor protein-tyrosine phosphatases," The Journal of Biological Chemistry, vol. 277, pp. 47263-47269 (2002).

Haase et al., "Intracellular zinc fluctuations modulate protein tyrosine phosphatase activity in insulin/insulin-like growth factor-1 signaling," Experimental Cell Research, vol. 291, pp. 289-298 (2003).

Liljebris et al., "Investigation of potential bioisosteric replacements for the carboxyl groups of peptidomimetic inhibitors of protein tyrosine phosphatase 1B: identification of a tetrazole-containing inhibitor with cellular activity," Journal of Medicinal Chemistry, vol. 45, pp. 1785-1798 (2002).

Frimurer et al., "Ligand-induced conformational changes: improved predictions of ligand binding conformations and affinities," Biophysical Journal, vol. 84, pp. 2273-2281 (2003).

Tjernberg et al., "Mechanism of action of pyridazine analogues on protein tyrosine phosphatase 1B (PTP1B)," Bioorganic & Medicinal Chemistry Letters, vol. 14, pp. 891-895 (2004).

Larsen et al., "Modification of the N-terminus of peptidomimetic protein tyrosine phosphatase 1B (PTP1B) Inhibitors: identification of analogues with cellular activity," Bioorganic & Medicinal Chemistry Letters, vol. 13, pp. 971-975 (2003).

Salmeen et al., "Molecular basis for the dephosphorylation of the activation segment of the insulin receptor by protein tyrosine phosphatase 1B," Molecular Cell, vol. 6, pp. 1401-1412 (2000).

Umezawa et al., "Molecular design and biological activities of protein-tyrosine phosphatase inhibitors," Pharmacology & Therapeutics, vol. 99, pp. 15-24 (2003).

Doman et al., "Molecular docking and high-throughput screening for novel inhibitors of protein tyrosine phosphatase-1B," Journal of Medicinal Chemistry, vol. 45, pp. 2213-2221 (2002).

Peters et al., "Molecular dynamics simulations of protein-tyrosine phosphatase 1B. I. ligand-induced changes in the protein motions," Biophysical Journal, vol. 77, pp. 505-515 (1999).

Peters et al., "Molecular dynamics simulations of protein-tyrosine phosphatase IB. II. Substrate-enzyme interactions and dynamics," Biophysical Journal, vol. 78, pp. 2191-2200 (2000).

Malamas et al., "New azolidinediones as inhibitors of protein tyrosine phosphatase 1B with antihyperglycemic properties," Journal of Medicinal Chemistry, vol. 43, pp. 995-1010 (2000).

Malamas et al., "Novel benzofuran and benzothiophene biphenyls as inhibitors of protein tyrosine phosphatase 1B with antihyperglycemic properties," Journal of Medicinal Chemistry, vol. 43, pp. 1293-1310 (2000).

Glover et al., "Nuclear magnetic resonance and restrained molecular dynamics studies of the interaction of an epidermal growth factor-derived peptide with protein tyrosine phosphatase 1B," Biochemistry, vol. 38, pp. 5256-5271 (1999).

Liljebris et al., "Oxidation of protein tyrosine phosphatases as a pharmaceutical mechanism of action: a study using 4-hydroxy-3,3-dimethyl-2H-benzo[g]indole-2,5(3H)-dione," The Journal of Pharmacology & Expremental Therapeutics, vol. 309, pp. 711-719 (2004).

Espanel et al., "The SPOT technique as a tool for studying protein tyrosine phosphatase substrate specificities," Protein Science, vol. 11, pp. 2326-2334 (2002).

Scapin et al., "The structural basis for the selectivity of benzotrizole inhibitors of PTP1B," Biochemistry, vol. 42, pp. 11451-11459 (2003).

Asante-Appiah et al., "The structure of PTP-1B in complex with a peptide inhibitor reveals an alternate binding mode for bisphosphonates," Biochemistry, vol. 41, pp. 9043-9051 (2002).

Bukczynska et al., "The T-cell protein tyrosine phosphatase is phosphorylated on Ser-304 by cyclin-dependent protein kinases in mitosis," Biochemical Journal, vol. 380, pp. 939-949 (2004).

Ragab et al., "The tyrosine phosphatase 1B regulates linker for activation of T-cell phosphorylation and platelet aggregation upon FcgammaRIIa cross-linking," The Journal of Biological Chemistry, vol. 278, pp. 40923-40932 (2003).

Zabolotny et al., "Trangenic Overexpression of Protein-tryosine Phosphatase 1B in Muscle Cause Insulin Resistance, but Overexpression with Leukocyte Antigen-related Phosphatase Does Not Additively Impair Insulin Action," The Journal of Biological Chemistry, vol. 279, pp. 24844-24851 (2004).

Lee et al., "Tripeptide inhibitors of Yersinia protein-tyrosine phosphatase," Bioorganic & Medicinal Chemistry Letters, vol. 13, pp. 2577-2581 (2003).

Sims et al, "Tyrosine phosphatase inhibitors selectively antagonize beta-adrenergic receptor-dependent regulation of cardiac ion channels," Molecular Phamacology, vol. 58, pp. 1213-1221 (2000).

Zhu et al., "Use of an Anaerobic Chamber Environment for the Assay of Endogenous Cellular Protein-Tyrosine Phosphatase Activities," Biological Procedures Online, vol. 4, pp. 1-9 (2002).

Database Caplus 'Online! Chemical Abstracts Service, Columbus, Ohio, US; Hoshino et al.: "Anti-infective agents and drug efflux pump inhibitors containing heteroaromatic compounds and" retrieved from STN Database accession No. 2002: 849289, RN 337903-96-5, RN 337904-05-9 abstract & JP 2002-322054, Japan; Nov. 8, 2002.

Nakayama et al., "MexAB-OprM-Specific Efflux Pump Inhibitors in *Pseudomonas aeruginosa*, Part 1: Discovery and Early Strategies for Lead Optimization," Bioorganic & Medicinal Chemistry Letters, vol. 13, pp. 4201-4204 (2003).

Lipshutz et al., "Metalation Studies of Trisubstituted Oxazoles," Journal of Organic Chemistry, vol. 46, pp. 1410-1413 (1981).

Cescon GR, "Some Properties of Triarylimidazolyl Radicals and Their Dimers," Journal of Organic Chemistry, vol. 36, No. 16, (1971).

Meanwell et al., "Nonprostanoid Prostacyclin Mimetics. 2. 4,5-Dipenyloxazole Derivatives," Journal of Medicinal Chemistry, vol. 35, pp. 3483-3497, (1992).

Cocco et al., "L-Acylaminoimidazoles Synthesis and Antimicrobial Activity," Farmaco, vol. 47, No. 2, pp. 229-238 (1992).

Covic et al., "Activation and inhibition of G protein-coupled receptors by cell-penetrating membrane-tethered peptides," Proceedings of the National Academy of Sciences, vol. 99, pp. 643-648 (2002).

Laufer et al., "Imidazole Inhibitors of Cytokine Release: Probing Substituents in the 2 Position," vol. 45, pp. 4695-4705 (2002).

Meanwell et al., "Nonprostanoid prostacyclin mimetics, 2, 4, 5-Diphenyloxazole derivatives," Journal of Medicinal Chemistry, vol. 35, No. 19, pp. 3483-3497 (1992).

Combs et al., "Structure-based design and discovery of protein tyrosine phosphatase inhibitors incorporating novel isothiazolidinone heterocyclic phosphotyrosine mimetics," Journal of Medicinal Chemistry, vol. 48, pp. 6544-6548 (2005).

Van Montfort et al., "Oxidation state of the active-site cysteine in protein tyrosine phosphatase 1B," Nature, vol. 423, pp. 773-777 (2003).

Chen et al., "Parallel synthesis of a library of bidentate protein tyrosine phosphatase inhibitors based on the alpha-ketoacid motif," Bioorganic & Medicinal Chemistry, vol. 12, pp. 3289-3298 (2004).

Chen et al., "Peptidic alpha-Ketocarboxylic Acids and Sulfonamides as inhibitors of Protein Tyrosine Phosphatases," Journal of Organic Chemistry, vol. 68, pp. 4123-4125 (2003).

Taing et al., "Potent and highly selective inhibitors of the protein tyrosine phosphatase 1B," Biochemistry, vol. 38, pp. 3793-3803 (1999).

Urbanek, "Potent Reversible Inhibitors of the Protein Tyrosine Phosphatase CD45," Journal of Medical Chemistry, vol. 44, pp. 1777-1793 (2001).

Xin et al., "Potent, selective inhibitors of protein tyrosine phosphatase 1B," Bioorganic & Medicinal Chemistry Letters, vol. 13, pp. 1887-1890 (2003).

Guo et al., "Probing the molecular basis for potent and selective protein-tyrosine phosphatase 1B inhibition," The Journal of Biological Chemistry, vol. 277, pp. 41014-41022 (2002).

Hooft Van Huijsduijnen et al., "Prospects for inhibitors of protein tyrosine phosphatase 1B as antidiabetic drugs," Journal of Medicinal Chemistry, vol. 47, pp. 4142-4146 (2004).

Liu et al., "Protein tyrosine phosphatase 1B inhibition: opportunities and challenges," Current Medicinal Chemistry, vol. 10, pp. 1407-1421 (2003).

Johnson et al., "Protein tyrosine phosphatase 1B inhibitors for diabetes," Nature Reviews Drug Discovery, vol. 1, pp. 696-709 (2002).

Rondinone et al., "Protein tyrosine phosphatase 1B reduction regulates adiposity and expression of genes involved in lipogenesis," Diabetes, vol. 51, pp. 2405-2411 (2002).

Ramachandran et al., "Protein tyrosine phospatase 1B: a novel target for type 2 diabetes and obesity," Current Topics in Medicinal Chemistry, vol. 3, pp. 749-757 (2003).

Romsicki et al., "Protein Tyrosine Phosphatase-1B Dephosphorylation of the Insulin Receptor Occurs in a Perinuclear Endosome Compartment in Human Embryonic Kidney 293 Cells," The Journal of Biological Chemistry, vol. 279, pp. 12666-12875 (2004).

Wu et al., "Protein tyrosine phosphatases are up-regulated and participate in cell death induced by polyglutamine expansion," The Journal of Biological Chemistry, vol. 277, pp. 44208-44213 (2002).

Alonso et al., "Protein tyrosine phosphatases in the human genome," Cell, vol. 117, pp. 699-711 (2004).

Zhang et al., "Protein Tyrosine Phophatases: Structure and Function, Substrate Specificity, and Inhibitor Development," Annual Review of Pharmacology and Toxicology, vol. 42, pp. 209-234 (2002).

Goldstein et al., "Protein-tyrosine phosphatase 1B (PTP1B): a novel therapeutic target for type 2 diabetes mellitus, obesity and related states of insulin resistance," Current Drug Targets—Immune, Endocrine & Metabolic Disorders, vol. 1, pp. 255-275 (2001).

Dadke et al., "Protein-Tyrosine Phophatase 1B as a Potential Drug Target for Obesity," Current Drug Targets—Immune, Endocrine & Metabolic Disorders, vol. 3, pp. 299-304 (2003).

Shimizu et al., "Protein-tyrosine Phosphatase 1B as New Activator for Hepatic Lipogenesis via Sterol Regulatory Element-binding Protein-1 Gene Expression," The Journal of Biological Chemistry, vol. 278, pp. 43095-43101 (2003).

Dadke et al., "Protein-tyrosine phosphatase 1B mediates the effects of insulin on the actin cytoskeleton in Immortalized fibroblasts," The Journal of Biological Chemistry, vol. 278, pp. 40607-40611 (2003).

Goldstein et al., "Protein-tyrosine phosphatases: emerging targets for therapeutic intervention in type 2 diabetes and related states of insulin resistance," The Journal of Clinical Endocrinology & Metabolism, vol. 87, pp. 2474-2480 (2002).

Moller et al., "Protein tyrosine phosphatases (PTPs) as drug targets: Inhibitors of PTP-1B for the treatment of diabetes," Current Opinion in Drug Discovery & Development, vol. 3, pp. 527-540 (2000).

Zinker et al, "PTP1B antisense oligonucleotide lowers PTP1B protein, normalizes blood glucose, and improves insulin sensitivity in diabetic mice," Proceedings of the National Academy of Sciences, vol. 99, pp. 11357-11362 (2002).

Waring et al., "PTP1B antisense-treated mice show regulation of genes involved in lipogenesis in liver and fat," Molecular and Cellular Endocrinology, vol. 203, pp. 155-168 (2003).

Tonks et al., "PTP1B: from the sidelines to the front lines," FEBS Letters, vol. 546, pp. 140-148 (2003).

Romsicki et al., "Purification and characterization of T cell protein tyrosine phosphatase reveals significant functional homology to protein tyrosine phosphatase-1B," Archives of Biochemistry and Biophysics, vol. 414, pp. 40-50 (2003).

Salmeen et al., "Redox regulation of protein tyrosine phosphatase 1B involves a sulphenyl-amide intermediate," Nature, vol. 423, pp. 769-773 (2003).

Gum et al., "Reduction of Protein tyrosine phosphatase 1B increases insulin-dependent signaling in ob/ob mice," Diabetes, vol. 52, pp. 21-28 (2003).

Galic et al., "Regulation of insulin receptor signaling by the protein tyrosine phosphatase TCPTP," Molecular and Cellular Biology, vol. 23, pp. 2096-2108 (2003).

Haj et al., "Regulation of receptor tyrosine kinase signaling by protein tyrosine phosphatase-1B," The Journal of Biological Chemistry, vol. 278, pp. 739-744 (2003).

Peters et al., "Residue 259 is a key determinant of substrate specificity of protein-tyrosine phosphatase 1B and alpha," The Journal of Biological Chemistry, vol. 275, pp. 18201-18209 (2000).

Liu et al., "Selective protein tyrosine phosphatase 1B inhibitors: targeting the second phosphotyrosine binding site with non-carboxylic acid-containing ligands," Journal of Medicinal Chemistry, vol. 46, pp. 3437-3440 (2003).

Milarski et al., "Sequence specificity in recognition of the epidermal growth factor receptor by protein tyrosine phosphatase 1B," The Journal of Biological Chemistry, vol. 268, pp. 23634-23639 (1993).

Halazy et al., "Signal Transduction: an Exciting Field of Investigation for Small Molecule Drug Discovery," Molecules, vol. 8, pp. 349-358 (2003).

Bleasdale et al., "Small molecule peptidomimetics containing a novel phosphotyrosine bioisostere inhibit protein tyrosine phosphatase 1B and augment insulin action," Biochemistry, vol. 40, pp. 5642-5654 (2001).

Xie et al., "Squaric Acids: A New Motif for Desigining Inhibitors of Protein Tyrosine Phosphatases," Organic Letters, vol. 6, pp. 83-86 (2004).

Dillet et al., "Stabilization of Charges and Protonation States in the Active Site of the Protein Tyrosine Phosphatases: A Computational Study," Journal of Physical Chemistry B, vol. 104, pp. 11321-11333 (2000).

Iverson et al., "Steric hindrance as a basis for structure-based design of selective inhibitors of protein-tyrosine phosphatases," Biochemistry, vol. 40, pp. 14812-14820 (2001).

Andersen et al., "Structural and evolutionary relationships among protein tyrosine phosphatase domains," Molecular and Cellular Biology, vol. 21, pp. 7117-7136 (2001).

Groves et al., "Structural Basis for Inhibition of the Protein Tyrosine Phosphatase 1B by Phosphotyrosine Peptide Mimetics," Biochemistry, vol. 37, pp. 17773-17783 (1998).

Sarmiento et al., "Structural basis of plasticity in protein tyrosine phosphatase 1B substrate recognition," Biochemistry, vol. 39, pp. 8171-8179 (2000).

Lau et al., "Structure based design of a series of potent and selective non peptide PTP-1B inhibitors," Bioorganic & Medicinal Chemistry Letters, vol. 14, pp. 1043-4048 (2004).

Iversen et al., "Structure determination of T cell protein-tyrosine phosphatase," The Journal of Biological Chemistry, vol. 277, pp. 19982-19990 (2002).

Jia et al., "Structure of protein tyrosine phosphatase 1B in complex with inhibitors bearing two phosphotyrosine mimetics," Journal of Medicinal Chemistry, vol. 44, pp. 4584-4594 (2001).

Iverson et al., "Structure-based design of a low molecular weight, nonphosphorus, nonpeptide, and highly selective inhibitor of protein-tyrosine phosphatase 1B," The Journal of Biological Chemistry, vol. 275, pp. 10300-10307 (2000).

Lund et al., "Structure-based design of selective and potent inhibitors of protein-tyrosine phosphatase beta," The Journal of Biological Chemistry, vol. 279, pp. 24226-24235 (2004).

Sarmiento et al., "Structure-based discovery of small molecular inhibitors targeted to protein tyrosine phosphatase 1B," Journal of Medicinal Chemistry, vol. 43, pp. 146-155 (2000).

Wang et al., "Structure-based Prediction of Free Energy Changes of binding of PTP-1B inhibitors," Journal of Computer-Aided Molecular Design, vol. 17, pp. 495-513 (2003).

McCain et al., "Suramin derivatives as inhibitors and activators of protein-tyrosine phosphatases," The Journal of Biological Chemistry, vol. 279, pp. 14713-14725 (2004).

Liljebris et al., "Synthesis and biological activity of a novel class of pyridazine analogues as non-competitive reversible inhibitors of protein tyrosine phosphatase 1B (PTP1B)," Bioorganic & Medicinal Chemistry, vol. 10, pp. 3197-3212 (2002).

Larsen et al., "Synthesis and biological activity of a novel class of small molecular weight peptidomimetic competitive inhibitors of protein tyrosine phosphatase 1B," Journal of Medicinal Chemistry, vol. 45, pp. 598-622 (2002).

Therien et al., "Synthesis of a novel peptidic photoaffinity probe for the PTP-1B enzyme," Bioorganic & Medicinal Chemistry Letters, vol. 14, pp. 2319-2322 (2004).

Dufresne et al., "The development of potent non-peptidic PTP-1B inhibitors," Bioorganic & Medicinal Chemistry Letters, vol. 14, pp. 1039-1042 (2004).

Leung et al. "The difluoromethylenesulfonic acid group as a monoanionic phosphate surrogate for obtaining PTP1B inhibitors," Bioorganic & Medicinal Chemistry, vol. 10, pp. 2309-2323 (2002).

Mooney et al., "The leukocyte common antigen-related protein LAR: candidate PTP for inhibitory targeting," Current Topics in Medicinal Chemistry, vol. 3, pp. 809-819 (2003).

Wasserman et al., "The Oxazole-Triamide Rearrangement Application Peptide Synthesis," Tetrahedron Letters, vol. 23, pp. 3831-3834 (1982).

Tiganis et al., "The protein-tyrosine phosphatase TCPTP regulates epidermal growth factor receptor-mediated and phosphatidylinositol 3-kinase-dependent signaling," The Journal of Biological Chemistry, vol. 274, pp. 27768-27775 (1999).

Widlanski et al., "The road less traveled: taming phosphatases," Chemistry & Biology, vol. 4, pp. 489-492 (1997).

Dube et al., "The role of protein tyrosine phosphatase 1B in Ras signaling," Proceedings of the National Academy of Sciences, vol. 101, pp. 1834-1839 (2004).

Andersen et al., "2-(oxalylamino)-benzoic acid is a general, competitive inhibitor of protein-tyrosine phosphatases," The Journal of Biological Chemistry, vol. 275, pp. 7101-7108 (2000).

Murthy et al., "3D-QSAR CoMFA and CoMSIA on Protein Tyrosine Phosphatase 1B Inhibitors," Bioorganic & Medicinal Chemistry, vol. 10, pp. 2267-2282 (2002).

Mok et al., "A single nucleotide polymorphism in protein tyrosine phosphatase PTP-1B is associated with protection from diabetes or impaired glucose Tolerance in Oji-Cree," The Journal of Clinical Endocrinology & Metabolism, vol. 87, pp. 724-727 (2002).

Shen et al., "Acquisition of a specific and potent PTP1B inhibitor from a novel combinatorial library and screening procedure," The Journal of Biological Chemistry, vol. 276, pp. 47311-47319 (2001).

International Search Report for related PCT application PCT/US2004/004076 mailed Aug. 24, 2004.

International Search Report for related PCT application PCT/US2004/004074 mailed Nov. 9, 2004.

International Search Report for related PCT application PCT/US2005/004590 mailed Aug. 9, 2005.

PCT partial International Search Report for related PCT application PCT/US2007/002675 mailed Jun. 6, 2007.

Claims from U.S. Appl. No. 11/056,498 as currently pending.

Prosecution History from U.S. Appl. No. 11/056,498.

Written Opinion of the International Searching Authority, PCT Patent Application PCT/US2007/002675 mailed Aug. 14, 2008.

International Search Report for related PCT application PCT/US2007/002675 mailed May 13, 2008.

Written Opinion for related PCT application PCT/US2007/002675 mailed May 13, 2008.

First Examination Report mailed Mar. 10, 2010 for New Zealand application 569329.

Written Opinion Report mailed Aug. 24, 2009 for Singapore application 200804987-6.

* cited by examiner

SUBSTITUTED IMIDAZOLE DERIVATIVES, COMPOSITIONS, AND METHODS OF USE AS PTPASE INHIBITORS

STATEMENT OF RELATED APPLICATION

The present application is a divisional application and claims priority under 35 USC §§120 and 121 to U.S. application Ser. No. 11/699,780 filed Jan. 30, 2007, and claims the benefit of priority to U.S. Provisional Application Ser. No. 60/763,256, filed Jan. 30, 2006, all of which are incorporated herein by reference.

FIELD OF THE INVENTION

This invention relates to substituted imidazole derivatives, compositions, and methods of treatment using the compounds and compositions which may be useful for the management, treatment, control, or adjunct treatment of diseases caused by activity of a protein phosphatase.

BACKGROUND OF THE INVENTION

Protein phosphorylation is now recognized as central to the fundamental processes of cellular signal transduction. Alterations in protein phosphorylation may therefore constitute either a physiological or pathological change in an in vivo system. Protein de-phosphorylation, mediated by phosphatases, is also central to certain signal transduction processes.

The two major classes of phosphatases are (a) protein serine/threonine phosphatases (PSTPases), which catalyze the dephosphorylation of serine and/or threonine residues on proteins or peptides; and (b) the protein tyrosine phosphatases (PTPases), which catalyze the dephosphorylation of tyrosine residues on proteins and/or peptides. A third class of phosphatases is the dual specificity phosphatases, or DSP's, which possess the ability to act both as PTPases and as PSTPases.

Among the PTPases there exist two important families, the intracellular PTPases, and the transmembrane PTPases. The intracellular PTPases include PTP1B, STEP, PTPD1, PTPD2, PTPMEG1, T-cell PTPase, PTPH1, FAP-1/BAS, PTP1D, and PTP1C. The transmembrane PTPases include LAR, CD45, PTPα, PTPβ, PTPδ, PTPε, PTPξ, PTPκ, PTPμ, PTPσ, HePTP, SAP-1, and PTP-U2. The dual-specificity phosphatases include KAP, cdc25, MAPK phosphatase, PAC-1, and rVH6.

The PTPases, especially PTP1B, are implicated in insulin insensitivity characteristic of type II diabetes (Kennedy, B. P.; Ramachandran, C. *Biochem. Pharm.* 2000, 60, 877-883). The PTPases, notably CD45 and HePTP, are also implicated in immune system function, and in particular T-cell function. Certain PTPases, notably TC-PTP, DEP-1, SAP-1, and CDC25, are also implicated in certain cancers. Certain PTPases, notably the bone PTPase OST-PTP, are implicated in osteoporosis. PTPases are implicated in mediating the actions of somatostatin on target cells, in particular the secretion of hormone and/or growth factor secretion.

Thus, there is a need for agents which inhibit the action of protein tyrosine phosphatases. Such agents may be useful for the treatment of glucose intolerance including Type I diabetes and Type II diabetes, immune dysfunction including AIDS, allergic diseases, inflammatory diseases, and autoimmunity such as psoriasis, infectious diseases, obesity, cancer, diseases involving the modulated synthesis of growth hormone or the modulated synthesis of growth factors or cytokines which affect the production of growth hormone, or Alzheimer's disease.

SUMMARY OF THE INVENTION

This invention provides substituted imidazole derivatives and compositions which inhibit PTP1B. In an embodiment, the present invention provides compounds of Formula (I-IV) as depicted below. In another embodiment, the present invention provides methods of preparation of compounds of Formula (I-IV). In another embodiment, the present invention provides pharmaceutical compositions comprising the compounds of Formula (I-IV). In another embodiment, the present invention provides methods of using the compounds of Formula (I-IV) in treating human or animal disorders. The compounds of the invention are useful as inhibitors of protein tyrosine phosphatases and thus may be useful for the management, treatment, control and adjunct treatment of a disease mediated by PTPase activity. Such diseases may comprise glucose intolerance including Type I diabetes and Type II diabetes, immune dysfunction including AIDS, allergic diseases, inflammatory diseases, and autoimmunity such as psoriasis, infectious diseases, obesity, cancer, diseases involving the modulated synthesis of growth hormone or the modulated synthesis of growth factors or cytokines which affect the production of growth hormone, or Alzheimer's disease.

DETAILED DESCRIPTION

Embodiments of the present invention comprise substituted imidazole derivatives, compositions, and methods of use. The present invention may be embodied in a variety of ways.

In a first aspect, the present invention provides imidazole inhibitors of protein tyrosine phosphatases (PTPases) which are useful for the management and treatment of disease caused by PTPases.

In another aspect, the present invention provides a compound of Formula I, II, III, or IV:

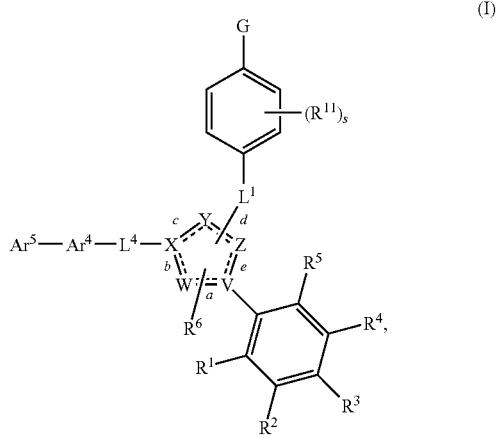

-continued

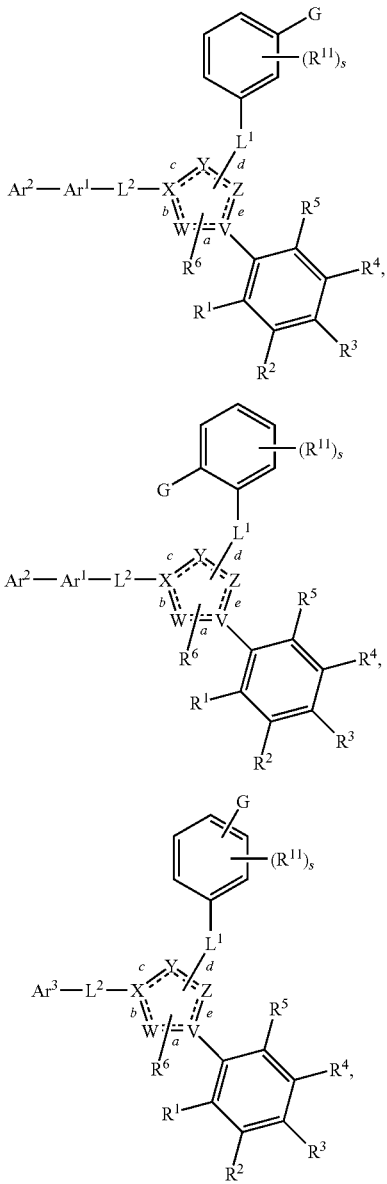

(II)

(III)

(IV)

wherein
Ar$^1$, Ar$^2$, Ar$^4$, and Ar$^5$ are independently selected from the group consisting of: phenyl, indanyl, tetrahydronaphthyl, pyridazine, pyrimidine, pyrazine, pyridine, piperidine, 4,5-diaza-indanyl, 5,6,7,8-tetrahydro-cinnoline, and 1-H-pyridin-2-one, and
Ar$^3$ is phenyl, naphthalene, indanyl, tetrahydronaphthyl, pyridazine, pyrimidine, pyrazine, pyridine, piperidine, 4,5-diaza-indanyl, or 5,6,7,8-tetrahydro-cinnoline,
  wherein
    Ar$^1$, Ar$^2$, Ar$^3$, and Ar$^4$ are each optionally substituted 1 to 4 times with a group independently selected from R$^b$, and
    Ar$^5$ is optionally substituted 1 to 4 times with a group selected from R$^a$;
V is C, W is C, X is N, Y is C, Z is N,
  when sides b, c, and e are single bonds, and sides a and d are double bonds; or
V is C, W is N, X is C, Y is N, Z is C,
  when sides a, c, and d are single bonds, and sides b and e are double bonds; or
V is C, W is N, X is C, Y is C, Z is N,
  when sides a, b, and d are single bonds, and sides c and e are double bonds;
L$^1$ is -T$^1$-L$^3$-T$^2$-,
  wherein
    L$^3$ is a direct bond, —C$_{1-10}$ alkylene, —C$_{2-10}$ alkenylene, or —C$_{2-10}$ alkynylene;
    T$^1$ and T$^2$ are independently selected from the group consisting of a direct bond, —CH$_2$—, —O—, —N(R$^{16}$)—, —C(O)—, —CON(R$^{16}$)—, —N(R$^{16}$)C(O)—, —N(R$^{16}$)CON(R$^{17}$)—, —N(R$^{16}$)C(O)O—, —OC(O)N(R$^{16}$)—, —N(R$^{16}$)SO$_2$—, —SO$_2$N(R$^{16}$)—, —C(O)—O—, —O—C(O)—, —S—, —S(O)—, —S(O)$_2$—, —N(R$^{16}$)SO$_2$N(R$^{17}$)—, —N═N—, and —N(R$^{16}$)—N(R$^{17}$)—;
    wherein
      R$^{16}$ and R$^{17}$ are independently selected from the group consisting of: -hydrogen, —C$_{1-10}$ alkyl, -aryl, -arylene-C$_{1-10}$ alkyl, and —C$_{1-10}$ alkylene-aryl, wherein alkyl and aryl are optionally substituted with R$^c$;
L$^2$ is selected from the group consisting of: —CH(R$^{18}$)—CH(R$^{19}$)—, —N(R$^{18}$)C(O)—, —N(R$^{18}$)—, —N(R$^{18}$)S(O)$_2$—, —C(O)N(R$^{18}$)—, —S(O)$_2$N(R$^{18}$), (trans)-C(R$^{18}$)═C(R$^{19}$)—, (cis)-C(R$^{18}$)═C(R$^{19}$)—, —C≡C—, —C(O)—, —O—, —C$_{1-5}$ alkylene-O—, O—C$_{1-5}$ alkylene, —(CH$_2$)$_r$—, 1,1 cycloalkylmethylene, or a direct bond,
  wherein
    R$^{18}$ and R$^{19}$ are independently selected from the group consisting of: -hydrogen, —C$_{1-10}$ alkyl, -aryl, -arylene-C$_{1-10}$ alkyl, and —C$_{1-10}$ alkylene-aryl, wherein alkyl and aryl are optionally substituted with R$^c$;
L$^4$ is selected from the group consisting of: a direct bond and —CH$_2$—,
R$^1$, R$^2$, R$^3$, R$^4$, and R$^5$ are independently selected from the group consisting of hydrogen and R$^b$,
R$^6$ is selected from the group consisting of hydrogen and R$^b$,
R$^{11}$ is selected from the group consisting of R$^b$,
G is

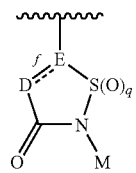

wherein
  a) D is C(R$^7$)(R$^8$), and
     E is C(R$^7$) or N,
     when side f is a single bond, or
  b) D is C(R$^7$), and
     E is C,
     when side f is a double bond,
     wherein
       R$^7$ and R$^8$ are independently selected from the group consisting of halo, hydroxy, amino, cyano, nitro, carboxy, —SO$_3$H, R$^f$ and R$^g$;

or

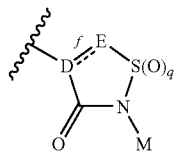

wherein
   a) D is $C(R^7)$, and
      E is $C(R^7)(R^8)$ or $N(R^9)$,
      when side f is a single bond, or
   b) D is C, and
      E is $C(R^7)$ or N,
      when side f is a double bond,
      wherein
         $R^7$ and $R^9$ are independently selected from the group consisting of: halo, hydroxy, amino, cyano, nitro, carboxy, —$SO_3H$, $R^f$ and $R^g$; and
         $R^9$ is $R^d$, M is hydrogen or a counter ion selected from the group consisting of: $Na^+$, $K^+$, and other pharmaceutically acceptable counter ions;

$R^a$ is
   a) -cycloalkyl,
   b) -cyano,
   c) —$OR^d$,
   d) —$NO_2$,
   e) -halogen,
   f) —$S(O)_m C_{2-10}$alkyl,
   g) —$SR^d$,
   h) —$S(O)_2OR^d$,
   i) —$S(O)_mNR^dR^e$,
   j) —$NR^dS(O)_mR^e$,
   k) —$NR^dR^e$,
   l) —$O(CR^fR^g)_nNR^dR^e$,
   m) —$C(O)R^d$,
   n) —$CO_2R^d$,
   o) —$CO_2(CR^fR^g)_nCONR^dR^e$,
   p) —$OC(O)R^d$,
   q) —$C(O)NR^dR^e$,
   r) —$NR^dC(O)R^e$,
   s) —$OC(O)NR^dR^e$,
   t) —$NR^dC(O)OR^e$,
   u) —$NR^dC(O)NR^dR^e$,
   v) —$CF_3$,
   w) —$OCF_3$
   x) —$C_{1-10}$ alkyl,
   y) —$C_{2-10}$ alkenyl,
   z) —$C_{2-10}$ alkynyl,
   aa) —$C_{1-10}$ alkylene-aryl,
   bb) —$C_{1-10}$ alkylene-heteroaryl,
   cc) -heteroaryl,
   dd) —$C(R^f)$=$C(R^g)$—$R^f$, or
   ee) —C≡C—$R^f$,
   wherein alkyl, alkenyl, alkynyl, aryl, heteroaryl, and cycloalkyl groups are optionally substituted 1-4 times with a group independently selected from $R^c$;

$R^b$ is
   a) -cycloalkyl,
   b) -cyano,
   c) —$OR^d$,
   d) —$NO_2$,
   e) -halogen,
   f) —$S(O)_mR^d$,
   g) —$SR^d$,
   h) —$S(O)_2OR^d$,
   i) —$S(O)_mNR^dR^e$,
   j) —$NR^dS(O)_mR^e$,
   k) —$NR^dR^e$,
   l) —$O(CR^fR^g)_nNR^dR^e$,
   m) —$C(O)R^d$,
   n) —$CO_2R^d$,
   o) —$CO_2(CR^fR^g)_nCONR^dR^e$,
   p) —$OC(O)R^d$,
   q) —$C(O)NR^dR^e$,
   r) —$NR^dC(O)R^e$,
   s) —$OC(O)NR^dR^e$,
   t) —$NR^dC(O)OR^e$,
   u) —$NR^dC(O)NR^dR^e$,
   v) —$CF_3$,
   w) —$OCF_3$
   x) —$C_{1-10}$ alkyl,
   y) —$C_{2-10}$ alkenyl,
   z) —$C_{2-10}$ alkynyl,
   aa) —$C_{1-10}$ alkylene-aryl,
   bb) —$C_{1-10}$ alkylene-heteroaryl,
   cc) -heteroaryl,
   dd) —$C(R^f)$=$C(R^g)$—$R^f$, or
   ee) —C≡C—$R^f$,
   wherein alkyl, alkenyl, alkynyl, aryl, heteroaryl, and cycloalkyl groups are optionally substituted 1-4 times with a group independently selected from $R^c$;

$R^c$ is
   a) -halogen,
   b) -amino,
   c) -carboxy,
   d) —$C_{1-4}$ alkyl,
   e) —O—$C_{1-4}$ alkyl,
   f) -cycloalkyl,
   g) —O-cycloalkyl,
   h) -aryl,
   i) —$C_{1-4}$ alkylene-aryl,
   j) -hydroxy,
   k) —$CF_3$,
   l) —O-aryl,
   m) -heteroaryl,
   n) -heteroaryl-$C_{1-10}$ alkyl,
   o) heterocyclyl,
   p) —$CO_2$—$C_{1-10}$ alkyl, or
   q) —$CO_2$—$C_{1-10}$ alkyl-aryl, $R^d$ and $R^e$ are independently selected from hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heterocyclyl, wherein alkyl, alkenyl, alkynyl, cycloalkyl, aryl, heterocyclyl groups are optionally substituted with one to four substituents independently selected from $R^c$; or $R^d$ and $R^e$ together with the atoms to which they are attached form a heterocyclic ring of 5 to 7 members containing 0-2 additional heteroatoms independently selected from oxygen, sulfur and nitrogen and optionally substituted with 1-3 times with $R^c$, and wherein 1 or 2 carbon atoms in the heterocyclic ring may be oxidized, $R^f$ and $R^g$ are independently selected from hydrogen, $C_{1-10}$ alkyl, cycloalkyl, —$C_{1-10}$ alkylene-cycloalkyl, and aryl, wherein alkyl, cycloalkyl, and aryl groups are optionally substituted with one to four substituents independently selected from $R^c$; or $R^f$ and $R^g$ together with the carbon to which they are attached form a ring of 5 to 7 members containing 0-2 heteroatoms independently selected from oxygen, sulfur and nitrogen optionally substituted with 1-3 times with $R^c$, and wherein 1 or 2 carbon atoms in the heterocyclic ring may be oxidized;

m is an integer from 1 to 2, n is an integer from 1 to 10, q is an integer from 1 to 2, r is an integer from 1 to 5, and s is an integer from 0 to 3, or pharmaceutically acceptable salt, solvate, or prodrug thereof.

In an embodiment, M is hydrogen or a counter ion selected from the group consisting of: sodium (Na$^+$), potassium (K$^+$), ammonium, morpholinium, barium, calcium salt. In another embodiment, M is hydrogen. In another embodiment, M is selected from the group consisting of: hydrogen, sodium and potassium. In another embodiment, M is selected from the group consisting of: sodium and potassium.

In another embodiment, the present invention provides a compound of Formula I, II, III, or IV, having the formula:

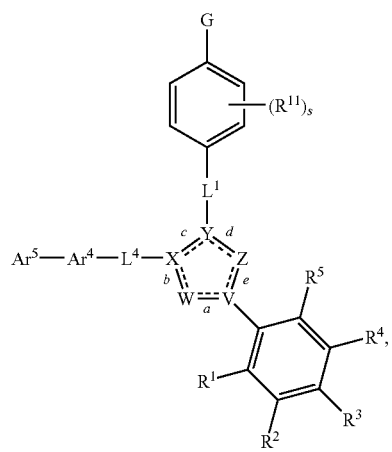
(Ia)

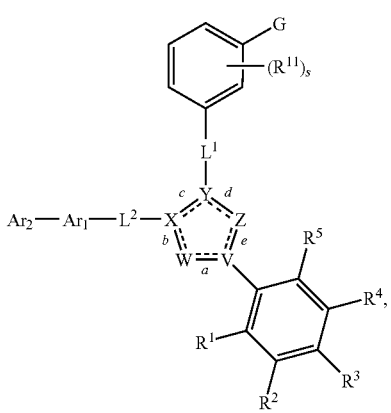
(IIa)

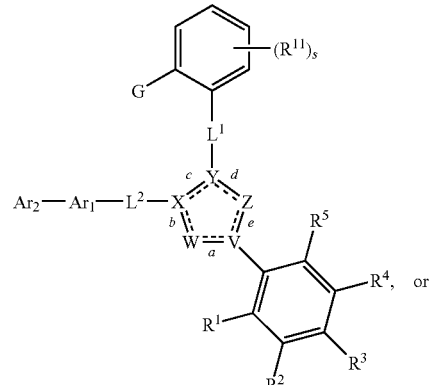
(IIIa)

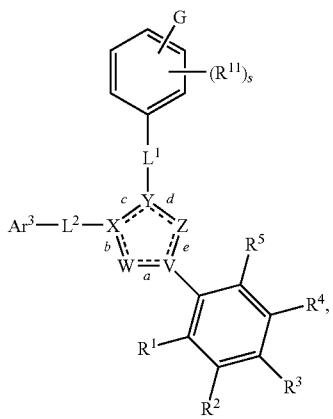
(IVa)

wherein
V is C, W is C—R$^6$, X is N, Y is C, Z is N,
when sides b, c, and e are single bonds, and sides a and d are double bonds; or
V is C, W is N, X is C, Y is N, Z is C—R$^6$,
when sides a, c, and d are single bonds, and sides b and e are double bonds; or
V is C, W is N—R$^6$, X is C, Y is C, Z is N,
when sides a, b, and d are single bonds, and sides c and e are double bonds;
R$^6$ is selected from the group consisting of hydrogen and R$^b$.

In another embodiment, the present invention provides a compound of Formula I, II, III, or IV, having the formula:

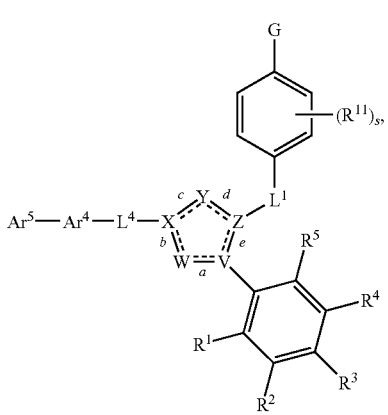
(Ib)

-continued

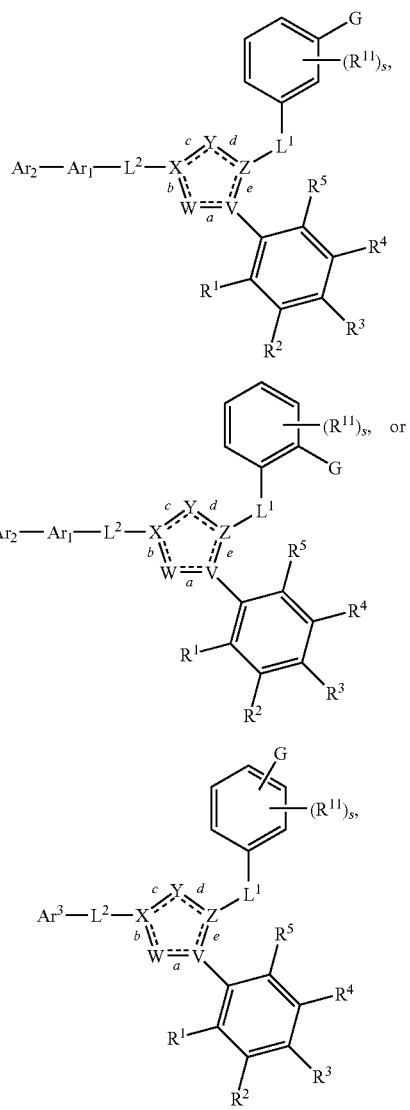

(IIb)

(IIIb)

(IVb)

wherein
V is C, W is N, X is C, Y is N—R⁶, Z is C,
and sides a, c, and d are single bonds, and sides b and e are double bonds; and
R⁶ is selected from the group consisting of hydrogen and R$^b$.

In another embodiment, $Ar^1$ and $Ar^4$ are independently selected from the group consisting of: phenyl-1,4-yl, pyridazine-3,6-yl, pyrimidine-2,5-yl, and pyrazine-2,5-yl.

In another embodiment, $Ar^1$, $Ar^2$, $Ar^4$, and $Ar^5$ are independently selected from the group consisting of: phenyl and pyridazine.

In another embodiment, one of $Ar^1$ and $Ar^2$ is phenyl and the other is pyridazine.

In another embodiment, both of $Ar^1$ and $Ar^2$ are either phenyl or pyridazine.

In another embodiment, $Ar^2$ is phenyl and $Ar^1$ is pyridazine-3,6-yl.

In another embodiment, $Ar^1$ is phenyl-1,4-yl and $Ar^2$ is pyridazine-3-yl.

In another embodiment, one of $Ar^4$ and $Ar^5$ is phenyl and the other is pyridazine.

In another embodiment, both of $Ar^4$ and $Ar^5$ are either phenyl or pyridazine.

In another embodiment, $Ar^5$ is phenyl and $Ar^4$ is pyridazine-3,6-yl.

In another embodiment, $Ar^4$ is phenyl-1,4-yl and $Ar^5$ is pyridazine-3-yl.

In another embodiment, $Ar^3$ is phenyl and substituted with a halogen.

In another embodiment, $Ar^2$, $Ar^3$, and $Ar^5$ are substituted with at least one lipophilic group.

In an embodiment, said compound has Formula Ia. In another embodiment, said compound has Formula IIa. In another embodiment, said compound has Formula IIIa. In another embodiment, said compound has Formula IVa.

In an embodiment wherein said compound has Formula Ia, IIa, IIIa, or IVa, V is C, W is C—R⁶, X is N, Y is C, Z is N, sides b, c, and e are single bonds, and sides a and d are double bonds.

In another embodiment where said compound has Formula Ia, IIa, IIIa, or IVa, V is C, W is N, X is C, Y is N, Z is C—R⁶, and sides a, c, and d are single bonds, and sides b and e are double bonds.

In another embodiment where said compound has Formula Ia, IIa, IIIa, or IVa, V is C, W is N—R⁶, X is C, Y is C, Z is N, and sides a, b, and d are single bonds, and sides c and e are double bonds.

In another embodiment, R⁶ is selected from the group consisting of hydrogen and $C_{1-4}$ alkyl.

In another embodiment wherein said compound has Formula Ia, IIa, IIIa, or IVa, V is C, W is N, X is C, Y is N, Z is C—R⁶, and sides a, c, and d are single bonds, and sides b and e are double bonds, and R⁶ is selected from the group consisting of hydrogen and $C_{1-10}$ alkyl.

In another embodiment, $L^1$ is $-T^1-L^3-T^2-$, wherein $L^3$, $T^1$ and $T^2$ are direct bonds.

In another embodiment, $L^1$ is $-T^1-L^3-T^2-$, wherein $T^1$ and $T^2$ are direct bonds and $L^3$ is —CH₂—

In another embodiment, $L^1$ is $-T^1-L^3-T^2-$, wherein $L^3$ is a direct bond or $C_{1-10}$ alkylene, $T^1$ is a direct bond, and $T^2$ is selected from the group consisting of —O—, —N(R¹⁶)—, —C(O)—, —CON(R¹⁶)—, —N(R¹⁷)C(O)—, —N(R₆)CON (R¹⁶)—, —N(R¹⁶)C(O)O—, —OC(O)N(R¹⁶)—, —N(R¹⁶)SO₂—, —SO₂N(R¹⁶)—, —C(O)—O—, —O—C(O)—, —S—, —S(O)—, —S(O)₂—, and —N(R¹⁶)SO₂N(R¹⁷)—.

In another embodiment, $L^1$ is $-T^1-L^3-T^2-$, wherein $L^3$ is a direct bond or $C_{1-10}$ alkylene, $T^2$ is a direct bond, and $T^1$ is selected from the group consisting of —O—, —N(R¹⁶)—, —C(O)—, —CON(R¹⁶)—, —N(R¹⁷)C(O)—, —N(R₆)CON (R¹⁶)—, —N(R¹⁶)C(O)O—, —OC(O)N(R¹⁶)—, —N(R¹⁶)SO₂—, —SO₂N(R¹⁶)—, —C(O)—O—, —O—C(O)—, —S—, —S(O)—, —S(O)₂—, and —N(R¹⁶)SO₂N(R¹⁷)—.

In another embodiment, $L^2$ is selected from the group consisting of —CH₂— or —CH₂—O—. In another embodiment, $L^2$ is —CH₂—. In another embodiment, $L^4$ is —CH₂—

In an embodiment, $R^1$, $R^2$, $R^3$, $R^4$, and $R^5$ are independently selected from the group consisting of:
a) -hydrogen;
b) -fluoro;
c) -chloro;
d) trifluoromethyl;
e) trifluoromethoxy;
f) —SO₂—$C_{1-6}$ alkyl;
g) -cyano;
h) -nitro; and
i) -phenyl.

In another embodiment, at least one of $R^1$, $R^2$, $R^3$, $R^4$, and $R^5$ is not hydrogen. In another embodiment, $R^1$, $R^2$, $R^3$, $R^4$, and $R^5$ are independently selected from the group consisting of hydrogen, fluoro, and chloro, wherein at least one of at least one of $R^1$, $R^2$, $R^3$, $R^4$, and $R^5$ is not hydrogen. In another embodiment, $R^1$ and $R^3$ are chloro or fluoro, and $R^2$, $R^4$, and $R^5$ are hydrogen.

In an embodiment, s is an integer from 1 to 3 and $R^{11}$ is independently selected from the group consisting of: methyl, methoxy, chloro, fluoro, nitro, cyano, hydroxy, trifluoromethyl, trifluoromethoxy, —$SO_2$—$CH_3$, —$SO_2$—$CF_3$, —$NHSO_2$—$CH_3$, —$NHSO_2$—$CF_3$, and cyclopropyl. In another embodiment, s is zero.

In an embodiment, G is

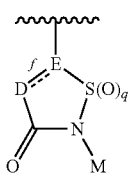

wherein
a) q is 2, D is $C(R^7)(R^8)$, E is $C(R^7)$ or N, when side f is a single bond, or
b) q is 2, D is $C(R^7)$, E is C, when side f is a double bond.

In a further embodiment, $R^7$ and $R^8$ are selected from the group consisting of: hydrogen and $C_{1-4}$ alkyl.

In another embodiment, G is

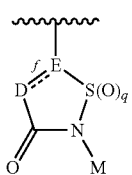

wherein
q is 2, D is $C(R^7)(R^8)$, E is N, and side f is a single bond.

In a further embodiment, $R^7$ and $R^8$ are selected from the group consisting of: hydrogen and $C_{1-4}$ alkyl.

In another embodiment, G is

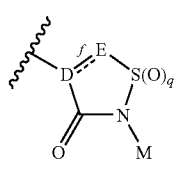

wherein
a) q is 2, D is $C(R^7)$, E is $C(R^7)(R^8)$ or $N(R^9)$, when side f is a single bond, or
b) q is 2, D is C, E is $C(R^7)$ or N, when side f is a double bond.

In a further embodiment, $R^7$, $R^8$, and $R^9$ are selected from the group consisting of: hydrogen and $C_{1-4}$ alkyl.

In an embodiment wherein the compound has the Formula IV, $Ar^3$ is naphthyl-2-yl and is substituted at the 6 position with a group selected from $R^b$ and may be further optionally substituted with 1 to 2 groups independently selected from $R^b$.

In another embodiment wherein the compound has the Formula IV, $Ar^3$ is phenyl and is substituted at the 4 position with a group selected from —$C(R^f)$=$C(R^g)$—$R^f$, and —C≡C—$R^f$, and the phenyl group may be further optionally substituted with 1 to 2 groups independently selected from $R^b$.

In an embodiment wherein the compound has the Formula II or III, $Ar^2$ is substituted with 1 to 3 groups independently selected from $R^b$.

In an embodiment wherein the compound has the Formula I, $Ar^5$ is substituted with 1 to 3 groups independently selected from $R^a$.

In another embodiment, $Ar^1$ and $Ar^4$ are unsubstituted, and $Ar^2$, $Ar^3$, and $Ar^5$ are each substituted with 1 to 3 groups independently selected from the group consisting of:
—$C_{1-10}$ alkyl,
-cycloalkyl,
-heterocyclyl,
-trifluoroalkyl,
-halogen,
-nitro,
-carboxy,
—$CO_2$—$C_{1-10}$ alkyl,
—$C_{1-10}$ alkylene-$CO_2$—$C_{1-10}$ alkyl,
—$C_{2-10}$ alkenylene-$CO_2$—$C_{1-10}$ alkyl,
—$C_{1-10}$ alkylene-$CO_2H$,
—$C_{2-10}$ alkenylene-$CO_2H$,
—O—$C_{1-10}$ alkylene-C(O)NH—$C_{1-10}$ alkyl,
—C(O)—$C_{1-10}$ alkyl,
—C(O)NH—$C_{1-10}$ alkyl,
—O-heterocyclyl,
—O—$C_{1-10}$ alkyl,
—O—$C_{1-10}$ haloalkyl,
—O—$C_{1-10}$ perhaloalkyl,
—O-cycloalkyl,
—O-phenyl,
-hydroxy,
—O—$C_{1-10}$ alkylene-cycloalkyl,
—O—$C_{1-10}$ alkylene-phenyl,
—S-heterocyclyl,
—S—$C_{1-10}$ alkyl,
—S—$C_{1-10}$ haloalkyl,
—S—$C_{1-10}$ perhaloalkyl,
—S-cycloalkyl,
—S-phenyl,
—S—$C_{1-10}$ alkylene-cycloalkyl,
—S—$C_{1-10}$ alkylene-phenyl,
—$C_{1-10}$ alkylene-cycloalkyl,
—$C_{1-10}$ alkylene-phenyl,
-amino,
—NH($C_{1-10}$ alkyl),
—N($C_{1-10}$ alkyl)$_2$,
—N($C_{1-10}$ alkyl)($C_{1-10}$ alkylene-cycloalkyl),
—$NHCO_2$—$C_{1-10}$ alkyl,
—NH($C_{1-10}$ alkylene-cycloalkyl),
—$S(O)_2$—$C_{2-10}$ alkyl,
—$SO_2$-cycloalkyl,
—$SO_2$—$C_{1-10}$ alkylene-cycloalkyl,
—S(O)—$C_{1-10}$ alkyl,
—S(O)-cycloalkyl, and
—S(O)—$C_{1-10}$ alkylene-cycloalkyl,
wherein alkyl, alkenyl, aryl, heteroaryl, and cycloalkyl groups are optionally substituted 1-4 times with a group independently selected from $R^c$.

In another embodiment, $Ar^1$ and $Ar^4$ are unsubstituted, and $Ar^2$, $Ar^3$, and $Ar^5$ are each substituted with 1 to 3 groups independently selected from the group consisting of:
—$C_{1-10}$ alkyl,
-cycloalkyl,
-heterocyclyl, -trifluoroalkyl,
-halogen,
-nitro,
—$CO_2$—$C_{1-10}$ alkyl,
—$C_{1-10}$ alkylene-$CO_2$—$C_{1-10}$ alkyl,
—$C_{2-10}$ alkenylene-$CO_2$—$C_{1-10}$ alkyl,
—O—$C_{1-10}$ alkylene-C(O)NH—$C_{1-10}$ alkyl,
—C(O)—$C_{1-10}$ alkyl,
—C(O)NH—$C_{1-10}$ alkyl,
—O-heterocyclyl,
—O—$C_{1-10}$ alkyl,
—O—$C_{1-10}$ haloalkyl,
—O—$C_{1-10}$ perhaloalkyl,
—O-cycloalkyl,
—O-phenyl,
—O—$C_{1-10}$ alkylene-cycloalkyl,
—O—$C_{1-10}$ alkylene-phenyl,
—S-heterocyclyl,
—S—$C_{1-10}$ alkyl,
—S—$C_{1-10}$ haloalkyl,
—S—$C_{1-10}$ perhaloalkyl,
—S-cycloalkyl,
—S-phenyl,
—S—$C_{1-10}$ alkylene-cycloalkyl,
—S—$C_{1-10}$ alkylene-phenyl,
—$C_{1-10}$ alkylene-cycloalkyl,
—$C_{1-10}$ alkylene-phenyl,
—NH($C_{1-10}$ alkyl),
—N($C_{1-10}$ alkyl)$_2$,
—N($C_{1-10}$ alkyl)($C_{1-10}$ alkylene-cycloalkyl),
—$NHCO_2$—$C_{1-10}$ alkyl,
—NH($C_{1-10}$ alkylene-cycloalkyl),
—$S(O)_2$—$C_{2-10}$ alkyl,
—$SO_2$-cycloalkyl,
—$SO_2$—$C_{1-10}$ alkylene-cycloalkyl,
—S(O)—$C_{1-10}$ alkyl,
—S(O)-cycloalkyl, and
—S(O)—$C_{1-10}$ alkylene-cycloalkyl.

In another embodiment, $Ar^1$ and $Ar^4$ are unsubstituted, and $Ar^2$, $Ar^3$, and $Ar^5$ are each substituted with 1 to 3 groups independently selected from the group consisting of:
—$C_{1-10}$ alkyl,
-cycloalkyl,
-trifluoroalkyl,
-halogen,
—$CO_2$—$C_{1-10}$ alkyl,
—$C_{1-10}$ alkylene-$CO_2$—$C_{1-10}$ alkyl,
—$C_{2-10}$ alkenylene-$CO_2$—$C_{1-10}$ alkyl,
—O—$C_{1-10}$ alkylene-C(O)NH—$C_{1-10}$ alkyl,
—C(O)—$C_{1-10}$ alkyl,
—O—$C_{1-10}$ alkyl,
—O—$C_{1-10}$ haloalkyl,
—O—$C_{1-10}$ perhaloalkyl,
—O-cycloalkyl,
—O-phenyl,
—O—$C_{1-10}$ alkylene-cycloalkyl,
—O—$C_{1-10}$ alkylene-phenyl,
—S—$C_{1-10}$ alkyl,
—S—$C_{1-10}$ haloalkyl,
—S—$C_{1-10}$ perhaloalkyl,
—S-cycloalkyl,
—S-phenyl,
—S—$C_{1-10}$ alkylene-cycloalkyl,
—S—$C_{1-10}$ alkylene-phenyl,
—$C_{1-10}$ alkylene-cycloalkyl,
—$C_{1-10}$ alkylene-phenyl,
—$S(O)_2$—$C_{2-10}$ alkyl,
—$SO_2$-cycloalkyl,
—$SO_2$—$C_{1-10}$ alkylene-cycloalkyl,
—S(O)—$C_{1-10}$ alkyl,
—S(O)-cycloalkyl, and
—S(O)—$C_{1-10}$ alkylene-cycloalkyl.

In another embodiment, $Ar^1$ and $Ar^4$ are unsubstituted, and $Ar^2$, $Ar^3$, and $Ar^5$ are each substituted with 1 to 3 groups independently selected from the group consisting of:
morpholine-4-yl,
piperidine-4-yl,
piperidine-1-yl,
4-piperidinyl-oxy,
3-piperidinyl-oxy,
2-oxo-piperidine-1-yl,
3-oxo-piperidine-1-yl,
[1-($C_{1-10}$ alkylsulfonyl)-piperidine-4-yl]-oxy,
[1-($C_{1-10}$ alkyloxycarbonyl)-piperidine-4-yl]-oxy,
[1-($C_{1-10}$ alkyloxycarbonyl)-piperidine-3-yl]-oxy,
piperazine-1-yl,
4-($C_{1-10}$ alkyl)-piperazine-1-yl,
2-oxo-piperazine-4-yl,
1-$C_{1-10}$ alkyl-2-oxo-piperazine-4-yl,
1-cycloalkyl-2-oxo-piperazine-4-yl,
4-tetrahydropyranyloxy,
3-tetrahydrofuranyloxy,
4-($C_{1-10}$ alkyloxycarbonyl)piperazine-1-yl,
pyrrolidine-1-yl,
3-phenyl-pyrrolidine-1-yl,
3-cycloalkyl-pyrrolidine-1-yl,
[1-($C_{1-10}$ alkoxycarbonyl)-pyrrolidine-3-yl]-oxy,
2-thiophenyloxy,
2-thiazolyloxy,
(1,2,4-oxadiazole-3-yl)-oxy,
(1-methyl-imidazole-2-yl)-oxy, and
(imidazole-2-yl)-$C_{1-10}$ alkyoxy,
wherein the alkyl, phenyl, cycloalkyl, morpholine, piperidine, piperazine, cycloalkyl, tetrahydropyran, tetrahydrofuran, pyrrolidine, thiazole, imidazole groups are optionally substituted 1-4 times with a group independently selected from $R^c$.

In another embodiment where the compound has the Formula Ia, IIa, IIIa, or IVa, $Ar^1$, $Ar^2$, $Ar^4$, and $Ar^5$ are independently selected from the group consisting of:
phenyl and pyridazine,
$L^1$ is a direct bond or —$CH_2$—,
$L^2$ is —$CH_2$—,
$L^4$ is —$CH_2$—,
V is C, W is N, X is C, Y is N, Z is C—$R^6$, and sides a, c, and d are single bonds,
and sides b and e are double bonds, and
G is

wherein
q is 2, D is C($R^7$)($R^8$), E is N, and side f is a single bond.

In another embodiment, $Ar^1$ and $Ar^4$ are unsubstituted, and $Ar^2$, $Ar^3$, and $Ar^5$ are substituted with at least one group selected from the group consisting of: methyl, ethyl, propyl, butyl, pentyl, hexyl, 1-ethyl-propyl, 1-propyl-butyl, 3,3-dimethyl-butyl, 4-methyl-pentyl, 4,4-dimethyl-pentyl, 1-(3,3-dimethyl-butyl)-4,4-dimethyl-pentyl, isobutyl, isopropyl, sec-butyl, tert-butyl, trifluoromethyl, 4,4,4-trifluorobutoxy, methoxy, ethoxy, propoxy, butoxy, pentoxy, hexyloxy, isobutoxy, isopropoxy, tert-butoxy, 2-phenethoxy, 2,2-dimethyl-propoxy, 3-methyl-butoxy, 3,3-dimethyl-butoxy, 3'-phenethyloxy, 2-cyclohexyl-ethanesulfonyl, 3,3-dimethyl-butane-1-sulfonyl, cyclohexanesulfonyl, cyclohexylmethanesulfonyl, cyclohexylmethylsulfonyl, 2-cyclohexyl-ethanesulfinyl, 3,3-dimethyl-butane-1-sulfinyl, cyclohexylmethylsulfinyl, 2-cyclohexyl-ethylsulfanyl, 3,3-dimethyl-butylsulfanyl, phenethylsulfanyl, cyclohexylmethylsulfanyl, cyclopentyl, cyclohexyl, cyclopentyloxy, cyclohexyloxy, cyclopentylmethyl, cyclohexylmethyl, 2-cyclopentylethyl, 2-cyclohexylethyl, cyclopentylmethoxy, cyclohexylmethoxy, 2-cyclopentylethoxy, 2-cyclohexylethoxy, 2-cyclohexyl-vinyl, 3-ethyl-cyclobutyl, amino, butylamino, diethylamino, Bis-(3,3-dimethyl-butyl)-amino, cyclohexylmethyl-amino, cyclohexylmethyl-ethyl-amino, 3-phenyl-pyrrolidin-1-yl, cyclohexyl-pyrrolidin-1-yl, piperidin-1-yl, piperidin-2-one-1-yl, piperazin-1-yl, piperazin-2-one-1-yl, piperazin-2-one-4-yl, piperazine-1-carboxylic acid 2,2-dimethyl-propyl ester, 1-cyclohexyl-piperazin-2-one-4-yl, 1-ethyl-piperazin-2-one-4-yl, 1-isopropyl-piperazin-2-one-4-yl, 1-methyl-piperazin-2-one-4-yl, 4-methyl-piperazin-1-yl, chloro, fluoro, nitro, phenyl, propionyl, carboxy, carboxymethyl, and morpholin-4-yl.

In another embodiment, $Ar^1$ and $Ar^4$ are unsubstituted, and $Ar^2$, $Ar^3$, and $Ar^5$ are substituted with at least one group selected from the group consisting of: methyl, ethyl, propyl, butyl, pentyl, hexyl, 1-ethyl-propyl, 1-propyl-butyl, 3,3-dimethyl-butyl, 4-methyl-pentyl, 4,4-dimethyl-pentyl, 1-(3,3-dimethyl-butyl)-4,4-dimethyl-pentyl, isobutyl, isopropyl, sec-butyl, tert-butyl, trifluoromethyl, 4,4,4-trifluorobutoxy, methoxy, ethoxy, propoxy, butoxy, pentoxy, hexyloxy, isobutoxy, isopropoxy, tert-butoxy, 2-phenethoxy, 2,2-dimethyl-propoxy, 3-methyl-butoxy, 3,3-dimethyl-butoxy, 3'-phenethyloxy, 2-cyclohexyl-ethanesulfonyl, 3,3-dimethyl-butane-1-sulfonyl, cyclohexanesulfonyl, cyclohexylmethanesulfonyl, cyclohexylmethylsulfonyl, 2-cyclohexyl-ethanesulfinyl, 3,3-dimethyl-butane-1-sulfinyl, cyclohexylmethylsulfinyl, 2-cyclohexyl-ethylsulfanyl, 3,3-dimethyl-butylsulfanyl, phenethylsulfanyl, cyclohexylmethylsulfanyl, cyclopentyl, cyclohexyl, cyclopentyloxy, cyclohexyloxy, cyclopentylmethyl, cyclohexylmethyl, 2-cyclopentylethyl, 2-cyclohexylethyl, cyclopentylmethoxy, cyclohexylmethoxy, 2-cyclopentylethoxy, 2-cyclohexylethoxy, 2-cyclohexyl-vinyl, 3-ethyl-cyclobutyl, chloro, fluoro, and phenyl.

In another embodiment, the present invention provides a compound of Formula IIa having the formula:

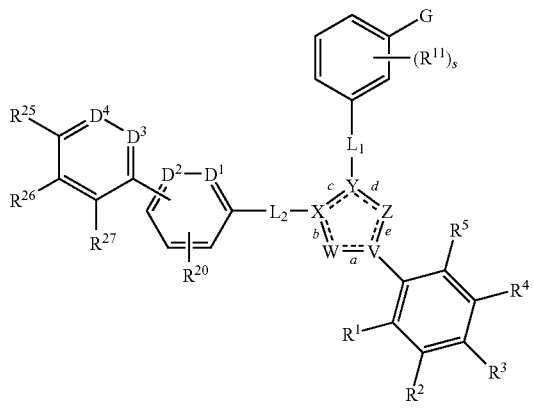

(IIc)

wherein
V is C, W is C—$R^6$, X is N, Y is C, Z is N,
  when sides b, c, and e are single bonds, and sides a and d are double bonds; or
V is C, W is N, X is C, Y is N, Z is C—$R^6$,
  when sides a, c, and d are single bonds, and sides b and e are double bonds; or
V is C, W is N—$R^6$, X is C, Y is C, Z is N,
  when sides a, b, and d are single bonds, and sides c and e are double bonds;
  wherein $R^6$ is hydrogen or $R^b$,
$D^1$ is C—$R^{21}$ and $D^2$ is C—$R^{22}$, or $D^1$ and $D^2$ are N;
$D^3$ is C—$R^{23}$ and $D^4$ is C—$R^{24}$, or $D^3$ and $D^4$ are N;
$L^1$ is -$T^1$-$L^3$-$T^2$-,
  wherein
    $L^3$ is a direct bond, —$C_{1-10}$ alkylene, —$C_{2-10}$ alkenylene, or —$C_{2-10}$ alkynylene;
    $T^1$ and $T^2$ are independently selected from the group consisting of a direct bond, —$CH_2$—, —O—, —N($R^{16}$)—, —C(O)—, —CON($R^{16}$)—, —N($R^{16}$)C(O)—, —N($R^{16}$)CON($R^{17}$)—, —N($R^{16}$)C(O)O—, —OC(O)N($R^{16}$)—, —N($R^{16}$)$SO_2$—, —$SO_2$N($R^{16}$)—, —C(O)—O—, —O—C(O)—, —S—, —S(O)—, —S(O)$_2$—, —N($R^{16}$)$SO_2$N($R^{17}$)—, —N═N—, or —N($R^{16}$)—N($R^{17}$)—;
    wherein
      $R^{16}$ and $R^{17}$ are independently selected from the group consisting of: -hydrogen, —$C_{1-10}$ alkyl, -aryl, -arylene-$C_{1-10}$ alkyl, or —$C_{1-10}$ alkylene-aryl, wherein alkyl and aryl are optionally substituted with $R^c$;
$L^2$ is selected from the group consisting of: —CH($R^{18}$)—CH($R^{19}$)—, —N($R^{18}$)C(O)—, —N($R^{18}$)—, —N($R^{18}$)S(O)$_2$—, —C(O)N($R^{18}$)—, —S(O)$_2$N($R^{18}$), (trans)-C($R^{18}$)═C($R^{19}$)—, (cis)-C($R^{18}$)═C($R^{19}$)—, —C≡C—, —C(O)—, —O—, -alkylene-O—, -alkylene-O—, —(CH$_2$)$_r$—, 1,1cycloalkylmethylene, or a direct bond,
  wherein
    $R^{18}$ and $R^{19}$ are independently selected from the group consisting of: -hydrogen, —$C_{1-10}$ alkyl, -aryl, -arylene-$C_{1-10}$ alkyl, or —$C_{1-10}$ alkylene-aryl, wherein alkyl and aryl are optionally substituted with $R^c$;
$R^1$, $R^2$, $R^3$, $R^4$, and $R^5$ are independently selected from the group consisting of hydrogen and $R^b$;
$R^{11}$ is selected from the group consisting of $R^b$;
$R^{20}$, $R^{21}$, $R^{22}$, $R^{23}$, $R^{24}$, $R^{25}$, $R^{26}$, and $R^{27}$ are independently selected from the group consisting of hydrogen and $R^b$;
G is

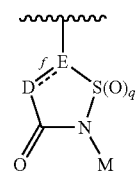

wherein
a) D is C($R^7$)($R^8$), E is C($R^7$) or N, when side f is a single bond, or
b) D is C($R^7$), E is C, when side f is a double bond,
  wherein
    $R^7$ and $R^8$ are independently selected from the group consisting of halo, hydroxy, amino, cyano, nitro, carboxy, —$SO_3$H, —$R^f$ and $R^g$;

or

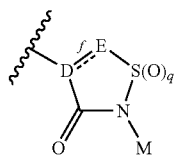

wherein
a) D is $C(R^7)$, E is $C(R^7)(R^8)$ or $N(R^9)$, when side f is a single bond, or
b) D is C, E is $C(R^7)$ or N, when side f is a double bond, wherein
   $R^7$ and $R^8$ are independently selected from the group consisting of: halo, hydroxy, amino, cyano, nitro, carboxy, —$SO_3H$, $R^3$ and $R^9$; and
   $R^9$ is $R^d$;
M is hydrogen or a counter ion selected from the group consisting of: $Na^+$, $K^+$, and other pharmaceutically acceptable counter ions;
$R^b$ is
a) -cycloalkyl,
b) -cyano,
c) —$OR^d$,
d) —$NO_2$,
e) -halogen,
f) —$S(O)_rR^d$,
g) —$SR^d$,
h) —$S(O)_2OR^d$,
i) —$S(O)_mNR^dR^e$,
j) —$NR^dS(O)_mR^e$,
k) —$NR^dR^e$,
l) —$O(CR^fR^g)_nNR^dR^e$,
m) —$C(O)R^d$,
n) —$CO_2R^d$,
o) —$CO_2(CR^fR^g)_nCONR^dR^e$,
p) —$OC(O)R^d$,
q) —$C(O)NR^dR^e$,
r) —$NR^dC(O)R^e$,
s) —$OC(O)NR^dR^e$,
t) —$NR^dC(O)OR^e$,
u) —$NR^dC(O)NR^dR^e$,
v) —$CF_3$,
w) —$OCF_3$
x) —$C_{1-10}$ alkyl,
y) —$C_{2-10}$ alkenyl,
z) —$C_{2-10}$ alkynyl,
aa) —$C_{1-10}$ alkylene-aryl,
bb) —$C_{1-10}$ alkylene-heteroaryl,
cc) -heteroaryl,
dd) —$C(R^f)$=$C(R^g)$—$R^f$, or
ee) —C≡C—$R^f$,
   wherein alkyl, alkenyl, alkynyl, aryl, heteroaryl, and cycloalkyl groups are optionally substituted 1-4 times with a group independently selected from $R^c$;
$R^c$ is
a) -halogen,
b) -amino,
c) -carboxy,
d) —$C_{1-4}$ alkyl,
e) —O—$C_{1-4}$ alkyl,
f) -cycloalkyl,
g) —O-cycloalkyl,
h) -aryl,
i) —$C_{1-4}$ alkylene-aryl,
j) -hydroxy,
k) —$CF_3$,
l) —O-aryl,
m) -heteroaryl,
n) -heteroaryl-$C_{1-10}$ alkyl,
o) heterocyclyl,
p) —$CO_2$—$C_{1-10}$ alkyl, or
q) —$CO_2$—$C_{1-10}$ alkyl-aryl,
$R^d$ and $R^e$ are independently selected from hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heterocyclyl, wherein alkyl, alkenyl, alkynyl, cycloalkyl, aryl, heterocyclyl groups are optionally substituted with one to four substituents independently selected from $R^c$; or $R^d$ and $R^e$ together with the atoms to which they are attached form a heterocyclic ring of 5 to 7 members containing 0-2 additional heteroatoms independently selected from oxygen, sulfur and nitrogen and optionally substituted with 1-3 times with $R^c$, and wherein 1 or 2 carbon atoms in the heterocyclic ring may be oxidized,
$R^f$ and $R^g$ are independently selected from hydrogen, $C_{1-10}$ alkyl, cycloalkyl, —$C_{1-10}$ alkylene-cycloalkyl, and aryl, wherein alkyl, cycloalkyl, and aryl groups are optionally substituted with one to four substituents independently selected from $R^c$; or $R^f$ and $R^g$ together with the carbon to which they are attached form a ring of 5 to 7 members containing 0-2 heteroatoms independently selected from oxygen, sulfur and nitrogen optionally substituted with 1-3 times with $R^c$, and wherein 1 or 2 carbon atoms in the heterocyclic ring may be oxidized;
m is an integer from 1 to 2,
n is an integer from 1 to 10,
q is an integer from 1 to 2,
r is an integer from 1 to 5,
s is an integer from 0 to 3.

In an embodiment of the compound of Formula (IIc), $L^1$ is -$T^1$-$L^3$-$T^2$-, wherein $L^3$, $T^1$ and $T^2$ are direct bonds. In another embodiment, $L^1$ is -$T^1$-$L^3$-$T^2$-, wherein $T^1$ and $T^2$ are direct bonds and $L^3$ is —$CH_2$—. In another embodiment, $L^1$ is -$T^1$-$L^3$-$T^2$-, wherein $L^3$ is a direct bond or alkylene, $T^1$ is a direct bond, and $T^2$ is selected from the group consisting of —O—, —$N(R^{16})$—, —C(O)—, —$CON(R^{16})$—, —$N(R^{17})$C(O)—, —$N(R_6)CON(R^{16})$—, —$N(R^{16})C(O)O$—, —OC(O)$N(R^{16})$—, —$N(R^{16})SO_2$—, —$SO_2N(R^{16})$—, —C(O)—O—, —O—C(O)—, —S—, —S(O)—, —$S(O)_2$—, and —$N(R^{16})SO_2N(R^{17})$—. In another embodiment, $L^1$ is -$T^1$-$L^3$-$T^2$-, wherein $L^3$ is a direct bond or alkylene, $T^2$ is a direct bond, and $T^1$ is selected from the group consisting of —O—, —$N(R^{16})$—, —C(O)—, —$CON(R^{16})$—, —$N(R^{17})C(O)$—, —$N(R_6)CON(R^{16})$—, —$N(R^{16})C(O)O$—, —OC(O)N$(R^{16})$—, —$N(R^{16})SO_2$—, —$SO_2N(R^{16})$—, —C(O)—O—, —O—C(O)—, —S—, —S(O)—, —$S(O)_2$—, and —$N(R^{16})SO_2N(R^{17})$—.

In another embodiment of the compound of Formula (IIc), $L^2$ is selected from the group consisting of —$CH_2$— or —$CH_2$—O—. In another embodiment, $L^2$ is —$CH_2$—.

In another embodiment of the compound of Formula (IIc), $R^1$, $R^2$, $R^3$, $R^4$, and $R^5$ are independently selected from the group consisting of:
a) -hydrogen;
b) -fluoro;
c) -chloro;
d) trifluoromethyl;
e) trifluoromethoxy;
f) —$SO_2$—$C_{1-6}$alkyl;
g) -cyano;

h) -nitro; and i) -phenyl.

In another embodiment, at least one of $R^1$, $R^2$, $R^3$, $R^4$, and $R^5$ is not hydrogen. In another embodiment, $R^1$, $R^2$, $R^3$, $R^4$, and $R^5$ are independently selected from the group consisting of hydrogen, fluoro, and chloro, wherein at least one of at least one of $R^1$, $R^2$, $R^3$, $R^4$, and $R^5$ is not hydrogen. In another embodiment, $R^1$ and $R^3$ are chloro or fluoro, and $R^2$, $R^4$, and $R^5$ are hydrogen.

In another embodiment of the compound of Formula (IIc), s is an integer from 1 to 3 and $R^{11}$ is independently selected from the group consisting of: methyl, methoxy, chloro, fluoro, nitro, cyano, hydroxy, trifluoromethyl, trifluoromethoxy, —$SO_2$—$CH_3$, —$SO_2$—$CF_3$, —$NHSO_2$—$CH_3$, —$NHSO_2$—$CF_3$, and cyclopropyl. In another embodiment, s is zero.

In another embodiment of the compound of Formula (IIc), $R^{20}$, $R^{21}$, and $R^{22}$ are hydrogen, and one or more of $R^{23}$-$R^{27}$ is independently selected from the group consisting of:
- —$C_{1-10}$ alkyl,
- -cycloalkyl,
- -heterocyclyl,
- -trifluoroalkyl,
- -halogen,
- -nitro,
- -carboxy,
- —$CO_2$—$C_{1-10}$ alkyl,
- —$C_{1-10}$ alkylene-$CO_2$—$C_{1-10}$ alkyl,
- —$C_{2-10}$ alkenylene-$CO_2$—$C_{1-10}$ alkyl,
- —$C_{1-10}$ alkylene-$CO_2H$,
- —$C_{2-10}$ alkenylene-$CO_2H$,
- —O—$C_{1-10}$ alkylene-C(O)NH—$C_{1-10}$ alkyl,
- —C(O)—$C_{1-10}$ alkyl,
- —C(O)NH—$C_{1-10}$ alkyl,
- —O-heterocyclyl,
- —O—$C_{1-10}$ alkyl,
- —O—$C_{1-10}$ haloalkyl,
- —O—$C_{1-10}$ perhaloalkyl,
- —O-cycloalkyl,
- —O-phenyl,
- -hydroxy,
- —O—$C_{1-10}$ alkylene-cycloalkyl,
- —O—$C_{1-10}$ alkylene-phenyl,
- —S-heterocyclyl,
- —S—$C_{1-10}$ alkyl,
- —S—$C_{1-10}$ haloalkyl,
- —S—$C_{1-10}$ perhaloalkyl,
- —S-cycloalkyl,
- —S-phenyl,
- —S—$C_{1-10}$ alkylene-cycloalkyl,
- —S—$C_{1-10}$ alkylene-phenyl,
- —$C_{1-10}$ alkylene-cycloalkyl,
- —$C_{1-10}$ alkylene-phenyl,
- -amino,
- —NH($C_{1-10}$ alkyl),
- —N($C_{1-10}$ alkyl)$_2$,
- —N($C_{1-10}$ alkyl)($C_{1-10}$ alkylene-cycloalkyl),
- —$NHCO_2$—$C_{1-10}$ alkyl,
- —NH($C_{1-10}$ alkylene-cycloalkyl),
- —S(O)$_2$—$C_{2-10}$ alkyl,
- —$SO_2$-cycloalkyl,
- —$SO_2$—$C_{1-10}$ alkylene-cycloalkyl,
- —S(O)—$C_{1-10}$ alkyl,
- —S(O)-cycloalkyl, and
- —S(O)—$C_{1-10}$ alkylene-cycloalkyl, wherein alkyl, alkenyl, aryl, heteroaryl, and cycloalkyl groups are optionally substituted 1-4 times with a group independently selected from $R^c$.

In another embodiment of the compound of Formula (IIc), $R^{20}$, $R^{21}$, and $R^{22}$ are hydrogen, and one or more of $R^{23}$-$R^{27}$ is independently selected from the group consisting of:
- —$C_{1-10}$ alkyl,
- -cycloalkyl,
- -heterocyclyl,
- -trifluoroalkyl,
- -halogen,
- -nitro,
- —$CO_2$—$C_{1-10}$ alkyl,
- —$C_{1-10}$ alkylene-$CO_2$—$C_{1-10}$ alkyl,
- —$C_{2-10}$ alkenylene-$CO_2$—$C_{1-10}$ alkyl,
- —O—$C_{1-10}$ alkylene-C(O)NH—$C_{1-10}$ alkyl,
- —C(O)—$C_{1-10}$ alkyl,
- —C(O)NH—$C_{1-10}$ alkyl,
- —O-heterocyclyl,
- —O—$C_{1-10}$ alkyl,
- —O—$C_{1-10}$ haloalkyl,
- —O—$C_{1-10}$ perhaloalkyl,
- —O-cycloalkyl,
- —O-phenyl,
- —O—$C_{1-10}$ alkylene-cycloalkyl,
- —O—$C_{1-10}$ alkylene-phenyl,
- —S-heterocyclyl,
- —S—$C_{1-10}$ alkyl,
- —S—$C_{1-10}$ haloalkyl,
- —S—$C_{1-10}$ perhaloalkyl,
- —S-cycloalkyl,
- —S-phenyl,
- —S—$C_{1-10}$ alkylene-cycloalkyl,
- —S—$C_{1-10}$ alkylene-phenyl,
- —$C_{1-10}$ alkylene-cycloalkyl,
- —$C_{1-10}$ alkylene-phenyl,
- —NH($C_{1-10}$ alkyl),
- —N($C_{1-10}$ alkyl)$_2$,
- —N($C_{1-10}$ alkyl)($C_{1-10}$ alkylene-cycloalkyl),
- —$NHCO_2$—$C_{1-10}$ alkyl,
- —NH($C_{1-10}$ alkylene-cycloalkyl),
- —S(O)$_2$—$C_{2-10}$ alkyl,
- —$SO_2$-cycloalkyl,
- —$SO_2$—$C_{1-10}$ alkylene-cycloalkyl,
- —S(O)—$C_{1-10}$ alkyl,
- —S(O)-cycloalkyl, and
- —S(O)—$C_{1-10}$ alkylene-cycloalkyl.

In another embodiment of the compound of Formula (IIc), $R^{20}$, $R^{21}$, and $R^{22}$ are hydrogen, and one or more of $R^{23}$-$R^{27}$ is independently selected from the group consisting of:
- —$C_{1-10}$ alkyl,
- -cycloalkyl,
- -trifluoroalkyl,
- -halogen,
- —$CO_2$—$C_{1-10}$ alkyl,
- —$C_{1-10}$ alkylene-$CO_2$—$C_{1-10}$ alkyl,
- —$C_{2-10}$ alkenylene-$CO_2$—$C_{1-10}$ alkyl,
- —O—$C_{1-10}$ alkylene-C(O)NH—$C_{1-10}$ alkyl,
- —C(O)—$C_{1-10}$ alkyl,
- —O—$C_{1-10}$ alkyl,
- —O—$C_{1-10}$ haloalkyl,
- —O—$C_{1-10}$ perhaloalkyl,
- —O-cycloalkyl,
- —O-phenyl,
- —O—$C_{1-10}$ alkylene-cycloalkyl,
- —O—$C_{1-10}$ alkylene-phenyl,
- —S—$C_{1-10}$ alkyl, —S—$C_{1-10}$ haloalkyl,
—S—$C_{1-10}$ perhaloalkyl,
—S-cycloalkyl,
—S-phenyl,
—S—$C_{1-10}$ alkylene-cycloalkyl,
—S—$C_{1-10}$ alkylene-phenyl,
—$C_{1-10}$ alkylene-cycloalkyl,
—$C_{1-10}$ alkylene-phenyl,
—$S(O)_2$—$C_{2-10}$ alkyl,
—$SO_2$-cycloalkyl,
—$SO_2$—$C_{1-10}$ alkylene-cycloalkyl,
—S(O)—$C_{1-10}$ alkyl,
—S(O)-cycloalkyl, and
—S(O)—$C_{1-10}$ alkylene-cycloalkyl.

In another embodiment of the compound of Formula (IIc), $R^{20}$, $R^{21}$, and $R^{22}$ are hydrogen, and one or more of $R^{23}$-$R^{27}$ is independently selected from the group consisting of:
morpholine-4-yl,
piperidine-4-yl,
piperidine-1-yl,
4-piperidinyl-oxy,
3-piperidinyl-oxy,
2-oxo-piperidine-1-yl,
3-oxo-piperidine-1-yl,
[1-($C_{1-10}$ alkylsulfonyl)-piperidine-4-yl]-oxy,
[1-($C_{1-10}$ alkyloxycarbonyl)-piperidine-4-yl]-oxy,
[1-($C_{1-10}$ alkyloxycarbonyl)-piperidine-3-yl]-oxy,
piperazine-1-yl,
4-($C_{1-10}$ alkyl)-piperazine-1-yl,
2-oxo-piperazine-4-yl,
1-$C_{1-10}$ alkyl-2-oxo-piperazine-4-yl,
1-cycloalkyl-2-oxo-piperazine-4-yl,
4-tetrahydropyranyloxy,
3-tetrahydrofuranyloxy,
4-($C_{1-10}$ alkyloxycarbonyl)piperazine-1-yl,
pyrrolidine-1-yl,
3-phenyl-pyrrolidine-1-yl,
3-cycloalkyl-pyrrolidine-1-yl,
[1-($C_{1-10}$ alkoxycarbonyl)-pyrrolidine-3-yl]-oxy,
2-thiophenyloxy,
2-thiazolyloxy,
(1,2,4-oxadiazole-3-yl)-oxy,
(1-methyl-imidazole-2-yl)-oxy, and
(imidazole-2-yl)-$C_{1-10}$ alkyoxy,
wherein the alkyl, phenyl, cycloalkyl, morpholine, piperidine, piperazine, cycloalkyl, tetrahydropyran, tetrahydrofuran, pyrrolidine, thiazole, imidazole groups are optionally substituted with a group independently selected from $R^c$.

In another embodiment of the compound of Formula (IIc), $R^{20}$, $R^{21}$, and $R^{22}$ are hydrogen, and one or more of $R^{23}$-$R^{27}$ is independently selected from the group consisting of: methyl, ethyl, propyl, butyl, pentyl, hexyl, 1-ethyl-propyl, 1-propyl-butyl, 3,3-dimethyl-butyl, 4-methyl-pentyl, 4,4-dimethyl-pentyl, 1-(3,3-dimethyl-butyl)-4,4-dimethyl-pentyl, isobutyl, isopropyl, sec-butyl, tert-butyl, trifluoromethyl, 4,4,4-trifluorobutoxy, methoxy, ethoxy, propoxy, butoxy, pentoxy, hexyloxy, isobutoxy, isopropoxy, tert-butoxy, 2-phenethoxy, 2,2-dimethylpropoxy, 3-methyl-butoxy, 3,3-dimethyl-butoxy, 3'-phenethyloxy, 2-cyclohexyl-ethanesulfonyl, 3,3-dimethyl-butane-1-sulfonyl, cyclohexanesulfonyl, cyclohexylmethanesulfonyl, cyclohexylmethylsulfonyl, 2-cyclohexyl-ethanesulfinyl, 3,3-dimethyl-butane-1-sulfinyl, cyclohexylmethylsulfinyl, 2-cyclohexyl-ethylsulfanyl, 3,3-dimethyl-butylsulfanyl, phenethylsulfanyl, cyclohexylmethylsulfanyl, cyclopentyl, cyclohexyl, cyclopentyloxy, cyclohexyloxy, cyclopentylmethyl, cyclohexylmethyl, 2-cyclopentylethyl, 2-cyclohexylethyl, cyclopentylmethoxy, cyclohexylmethoxy, 2-cyclopentylethoxy, 2-cyclohexylethoxy, 2-cyclohexyl-vinyl, 3-ethyl-cyclobutyl, chloro, fluoro, and phenyl.

In another embodiment of the compound of Formula (IIc), V is C, W is N, X is C, Y is N, Z is C—$R^6$, and sides a, c, and d are single bonds, and sides b and e are double bonds, and $R^6$ is selected from the group consisting of hydrogen and —$C_{1-10}$ alkyl.

In another embodiment of the compound of Formula (IIc), $D^1$ is C—$R^{21}$, $D^2$ is C—$R^{22}$, $R^{21}$ and $R^{22}$ are hydrogen, $D^3$ is C—$R^{23}$ and $D^4$ is C—$R^{24}$. In another embodiment, $D^1$ is C—$R^{21}$, $D^2$ is C—$R^{22}$, $R^{21}$ and $R^{22}$ are hydrogen, and $D^3$ and $D^4$ are N.

In an embodiment of the compound of Formula (IIc), G is

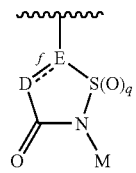

wherein
a) q is 2, D is $C(R^7)(R^8)$, E is $C(R^7)$ or N, when side f is a single bond, or
b) q is 2, D is $C(R^7)$, E is C, when side f is a double bond.

In a further embodiment, $R^7$ and $R^8$ are selected from the group consisting of: hydrogen and $C_{1-4}$ alkyl.

In another embodiment of the compound of Formula (IIc), G is

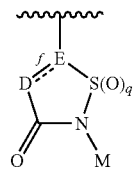

wherein
q is 2, D is $C(R^7)(R^8)$, E is N, and side f is a single bond.

In a further embodiment, $R^7$ and $R^8$ are selected from the group consisting of: hydrogen and $C_{1-4}$ alkyl.

In another embodiment, G is

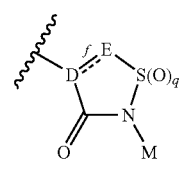

wherein
a) q is 2, D is $C(R^7)$, E is $C(R^7)(R^8)$ or $N(R^9)$, when side f is a single bond, or
b) q is 2, D is C, E is $C(R^7)$ or N, when side f is a double bond.

In a further embodiment, $R^7$, $R^8$, and $R^9$ are selected from the group consisting of: hydrogen and $C_{1-4}$ alkyl.

In another embodiment of the compound of Formula (IIc), the compound has the formula:

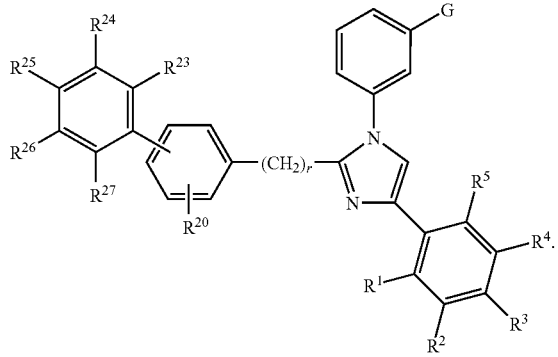

(IId)

In another embodiment of the compound of Formula (IIc), the compound has the formula:

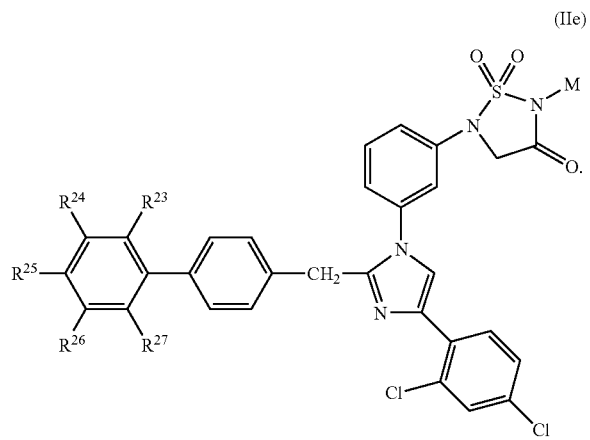

(IIe)

In the compounds of Formula (I-IV), the various functional groups represented should be understood to have a point of attachment at the functional group having the hyphen. In other words, in the case of -alkylene-aryl, it should be understood that the point of attachment is the alkylene group; an example would be benzyl. In the case of a group such as —C(O)—NH— alkylene-aryl, the point of attachment is the carbonyl carbon.

Also included within the scope of the invention are the individual enantiomers of the compounds represented by Formula (I-IV) above as well as any wholly or partially racemic mixtures thereof. The present invention also covers the individual enantiomers of the compounds represented by formula above as mixtures with diastereoisomers thereof in which one or more stereocenters are inverted. Unless otherwise stated, structures depicted herein are also meant to include compounds that differ only in the presence of one or more isotopically enriched atoms. For example, compounds having the present structure except for the replacement of a hydrogen atom by a deuterium or tritium, or the replacement of a carbon atom by a $^{13}C$ or $^{14}C$-enriched carbon are within the scope of the invention.

In another aspect, the present invention provides a pharmaceutically acceptable salt, solvate, or prodrug of compounds of Formula (I-IV). In an embodiment, the prodrug comprises a biohydrolyzable ester or biohydrolyzable amide of a compound of Formula (I-IV).

Examples of compounds of Formula (I-IV) of the present invention having potentially useful biological activity are listed by name below in Table 1. The ability of compounds Formula (I-IV) to inhibit PTP-1B was established with representative compounds of Formula (I-IV) listed in Table I using a standard primary/secondary assay test procedure that measures the inhibition of PTP-1B activity. The compounds of Formula I in Table I may inhibit PTP-IB with an IC50 of less than 10 microMolar ($\mu M$; $10^{-6}$ M).

Compounds that inhibit PTP-1B activity are potentially useful in treating metabolic disorders related to insulin resistance or hyperglycemia, typically associated with obesity or glucose intolerance. The compounds of Formula (I-IV) of the present invention may therefore be particularly useful in the treatment or inhibition of Type II diabetes. The compounds of this invention may also potentially be useful in modulating glucose levels in disorders such as Type I diabetes.

TABLE 1

| Ex. | Structure | Name |
| --- | --- | --- |
| 1 | 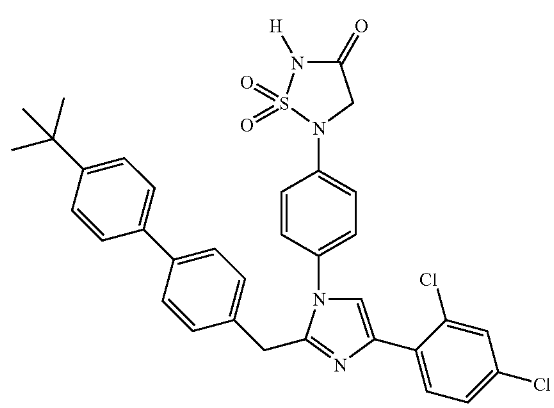 [SMILES: CC(C)(C)c1ccc(-c2ccc(Cc3nc(-c4ccc(Cl)cc4Cl)cn3-c3ccc(N4CC(=O)NS4(=O)=O)cc3)cc2)cc1] | 5-{4-[2-(4'-Tert-butyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 2 | 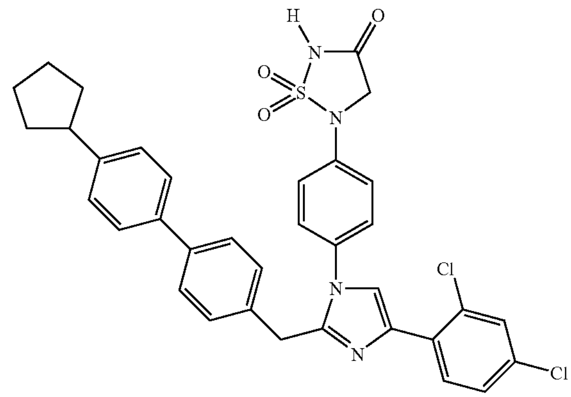 [SMILES: O=C1CN(c2ccc(-n3cc(-c4ccc(Cl)cc4Cl)nc3Cc3ccc(-c4ccc(C5CCCC5)cc4)cc3)cc2)S(=O)(=O)N1] | 5-{4-[2-(4'-Cyclopentyl-biphenyl-4-ylmethyl)-4-(2,4-dichloro-phenyl)-imidazol-1-yl]-phenyl}-1,2,5-thiadiazolidine-3-one-1,1-dioxide |
| 3 | 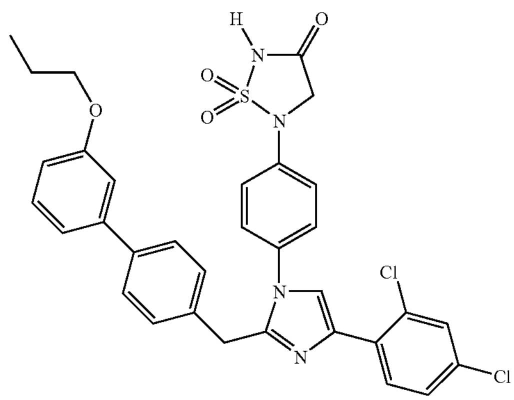 [SMILES: CCCOc1cccc(-c2ccc(Cc3nc(-c4ccc(Cl)cc4Cl)cn3-c3ccc(N4CC(=O)NS4(=O)=O)cc3)cc2)c1] | 5-{4-[4-(2,4-Dichloro-phenyl)-2-(3'-propoxy-biphenyl-4-ylmethyl)-imidazol-1-yl]-phenyl}-1,2,5-thiadiazolidine-3-one-1,1-dioxide |
| 4 | 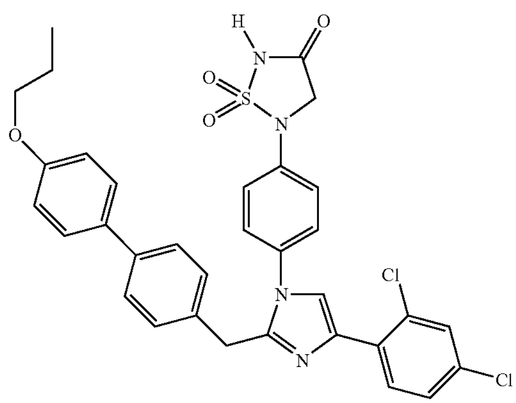 [SMILES: CCCOc1ccc(-c2ccc(Cc3nc(-c4ccc(Cl)cc4Cl)cn3-c3ccc(N4CC(=O)NS4(=O)=O)cc3)cc2)cc1] | 5-{4-[4-(2,4-Dichloro-phenyl)-2-(4'-propoxy-biphenyl-4-ylmethyl)-imidazol-1-yl]-phenyl}-1,2,5-thiadiazolidine-3-one-1,1-dioxide |
| 5 | 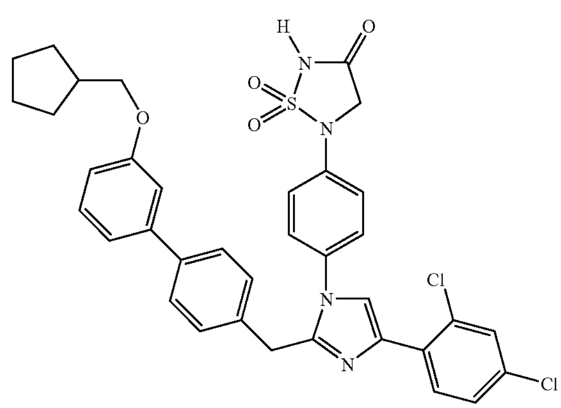 [SMILES: O=C1CN(c2ccc(-n3cc(-c4ccc(Cl)cc4Cl)nc3Cc3ccc(-c4cccc(OCC5CCCC5)c4)cc3)cc2)S(=O)(=O)N1] | 5-{4-[2-(3'-cyclopentylmethoxy-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 6 | 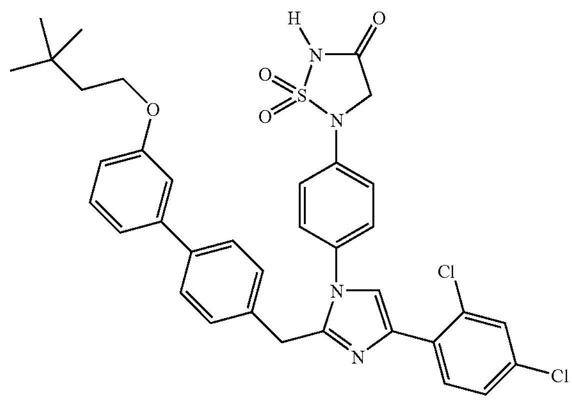 [SMILES: CC(C)(C)CCOc1cccc(-c2ccc(Cc3nc(-c4ccc(Cl)cc4Cl)cn3-c3ccc(N4CC(=O)NS4(=O)=O)cc3)cc2)c1] | 5-(4-{4-(2,4-Dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide |
| 7 | 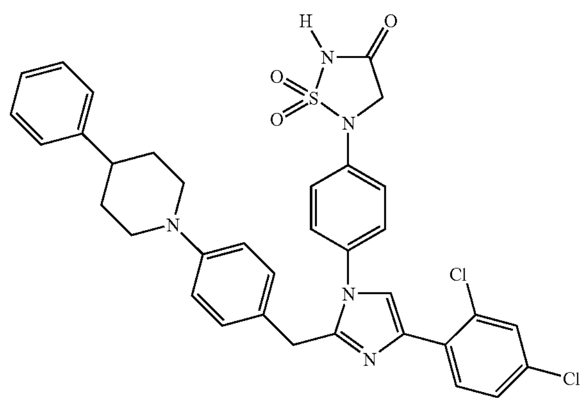 [SMILES: O=C1CN(c2ccc(-n3cc(-c4ccc(Cl)cc4Cl)nc3Cc3ccc(N4CCC(c5ccccc5)CC4)cc3)cc2)S(=O)(=O)N1] | 5-(4-{4-(2,4-Dichloro-phenyl)-2-[4-(4-phenyl-piperidin-1-yl)-benzyl]-imidazol-1-yl}-phenyl)-1,2,5-thiadiazolidine-3-one-1,1-dioxide |
| 8 | 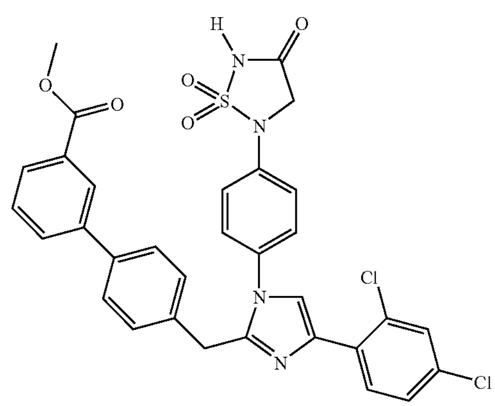 [SMILES: COC(=O)c1cccc(-c2ccc(Cc3nc(-c4ccc(Cl)cc4Cl)cn3-c3ccc(N4CC(=O)NS4(=O)=O)cc3)cc2)c1] | 4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-3-carboxylic acid methyl ester |
| 9 | 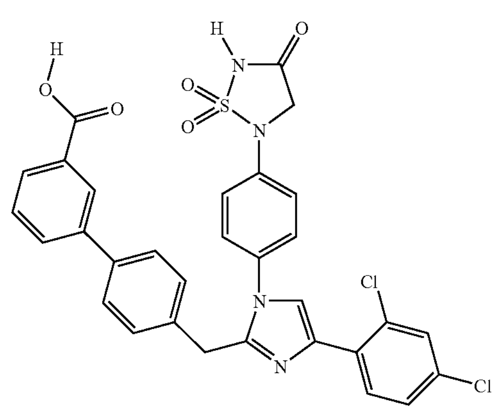 [SMILES: O=C1CN(c2ccc(-n3cc(-c4ccc(Cl)cc4Cl)nc3Cc3ccc(-c4cccc(C(=O)O)c4)cc3)cc2)S(=O)(=O)N1] | 4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-3-carboxylic acid |

TABLE 1-continued

| Ex. | Structure | Name |
|---|---|---|
| 10 | 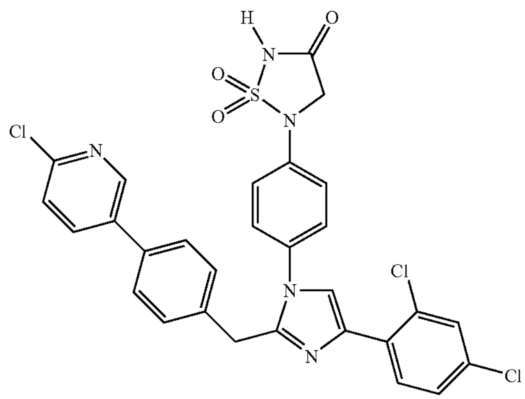 [SMILES: O=C1CN(c2ccc(-n3cc(-c4ccc(Cl)cc4Cl)nc3Cc3ccc(-c4ccc(Cl)nc4)cc3)cc2)S(=O)(=O)N1] | 5-{4-[2-[4-(6-Chloro-pyridin-3-yl)-benzyl]-4-(2,4-dichloro-phenyl)-imidazol-1-yl]-phenyl}-1,2,5-thiadiazolidine-3-one-1,1-dioxide |
| 11 | 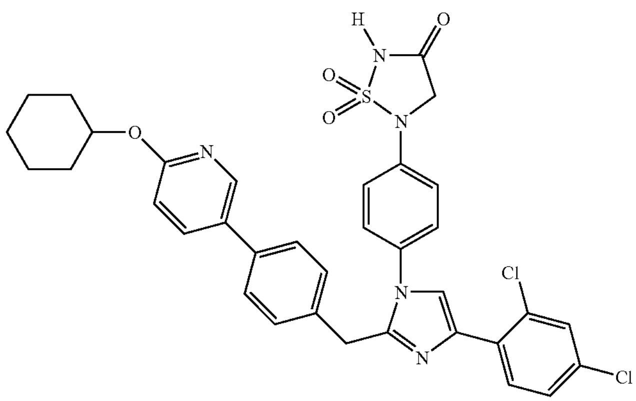 [SMILES: O=C1CN(c2ccc(-n3cc(-c4ccc(Cl)cc4Cl)nc3Cc3ccc(-c4ccc(OC5CCCCC5)nc4)cc3)cc2)S(=O)(=O)N1] | 5-{4-[2-[4-(6-Cyclohexyloxy-pyridin-3-yl)-benzyl]-4-(2,4-dichloro-phenyl)-imidazol-1-yl]-phenyl}-1,2,5-thiadiazolidine-3-one-1,1-dioxide |
| 12 | 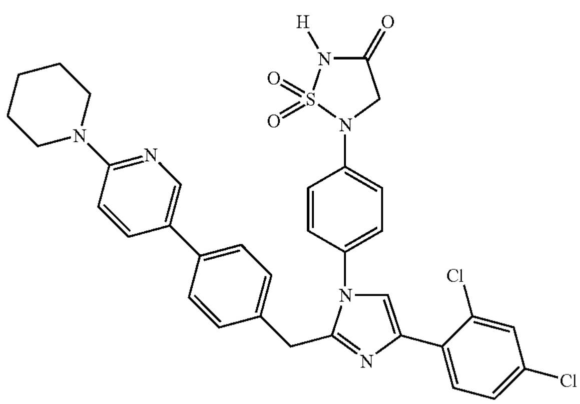 | 5-(4-{4-(2,4-Dichloro-phenyl)-2-[4-(3,4,5,6-tetrahydro-2H-[1,2']bipyridinyl-5'-yl)-benzyl]-imidazol-1-yl}-phenyl)-1,2,5-thiadiazolidine-3-one-1,1-dioxide |
| 13 | 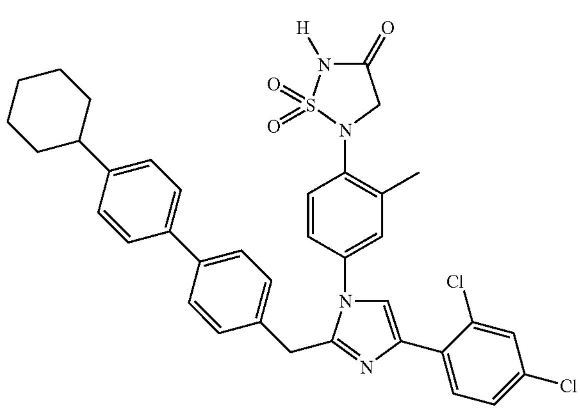 [SMILES: Cc1cc(-n2cc(-c3ccc(Cl)cc3Cl)nc2Cc2ccc(-c3ccc(C4CCCCC4)cc3)cc2)ccc1N1CC(=O)NS1(=O)=O] | 5-{4-[2-(4'-Cyclohexyl-biphenyl-4-ylmethyl)-4-(2,4-dichloro-phenyl)-imidazol-1-yl]-2-methyl-phenyl}-1,2,5-thiadiazolidine-3-one-1,1-dioxide |

TABLE 1-continued

| Ex. | Structure | Name |
|---|---|---|
| 14 | 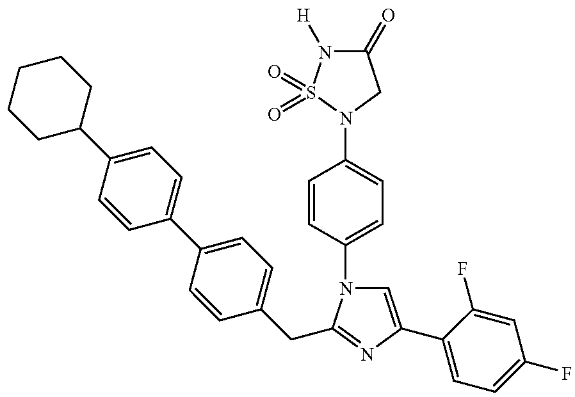 [SMILES: O=C1CN(c2ccc(-n3cc(-c4ccc(F)cc4F)nc3Cc3ccc(-c4ccc(C5CCCCC5)cc4)cc3)cc2)S(=O)(=O)N1] | 5-{4-[2-(4'-Cyclohexyl-biphenyl-4-ylmethyl)-4-(2,4-difluoro-phenyl)-imidazol-1-yl]-phenyl}-1,2,5-thiadiazolidine-3-one-1,1-dioxide |
| 15 | 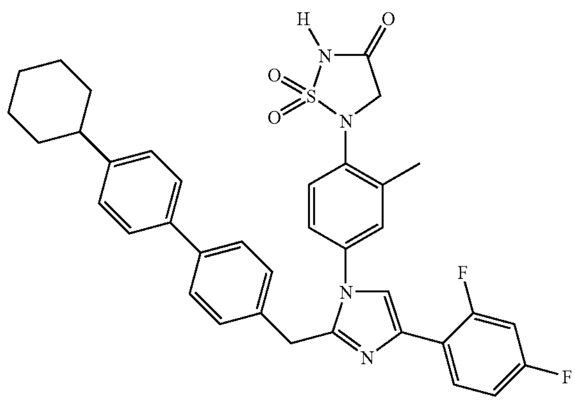 [SMILES: Cc1cc(-n2cc(-c3ccc(F)cc3F)nc2Cc2ccc(-c3ccc(C4CCCCC4)cc3)cc2)ccc1N1CC(=O)NS1(=O)=O] | 5-{4-[2-(4'-Cyclohexyl-biphenyl-4-ylmethyl)-4-(2,4-difluoro-phenyl)-imidazol-1-yl]-2-methyl-phenyl}-1,2,5-thiadiazolidine-3-one-1,1-dioxide |
| 16 | 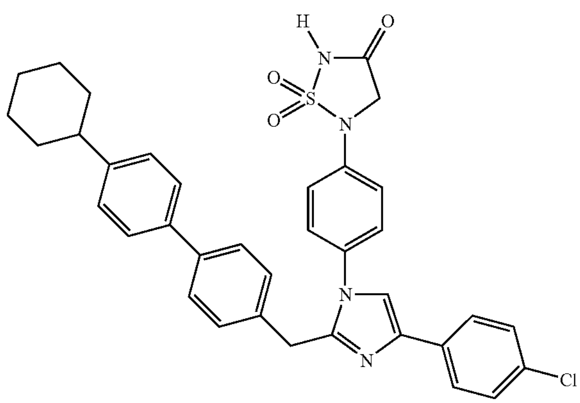 [SMILES: O=C1CN(c2ccc(-n3cc(-c4ccc(Cl)cc4)nc3Cc3ccc(-c4ccc(C5CCCCC5)cc4)cc3)cc2)S(=O)(=O)N1] | 5-{4-[4-(4-Chloro-phenyl)-2-(4'-cyclohexyl-biphenyl-4-ylmethyl)-imidazol-1-yl]-phenyl}-1,2,5-thiadiazolidine-3-one-1,1-dioxide |
| 17 | 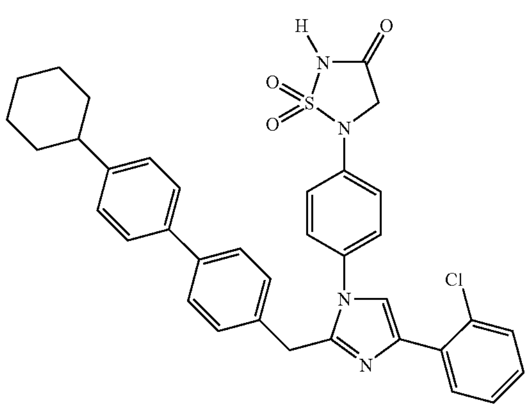 [SMILES: O=C1CN(c2ccc(-n3cc(-c4ccccc4Cl)nc3Cc3ccc(-c4ccc(C5CCCCC5)cc4)cc3)cc2)S(=O)(=O)N1] | 5-{4-[4-(2-Chloro-phenyl)-2-(4'-cyclohexyl-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 18 | 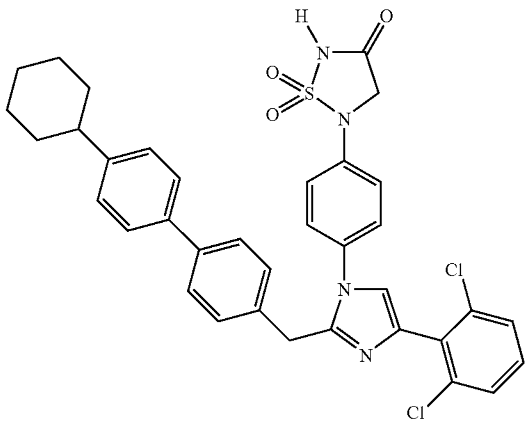 [SMILES: O=C1CN(c2ccc(-n3cc(-c4c(Cl)cccc4Cl)nc3Cc3ccc(-c4ccc(C5CCCCC5)cc4)cc3)cc2)S(=O)(=O)N1] | 5-{4-[2-(4'-Cyclohexyl-biphenyl-4-ylmethyl)-4-(2,6-dichloro-phenyl)-imidazol-1-yl]-phenyl}-1,2,5-thiadiazolidine-3-one-1,1-dioxide |
| 19 | 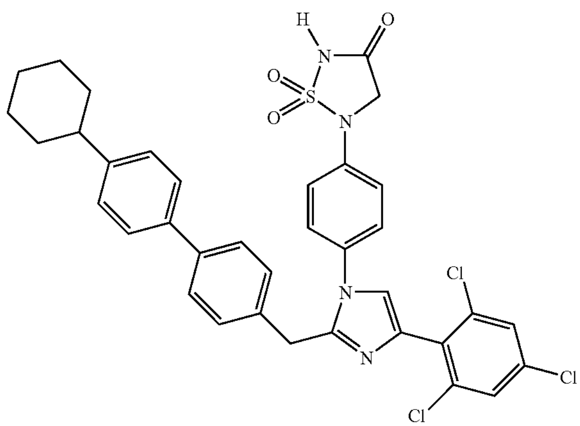 [SMILES: O=C1CN(c2ccc(-n3cc(-c4c(Cl)cc(Cl)cc4Cl)nc3Cc3ccc(-c4ccc(C5CCCCC5)cc4)cc3)cc2)S(=O)(=O)N1] | 5-{4-[2-(4'-Cyclohexyl-biphenyl-4-ylmethyl)-4-(2,4,6-trichloro-phenyl)-imidazol-1-yl]-phenyl}-1,2,5-thiadiazolidine-3-one-1,1-dioxide |
| 20 | 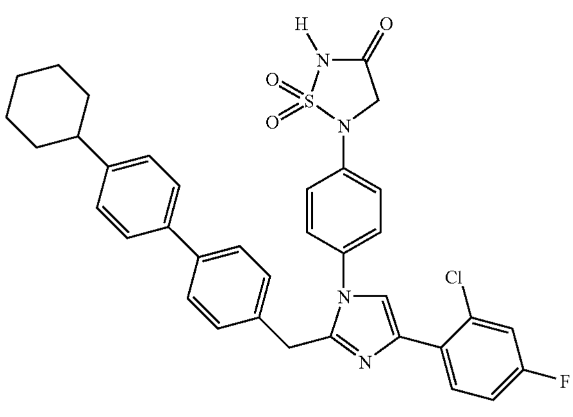 [SMILES: O=C1CN(c2ccc(-n3cc(-c4ccc(F)cc4Cl)nc3Cc3ccc(-c4ccc(C5CCCCC5)cc4)cc3)cc2)S(=O)(=O)N1] | 5-{4-[4-(2-Chloro-4-fluoro-phenyl)-2-(4'-cyclohexyl-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 21 | 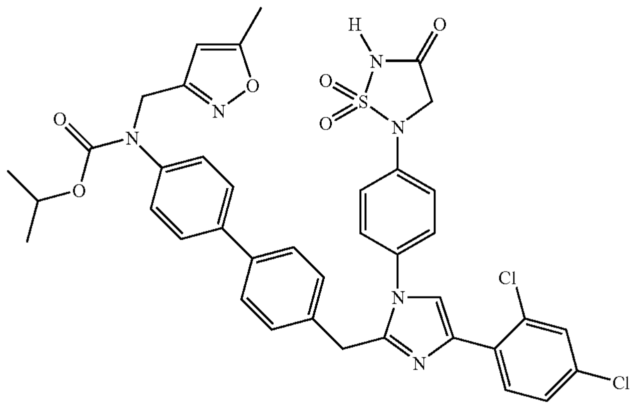 [SMILES: Cc1cc(CN(C(=O)OC(C)C)c2ccc(-c3ccc(Cc4nc(-c5ccc(Cl)cc5Cl)cn4-c4ccc(N5CC(=O)NS5(=O)=O)cc4)cc3)cc2)no1] | (4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-(5-methyl-isoxazol-3-ylmethyl)-carbamic acid isopropyl ester |
| 22 | 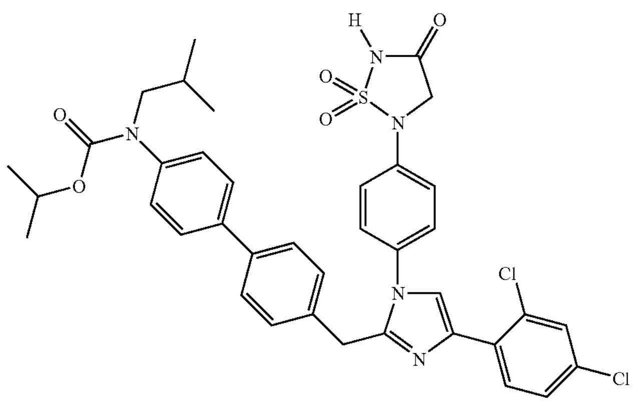 [SMILES: CC(C)CN(C(=O)OC(C)C)c1ccc(-c2ccc(Cc3nc(-c4ccc(Cl)cc4Cl)cn3-c3ccc(N4CC(=O)NS4(=O)=O)cc3)cc2)cc1] | (4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-isobutyl-carbamic acid isopropyl ester |
| 23 | 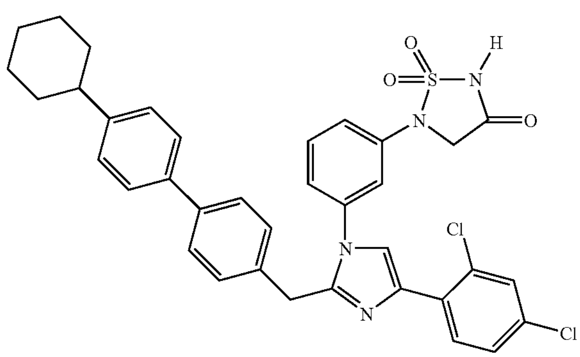 | 5-{3-[2-(4'-Cyclohexyl-biphenyl-4-ylmethyl)-4-(2,4-dichloro-phenyl)-imidazol-1-yl]-phenyl}-1,2,5-thiadiazolidine-3-one-1,1-dioxide |
| 24 | 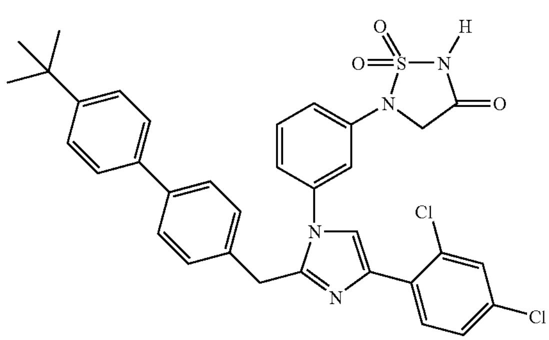 [SMILES: CC(C)(C)c1ccc(-c2ccc(Cc3nc(-c4ccc(Cl)cc4Cl)cn3-c3cccc(N4CC(=O)NS4(=O)=O)c3)cc2)cc1] | 5-{3-[2-(4'-Tert-butyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 25 | 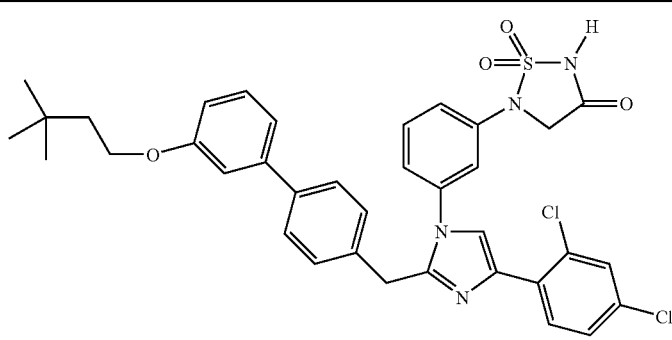 | 5-(3-{4-(2,4-Dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide |
| 26 | 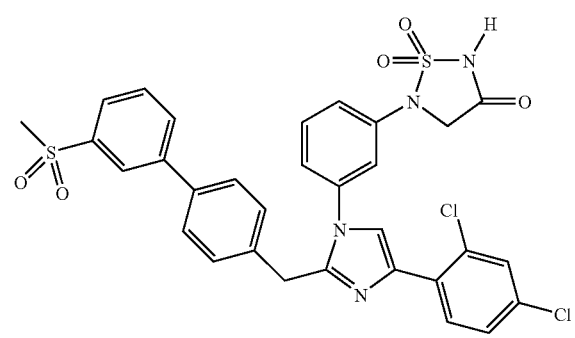 [SMILES: CS(=O)(=O)c1cccc(-c2ccc(Cc3nc(-c4ccc(Cl)cc4Cl)cn3-c3cccc(N4CC(=O)NS4(=O)=O)c3)cc2)c1] | 5-{3-[4-(2,4-Dichloro-phenyl)-2-(3'-methanesulfonyl-biphenyl-4-ylmethyl)-imidazol-1-yl]-phenyl}-1,2,5-thiadiazolidine-3-one-1,1-dioxide |
| 27 | 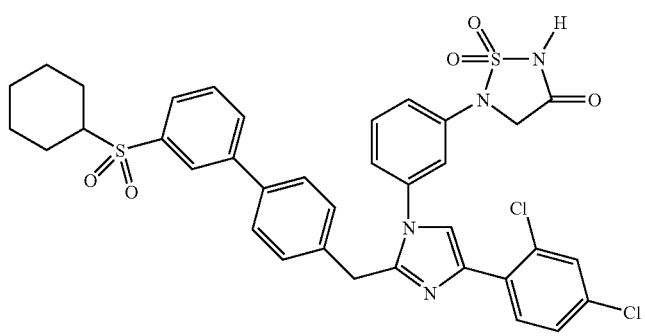 [SMILES: O=C1CN(c2cccc(-n3cc(-c4ccc(Cl)cc4Cl)nc3Cc3ccc(-c4cccc(S(=O)(=O)C5CCCCC5)c4)cc3)c2)S(=O)(=O)N1] | 5-{3-[2-(3'-Cyclohexanesulfonyl-biphenyl-4-ylmethyl)-4-(2,4-dichloro-phenyl)-imidazol-1-yl]-phenyl}-1,2,5-thiadiazolidine-3-one-1,1-dioxide |
| 28 | 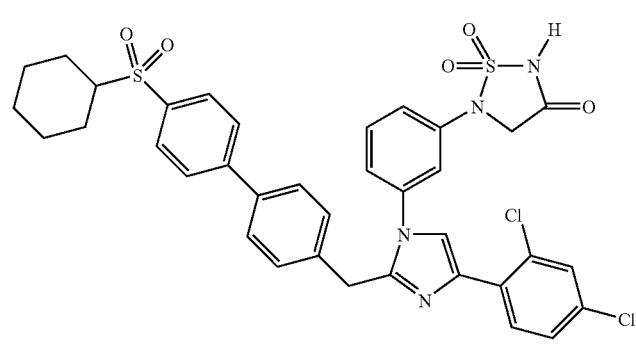 [SMILES: O=C1CN(c2cccc(-n3cc(-c4ccc(Cl)cc4Cl)nc3Cc3ccc(-c4ccc(S(=O)(=O)C5CCCCC5)cc4)cc3)c2)S(=O)(=O)N1] | 5-{3-[2-(4'-Cyclohexanesulfonyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 29 | 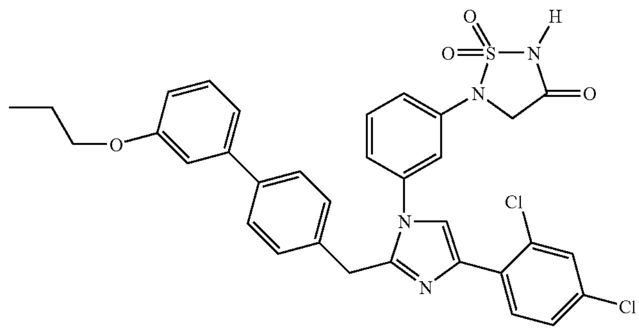 [SMILES: CCCOc1cccc(-c2ccc(Cc3nc(-c4ccc(Cl)cc4Cl)cn3-c3cccc(N4CC(=O)NS4(=O)=O)c3)cc2)c1] | 5-{3-[4-(2,4-Dichloro-phenyl)-2-(3'-propoxy-biphenyl-4-ylmethyl)-imidazol-1-yl]-phenyl}-1,2,5-thiadiazolidine-3-one-1,1-dioxide |
| 30 | 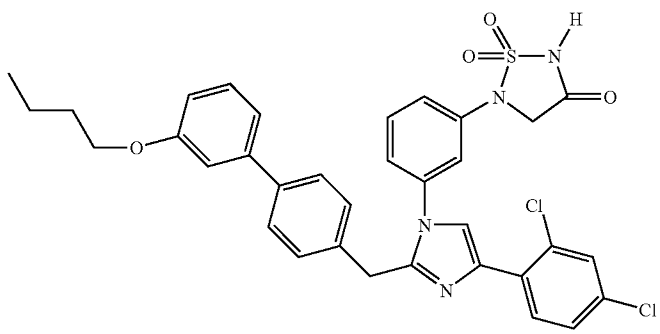 [SMILES: CCCCOc1cccc(-c2ccc(Cc3nc(-c4ccc(Cl)cc4Cl)cn3-c3cccc(N4CC(=O)NS4(=O)=O)c3)cc2)c1] | 5-{3-[2-(3'-Butoxy-biphenyl-4-ylmethyl)-4-(2,4-dichloro-phenyl)-imidazol-1-yl]-phenyl}-1,2,5-thiadiazolidine-3-one-1,1-dioxide |
| 31 | 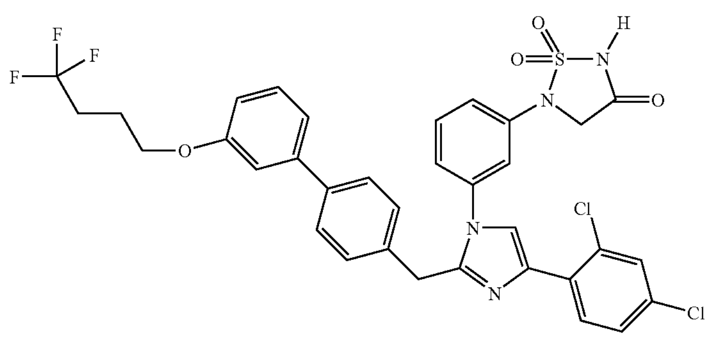 [SMILES: O=C1CN(c2cccc(-n3cc(-c4ccc(Cl)cc4Cl)nc3Cc3ccc(-c4cccc(OCCCC(F)(F)F)c4)cc3)c2)S(=O)(=O)N1] | 5-(3-{4-(2,4-Dichloro-phenyl)-2-[3'-(4,4,4-trifluoro-butoxy)-biphenyl-4-ylmethyl]-imidazol-1-yl}-phenyl)-1,2,5-thiadiazolidine-3-one-1,1-dioxide |
| 32 | 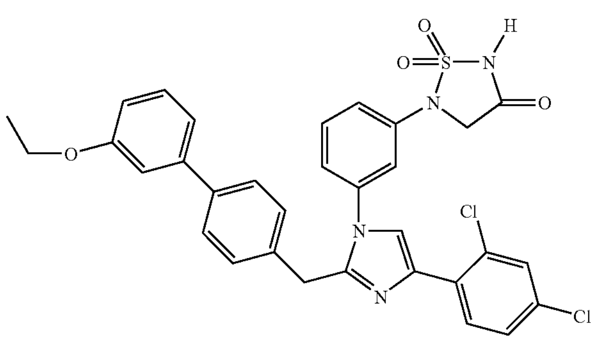 [SMILES: CCOc1cccc(-c2ccc(Cc3nc(-c4ccc(Cl)cc4Cl)cn3-c3cccc(N4CC(=O)NS4(=O)=O)c3)cc2)c1] | 5-{3-[4-(2,4-Dichloro-phenyl)-2-(3'-ethoxy-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 33 | 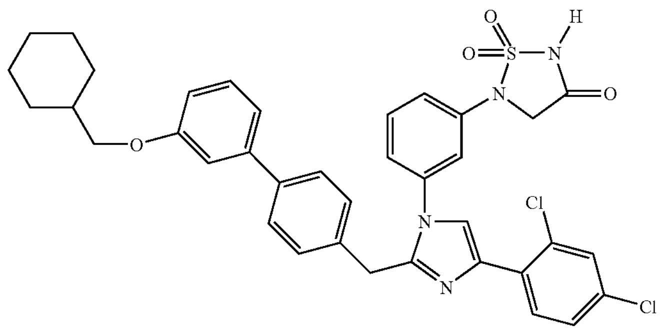 [SMILES: O=C1CN(c2cccc(-n3cc(-c4ccc(Cl)cc4Cl)nc3Cc3ccc(-c4cccc(OCC5CCCCC5)c4)cc3)c2)S(=O)(=O)N1] | 5-{3-[2-(3'-Cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide |
| 34 | 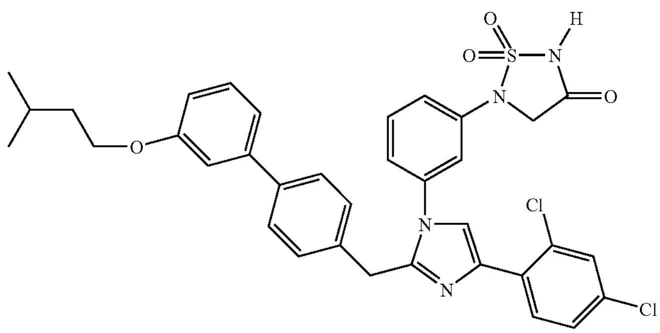 [SMILES: CC(C)CCOc1cccc(-c2ccc(Cc3nc(-c4ccc(Cl)cc4Cl)cn3-c3cccc(N4CC(=O)NS4(=O)=O)c3)cc2)c1] | 5-(3-{4-(2,4-Dichloro-phenyl)-2-[3'-(3-methyl-butoxy)-biphenyl-4-ylmethyl]-imidazol-1-yl}-phenyl)-1,2,5-thiadiazolidine-3-one-1,1-dioxide |
| 35 | 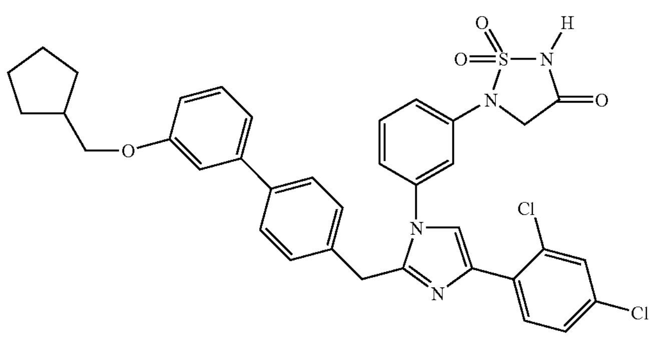 [SMILES: O=C1CN(c2cccc(-n3cc(-c4ccc(Cl)cc4Cl)nc3Cc3ccc(-c4cccc(OCC5CCCC5)c4)cc3)c2)S(=O)(=O)N1] | 5-{3-[2-(3'-Cyclopentylmethoxy-biphenyl-4-ylmethyl)-4-(2,4-dichloro-phenyl)-imidazol-1-yl]-phenyl}-1,2,5-thiadiazolidine-3-one-1,1-dioxide |
| 36 | 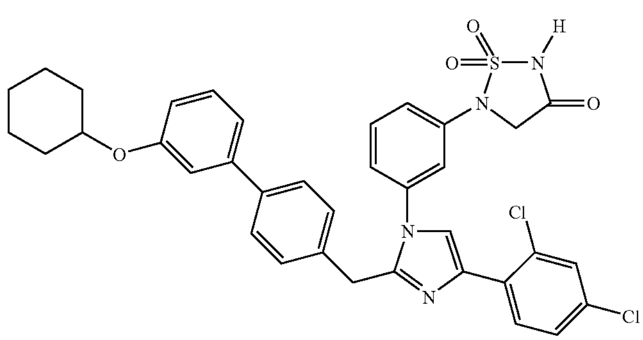 [SMILES: O=C1CN(c2cccc(-n3cc(-c4ccc(Cl)cc4Cl)nc3Cc3ccc(-c4cccc(OC5CCCCC5)c4)cc3)c2)S(=O)(=O)N1] | 5-{3-[2-(3'-Cyclohexyloxy-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 37 | 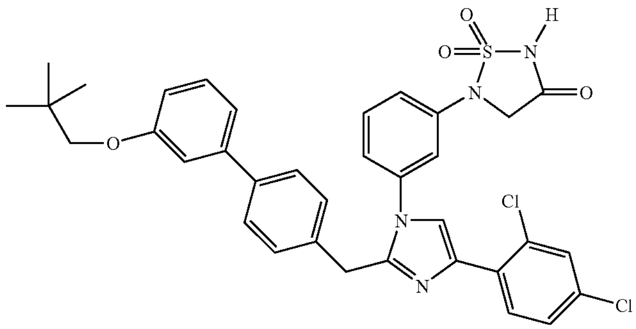 [SMILES: CC(C)(C)COc1cccc(-c2ccc(Cc3nc(-c4ccc(Cl)cc4Cl)cn3-c3cccc(N4CC(=O)NS4(=O)=O)c3)cc2)c1] | 5-(3-{4-(2,4-Dichloro-phenyl)-2-[3'-(2,2-dimethyl-propoxy)-biphenyl-4-ylmethyl]-imidazol-1-yl}-phenyl)-1,2,5-thiadiazolidine-3-one-1,1-dioxide |
| 38 | 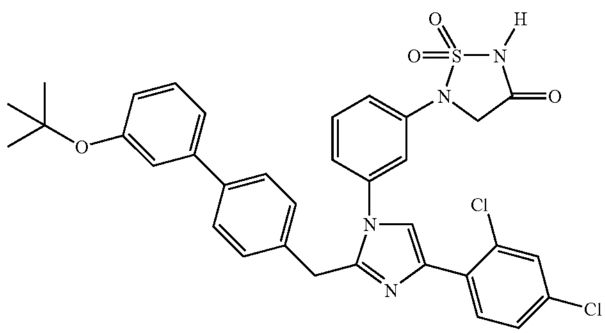 [SMILES: CC(C)(C)Oc1cccc(-c2ccc(Cc3nc(-c4ccc(Cl)cc4Cl)cn3-c3cccc(N4CC(=O)NS4(=O)=O)c3)cc2)c1] | 5-{3-[2-(3'-Tert-butoxy-biphenyl-4-ylmethyl)-4-(2,4-dichloro-phenyl)-imidazol-1-yl]-phenyl}-1,2,5-thiadiazolidine-3-one-1,1-dioxid |
| 39 | 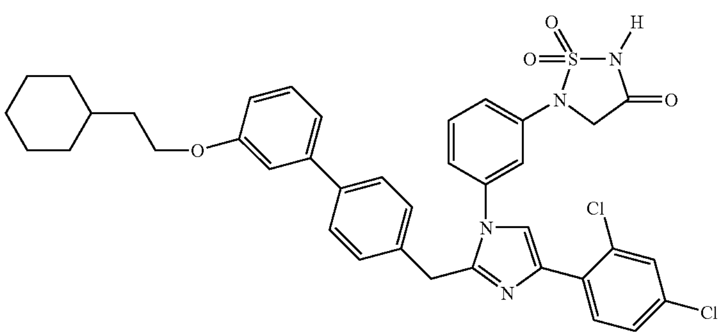 [SMILES: O=C1CN(c2cccc(-n3cc(-c4ccc(Cl)cc4Cl)nc3Cc3ccc(-c4cccc(OCCC5CCCCC5)c4)cc3)c2)S(=O)(=O)N1] | 5-{3-[2-[3'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide |
| 40 | 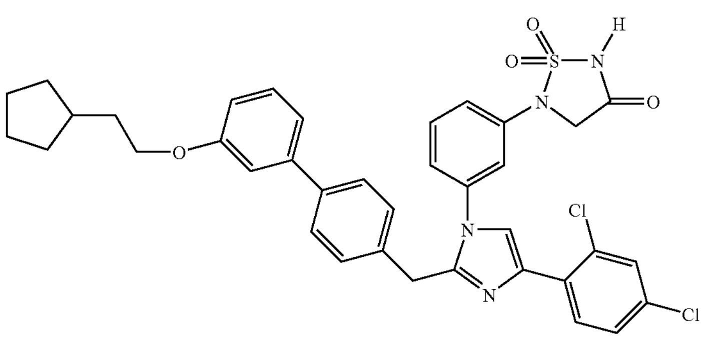 [SMILES: O=C1CN(c2cccc(-n3cc(-c4ccc(Cl)cc4Cl)nc3Cc3ccc(-c4cccc(OCCC5CCCC5)c4)cc3)c2)S(=O)(=O)N1] | 5-{3-[2-[3'-(2-Cyclopentyl-ethoxy)-biphenyl-4-ylmethyl]-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 41 | 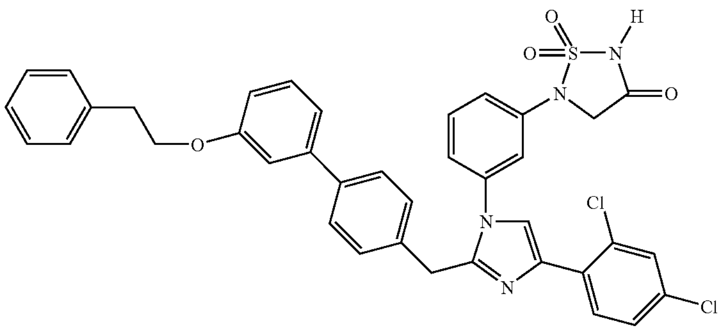 [SMILES: O=C1CN(c2cccc(-n3cc(-c4ccc(Cl)cc4Cl)nc3Cc3ccc(-c4cccc(OCCc5ccccc5)c4)cc3)c2)S(=O)(=O)N1] | 5-{3-[4-(2,4-Dichloro-phenyl)-2-(3'-phenethyloxy-biphenyl-4-ylmethyl)-imidazol-1-yl]-phenyl}-1,2,5-thiadiazolidine-3-one-1,1-dioxide |
| 42 | 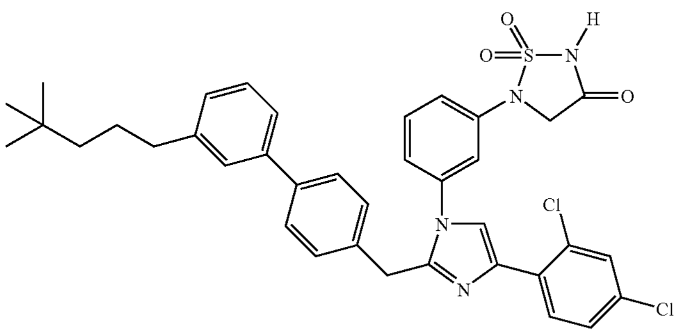 [SMILES: CC(C)(C)CCCc1cccc(-c2ccc(Cc3nc(-c4ccc(Cl)cc4Cl)cn3-c3cccc(N4CC(=O)NS4(=O)=O)c3)cc2)c1] | 5-(3-{4-(2,4-Dichloro-phenyl)-2-[3'-(4,4-dimethyl pentyl)-biphenyl-4-ylmethyl]-imidazol-1-yl}-phenyl)-1,2,5-thiadiazolidine-3-one-1,1-dioxide |
| 43 | 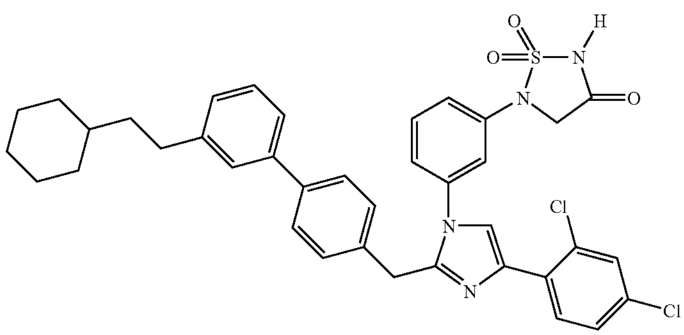 | 5-{3-[2-[3'-(2-Cyclohexyl-ethyl)-biphenyl-4-ylmethyl]-4-(2,4-dichloro-phenyl)-imidazol-1-yl]-phenyl}-1,2,5-thiadiazolidine-3-one-1,1-dioxide |
| 44 | 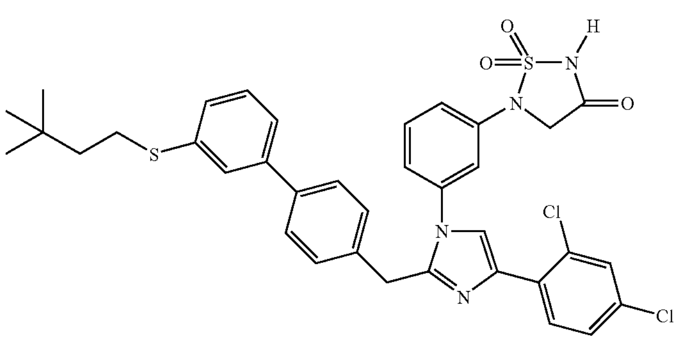 [SMILES: CC(C)(C)CCSc1cccc(-c2ccc(Cc3nc(-c4ccc(Cl)cc4Cl)cn3-c3cccc(N4CC(=O)NS4(=O)=O)c3)cc2)c1] | 5-(3-{4-(2,4-Dichloro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide |

TABLE 1-continued

| Ex. | Structure | Name |
|---|---|---|
| 45 | 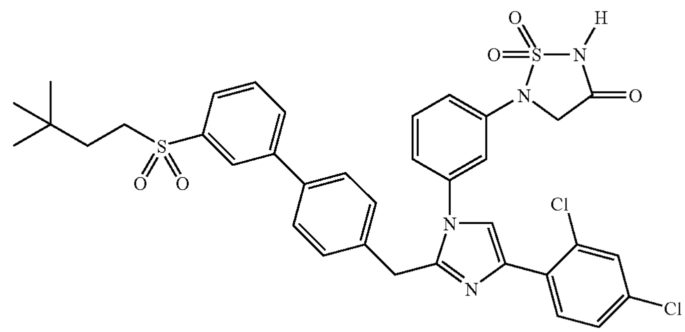 [SMILES: CC(C)(C)CCS(=O)(=O)c1cccc(-c2ccc(Cc3nc(-c4ccc(Cl)cc4Cl)cn3-c3cccc(N4CC(=O)NS4(=O)=O)c3)cc2)c1] | 5-(3-{4-(2,4-Dichloro-phenyl)-2-[3'-(3,3-dimethyl-butane-1-sulfonyl)-biphenyl-4-ylmethyl]-imidazol-1-yl}-phenyl)-1,2,5-thiadiazolidine-3-one-1,1-dioxide |
| 46 | 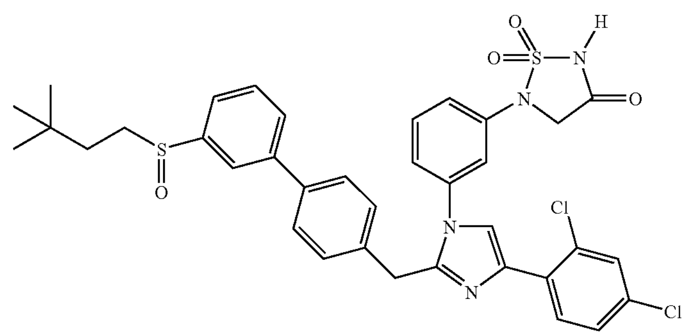 [SMILES: CC(C)(C)CCS(=O)c1cccc(-c2ccc(Cc3nc(-c4ccc(Cl)cc4Cl)cn3-c3cccc(N4CC(=O)NS4(=O)=O)c3)cc2)c1] | 5-(3-{4-(2,4-Dichloro-phenyl)-2-[3'-(3,3-dimethyl-butane-1-sulfinyl)-biphenyl-4-ylmethyl]-imidazol-1-yl}-phenyl)-1,2,5-thiadiazolidine-3-one-1,1-dioxide |
| 47 | 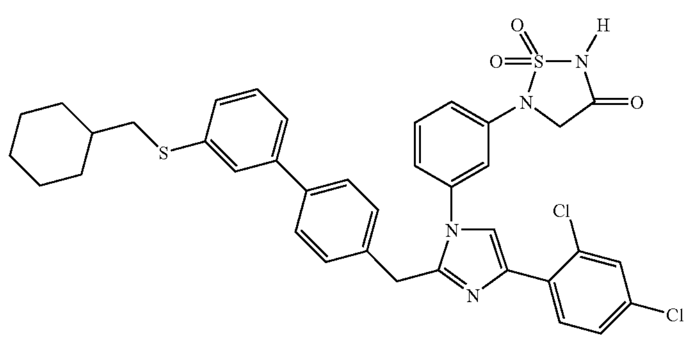 [SMILES: O=C1CN(c2cccc(-n3cc(-c4ccc(Cl)cc4Cl)nc3Cc3ccc(-c4cccc(SCC5CCCCC5)c4)cc3)c2)S(=O)(=O)N1] | 5-{3-[2-(3'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide |
| 48 | 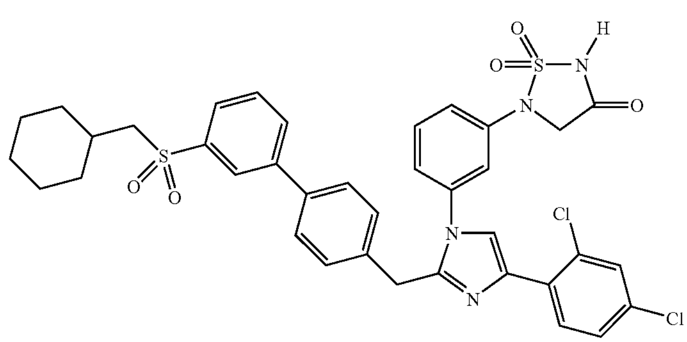 [SMILES: O=C1CN(c2cccc(-n3cc(-c4ccc(Cl)cc4Cl)nc3Cc3ccc(-c4cccc(S(=O)(=O)CC5CCCCC5)c4)cc3)c2)S(=O)(=O)N1] | 5-{3-[2-(3'-Cyclohexylmethylsulfonyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 49 | 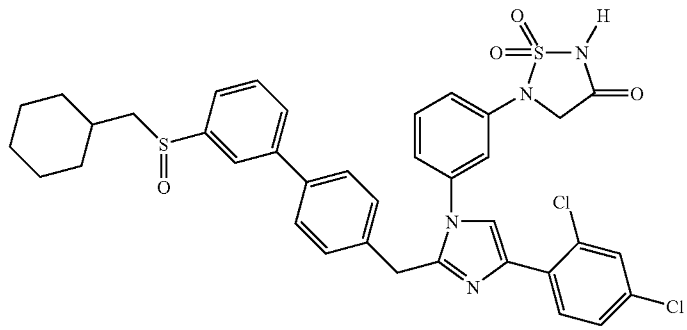 [SMILES: O=C1CN(c2cccc(-n3cc(-c4ccc(Cl)cc4Cl)nc3Cc3ccc(-c4cccc(S(=O)CC5CCCCC5)c4)cc3)c2)S(=O)(=O)N1] | 5-{3-[2-(3'-Cyclohexylmethylsulfinyl-biphenyl-4-ylmethyl)-4-(2,4-dichloro-phenyl)-imidazol-1-yl]-phenyl}-1,2,5-thiadiazolidine-3-one-1,1-dioxide |
| 50 | 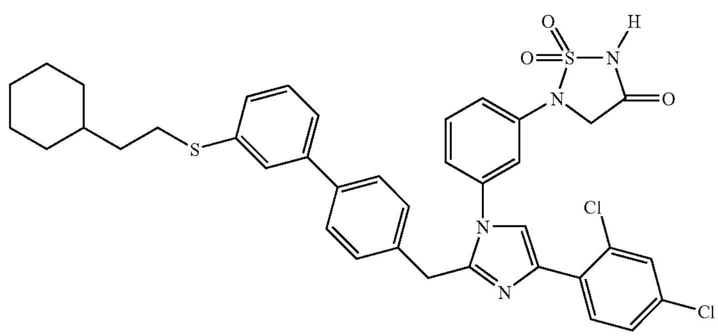 [SMILES: O=C1CN(c2cccc(-n3cc(-c4ccc(Cl)cc4Cl)nc3Cc3ccc(-c4cccc(SCCC5CCCCC5)c4)cc3)c2)S(=O)(=O)N1] | 5-{3-[2-(3'-(2-Cyclohexyl-ethylsulfanyl)-biphenyl-4-ylmethyl)-4-(2,4-dichloro-phenyl)-imidazol-1-yl]-phenyl}-1,2,5-thiadiazolidine-3-one-1,1-dioxide |
| 51 | 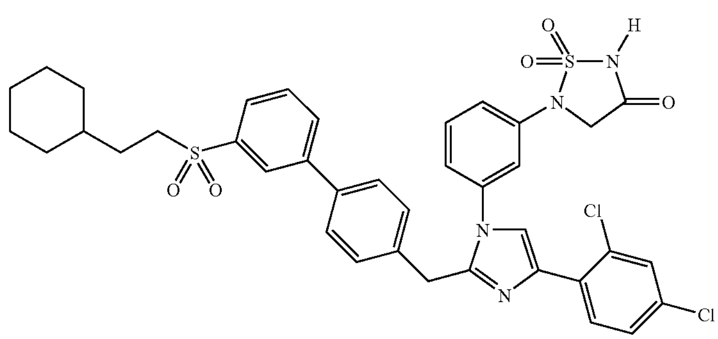 [SMILES: O=C1CN(c2cccc(-n3cc(-c4ccc(Cl)cc4Cl)nc3Cc3ccc(-c4cccc(S(=O)(=O)CCC5CCCCC5)c4)cc3)c2)S(=O)(=O)N1] | 5-{3-[2-(3'-(2-Cyclohexyl-ethanesulfonyl)-biphenyl-4-ylmethyl)-4-(2,4-dichloro-phenyl)-imidazol-1-yl]-phenyl}-1,2,5-thiadiazolidine-3-one-1,1-dioxide |
| 52 | 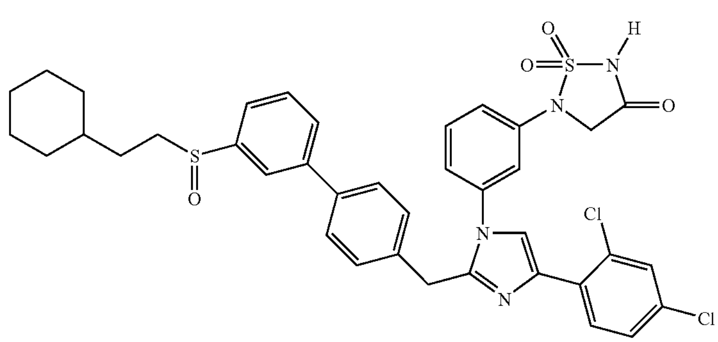 [SMILES: O=C1CN(c2cccc(-n3cc(-c4ccc(Cl)cc4Cl)nc3Cc3ccc(-c4cccc(S(=O)CCC5CCCCC5)c4)cc3)c2)S(=O)(=O)N1] | 5-{3-[2-(3'-(2-Cyclohexyl-ethanesulfinyl)-biphenyl-4-ylmethyl)-4-(2,4-dichloro-phenyl)-imidazol-1-yl]-phenyl}-1,2,5-thiadiazolidine-3-one-1,1-dioxide |

| Ex. | Structure | Name |
|---|---|---|
| 53 | 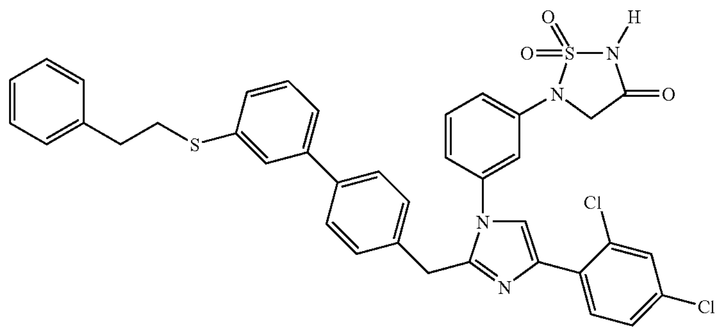 [SMILES: O=C1CN(c2cccc(-n3cc(-c4ccc(Cl)cc4Cl)nc3Cc3ccc(-c4cccc(SCCc5ccccc5)c4)cc3)c2)S(=O)(=O)N1] | 5-{3-[4-(2,4-Dichloro-phenyl)-2-(3'-phenethylsulfanyl-biphenyl-4-ylmethyl)-imidazol-1-yl]-phenyl}-1,2,5-thiadiazolidine-3-one-1,1-dioxide |
| 54 | 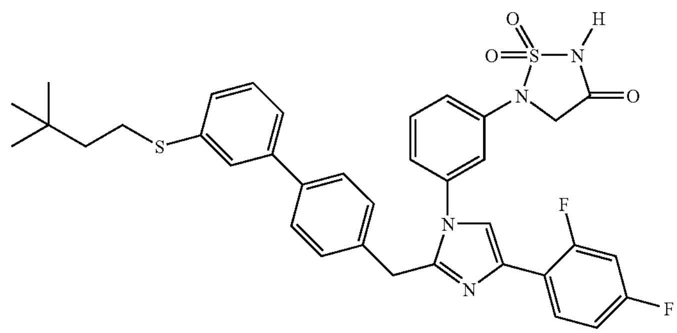 [SMILES: CC(C)(C)CCSc1cccc(-c2ccc(Cc3nc(-c4ccc(F)cc4F)cn3-c3cccc(N4CC(=O)NS4(=O)=O)c3)cc2)c1] | 5-(3-{4-(2,4-Difluoro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide |
| 55 | 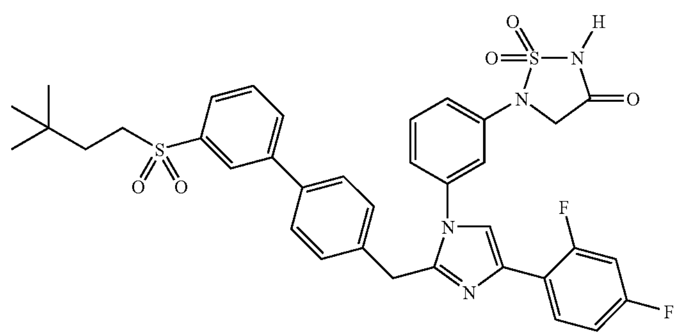 [SMILES: CC(C)(C)CCS(=O)(=O)c1cccc(-c2ccc(Cc3nc(-c4ccc(F)cc4F)cn3-c3cccc(N4CC(=O)NS4(=O)=O)c3)cc2)c1] | 5-(3-{4-(2,4-Difluoro-phenyl)-2-[3'-(3,3-dimethyl-butane-1-sulfonyl)-biphenyl-4-ylmethyl]-imidazol-1-yl}-phenyl)-1,2,5-thiadiazolidine-3-one-1,1-dioxide |
| 56 | 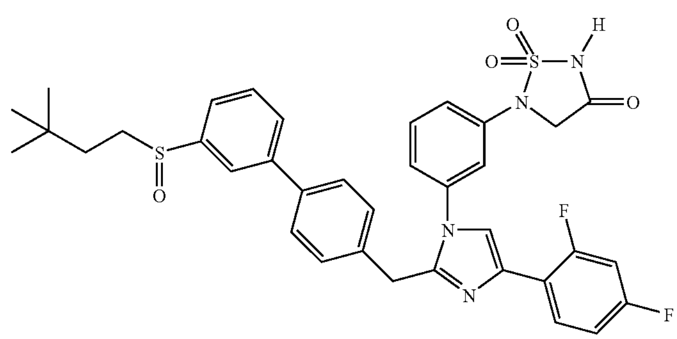 [SMILES: CC(C)(C)CCS(=O)c1cccc(-c2ccc(Cc3nc(-c4ccc(F)cc4F)cn3-c3cccc(N4CC(=O)NS4(=O)=O)c3)cc2)c1] | 5-(3-{4-(2,4-Difluoro-phenyl)-2-[3'-(3,3-dimethyl-butane-1-sulfinyl)-biphenyl-4-ylmethyl]-imidazol-1-yl}-phenyl)-1,2,5-thiadiazolidine-3-one-1,1-dioxide |

TABLE 1-continued

| Ex. | Structure | Name |
|---|---|---|
| 57 | 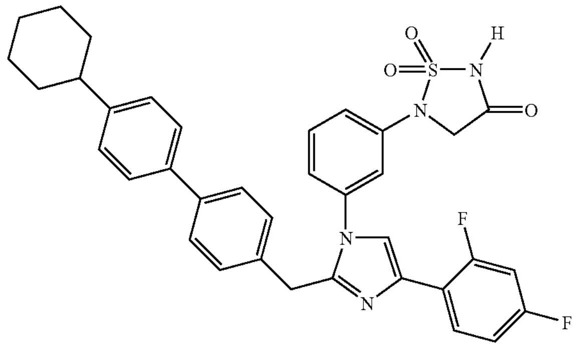 [SMILES: O=C1CN(c2cccc(-n3cc(-c4ccc(F)cc4F)nc3Cc3ccc(-c4ccc(C5CCCCC5)cc4)cc3)c2)S(=O)(=O)N1] | 5-{3-[2-(4'-Cyclohexyl-biphenyl-4-ylmethyl)-4-(2,4-difluoro-phenyl)-imidazol-1-yl]-phenyl}-1,2,5-thiadiazolidine-3-one-1,1-dioxide |
| 58 | 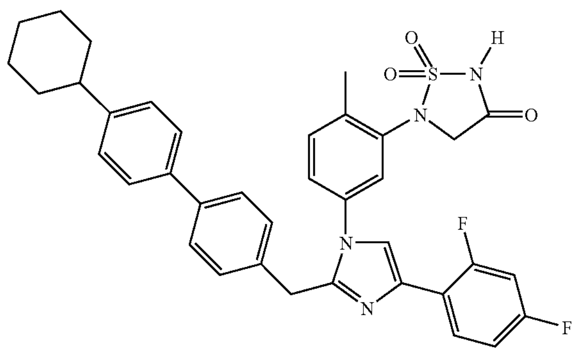 [SMILES: Cc1ccc(-n2cc(-c3ccc(F)cc3F)nc2Cc2ccc(-c3ccc(C4CCCCC4)cc3)cc2)cc1N1CC(=O)NS1(=O)=O] | 5-{5-[2-(4'-Cyclohexyl-biphenyl-4-ylmethyl)-4-(2,4-difluoro-phenyl)-imidazol-1-yl]-2-methyl-phenyl}-1,2,5-thiadiazolidine-3-one-1,1-dioxide |
| 59 | 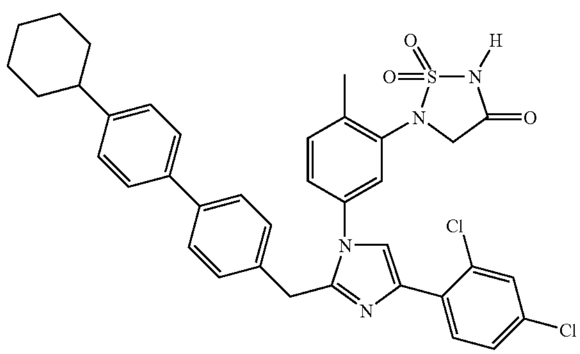 [SMILES: Cc1ccc(-n2cc(-c3ccc(Cl)cc3Cl)nc2Cc2ccc(-c3ccc(C4CCCCC4)cc3)cc2)cc1N1CC(=O)NS1(=O)=O] | 5-{5-[2-(4'-Cyclohexyl-biphenyl-4-ylmethyl)-4-(2,4-difluoro-phenyl)-imidazol-1-yl]-2-methyl-phenyl}-1,2,5-thiadiazolidine-3-one-1,1-dioxide |
| 60 | 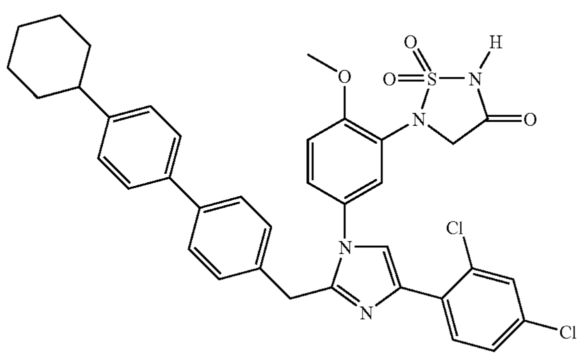 [SMILES: COc1ccc(-n2cc(-c3ccc(Cl)cc3Cl)nc2Cc2ccc(-c3ccc(C4CCCCC4)cc3)cc2)cc1N1CC(=O)NS1(=O)=O] | 5-{5-[2-(4'-Cyclohexyl-biphenyl-4-ylmethyl)-4-(2,4-difluoro-phenyl)-imidazol-1-yl]-2-methoxy-phenyl}-1,2,5-thiadiazolidine-3-one-1,1-dioxide |

TABLE 1-continued

| Ex. | Structure | Name |
|---|---|---|
| 61 | 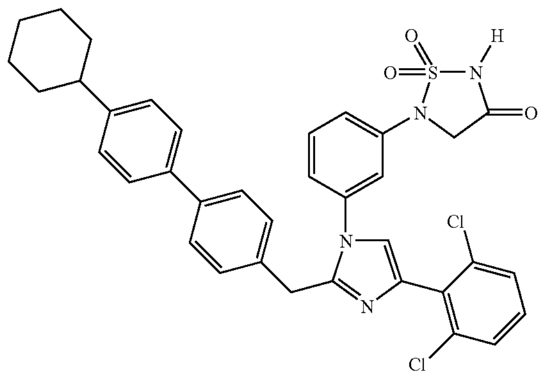 [SMILES: O=C1CN(c2cccc(-n3cc(-c4c(Cl)cccc4Cl)nc3Cc3ccc(-c4ccc(C5CCCCC5)cc4)cc3)c2)S(=O)(=O)N1] | 5-{3-[2-(4'-Cyclohexyl-biphenyl-4-ylmethyl)-4-(2,6-dichloro-phenyl)-imidazol-1-yl]-phenyl}-1,2,5-thiadiazolidine-3-one-1,1-dioxide |
| 62 | 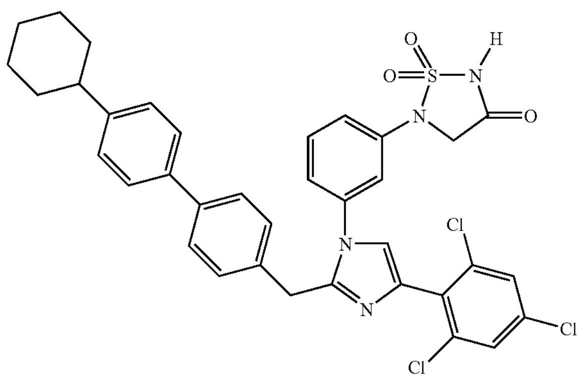 [SMILES: O=C1CN(c2cccc(-n3cc(-c4c(Cl)cc(Cl)cc4Cl)nc3Cc3ccc(-c4ccc(C5CCCCC5)cc4)cc3)c2)S(=O)(=O)N1] | 5-{3-[2-(4'-Cyclohexyl-biphenyl-4-ylmethyl)-4-(2,4,6-trichloro-phenyl)-imidazol-1-yl]-phenyl}-1,2,5-thiadiazolidine-3-one-1,1-dioxide |
| 63 | 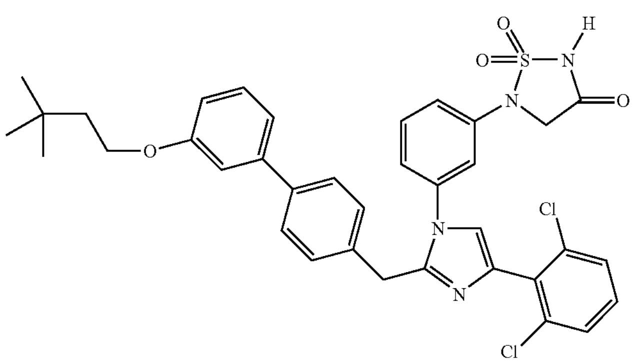 [SMILES: CC(C)(C)CCOc1cccc(-c2ccc(Cc3nc(-c4c(Cl)cccc4Cl)cn3-c3cccc(N4CC(=O)NS4(=O)=O)c3)cc2)c1] | 5-(3-{4-(2,6-Dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide |
| 64 | 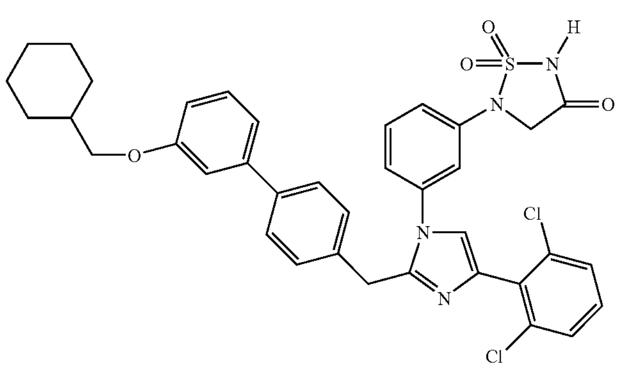 [SMILES: O=C1CN(c2cccc(-n3cc(-c4c(Cl)cccc4Cl)nc3Cc3ccc(-c4cccc(OCC5CCCCC5)c4)cc3)c2)S(=O)(=O)N1] | 5-{3-[2-(3'-Cyclohexylmethoxy-biphenyl-4-ylmethyl)-4-(2,6-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 65 | 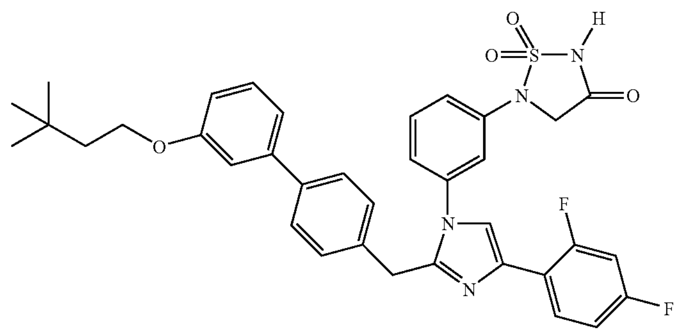 | 5-(3-{4-(2,4-Difluoro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide |
| 66 | 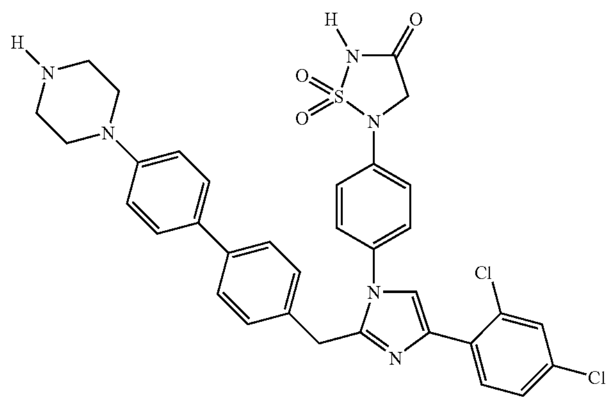 [SMILES: O=C1CN(c2ccc(-n3cc(-c4ccc(Cl)cc4Cl)nc3Cc3ccc(-c4ccc(N5CCNCC5)cc4)cc3)cc2)S(=O)(=O)N1] | 5-{4-[4-(2,4-Dichloro-phenyl)-2-(4'-piperazin-1-yl-biphenyl-4-ylmethyl)-imidazol-1-yl]-phenyl}-1,2,5-thiadiazolidine-3-one-1,1-dioxide |
| 67 | 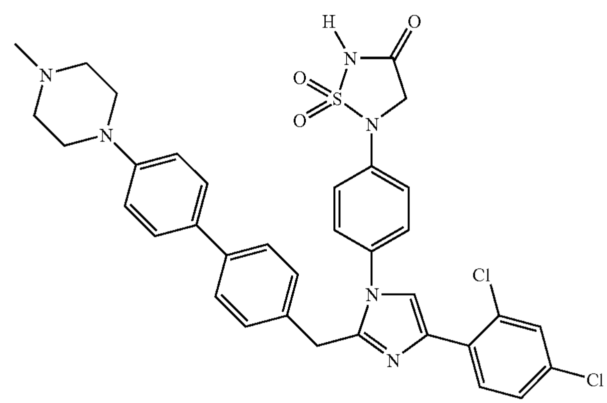 [SMILES: CN1CCN(c2ccc(-c3ccc(Cc4nc(-c5ccc(Cl)cc5Cl)cn4-c4ccc(N5CC(=O)NS5(=O)=O)cc4)cc3)cc2)CC1] | 5-(4-{4-(2,4-Dichloro-phenyl)-2-[4'-(4-methyl-piperazin-1-yl)-biphenyl-4-ylmethyl]-imidazol-1-yl}-phenyl)-1,2,5-thiadiazolidine-3-one-1,1-dioxide |
| 68 | 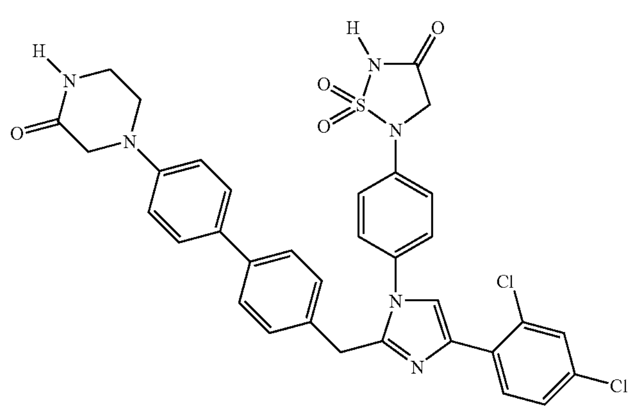 [SMILES: O=C1CN(c2ccc(-c3ccc(Cc4nc(-c5ccc(Cl)cc5Cl)cn4-c4ccc(N5CC(=O)NS5(=O)=O)cc4)cc3)cc2)CCN1] | 4-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-piperazin-2-one |

TABLE 1-continued

| Ex. | Structure | Name |
|---|---|---|
| 69 | 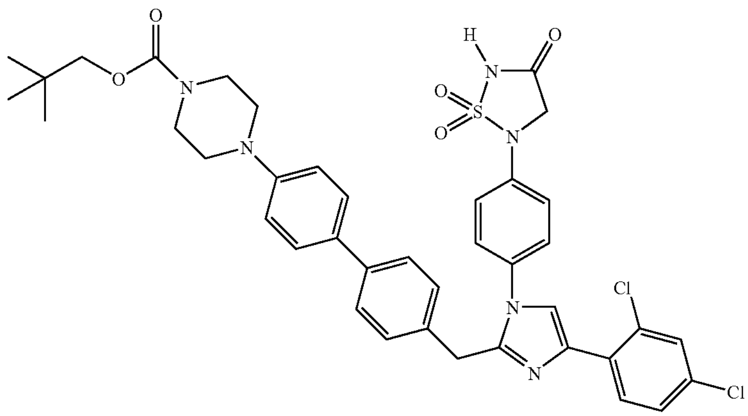 [SMILES: CC(C)(C)COC(=O)N1CCN(c2ccc(-c3ccc(Cc4nc(-c5ccc(Cl)cc5Cl)cn4-c4ccc(N5CC(=O)NS5(=O)=O)cc4)cc3)cc2)CC1] | 4-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-piperazine-1-carboxylic acid 2,2-dimethyl-propyl ester |
| 70 | 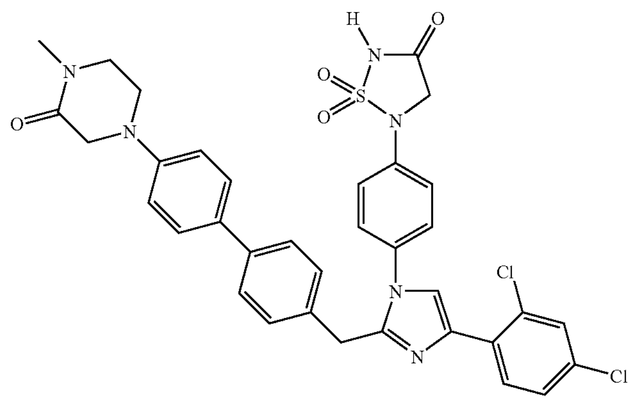 [SMILES: CN1CCN(c2ccc(-c3ccc(Cc4nc(-c5ccc(Cl)cc5Cl)cn4-c4ccc(N5CC(=O)NS5(=O)=O)cc4)cc3)cc2)CC1=O] | 4-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-1-methyl-piperazin-2-one |
| 71 | 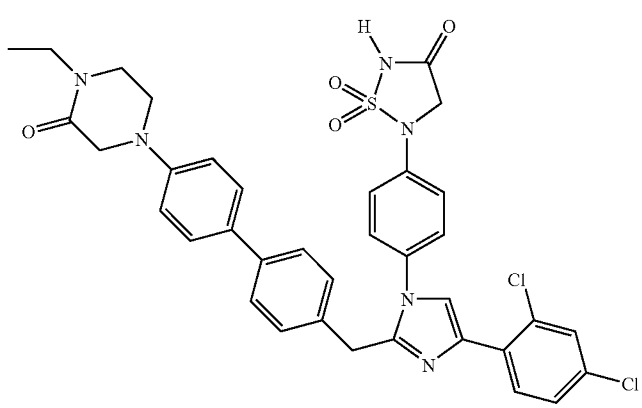 [SMILES: CCN1CCN(c2ccc(-c3ccc(Cc4nc(-c5ccc(Cl)cc5Cl)cn4-c4ccc(N5CC(=O)NS5(=O)=O)cc4)cc3)cc2)CC1=O] | 4-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-1-ethyl-piperazin-2-one |

TABLE 1-continued

| Ex. | Structure | Name |
|---|---|---|
| 72 | 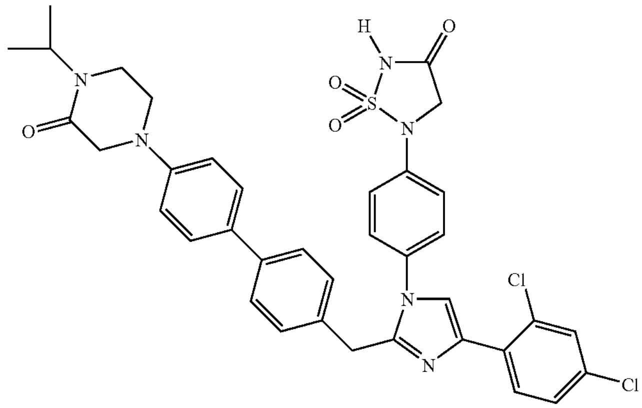 [SMILES: CC(C)N1CCN(c2ccc(-c3ccc(Cc4nc(-c5ccc(Cl)cc5Cl)cn4-c4ccc(N5CC(=O)NS5(=O)=O)cc4)cc3)cc2)CC1=O] | 4-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-1-isopropyl-piperazin-2-one |
| 73 | 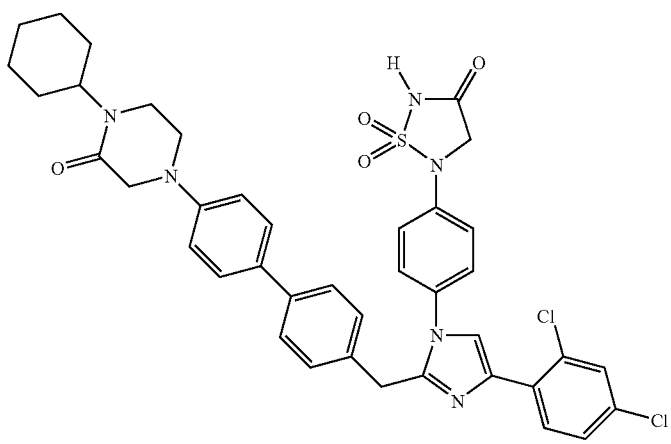 [SMILES: O=C1CN(c2ccc(-n3cc(-c4ccc(Cl)cc4Cl)nc3Cc3ccc(-c4ccc(N5CCN(C6CCCCC6)C(=O)C5)cc4)cc3)cc2)S(=O)(=O)N1] | 1-Cyclohexyl-4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-piperazin-2-one |
| 74 | 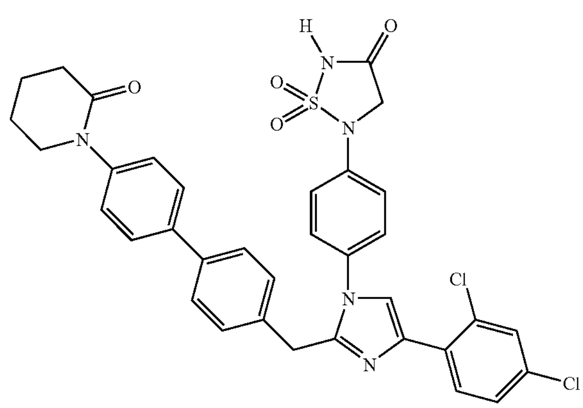 [SMILES: O=C1CN(c2ccc(-n3cc(-c4ccc(Cl)cc4Cl)nc3Cc3ccc(-c4ccc(N5CCCCC5=O)cc4)cc3)cc2)S(=O)(=O)N1] | 1-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-piperidin-2-one |

TABLE 1-continued

| Ex. | Structure | Name |
|---|---|---|
| 75 | 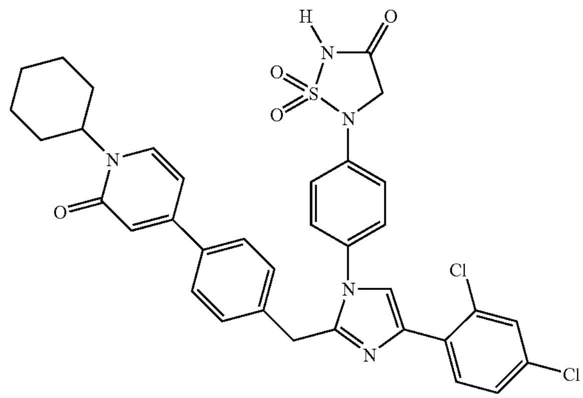 [SMILES: O=C1CN(c2ccc(-n3cc(-c4ccc(Cl)cc4Cl)nc3Cc3ccc(-c4ccn(C5CCCCC5)c(=O)c4)cc3)cc2)S(=O)(=O)N1] | 1-Cyclohexyl-4-(4-{4-(2,4-dichloro-phenyl)-1-[4-(1,1,4-trioxo-[1,2,5]thiadiazolidin-2-yl)-phenyl]-1H-imidazol-2-ylmethyl}-phenyl)-1H-pyridin-2-one |
| 76 | 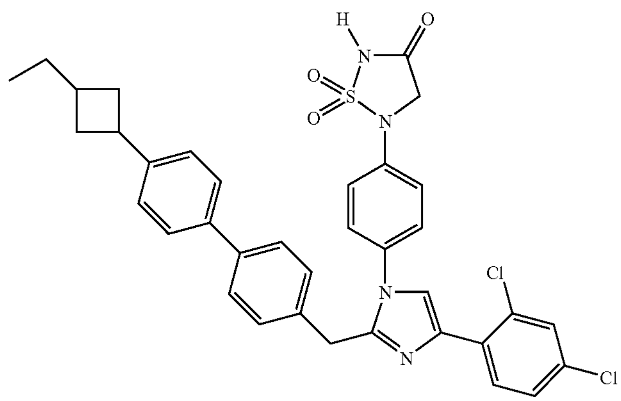 [SMILES: CCC1CC(c2ccc(-c3ccc(Cc4nc(-c5ccc(Cl)cc5Cl)cn4-c4ccc(N5CC(=O)NS5(=O)=O)cc4)cc3)cc2)C1] | 5-(4-{4-(2,4-Dichloro-phenyl)-2-[4'-(3-ethyl-cyclobutyl)-biphenyl-4-ylmethyl]-imidazol-1-yl}-phenyl)-1,2,5-thiadiazolidine-3-one-1,1-dioxide |
| 77 | 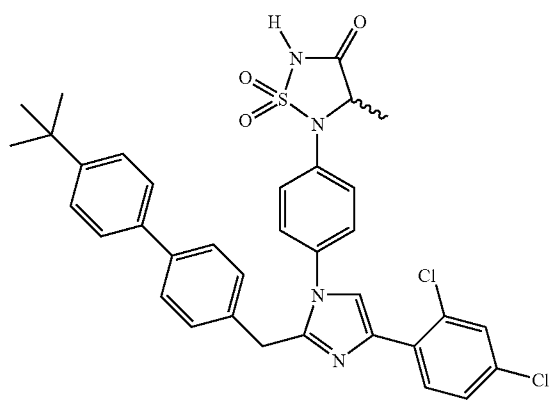 [SMILES: CC1C(=O)NS(=O)(=O)N1c1ccc(-n2cc(-c3ccc(Cl)cc3Cl)nc2Cc2ccc(-c3ccc(C(C)(C)C)cc3)cc2)cc1] | 5-{4-[2-(4'-Tert-butyl-biphenyl-4-ylmethyl)-4-(2,4-dichloro-phenyl)-imidazol-1-yl]-phenyl}-4-methyl-1,2,5-thiadiazolidine-3-one-1,1-dioxide |
| 78 | 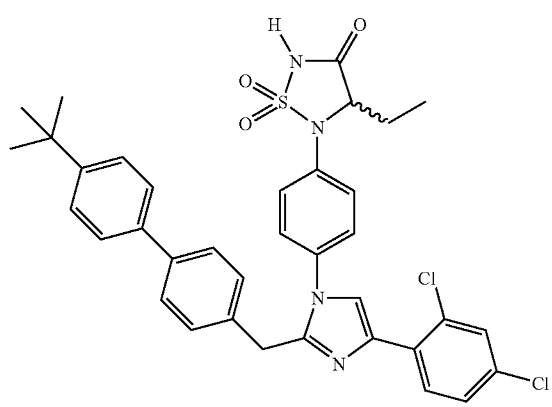 [SMILES: CCC1C(=O)NS(=O)(=O)N1c1ccc(-n2cc(-c3ccc(Cl)cc3Cl)nc2Cc2ccc(-c3ccc(C(C)(C)C)cc3)cc2)cc1] | 5-{4-[2-(4'-Tert-butyl-biphenyl-4-ylmethyl)-4-(2,4-dichloro-phenyl)-imidazol-1-yl]-phenyl}-4-ethyl-1,2,5-thiadiazolidine-3-one-1,1-dioxide |

TABLE 1-continued

| Ex. | Structure | Name |
|---|---|---|
| 79 | 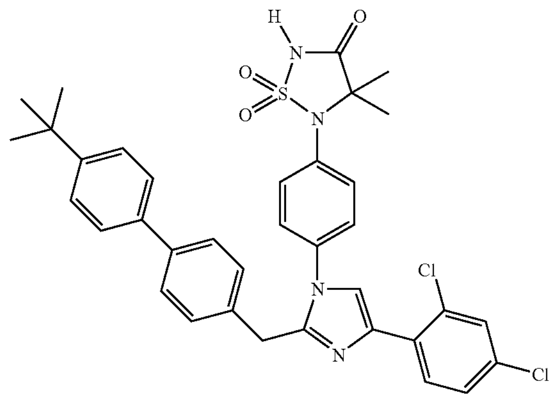 [SMILES: CC(C)(C)c1ccc(-c2ccc(Cc3nc(-c4ccc(Cl)cc4Cl)cn3-c3ccc(N4C(C)(C)C(=O)NS4(=O)=O)cc3)cc2)cc1] | 5-{4-[2-(4'-Tert-butyl-biphenyl-4-ylmethyl)-4-(2,4-dichloro-phenyl)-imidazol-1-yl]-phenyl}-4,4-dimethyl-1,2,5-thiadiazolidine-3-one-1,1-dioxide |
| 80 | 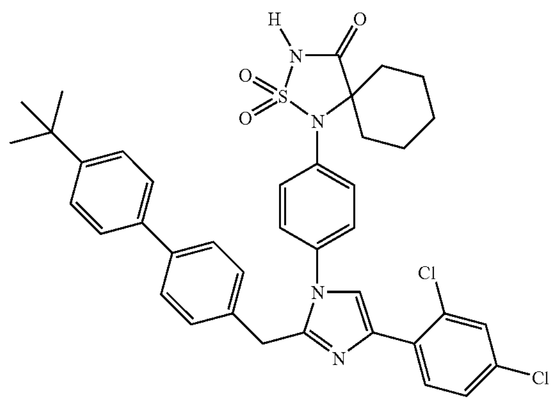 [SMILES: CC(C)(C)c1ccc(-c2ccc(Cc3nc(-c4ccc(Cl)cc4Cl)cn3-c3ccc(N4C5(CCCCC5)C(=O)NS4(=O)=O)cc3)cc2)cc1] | 1-{4-[2-(4'-Tert-Butyl-biphenyl-4-ylmethyl)-4-(2,4-dichloro-phenyl)-imidazol-1-yl]-phenyl}-2,2-dioxo-thia-1,3-diaza-spiro[4.5]decan-4-one |
| 81 | 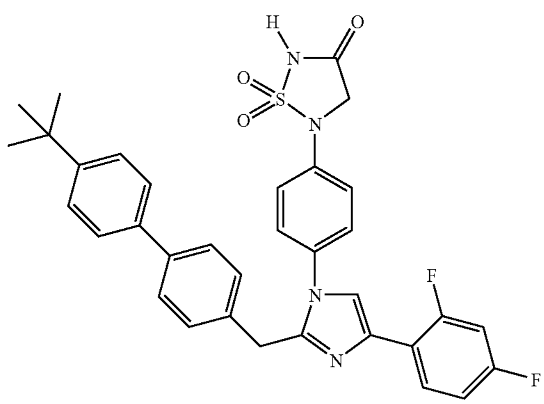 [SMILES: CC(C)(C)c1ccc(-c2ccc(Cc3nc(-c4ccc(F)cc4F)cn3-c3ccc(N4CC(=O)NS4(=O)=O)cc3)cc2)cc1] | 5-{4-[2-(4'-Tert-butyl-biphenyl-4-ylmethyl)-4-(2,4-difluoro-phenyl)-imidazol-1-yl]-phenyl}-1,2,5-thiadiazolidine-3-one-1,1-dioxide |
| 82 | 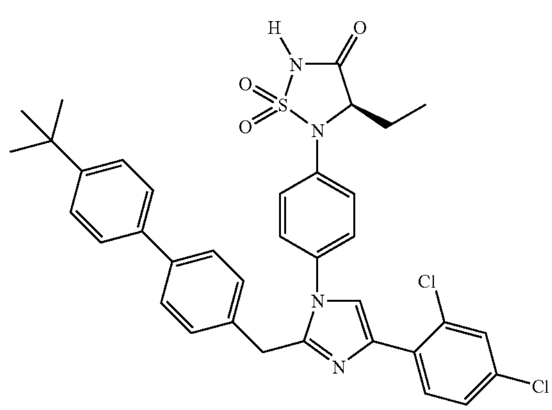 [SMILES: CC[C@@H]1C(=O)NS(=O)(=O)N1c1ccc(-n2cc(-c3ccc(Cl)cc3Cl)nc2Cc2ccc(-c3ccc(C(C)(C)C)cc3)cc2)cc1] | (4R)-5-{4-[2-(4'-Tert-butyl-biphenyl-4-ylmethyl)-4-(2,4-dichloro-phenyl)-imidazol-1-yl]-phenyl}-4-ethyl-1,2,5-thiadiazolidine-3-one-1,1-dioxide |

TABLE 1-continued

| Ex. | Structure | Name |
|---|---|---|
| 83 | 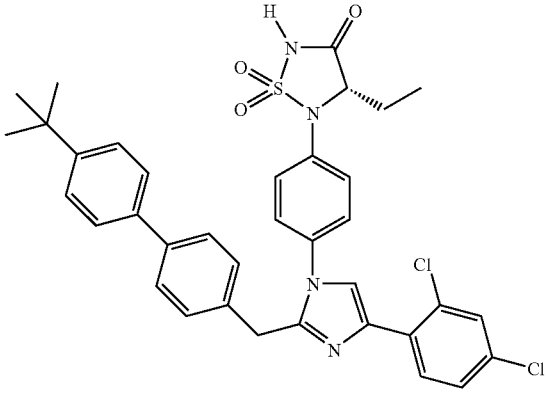 [SMILES: CC[C@H]1C(=O)NS(=O)(=O)N1c1ccc(-n2cc(-c3ccc(Cl)cc3Cl)nc2Cc2ccc(-c3ccc(C(C)(C)C)cc3)cc2)cc1] | (4S)-5-{4-[2-(4'-Tert-butyl-biphenyl-4-ylmethyl)-4-(2,4-dichloro-phenyl)-imidazol-1-yl]-phenyl}-4-ethyl-1,2,5-thiadiazolidine-3-one-1,1-dioxide |
| 84 | 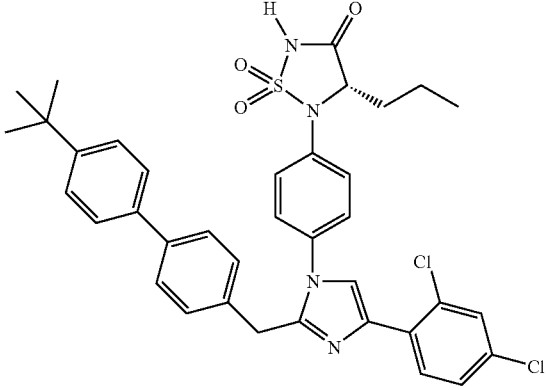 [SMILES: CCC[C@H]1C(=O)NS(=O)(=O)N1c1ccc(-n2cc(-c3ccc(Cl)cc3Cl)nc2Cc2ccc(-c3ccc(C(C)(C)C)cc3)cc2)cc1] | (4S)-5-{4-[2-(4'-Tert-butyl-biphenyl-4-ylmethyl)-4-(2,4-dichloro-phenyl)-imidazol-1-yl]-phenyl}-4-propyl-1,2,5-thiadiazolidine-3-one-1,1-dioxide |
| 85 | 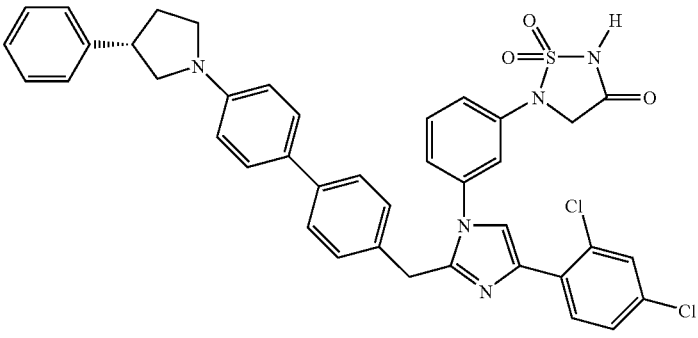 [SMILES: O=C1CN(c2cccc(-n3cc(-c4ccc(Cl)cc4Cl)nc3Cc3ccc(-c4ccc(N5CC[C@@H](c6ccccc6)C5)cc4)cc3)c2)S(=O)(=O)N1] | 5-(3-{4-(2,4-Dichloro-phenyl)-2-{4'-[(3S)-3-phenyl-pyrrolidin-1-yl]-biphenyl-4-ylmethyl}-imidazol-1-yl}-phenyl)-1,2,5-thiadiazolidine-3-one-1,1-dioxide |
| 86 | 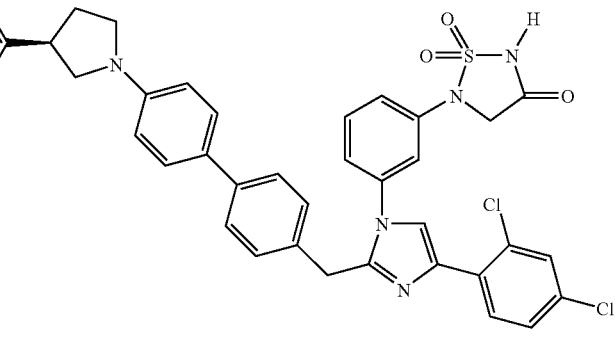 | 5-(3-{4-(2,4-Dichloro-phenyl)-2-{4'-[(3R)-3-phenyl-pyrrolidin-1-yl]-biphenyl-4-ylmethyl}-imidazol-1-yl}-phenyl)-1,2,5-thiadiazolidine-3-one-1,1-dioxide |

TABLE 1-continued

| Ex. | Structure | Name |
|---|---|---|
| 87 | 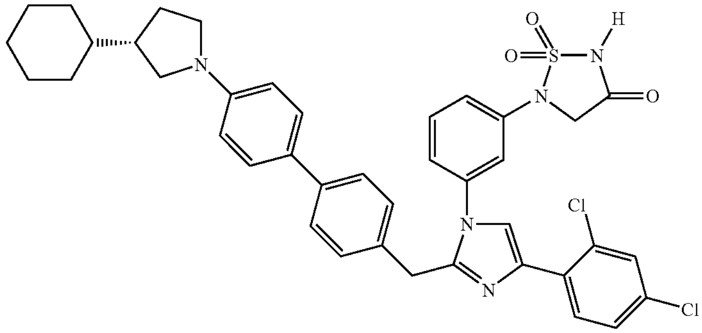 [SMILES: O=C1CN(c2cccc(-n3cc(-c4ccc(Cl)cc4Cl)nc3Cc3ccc(-c4ccc(N5CC[C@@H](C6CCCCC6)C5)cc4)cc3)c2)S(=O)(=O)N1] | 5-{3-[2-{4'-[(3S)-3-Cyclohexyl-pyrrolidin-1-yl]-biphenyl-4-ylmethyl}-4-(2,4-dichloro-phenyl)-imidazol-1-yl]-phenyl}-1,2,5-thiadiazolidine-3-one-1,1-dioxide |
| 88 | 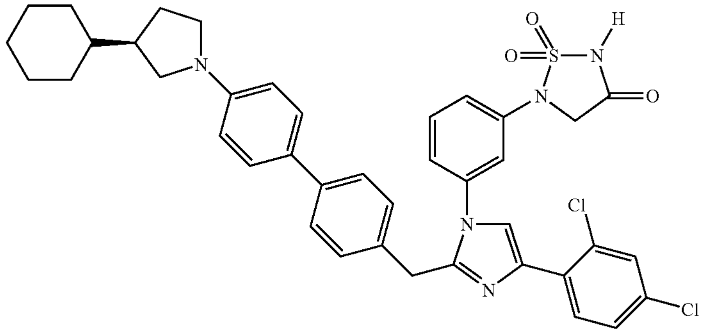 [SMILES: O=C1CN(c2cccc(-n3cc(-c4ccc(Cl)cc4Cl)nc3Cc3ccc(-c4ccc(N5CC[C@H](C6CCCCC6)C5)cc4)cc3)c2)S(=O)(=O)N1] | 5-{3-[2-{4'-[(3R)-3-Cyclohexyl-pyrrolidin-1-yl]-biphenyl-4-ylmethyl}-4-(2,4-dichloro-phenyl)-imidazol-1-yl]-phenyl}-1,2,5-thiadiazolidine-3-one-1,1-dioxide |
| 89 | 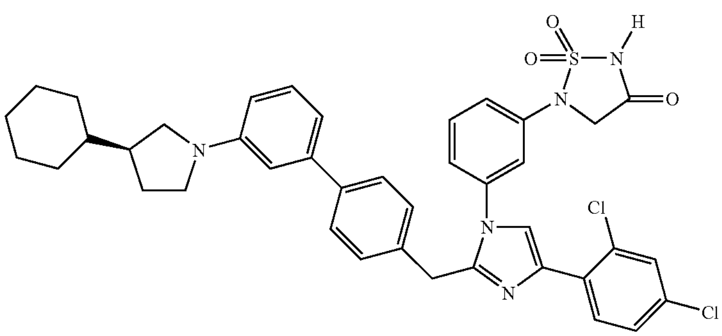 [SMILES: O=C1CN(c2cccc(-n3cc(-c4ccc(Cl)cc4Cl)nc3Cc3ccc(-c4cccc(N5CC[C@@H](C6CCCCC6)C5)c4)cc3)c2)S(=O)(=O)N1] | 5-{3-[2-{3'-[(3S)-3-Cyclohexyl-pyrrolidin-1-yl]-biphenyl-4-ylmethyl}-4-(2,4-dichloro-phenyl)-imidazol-1-yl]-phenyl}-1,2,5-thiadiazolidine-3-one-1,1-dioxide |
| 90 | 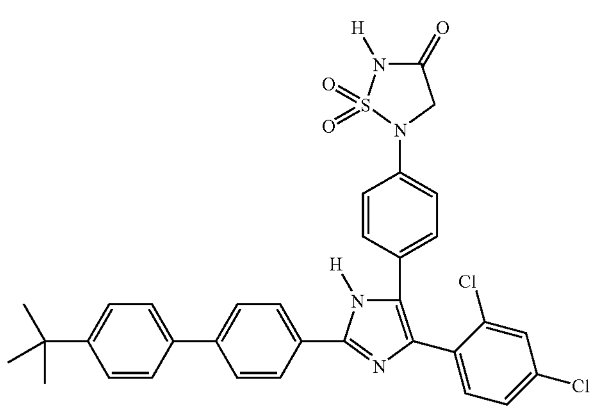 [SMILES: CC(C)(C)c1ccc(-c2ccc(-c3nc(-c4ccc(Cl)cc4Cl)c(-c4ccc(N5CC(=O)NS5(=O)=O)cc4)[nH]3)cc2)cc1] | 5-{4-[2-(4'-Tert-butyl-biphenyl-4-yl)-5-(2,4-dichloro-phenyl)-3H-imidazol-4-yl]-phenyl}-1,2,5-thiadiazolidine-3-one-1,1-dioxide |

TABLE 1-continued

| Ex. | Structure | Name |
|---|---|---|
| 91 | 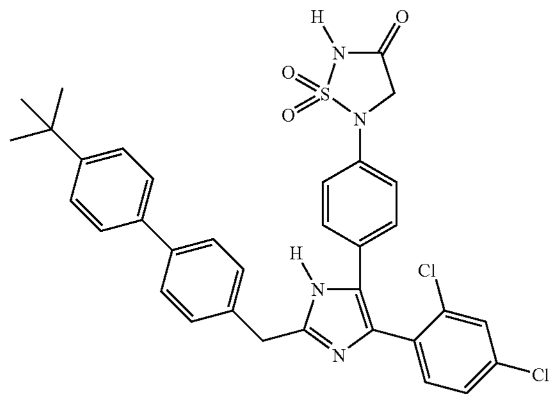 [SMILES: CC(C)(C)c1ccc(-c2ccc(Cc3nc(-c4ccc(Cl)cc4Cl)c(-c4ccc(N5CC(=O)NS5(=O)=O)cc4)[nH]3)cc2)cc1] | 5-{4-[2-(4'-Tert-butyl-biphenyl-4-ylmethyl)-5-(2,4-dichloro-phenyl)-3H-imidazol-4-yl]-phenyl}-1,2,5-thiadiazolidine-3-one-1,1-dioxide |
| 92 | 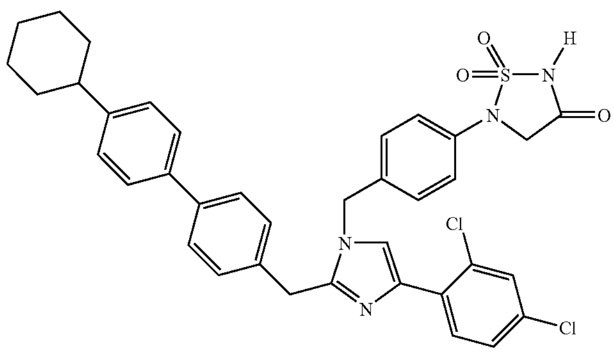 [SMILES: O=C1CN(c2ccc(Cn3cc(-c4ccc(Cl)cc4Cl)nc3Cc3ccc(-c4ccc(C5CCCCC5)cc4)cc3)cc2)S(=O)(=O)N1] | 5-{4-[2-(4'-Cyclohexyl-biphenyl-4-ylmethyl)-4-(2,4-dichloro-phenyl)-imidazol-1-ylmethyl]-phenyl}-1,2,5-thiadiazolidine-3-one-1,1-dioxide |
| 93 | 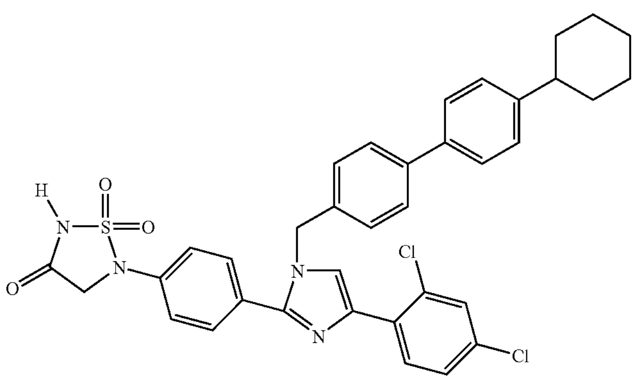 [SMILES: O=C1CN(c2ccc(-c3nc(-c4ccc(Cl)cc4Cl)cn3Cc3ccc(-c4ccc(C5CCCCC5)cc4)cc3)cc2)S(=O)(=O)N1] | 5-{4-[1-(4'-Cyclohexyl-biphenyl-4-ylmethyl)-4-(2,4-dichloro-phenyl)-1H-imidazol-2-yl]-phenyl}-1,2,5-thiadiazolidine-3-one-1,1-dioxide |
| 94 | 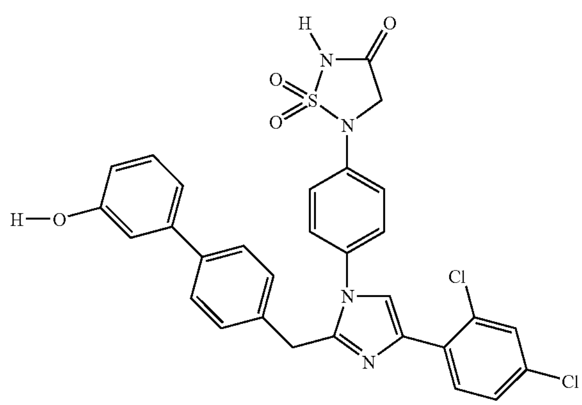 [SMILES: O=C1CN(c2ccc(-n3cc(-c4ccc(Cl)cc4Cl)nc3Cc3ccc(-c4cccc(O)c4)cc3)cc2)S(=O)(=O)N1] | 5-{4-[4-(2,4-Dichloro-phenyl)-2-(3'-hydroxy-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 95 | 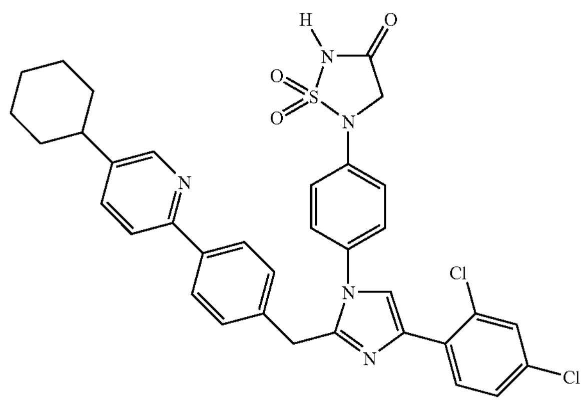 [SMILES: O=C1CN(c2ccc(-n3cc(-c4ccc(Cl)cc4Cl)nc3Cc3ccc(-c4ccc(C5CCCCC5)cn4)cc3)cc2)S(=O)(=O)N1] | 5-{4-[2-[4-(5-Cyclohexyl-pyridin-2-yl)-benzyl]-4-(2,4-dichloro-phenyl)-imidazol-1-yl]-phenyl}-1,2,5-thiadiazolidine-3-one-1,1-dioxide |
| 96 | 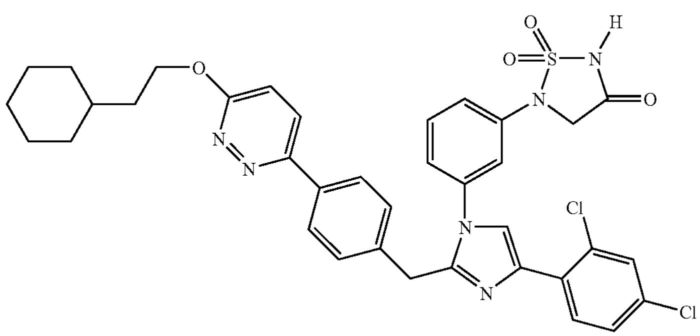 [SMILES: O=C1CN(c2cccc(-n3cc(-c4ccc(Cl)cc4Cl)nc3Cc3ccc(-c4ccc(OCCC5CCCCC5)nn4)cc3)c2)S(=O)(=O)N1] | 5-{3-[2-{4-[6-(2-Cyclohexyl-ethoxy)-pyridazin-3-yl]-benzyl}-4-(2,4-dichloro-phenyl)-imidazol-1-yl]-phenyl}-1,2,5-thiadiazolidine-3-one-1,1-dioxide |
| 97 | 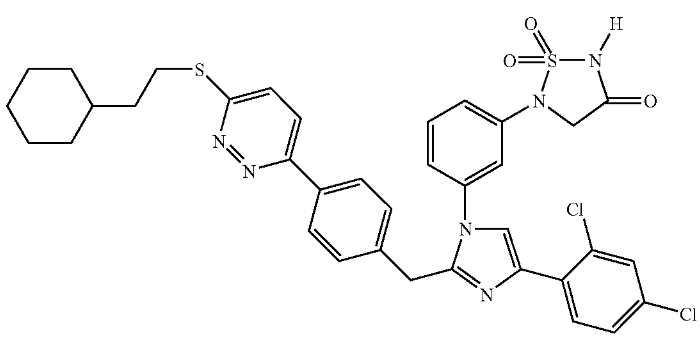 [SMILES: O=C1CN(c2cccc(-n3cc(-c4ccc(Cl)cc4Cl)nc3Cc3ccc(-c4ccc(SCCC5CCCCC5)nn4)cc3)c2)S(=O)(=O)N1] | 5-{3-[2-{4-[6-(2-Cyclohexyl-ethylsulfanyl)-pyridazin-3-yl]-benzyl}-4-(2,4-dichloro-phenyl)-imidazol-1-yl]-phenyl}-1,2,5-thiadiazolidine-3-one-1,1-dioxide |
| 98 | 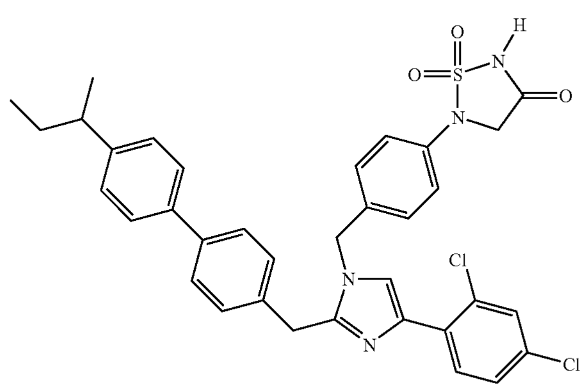 [SMILES: CCC(C)c1ccc(-c2ccc(Cc3nc(-c4ccc(Cl)cc4Cl)cn3Cc3ccc(N4CC(=O)NS4(=O)=O)cc3)cc2)cc1] | 5-{4-[2-(4'-sec-Butyl-biphenyl-4-ylmethyl)-4-(2,4-dichloro-phenyl)-imidazol-1-ylmethyl]-phenyl}-1,2,5-thiadiazolidine-3-one-1,1-dioxide |

TABLE 1-continued

| Ex. | Structure | Name |
|---|---|---|
| 99 | 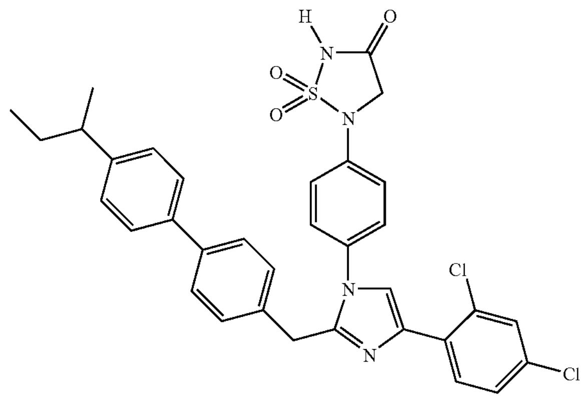 [SMILES: CCC(C)c1ccc(-c2ccc(Cc3nc(-c4ccc(Cl)cc4Cl)cn3-c3ccc(N4CC(=O)NS4(=O)=O)cc3)cc2)cc1] | 5-{4-[2-(4'-sec-Butyl-biphenyl-4-ylmethyl)-4-(2,4-dichloro-phenyl)-imidazol-1-yl]-phenyl}-1,2,5-thiadiazolidine-3-one-1,1-dioxide |
| 100 | 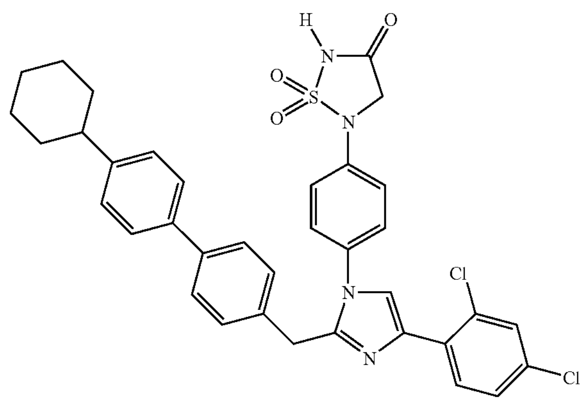 [SMILES: O=C1CN(c2ccc(-n3cc(-c4ccc(Cl)cc4Cl)nc3Cc3ccc(-c4ccc(C5CCCCC5)cc4)cc3)cc2)S(=O)(=O)N1] | 5-{4-[2-(4'-Cyclohexyl-biphenyl-4-ylmethyl)-4-(2,4-dichloro-phenyl)-imidazol-1-yl]-phenyl}-1,2,5-thiadiazolidine-3-one-1,1-dioxide |
| 101 | 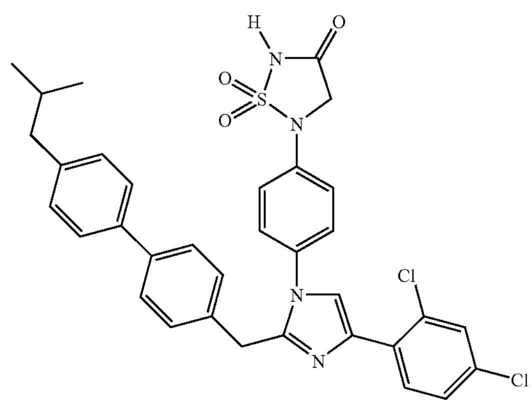 [SMILES: CC(C)Cc1ccc(-c2ccc(Cc3nc(-c4ccc(Cl)cc4Cl)cn3-c3ccc(N4CC(=O)NS4(=O)=O)cc3)cc2)cc1] | 5-{4-[4-(2,4-Dichloro-phenyl)-2-(4'-isobutyl-biphenyl-4-ylmethyl)-imidazol-1-yl]-phenyl}-1,2,5-thiadiazolidine-3-one-1,1-dioxide |
| 102 | 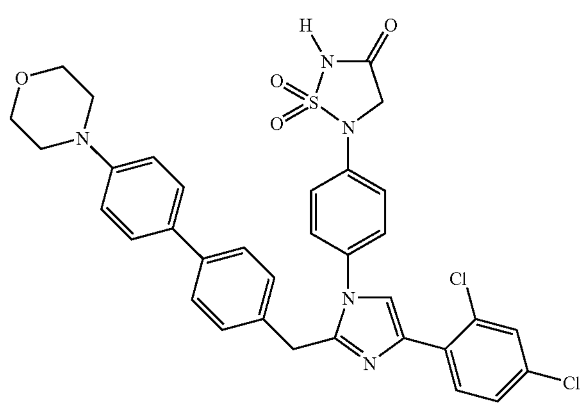 [SMILES: O=C1CN(c2ccc(-n3cc(-c4ccc(Cl)cc4Cl)nc3Cc3ccc(-c4ccc(N5CCOCC5)cc4)cc3)cc2)S(=O)(=O)N1] | 5-{4-[4-(2,4-Dichloro-phenyl)-2-(4'-morpholin-4-yl-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 103 | 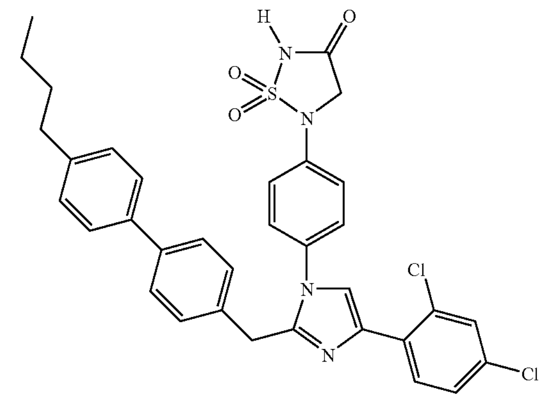 | 5-{4-[2-(4'-Butyl-biphenyl-4-ylmethyl)-4-(2,4-dichloro-phenyl)-imidazol-1-yl]-phenyl}-1,2,5-thiadiazolidine-3-one-1,1-dioxide |
| 104 | 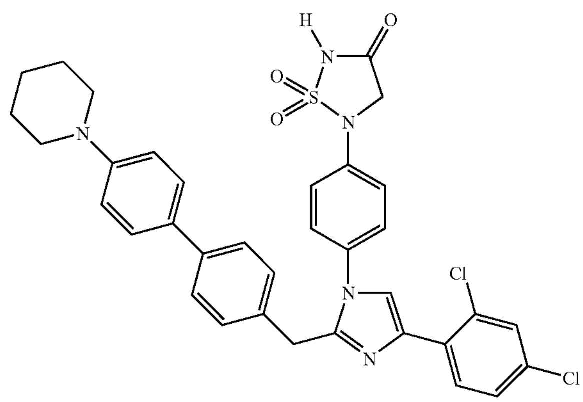 [SMILES: O=C1CN(c2ccc(-n3cc(-c4ccc(Cl)cc4Cl)nc3Cc3ccc(-c4ccc(N5CCCCC5)cc4)cc3)cc2)S(=O)(=O)N1] | 5-{4-[4-(2,4-Dichloro-phenyl)-2-(4'-piperidin-1-yl-biphenyl-4-ylmethyl)-imidazol-1-yl]-phenyl}-1,2,5-thiadiazolidine-3-one-1,1-dioxide |
| 105 | 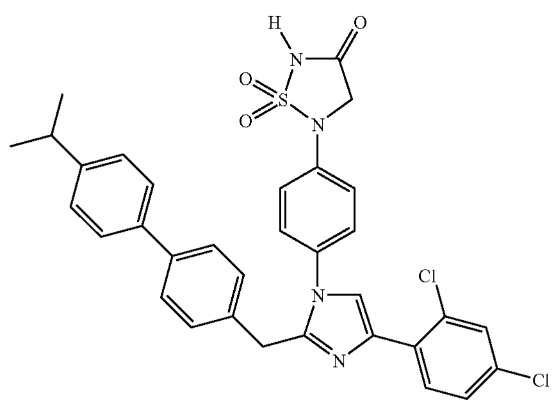 [SMILES: CC(C)c1ccc(-c2ccc(Cc3nc(-c4ccc(Cl)cc4Cl)cn3-c3ccc(N4CC(=O)NS4(=O)=O)cc3)cc2)cc1] | 5-{4-[4-(2,4-Dichloro-phenyl)-2-(4'-isopropyl-biphenyl-4-ylmethyl)-imidazol-1-yl]-phenyl}-1,2,5-thiadiazolidine-3-one-1,1-dioxide |
| 106 | 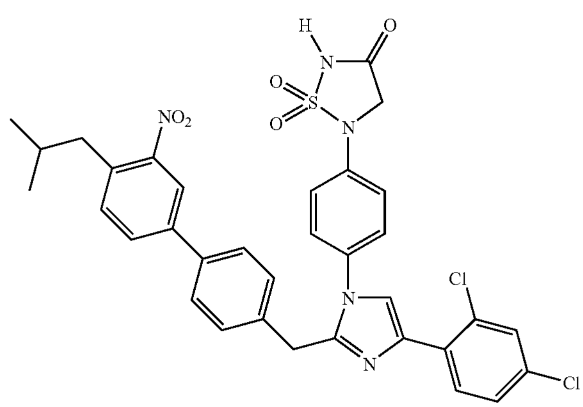 | 5-{4-[2-(3'-Nitro-4'-isobutyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 107 | 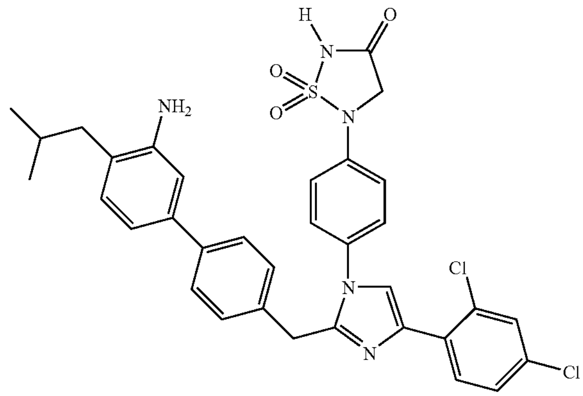 [SMILES: CC(C)Cc1ccc(-c2ccc(Cc3nc(-c4ccc(Cl)cc4Cl)cn3-c3ccc(N4CC(=O)NS4(=O)=O)cc3)cc2)cc1[N+](=O)[O-]] | 5-{4-[2-(3'-Amino-4'-isobutyl-biphenyl-4-ylmethyl)-4-(2,4-dichloro-phenyl)-imidazol-1-yl]-phenyl}-1,2,5-thiadiazolidine-3-one-1,1-dioxide |
| 108 | 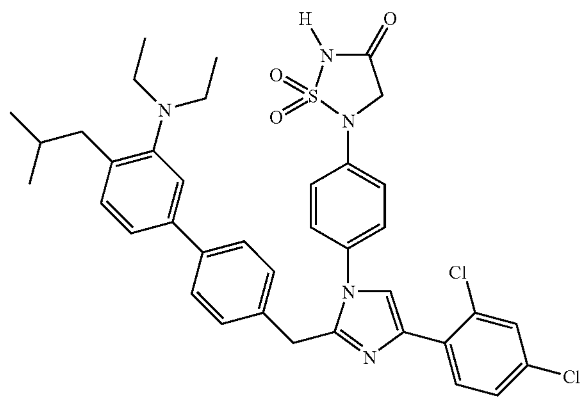 [SMILES: CCN(CC)c1cc(-c2ccc(Cc3nc(-c4ccc(Cl)cc4Cl)cn3-c3ccc(N4CC(=O)NS4(=O)=O)cc3)cc2)ccc1CC(C)C] | 5-{4-[4-(2,4-Dichloro-phenyl)-2-(3'-diethylamino-4'-isobutyl-biphenyl-4-ylmethyl)-imidazol-1-yl]-phenyl}-1,2,5-thiadiazolidine-3-one-1,1-dioxide |
| 109 | 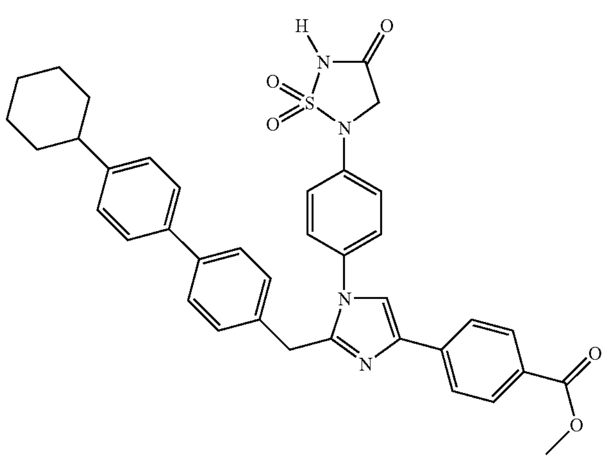 [SMILES: COC(=O)c1ccc(-c2cn(-c3ccc(N4CC(=O)NS4(=O)=O)cc3)c(Cc3ccc(-c4ccc(C5CCCCC5)cc4)cc3)n2)cc1] | 4-{2-(4'-Cyclohexyl-biphenyl-4-ylmethyl)-1-[4-(1,1,4-trioxo-1-[1,2,5]thiadiazolidin-2-yl)-phenyl]-1H-imidazol-4-yl}-benzoic acid methyl ester |

TABLE 1-continued

| Ex. | Structure | Name |
|---|---|---|
| 110 | 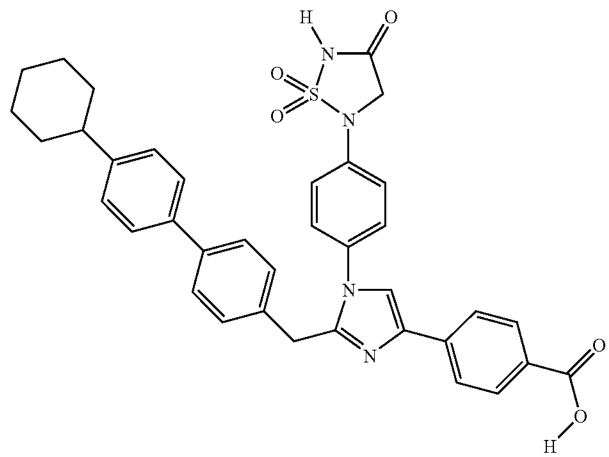 [SMILES: O=C1CN(c2ccc(-n3cc(-c4ccc(C(=O)O)cc4)nc3Cc3ccc(-c4ccc(C5CCCCC5)cc4)cc3)cc2)S(=O)(=O)N1] | 4-{2-(4'-Cyclohexyl-biphenyl-4-ylmethyl)-1-[4-(1,1,4-trioxo-1-[1,2,5] thiadiazolidin-2-yl)-phenyl]-1H-imidazol-4-yl}-benzoic acid |
| 111 | 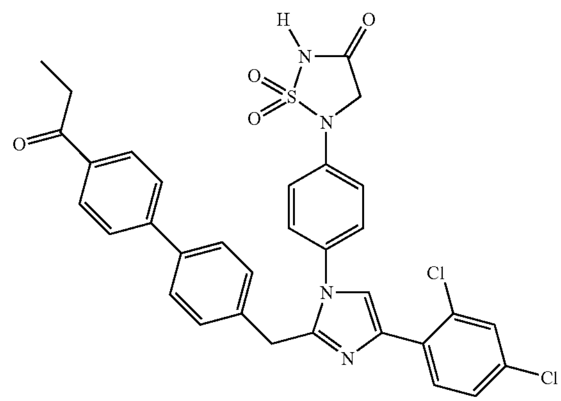 [SMILES: CCC(=O)c1ccc(-c2ccc(Cc3nc(-c4ccc(Cl)cc4Cl)cn3-c3ccc(N4CC(=O)NS4(=O)=O)cc3)cc2)cc1] | 5-{4-[4-(2,4-Dichloro-phenyl)-2-(4'-propionyl-biphenyl-4-ylmethyl)-imidazol-1-yl]-phenyl}-1,2,5-thiadiazolidine-3-one-1,1-dioxide |
| 112 | 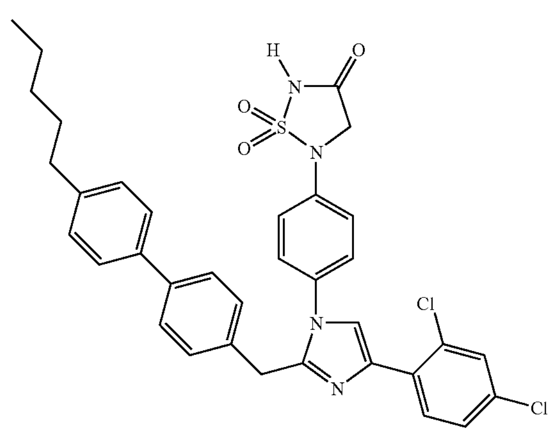 [SMILES: CCCCCc1ccc(-c2ccc(Cc3nc(-c4ccc(Cl)cc4Cl)cn3-c3ccc(N4CC(=O)NS4(=O)=O)cc3)cc2)cc1] | 5-{4-[4-(2,4-Dichloro-phenyl)-2-(4'-pentyl-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 113 | 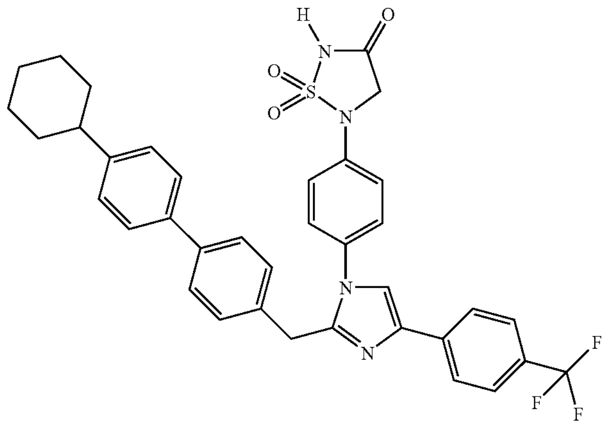 [SMILES: O=C1CN(c2ccc(-n3cc(-c4ccc(C(F)(F)F)cc4)nc3Cc3ccc(-c4ccc(C5CCCCC5)cc4)cc3)cc2)S(=O)(=O)N1] | 5-{4-[2-(4'-Cyclohexyl-biphenyl-4-ylmethyl)-4-(4-trifluoromethyl-phenyl)-imidazol-1-yl]-phenyl}-1,2,5-thiadiazolidine-3-one-1,1-dioxide |
| 114 | 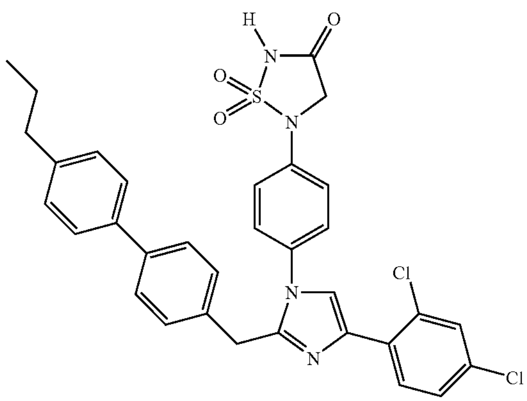 [SMILES: CCCc1ccc(-c2ccc(Cc3nc(-c4ccc(Cl)cc4Cl)cn3-c3ccc(N4CC(=O)NS4(=O)=O)cc3)cc2)cc1] | 5-{4-[4-(2,4-Dichloro-phenyl)-2-(4'-propyl-biphenyl-4-ylmethyl)-imidazol-1-yl]-phenyl}-1,2,5-thiadiazolidine-3-one-1,1-dioxide |
| 115 | 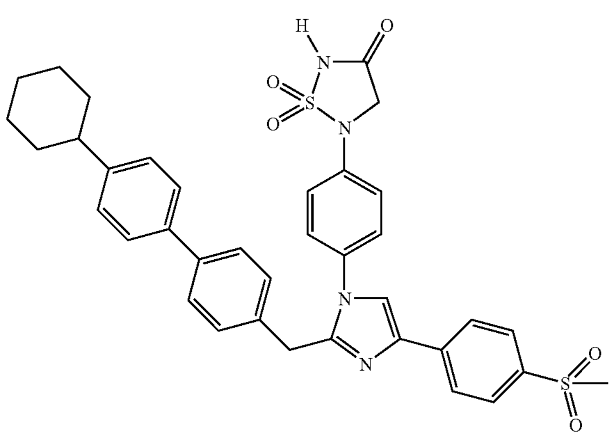 [SMILES: CS(=O)(=O)c1ccc(-c2cn(-c3ccc(N4CC(=O)NS4(=O)=O)cc3)c(Cc3ccc(-c4ccc(C5CCCCC5)cc4)cc3)n2)cc1] | 5-{4-[2-(4'-Cyclohexyl-biphenyl-4-ylmethyl)-4-(4-methanesulfonyl-phenyl)-imidazol-1-yl]-phenyl]-1,2,5-thiadiazolidine-3-one-1,1-dioxide |

TABLE 1-continued

| Ex. | Structure | Name |
|---|---|---|
| 116 | 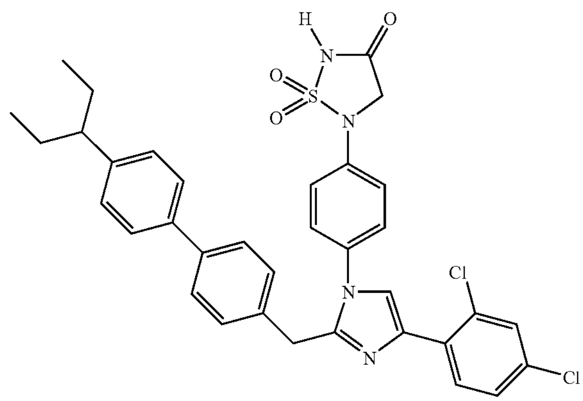 [SMILES: CCC(CC)c1ccc(-c2ccc(Cc3nc(-c4ccc(Cl)cc4Cl)cn3-c3ccc(N4CC(=O)NS4(=O)=O)cc3)cc2)cc1] | 5-(4-{4-(2,4-Dichloro-phenyl)-2-[4'-(1-ethyl-propyl)-biphenyl-4-ylmethyl]-imidazol-1-yl}-phenyl)-1,2,5-thiadiazolidine-3-one-1,1-dioxide |
| 117 | 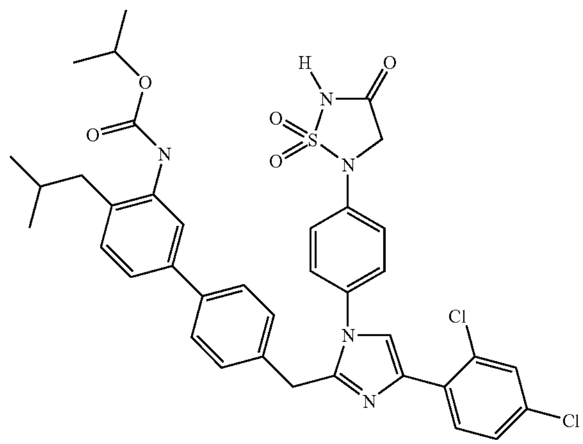 [SMILES: CC(C)Cc1ccc(-c2ccc(Cc3nc(-c4ccc(Cl)cc4Cl)cn3-c3ccc(N4CC(=O)NS4(=O)=O)cc3)cc2)cc1NC(=O)OC(C)C] | (4'-{4-(2,4-Dichloro-phenyl)-1-[4-(1,1,4-trioxo-1-[1,2,5]thiadiazolidin-2-yl)-phenyl]-1H-imidazol-2-ylmethyl}-4-isobutyl-biphenyl-3-yl)-carbamic acid isopropyl ester |
| 118 | 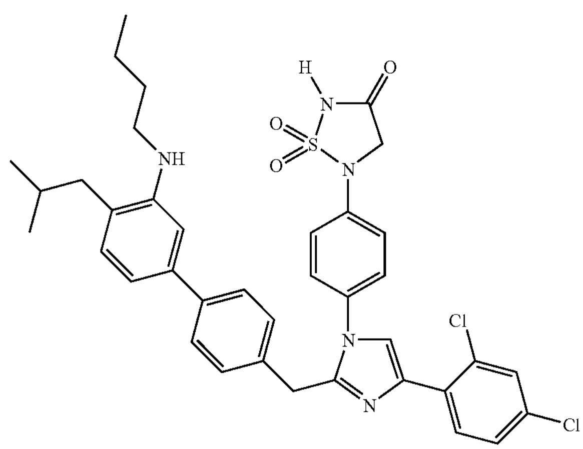 [SMILES: CCCCNc1cc(-c2ccc(Cc3nc(-c4ccc(Cl)cc4Cl)cn3-c3ccc(N4CC(=O)NS4(=O)=O)cc3)cc2)ccc1CC(C)C] | 5-{4-[2-(3'-Butylamino-4'-isobutyl-biphenyl-4-ylmethyl)-4-(2,4-dichloro-phenyl)-imidazol-1-yl]-phenyl}-1,2,5-thiadiazolidine-3-one-1,1-dioxide |
| 119 | 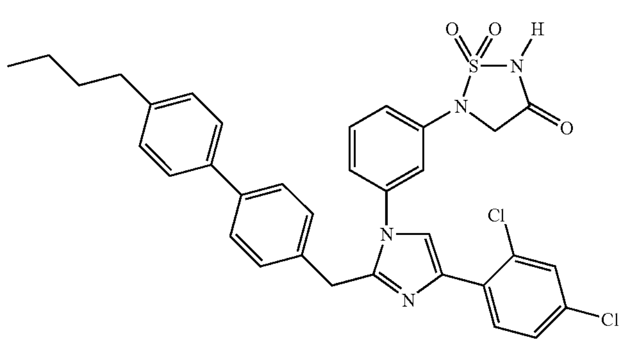 [SMILES: CCCCc1ccc(-c2ccc(Cc3nc(-c4ccc(Cl)cc4Cl)cn3-c3cccc(N4CC(=O)NS4(=O)=O)c3)cc2)cc1] | 5-{3-[2-(4'-Butyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 120 | 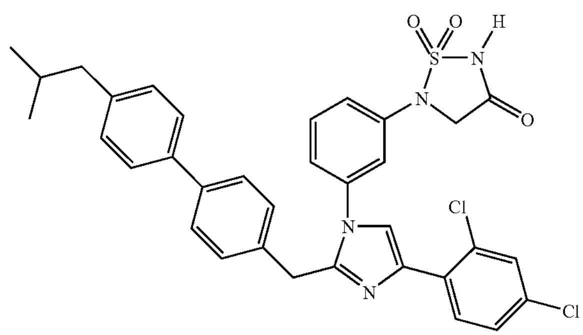 [SMILES: CC(C)Cc1ccc(-c2ccc(Cc3nc(-c4ccc(Cl)cc4Cl)cn3-c3cccc(N4CC(=O)NS4(=O)=O)c3)cc2)cc1] | 5-{3-[4-(2,4-Dichloro-phenyl)-2-(4'-isobutyl-biphenyl-4-ylmethyl)-imidazol-1-yl]-phenyl}-1,2,5-thiadiazolidine-3-one-1,1-dioxide |
| 121 | 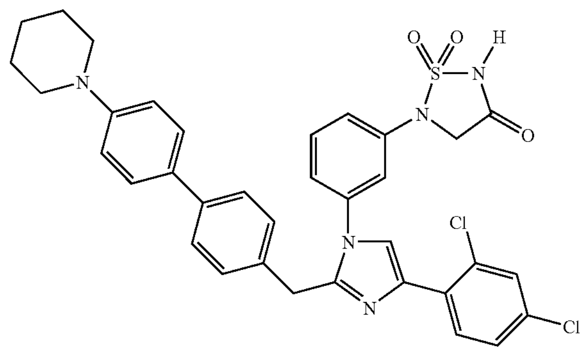 [SMILES: O=C1CN(c2cccc(-n3cc(-c4ccc(Cl)cc4Cl)nc3Cc3ccc(-c4ccc(N5CCCCC5)cc4)cc3)c2)S(=O)(=O)N1] | 5-{3-[4-(2,4-Dichloro-phenyl)-2-(4'-piperidin-1-yl-biphenyl-4-ylmethyl)-imidazol-1-yl]-phenyl}-1,2,5-thiadiazolidine-3-one-1,1-dioxide |
| 122 | 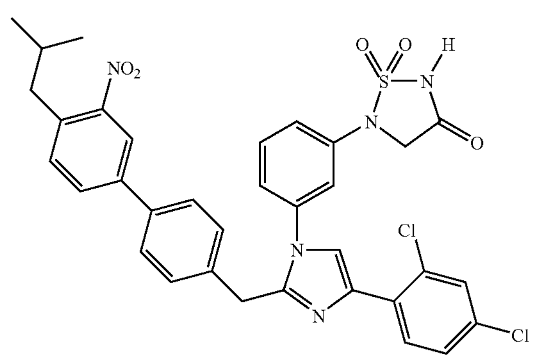 [SMILES: CC(C)Cc1ccc(-c2ccc(Cc3nc(-c4ccc(Cl)cc4Cl)cn3-c3cccc(N4CC(=O)NS4(=O)=O)c3)cc2)cc1[N+](=O)[O-]] | 5-{3-[2-(3'-Nitro-4'-isobutyl-biphenyl-4-ylmethyl)-4-(2,4-dichloro-phenyl)-imidazol-1-yl]-phenyl}-1,2,5-thiadiazolidine-3-one-1,1-dioxide |
| 123 | 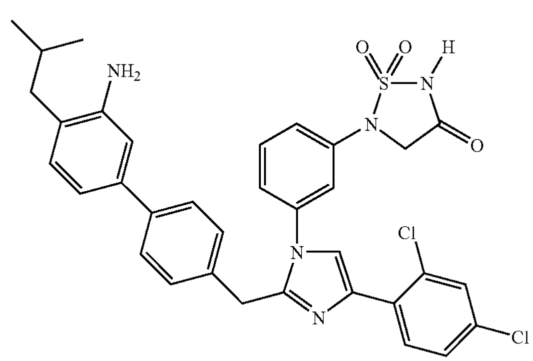 | 5-{3-[2-(3'-Amino-4'-isobutyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 124 | 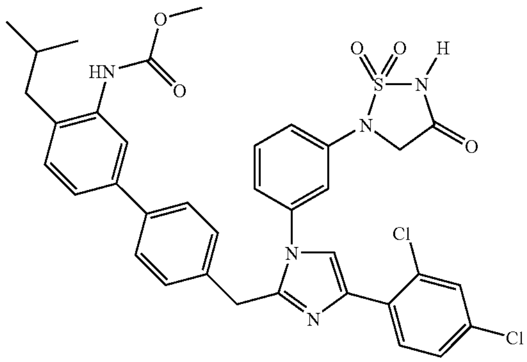 [SMILES: COC(=O)Nc1cc(-c2ccc(Cc3nc(-c4ccc(Cl)cc4Cl)cn3-c3cccc(N4CC(=O)NS4(=O)=O)c3)cc2)ccc1CC(C)C] | (4'-{4-(2,4-Dichloro-phenyl)-1-[3-(1,1,4-trioxo-1-[1,2,5]thiadiazolidin-2-yl)-phenyl]-1H-imidazol-2-ylmethyl}-4-isobutyl-biphenyl-3-yl)-carbamic acid methyl ester |
| 125 | 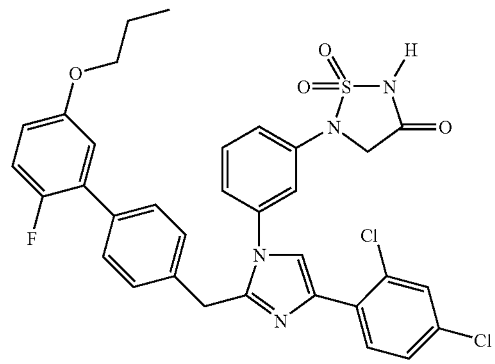 [SMILES: CCCOc1ccc(F)c(-c2ccc(Cc3nc(-c4ccc(Cl)cc4Cl)cn3-c3cccc(N4CC(=O)NS4(=O)=O)c3)cc2)c1] | 5-{3-[4-(2,4-Dichloro-phenyl)-2-(2'-fluoro-5'-propoxy-biphenyl-4-ylmethyl)-imidazol-1-yl]-phenyl}-1,2,5-thiadiazolidine-3-one-1,1-dioxide |
| 126 | 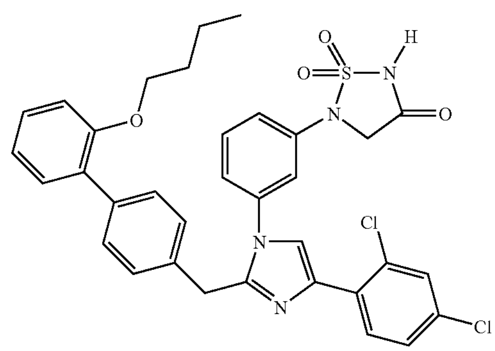 [SMILES: CCCCOc1ccccc1-c1ccc(Cc2nc(-c3ccc(Cl)cc3Cl)cn2-c2cccc(N3CC(=O)NS3(=O)=O)c2)cc1] | 5-{3-[2-(2'-Butoxy-biphenyl-4-ylmethyl)-4-(2,4-dichloro-phenyl)-imidazol-1-yl]-phenyl}-1,2,5-thiadiazolidine-3-one-1,1-dioxide |
| 127 | 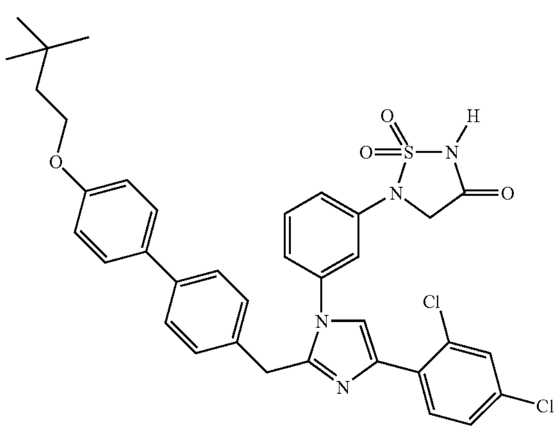 [SMILES: CC(C)(C)CCOc1ccc(-c2ccc(Cc3nc(-c4ccc(Cl)cc4Cl)cn3-c3cccc(N4CC(=O)NS4(=O)=O)c3)cc2)cc1] | 5-(3-{4-(2,4-Dichloro-phenyl)-2-[4'-(3,3-dimethyl-butoxy)-biphenyl-4-ylmethyl]-imidazol-1-yl}-phenyl)-1,2,5-thiadiazolidine-3-one-1,1-dioxide |

TABLE 1-continued

| Ex. | Structure | Name |
|---|---|---|
| 128 | 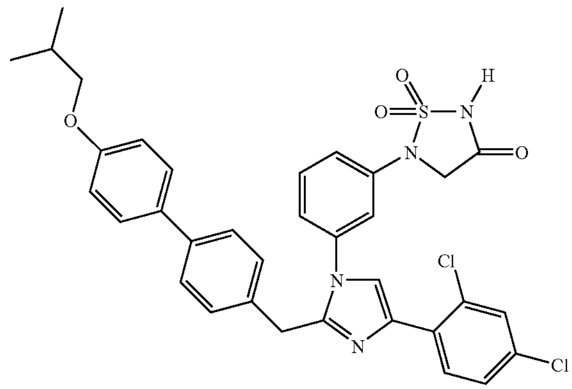 [SMILES: CC(C)COc1ccc(-c2ccc(Cc3nc(-c4ccc(Cl)cc4Cl)cn3-c3cccc(N4CC(=O)NS4(=O)=O)c3)cc2)cc1] | 5-{3-[4-(2,4-Dichloro-phenyl)-2-(4'-isobutoxy-biphenyl-4-ylmethyl)-imidazol-1-yl]-phenyl}-1,2,5-thiadiazolidine-3-one-1,1-dioxide |
| 129 | 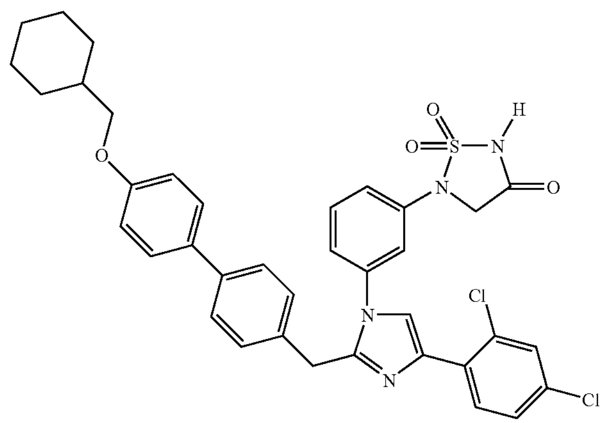 [SMILES: O=C1CN(c2cccc(-n3cc(-c4ccc(Cl)cc4Cl)nc3Cc3ccc(-c4ccc(OCC5CCCCC5)cc4)cc3)c2)S(=O)(=O)N1] | 5-{3-[2-{4'-Cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide |
| 130 | 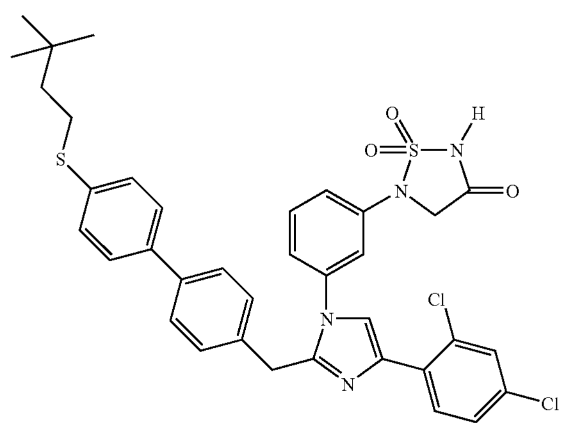 | 5-(3-{4-(2,4-Dichloro-phenyl)-2-[4'-(3,3-dimethyl-butylsulfanyl)-biphenyl-4-ylmethyl]-imidazol-1-yl}-phenyl)-1,2,5-thiadiazolidine-3-one-1,1-dioxide |

TABLE 1-continued

| Ex. | Structure | Name |
|---|---|---|
| 131 | 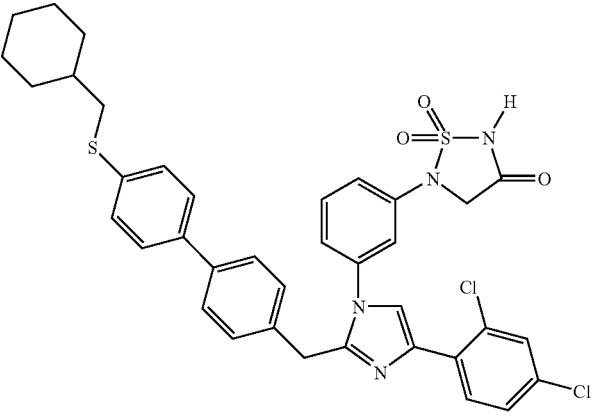 [SMILES: O=C1CN(c2cccc(-n3cc(-c4ccc(Cl)cc4Cl)nc3Cc3ccc(-c4ccc(SCC5CCCCC5)cc4)cc3)c2)S(=O)(=O)N1] | 5-{3-[2-{4'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide |
| 132 | 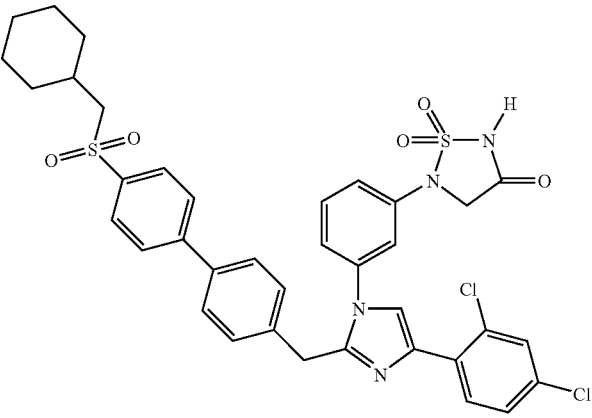 [SMILES: O=C1CN(c2cccc(-n3cc(-c4ccc(Cl)cc4Cl)nc3Cc3ccc(-c4ccc(S(=O)(=O)CC5CCCCC5)cc4)cc3)c2)S(=O)(=O)N1] | 5-{3-[2-{4'-Cyclohexylmethylsulfonyl-biphenyl-4-ylmethyl)-4-(2,4-dichloro-phenyl)-imidazol-1-yl]-phenyl}-1,2,5-thiadiazolidine-3-one-1,1-dioxide |
| 133 | 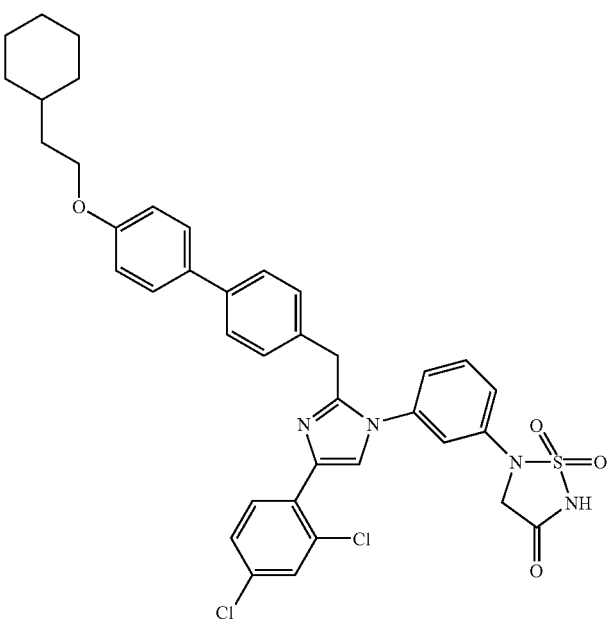 | 5-{3-[2-[4'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 134 | 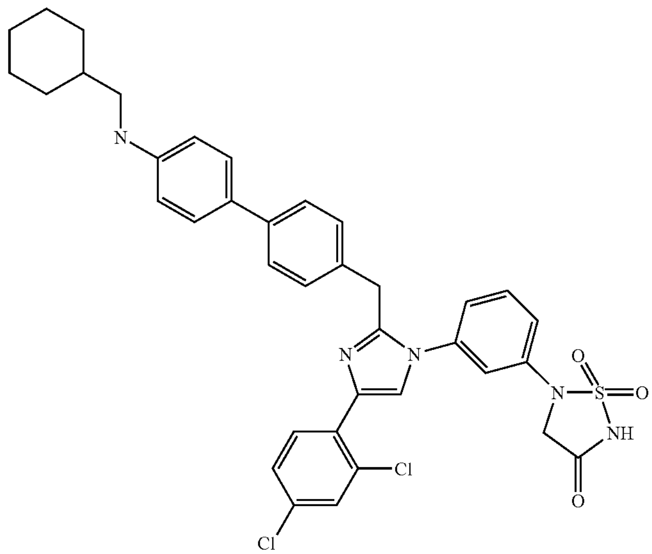 [SMILES: O=C1CN(c2cccc(-n3cc(-c4ccc(Cl)cc4Cl)nc3Cc3ccc(-c4ccc(NCC5CCCCC5)cc4)cc3)c2)S(=O)(=O)N1] | 5-{3-[2-{4'-(Cyclohexylmethyl-amino)-biphenyl-4-ylmethyl]-4-(2,4-dichloro-phenyl)-imidazol-1-yl]-phenyl}-1,2,5-thiadiazolidine-3-one-1,1-dioxide |
| 135 | 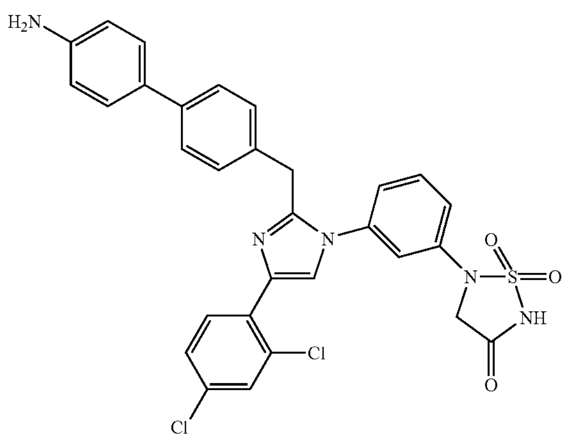 [SMILES: Nc1ccc(-c2ccc(Cc3nc(-c4ccc(Cl)cc4Cl)cn3-c3cccc(N4CC(=O)NS4(=O)=O)c3)cc2)cc1] | 5-{3-[2-(4'-Amino-biphenyl-4-ylmethyl)-4-(2,4-dichloro-phenyl)-imidazol-1-yl]-phenyl}-1,2,5-thiadiazolidine-3-one-1,1-dioxide |
| 136 | 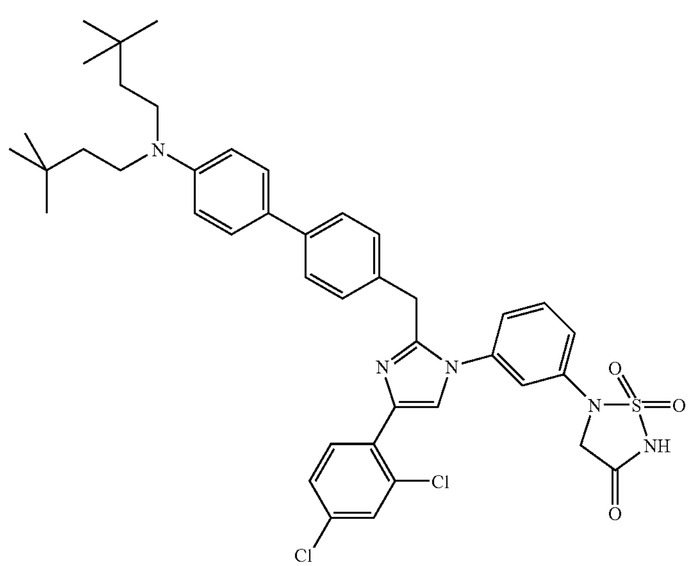 [SMILES: CC(C)(C)CCN(CCC(C)(C)C)c1ccc(-c2ccc(Cc3nc(-c4ccc(Cl)cc4Cl)cn3-c3cccc(N4CC(=O)NS4(=O)=O)c3)cc2)cc1] | 5-{3-[2-{4'-[Bis-(3,3-dimethyl-butyl)-amino]-biphenyl-4-ylmethyl}-4-(2,4-dichloro-phenyl)-imidazol-1-yl]-phenyl}-1,2,5-thiadiazolidine-3-one-1,1-dioxide |

//
TABLE 1-continued
| Ex. | Structure | Name |
|---|---|---|
| 137 | 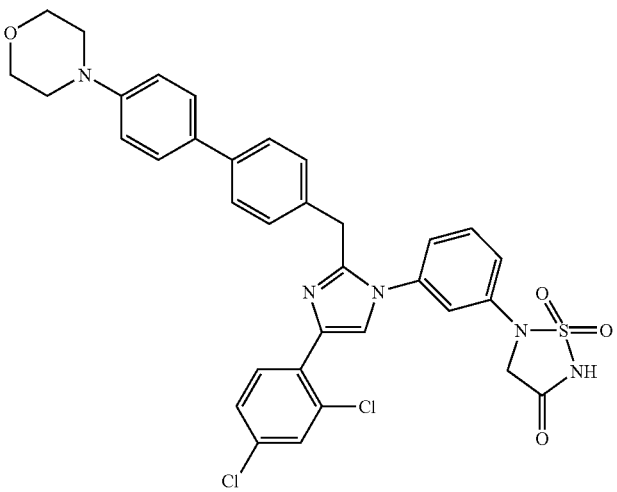 [SMILES: O=C1CN(c2cccc(-n3cc(-c4ccc(Cl)cc4Cl)nc3Cc3ccc(-c4ccc(N5CCOCC5)cc4)cc3)c2)S(=O)(=O)N1] | 5-{3-[4-(2,4-Dichloro-phenyl)-2-(4'-morpholin-4-yl-biphenyl-4-ylmethyl)-imidazol-1-yl]-phenyl}-1,2,5-thiadiazolidine-3-one-1,1-dioxide |
| 138 | 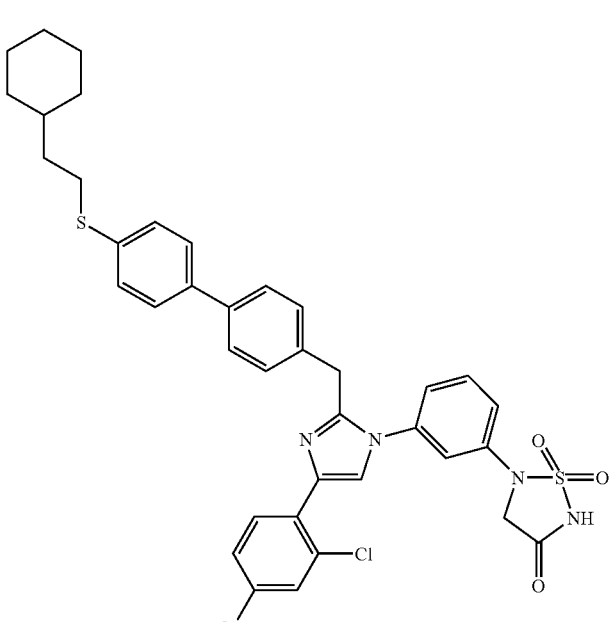 | 5-{3-[2-[4'-(2-Cyclohexyl-ethylsulfanyl)-biphenyl-4-ylmethyl]-4-(2,4-dichloro-phenyl)-imidazol-1-yl]-phenyl}-1,2,5-thiadiazolidine-3-one-1,1-dioxide |

| Ex. | Structure | Name |
|---|---|---|
| 139 | 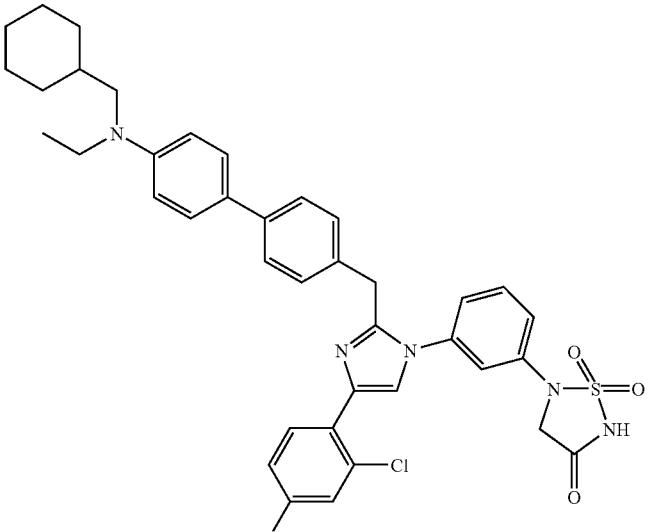 | 5-{3-[2-{4'-(Cyclohexylmethyl-ethyl)-amino)-biphenyl-4-ylmethyl]-4-(2,4-dichloro-phenyl)-imidazol-1-yl]-phenyl}-1,2,5-thiadiazolidine-3-one-1,1-dioxide |
| 140 | 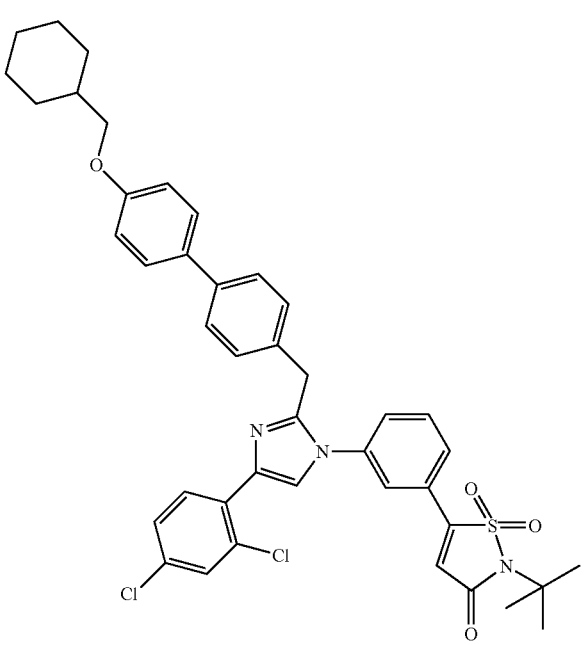 [SMILES: CC(C)(C)N1C(=O)C=C(c2cccc(-n3cc(-c4ccc(Cl)cc4Cl)nc3Cc3ccc(-c4ccc(OCC5CCCCC5)cc4)cc3)c2)S1(=O)=O] | 2-tert-Butyl-5-{3-[2-(4'-cyclohexylmethoxy-biphenyl-4-ylmethyl)-4-(2,4-dichloro-phenyl)-imidazol-1-yl]-phenyl}-isothiazol-3-one-1,1-dioxide |

TABLE 1-continued

| Ex. | Structure | Name |
|---|---|---|
| 141 | 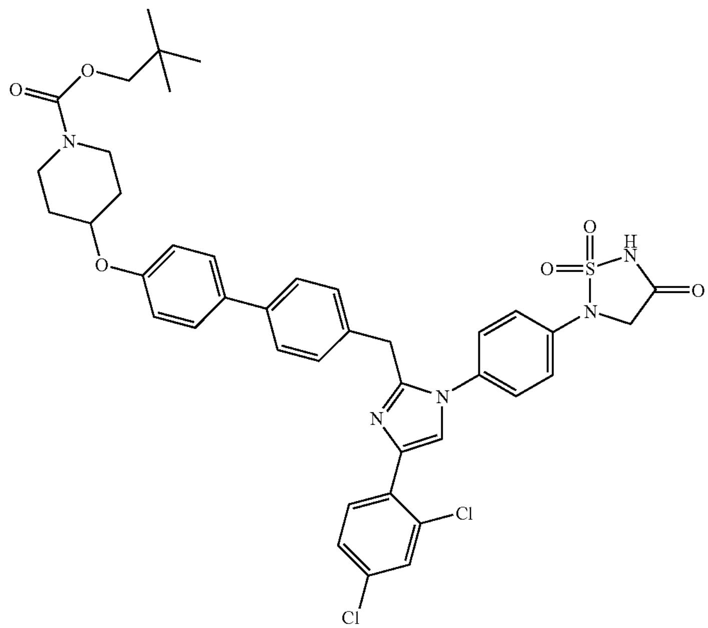 [SMILES: CC(C)(C)COC(=O)N1CCC(Oc2ccc(-c3ccc(Cc4nc(-c5ccc(Cl)cc5Cl)cn4-c4ccc(N5CC(=O)NS5(=O)=O)cc4)cc3)cc2)CC1] | 4-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yloxy)-piperidine-1-carboxylic acid 2,2-dimethyl-propyl ester |
| 142 | 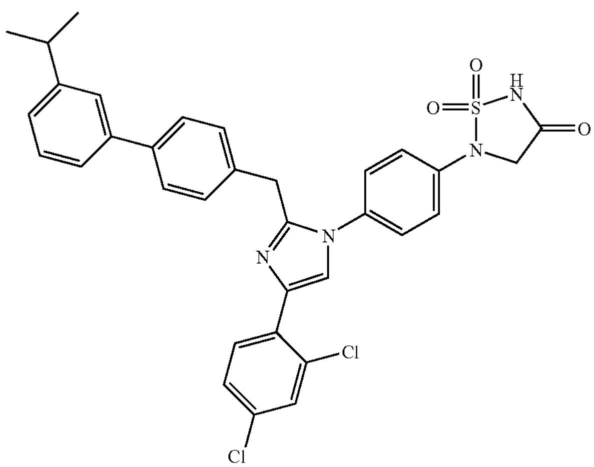 [SMILES: CC(C)c1cccc(-c2ccc(Cc3nc(-c4ccc(Cl)cc4Cl)cn3-c3ccc(N4CC(=O)NS4(=O)=O)cc3)cc2)c1] | 5-{4-[4-(2,4-Dichloro-phenyl)-2-(3'-isopropyl-biphenyl-4-ylmethyl)-imidazol-1-yl]-phenyl}-1,2,5-thiadiazolidine-3-one-1,1-dioxide |
| 143 | 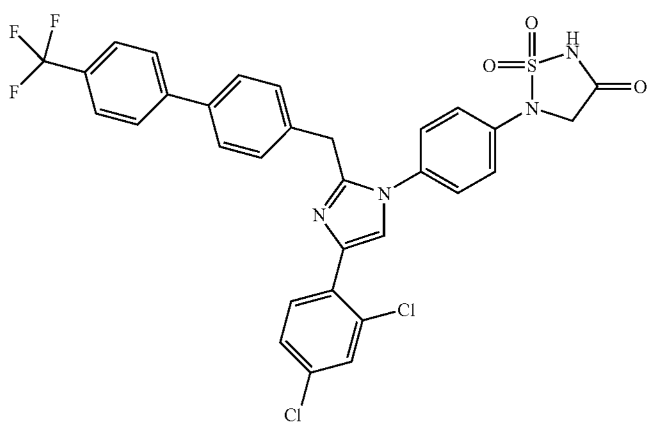 [SMILES: O=C1CN(c2ccc(-n3cc(-c4ccc(Cl)cc4Cl)nc3Cc3ccc(-c4ccc(C(F)(F)F)cc4)cc3)cc2)S(=O)(=O)N1] | 5-{4-[4-(2,4-Dichloro-phenyl)-2-(4'-trifluoromethyl-biphenyl-4-ylmethyl)-imidazol-1-yl]-phenyl}-1,2,5-thiadiazolidine-3-one-1,1-dioxide |

TABLE 1-continued

| Ex. | Structure | Name |
|---|---|---|
| 144 | 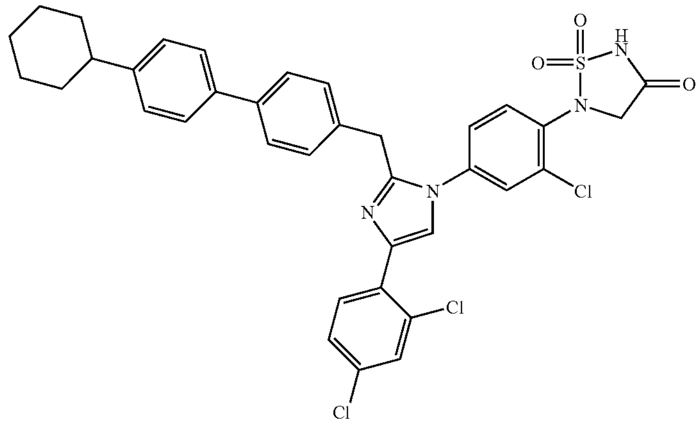 [SMILES: O=C1CN(c2ccc(-n3cc(-c4ccc(Cl)cc4Cl)nc3Cc3ccc(-c4ccc(C5CCCCC5)cc4)cc3)cc2Cl)S(=O)(=O)N1] | 5-{2-Chloro-4-[2-(4'-cyclohexyl-biphenyl-4-ylmethyl)-4-(2,4-dichloro-phenyl)-imidazol-1-yl]-phenyl}-1,2,5-thiadiazolidine-3-one-1,1-dioxide |
| 145 | 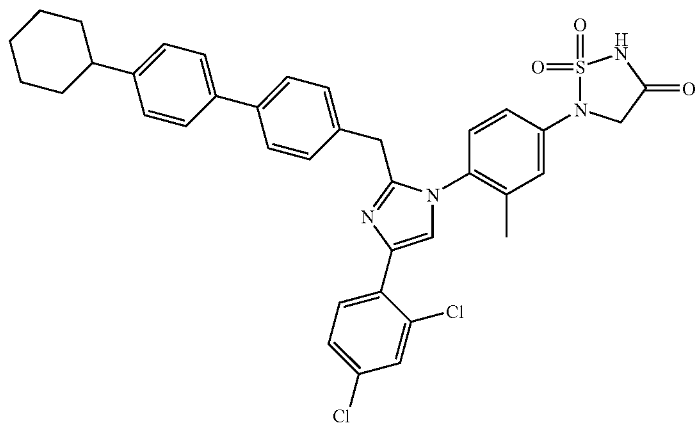 [SMILES: Cc1cc(N2CC(=O)NS2(=O)=O)ccc1-n1cc(-c2ccc(Cl)cc2Cl)nc1Cc1ccc(-c2ccc(C3CCCCC3)cc2)cc1] | 5-{4-[2-(4'-Cyclohexyl-biphenyl-4-ylmethyl)-4-(2,4-dichloro-phenyl)-imidazol-1-yl]-3-methyl-phenyl}-1,2,5-thiadiazolidine-3-one-1,1-dioxide |
| 146 | 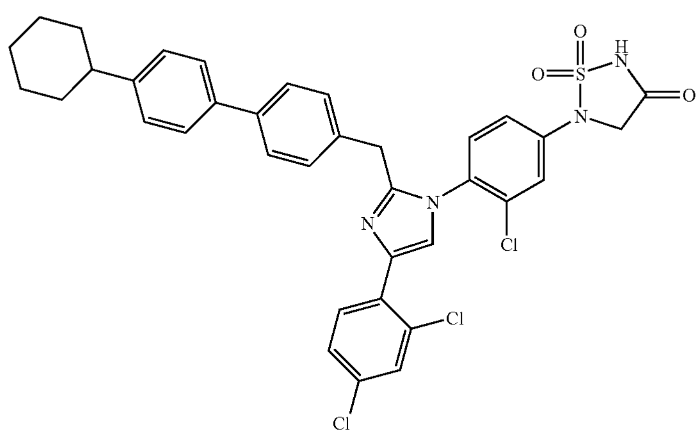 | 5-{3-Chloro-4-[2-(4'-cyclohexyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 147 | 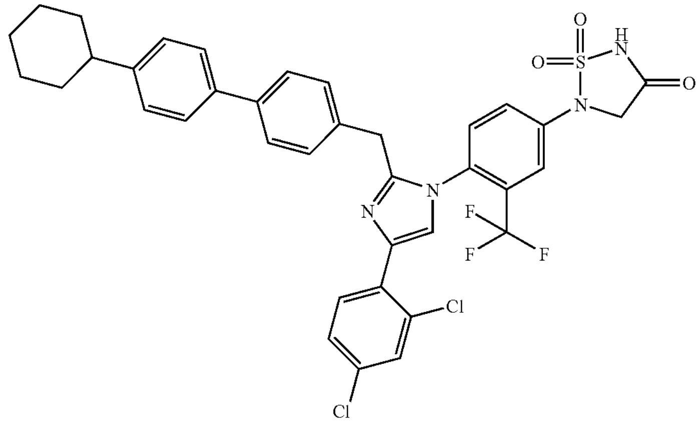 [SMILES: O=C1CN(c2ccc(-n3cc(-c4ccc(Cl)cc4Cl)nc3Cc3ccc(-c4ccc(C5CCCCC5)cc4)cc3)c(C(F)(F)F)c2)S(=O)(=O)N1] | 5-{4-[2-(4'-Cyclohexyl-biphenyl-4-ylmethyl)-4-(2,4-dichloro-phenyl)-imidazol-1-yl]-3-trifluoromethyl-phenyl}-1,2,5-thiadiazolidine-3-one-1,1-dioxide |
| 148 | 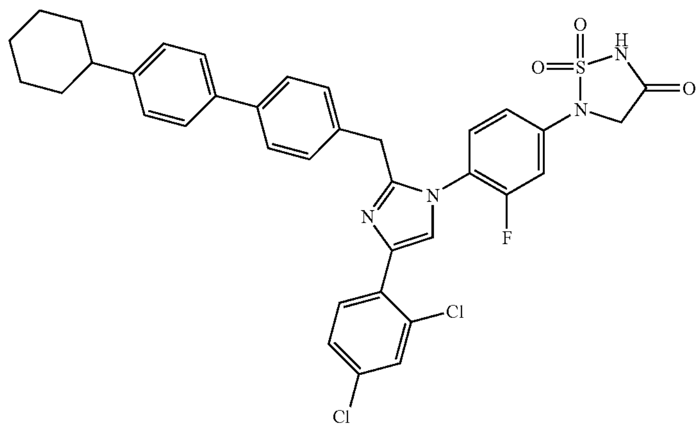 [SMILES: O=C1CN(c2ccc(-n3cc(-c4ccc(Cl)cc4Cl)nc3Cc3ccc(-c4ccc(C5CCCCC5)cc4)cc3)c(F)c2)S(=O)(=O)N1] | 5-{4-[2-(4'-Cyclohexyl-biphenyl-4-ylmethyl)-4-(2,4-dichloro-phenyl)-imidazol-1-yl]-3-fluoro-phenyl}-1,2,5-thiadiazolidine-3-one-1,1-dioxide |
| 149 | 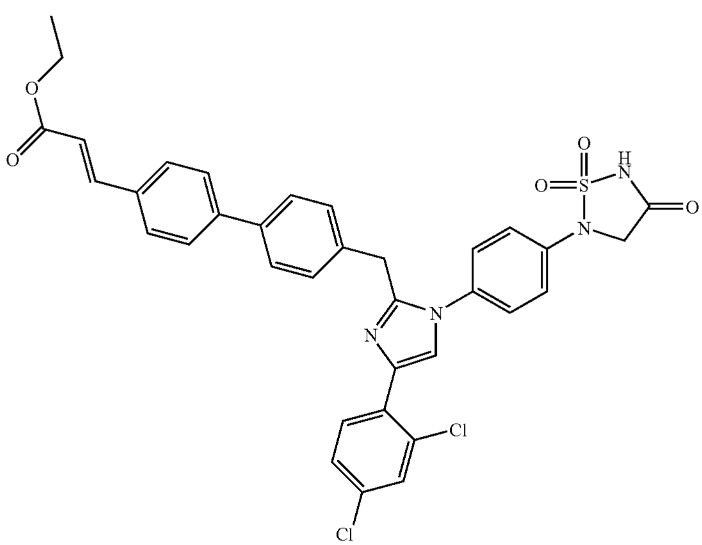 [SMILES: CCOC(=O)/C=C/c1ccc(-c2ccc(Cc3nc(-c4ccc(Cl)cc4Cl)cn3-c3ccc(N4CC(=O)NS4(=O)=O)cc3)cc2)cc1] | 3-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-acrylic acid ethyl ester |

TABLE 1-continued

| Ex. | Structure | Name |
|---|---|---|
| 150 | 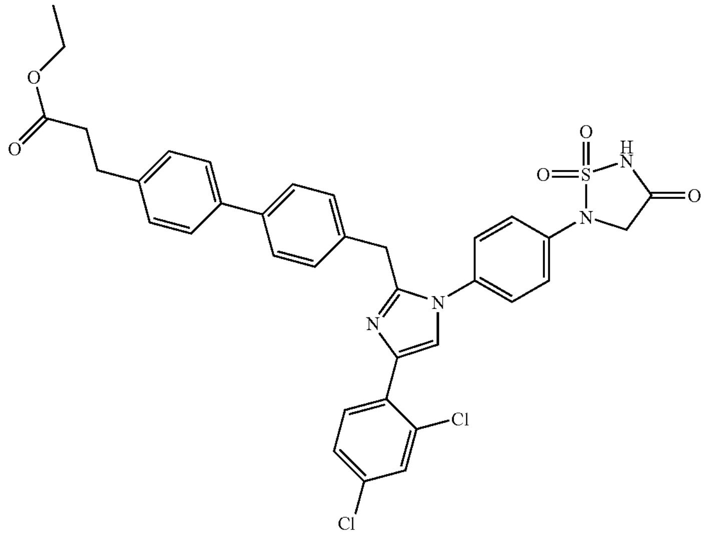 [SMILES: CCOC(=O)CCc1ccc(-c2ccc(Cc3nc(-c4ccc(Cl)cc4Cl)cn3-c3ccc(N4CC(=O)NS4(=O)=O)cc3)cc2)cc1] | 3-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-propionic acid ethyl ester |
| 151 | 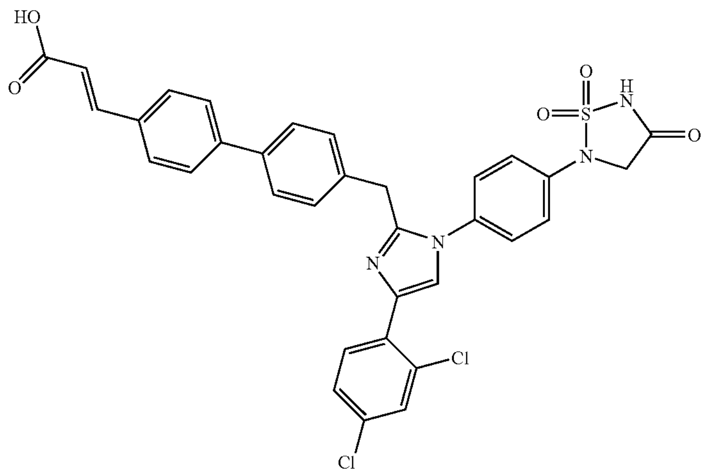 [SMILES: O=C(O)/C=C/c1ccc(-c2ccc(Cc3nc(-c4ccc(Cl)cc4Cl)cn3-c3ccc(N4CC(=O)NS4(=O)=O)cc3)cc2)cc1] | 3-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-acrylic acid |
| 152 | 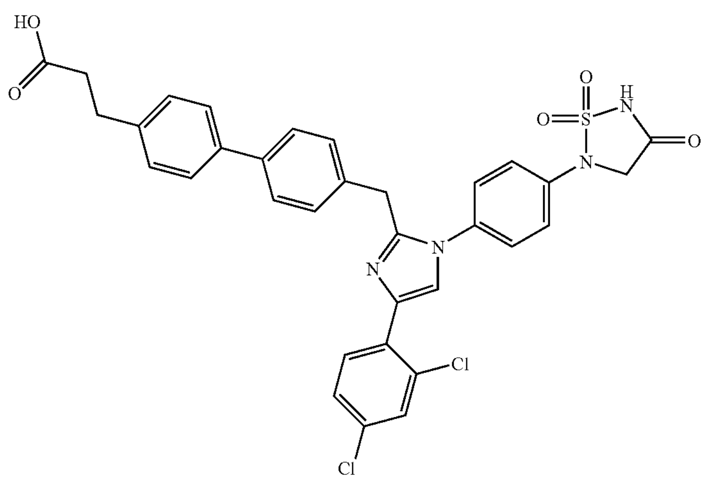 [SMILES: O=C(O)CCc1ccc(-c2ccc(Cc3nc(-c4ccc(Cl)cc4Cl)cn3-c3ccc(N4CC(=O)NS4(=O)=O)cc3)cc2)cc1] | 3-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-propionic acid |

TABLE 1-continued

| Ex. | Structure | Name |
|---|---|---|
| 153 | 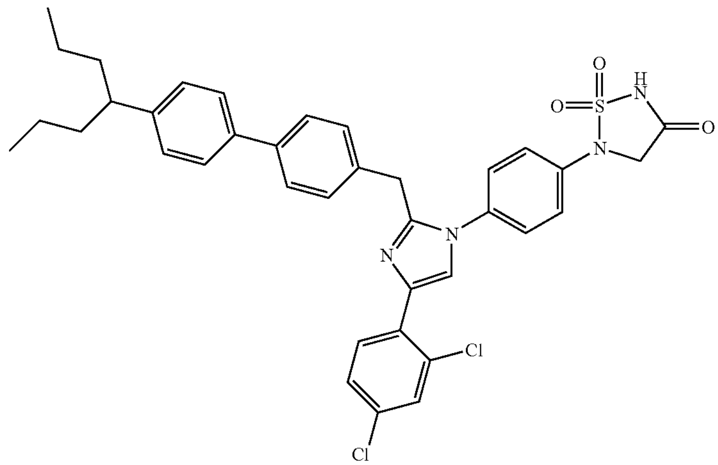 [SMILES: CCCC(CCC)c1ccc(-c2ccc(Cc3nc(-c4ccc(Cl)cc4Cl)cn3-c3ccc(N4CC(=O)NS4(=O)=O)cc3)cc2)cc1] | 5-(4-{4-(2,4-Dichloro-phenyl)-2-[4'-(1-propyl-butyl)-biphenyl-4-ylmethyl]-imidazol-1-yl}-phenyl)-1,2,5-thiadiazolidine-3-one-1,1-dioxide |
| 154 | 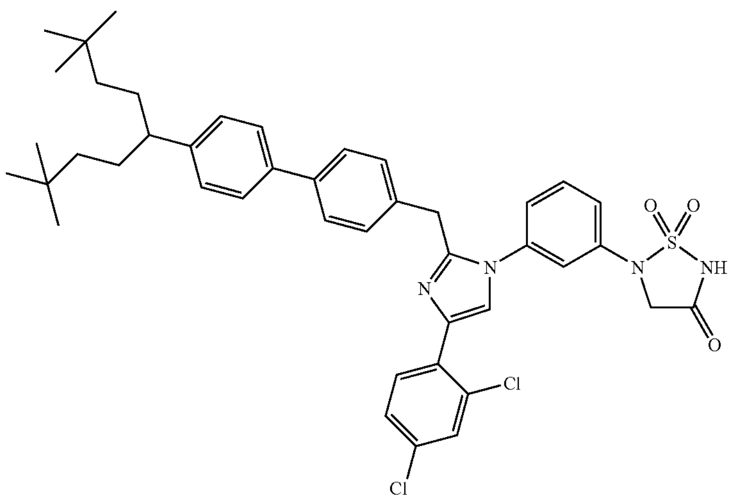 [SMILES: CC(C)(C)CCC(CCC(C)(C)C)c1ccc(-c2ccc(Cc3nc(-c4ccc(Cl)cc4Cl)cn3-c3cccc(N4CC(=O)NS4(=O)=O)c3)cc2)cc1] | 5-[3-(4-(2,4-Dichloro-phenyl)-2-{4'-[1-(3,3-dimethyl-butyl)-4,4-dimethyl-pentyl]-biphenyl-4-ylmethyl}-imidazol-1-yl)-phenyl]-1,2,5-thiadiazolidine-3-one-1,1-dioxide |
| 155 | 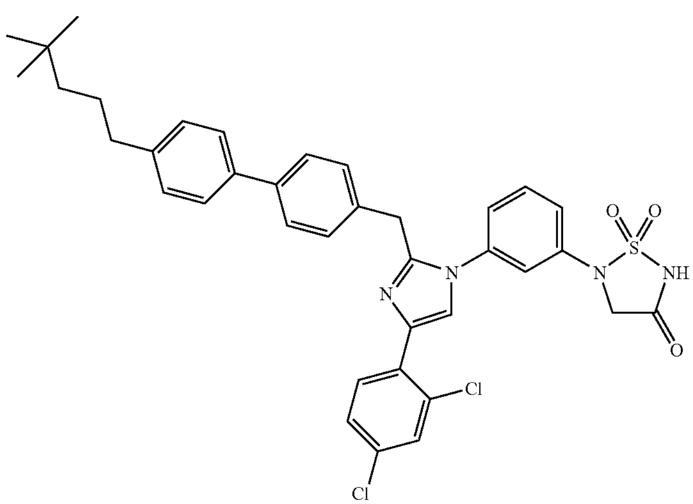 [SMILES: CC(C)(C)CCCc1ccc(-c2ccc(Cc3nc(-c4ccc(Cl)cc4Cl)cn3-c3cccc(N4CC(=O)NS4(=O)=O)c3)cc2)cc1] | 5-(3-{4-(2,4-Dichloro-phenyl)-2-[4'-(4,4-dimethyl-pentyl)-biphenyl-4-ylmethyl]-imidazol-1-yl}-phenyl)-1,2,5-thiadiazolidine-3-one-1,1-dioxide |

TABLE 1-continued

| Ex. | Structure | Name |
|---|---|---|
| 156 | 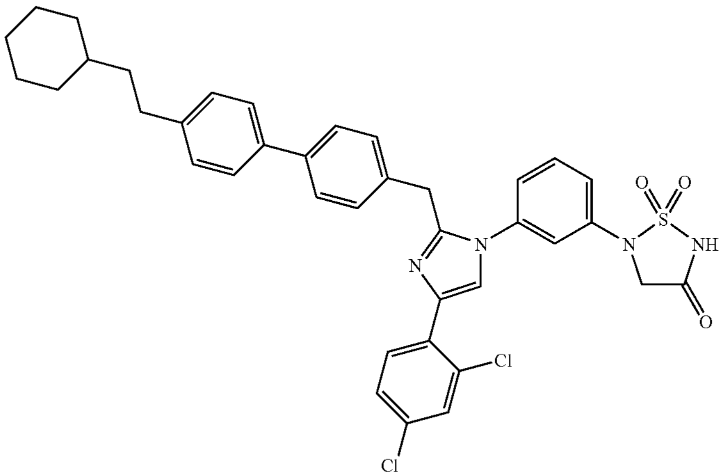 [SMILES: O=C1CN(c2cccc(-n3cc(-c4ccc(Cl)cc4Cl)nc3Cc3ccc(-c4ccc(CCC5CCCCC5)cc4)cc3)c2)S(=O)(=O)N1] | 5-{3-[2-[4'-(2-Cyclohexyl-ethyl)-biphenyl-4-ylmethyl]-4-(2,4-dichloro-phenyl)-imidazol-1-yl]-phenyl}-1,2,5-thiadiazolidine-3-one-1,1-dioxide |
| 157 | 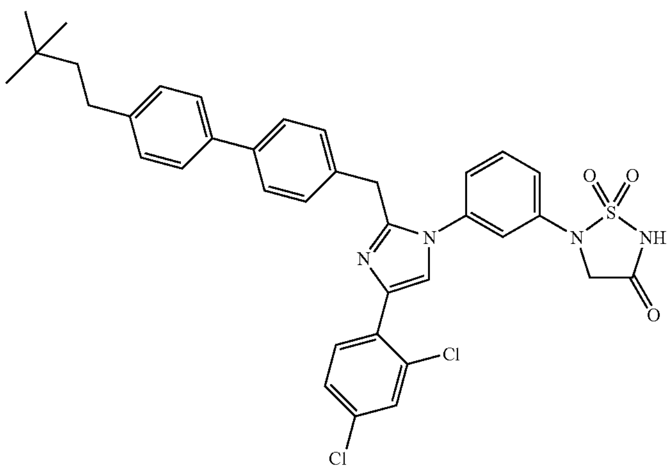 [SMILES: CC(C)(C)CCc1ccc(-c2ccc(Cc3nc(-c4ccc(Cl)cc4Cl)cn3-c3cccc(N4CC(=O)NS4(=O)=O)c3)cc2)cc1] | 5-(3-{4-(2,4-Dichloro-phenyl)-2-[4'-(3,3-dimethyl-butyl)-biphenyl-4-ylmethyl]-imidazol-1-yl}-phenyl)-1,2,5-thiadiazolidine-3-one-1,1-dioxide |
| 158 | 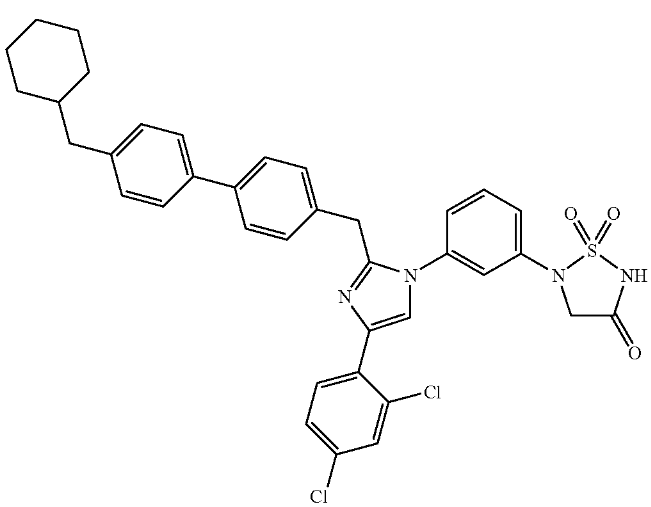 [SMILES: O=C1CN(c2cccc(-n3cc(-c4ccc(Cl)cc4Cl)nc3Cc3ccc(-c4ccc(CC5CCCCC5)cc4)cc3)c2)S(=O)(=O)N1] | 5-{3-[2-(4'-Cyclohexylmethyl-biphenyl-4-ylmethyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 159 | 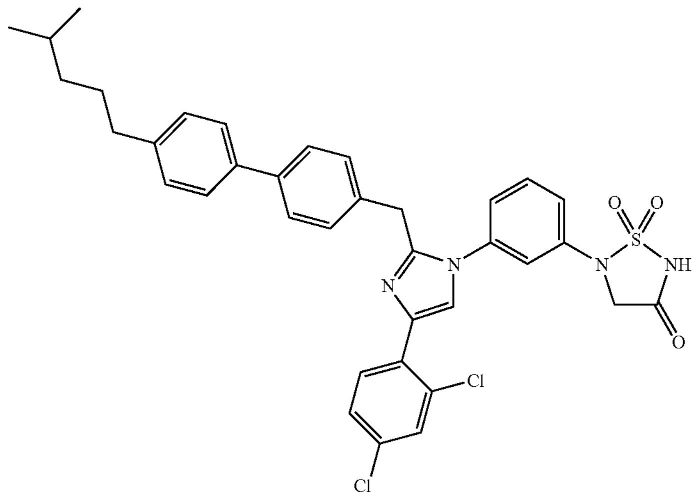 [SMILES: CC(C)CCCc1ccc(-c2ccc(Cc3nc(-c4ccc(Cl)cc4Cl)cn3-c3cccc(N4CC(=O)NS4(=O)=O)c3)cc2)cc1] | 5-(3-{4-(2,4-Dichloro-phenyl)-2-[4'-(4-methyl-pentyl)-biphenyl-4-ylmethyl]-imidazol-1-yl}-phenyl)-1,2,5-thiadiazolidine-3-one-1,1-dioxide |
| 160 | 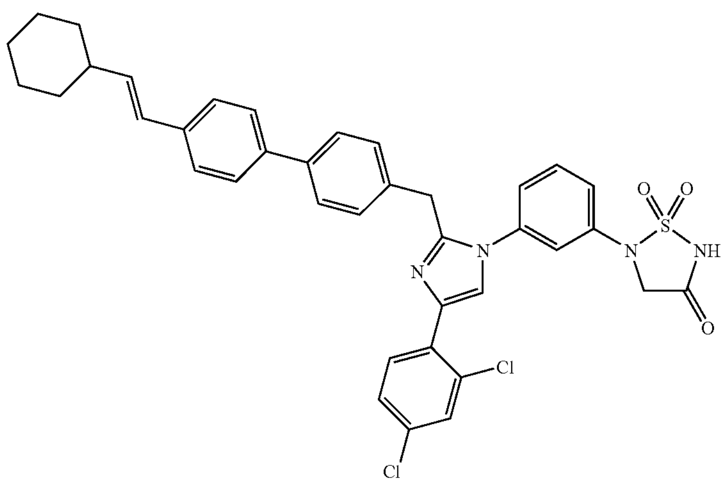 [SMILES: O=C1CN(c2cccc(-n3cc(-c4ccc(Cl)cc4Cl)nc3Cc3ccc(-c4ccc(/C=C/C5CCCCC5)cc4)cc3)c2)S(=O)(=O)N1] | 5-{3-[2-[4'-(2-Cyclohexyl-vinyl)-biphenyl-4-ylmethyl]-4-(2,4-dichloro-phenyl)-imidazol-1-yl]-phenyl}-1,2,5-thiadiazolidine-3-one-1,1-dioxide |
| 161 | 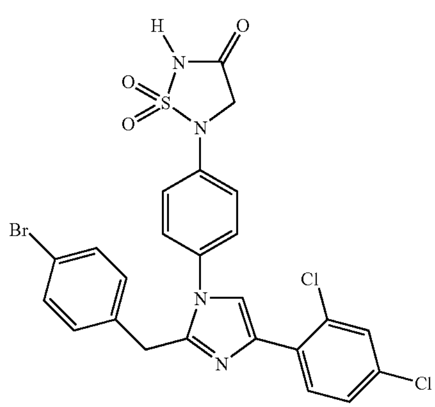 [SMILES: O=C1CN(c2ccc(-n3cc(-c4ccc(Cl)cc4Cl)nc3Cc3ccc(Br)cc3)cc2)S(=O)(=O)N1] | 5-{4-[2-(4-Bromo-benzyl)-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 162 | 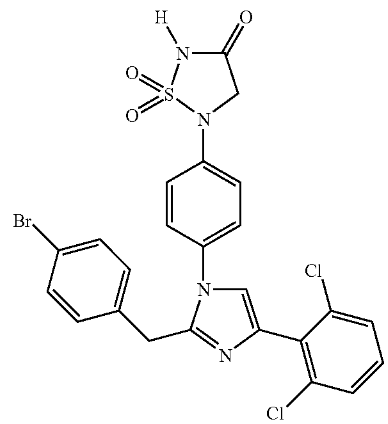 [SMILES: O=C1CN(c2ccc(-n3cc(-c4c(Cl)cccc4Cl)nc3Cc3ccc(Br)cc3)cc2)S(=O)(=O)N1] | 5-{4-[2-(4-Bromo-benzyl)-4-(2,6-dichloro-phenyl)-imidazol-1-yl]-phenyl}-1,2,5-thiadiazolidine-3-one-1,1-dioxide |
| 163 | 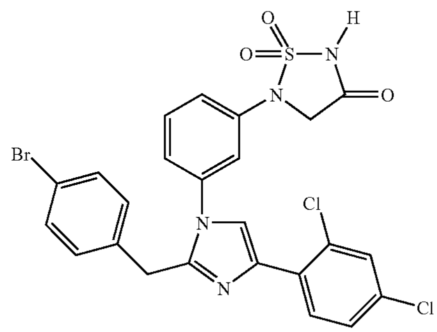 [SMILES: O=C1CN(c2cccc(-n3cc(-c4ccc(Cl)cc4Cl)nc3Cc3ccc(Br)cc3)c2)S(=O)(=O)N1] | 5-{3-[2-(4-Bromo-benzyl)-4-(2,4-dichloro-phenyl)-imidazol-1-yl]-phenyl}-1,2,5-thiadiazolidine-3-one-1,1-dioxide |
| 164 | 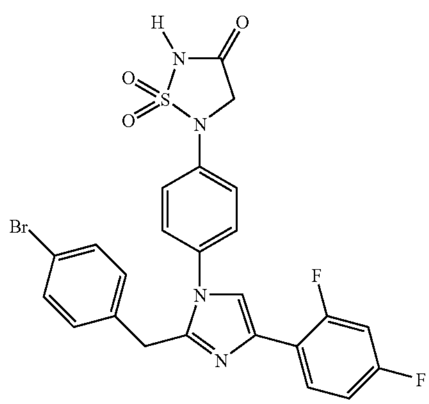 [SMILES: O=C1CN(c2ccc(-n3cc(-c4ccc(F)cc4F)nc3Cc3ccc(Br)cc3)cc2)S(=O)(=O)N1] | 5-{4-[2-(4-Bromo-benzyl)-4-(2,4-difluoro-phenyl)-imidazol-1-yl]-phenyl}-1,2,5-thiadiazolidine-3-one-1,1-dioxide |
| 165 | 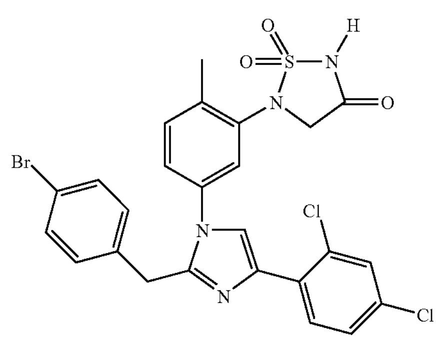 | 5-{5-[2-(4-Bromo-benzyl)-4-(2,4-dichloro-phenyl)-imidazol-1-yl]-2-methyl-phenyl}-1,2,5-thiadiazolidine-3-one-1,1-dioxide |

TABLE 1-continued

| Ex. | Structure | Name |
|---|---|---|
| 166 | 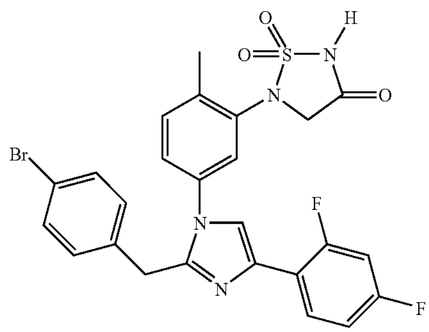 [SMILES: Cc1ccc(-n2cc(-c3ccc(F)cc3F)nc2Cc2ccc(Br)cc2)cc1N1CC(=O)NS1(=O)=O] | 5-{5-[2-(4-Bromo-benzyl)-4-(2,4-difluoro-phenyl)-imidazol-1-yl]-2-methyl-phenyl}-1,2,5-thiadiazolidine-3-one-1,1-dioxide |
| 167 | 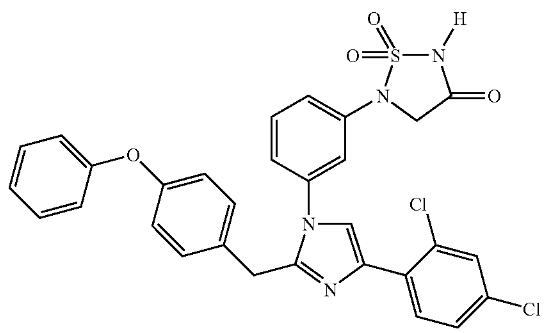 [SMILES: O=C1CN(c2cccc(-n3cc(-c4ccc(Cl)cc4Cl)nc3Cc3ccc(Oc4ccccc4)cc3)c2)S(=O)(=O)N1] | 5-{3-[4-(2,4-Dichloro-phenyl)-2-(4'-phenoxy-biphenyl-4-ylmethyl)-imidazol-1-yl]-phenyl}-1,2,5-thiadiazolidine-3-one-1,1-dioxide |
| 168 | 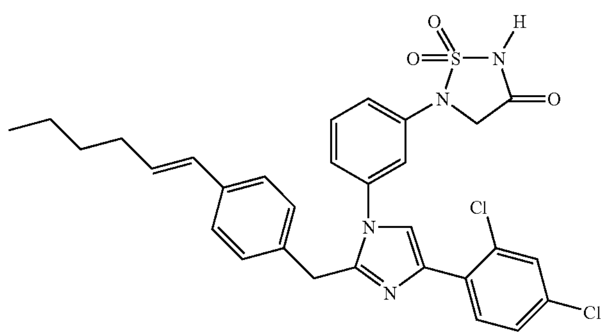 | 5-{3-[4-(2,4-Dichloro-phenyl)-2-(4-hex-1-enyl-benzyl)-imidazol-1-yl]-phenyl}-1,2,5-thiadiazolidine-3-one-1,1-dioxide |
| 169 | 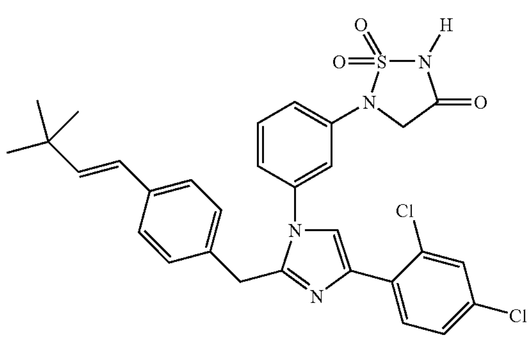 [SMILES: CC(C)(C)/C=C/c1ccc(Cc2nc(-c3ccc(Cl)cc3Cl)cn2-c2cccc(N3CC(=O)NS3(=O)=O)c2)cc1] | 5-(3-{4-(2,4-Dichloro-phenyl)-2-[4-(3,3-dimethyl-but-1-enyl)-benzyl]-imidazol-1-yl}-phenyl)-1,2,5-thiadiazolidine-3-one-1,1-dioxide |

TABLE 1-continued

| Ex. | Structure | Name |
|---|---|---|
| 170 | 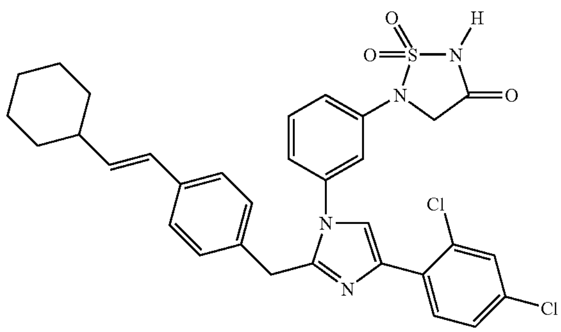 [SMILES: O=C1CN(c2cccc(-n3cc(-c4ccc(Cl)cc4Cl)nc3Cc3ccc(/C=C/C4CCCCC4)cc3)c2)S(=O)(=O)N1] | 5-{3-[2-[4-(2-Cyclohexyl-vinyl)-benzyl]-4-(2,4-dichloro-phenyl)-imidazol-1-yl]-phenyl}-1,2,5-thiadiazolidine-3-one-1,1-dioxide |
| 171 | 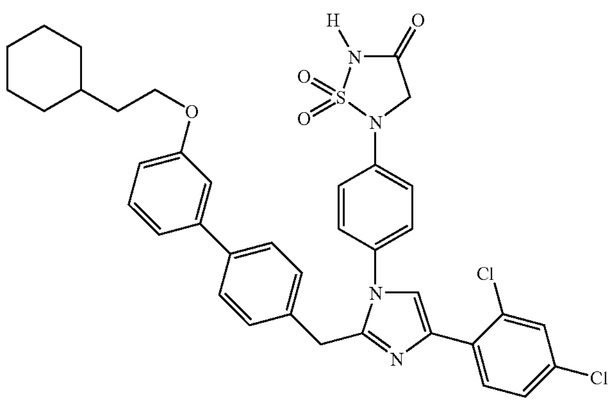 [SMILES: O=C1CN(c2ccc(-n3cc(-c4ccc(Cl)cc4Cl)nc3Cc3ccc(-c4cccc(OCCC5CCCCC5)c4)cc3)cc2)S(=O)(=O)N1] | 5-{4-[2-[3'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide |
| 172 | 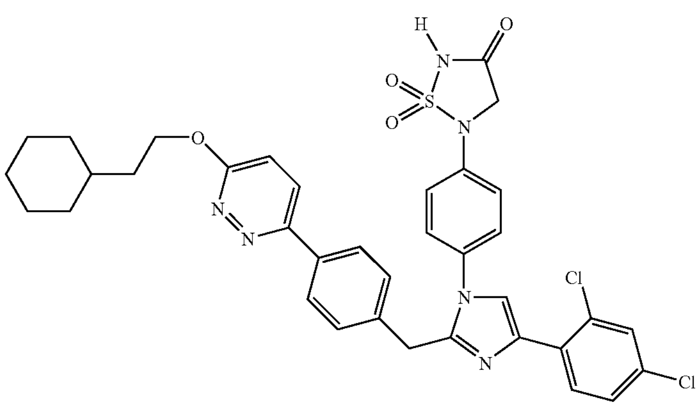 [SMILES: O=C1CN(c2ccc(-n3cc(-c4ccc(Cl)cc4Cl)nc3Cc3ccc(-c4ccc(OCCC5CCCCC5)nn4)cc3)cc2)S(=O)(=O)N1] | 5-{4-[2-{4-[6-(2-Cyclohexyl-ethoxy)-pyridazin-3-yl]-benzyl}-4-(2,4-dichloro-phenyl)-imidazol-1-yl]-phenyl}-1,2,5-thiadiazolidine-3-one-1,1-dioxide |
| 173 | 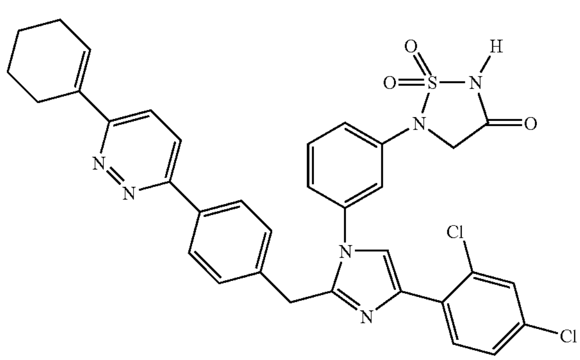 [SMILES: O=C1CN(c2cccc(-n3cc(-c4ccc(Cl)cc4Cl)nc3Cc3ccc(-c4ccc(C5=CCCCC5)nn4)cc3)c2)S(=O)(=O)N1] | 5-{3-[2-[4-(6-Cyclohex-1-enyl-pyridazin-3-yl)-benzyl]-4-(2,4-dichloro-phenyl)-imidazol-1-yl]-phenyl}-1,2,5-thiadiazolidine-3-one-1,1-dioxide |

TABLE 1-continued

| Ex. | Structure | Name |
|---|---|---|
| 174 | 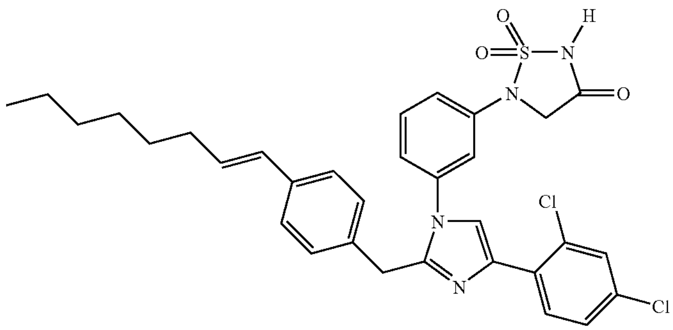 [SMILES: CCCCCC/C=C/c1ccc(Cc2nc(-c3ccc(Cl)cc3Cl)cn2-c2cccc(N3CC(=O)NS3(=O)=O)c2)cc1] | 5-{3-[4-(2,4-Dichloro-phenyl)-2-(4-oct-1-enyl-benzyl)-imidazol-1-yl]-phenyl}-1,2,5-thiadiazolidine-3-one-1,1-dioxide |
| 175 | 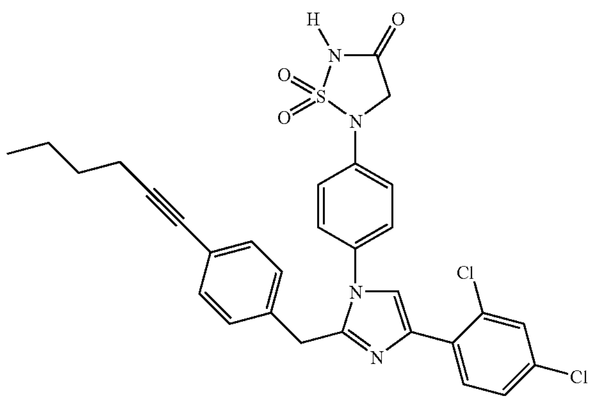 [SMILES: CCCCC#Cc1ccc(Cc2nc(-c3ccc(Cl)cc3Cl)cn2-c2ccc(N3CC(=O)NS3(=O)=O)cc2)cc1] | 5-{4-[4-(2,4-Dichloro-phenyl)-2-(4-hex-1-ynyl-benzyl)-imidazol-1-yl]-phenyl}-1,2,5-thiadiazolidine-3-one-1,1-dioxide |
| 176 | 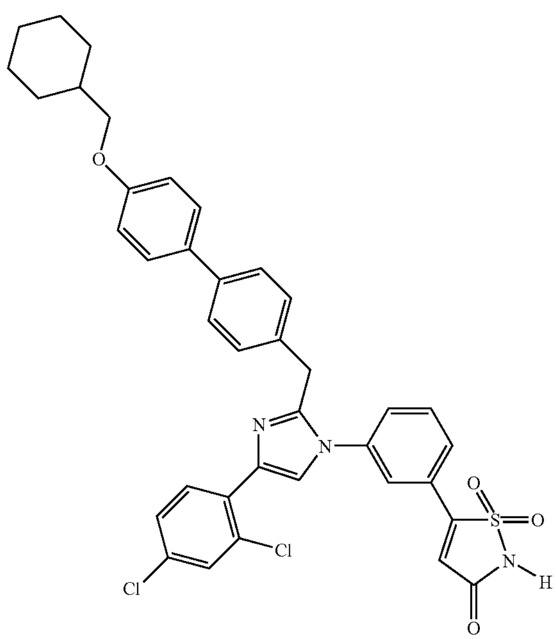 [SMILES: O=C1C=C(c2cccc(-n3cc(-c4ccc(Cl)cc4Cl)nc3Cc3ccc(-c4ccc(OCC5CCCCC5)cc4)cc3)c2)S(=O)(=O)N1] | 5-{3-[2-(4'-Cyclohexylmethoxy-biphenyl-4-ylmethyl)-4-(2,4-dichloro-phenyl)-imidazol-1-yl]-phenyl}-isothiazol-3-one-1,1-dioxide |

TABLE 1-continued

| Ex. | Structure | Name |
|---|---|---|
| 177 | 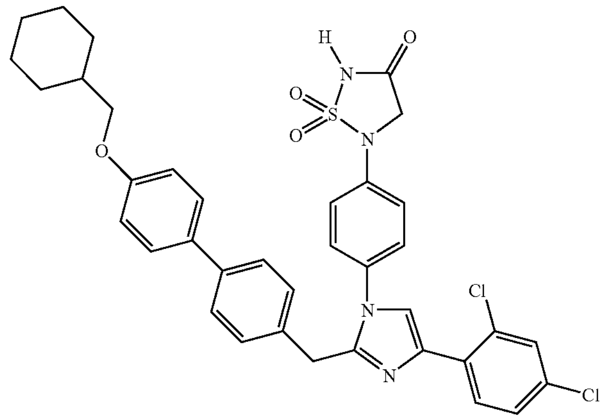 [SMILES: O=C1CN(c2ccc(-n3cc(-c4ccc(Cl)cc4Cl)nc3Cc3ccc(-c4ccc(OCC5CCCCC5)cc4)cc3)cc2)S(=O)(=O)N1] | 5-{4-[2-(4'-Cyclohexylmethoxy-biphenyl-4-ylmethyl)-4-(2,4-dichloro-phenyl)-imidazol-1-yl]-phenyl}1,2,5]-thiadiazolidin-3-one-1,1-dioxide |
| 178 | 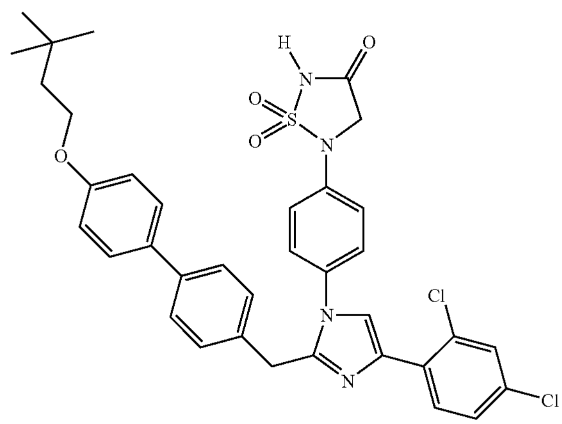 [SMILES: CC(C)(C)CCOc1ccc(-c2ccc(Cc3nc(-c4ccc(Cl)cc4Cl)cn3-c3ccc(N4CC(=O)NS4(=O)=O)cc3)cc2)cc1] | 5-(4-{4-(2,4-Dichloro-phenyl)-2-[4'-(3,3-dimethyl-butoxy)-biphenyl-4-yl methyl]-imidazol-1-yl}-phenyl)-1,2,5]-thiadiazolidin-3-one-1,1-dioxide |
| 179 | 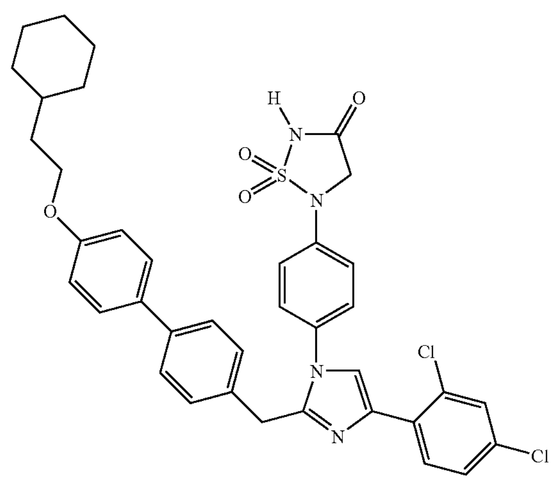 [SMILES: O=C1CN(c2ccc(-n3cc(-c4ccc(Cl)cc4Cl)nc3Cc3ccc(-c4ccc(OCCC5CCCCC5)cc4)cc3)cc2)S(=O)(=O)N1] | 5-{4-[2-[4'-(2-Cyclohexyl-ethoxy)-biphenyl-4-ylmethyl]-4-(2,4-dichloro-phenyl)-imidazol-1-yl]-phenyl}-1,2,5]-thiadiazolidin-3-one-1,1-dioxide |

TABLE 1-continued

| Ex. | Structure | Name |
|---|---|---|
| 180 | 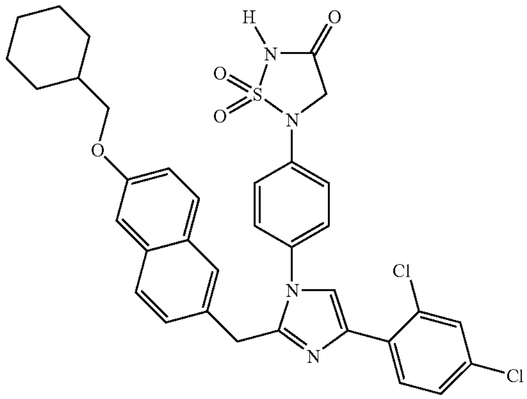 [SMILES: O=C1CN(c2ccc(-n3cc(-c4ccc(Cl)cc4Cl)nc3Cc3ccc4cc(OCC5CCCCC5)ccc4c3)cc2)S(=O)(=O)N1] | 5-{4-[2-(6 Cyclohexylmethoxy-naphthalen-2-ylmethyl)-4-(2,4-dichloro-phenyl)-imidazol-1-yl]-phenyl}1,2,5]-thiadiazolidin-3-one-1,1-dioxide |
| 181 | 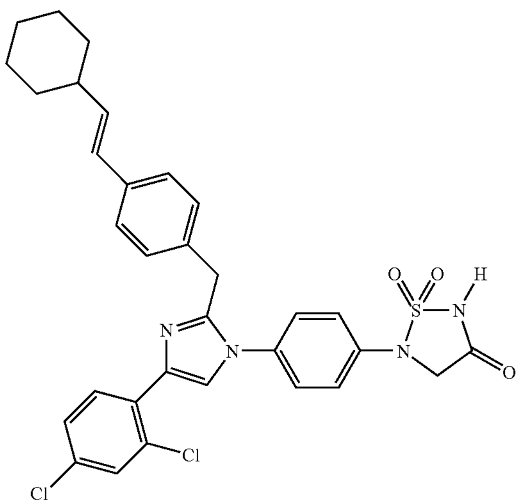 [SMILES: O=C1CN(c2ccc(-n3cc(-c4ccc(Cl)cc4Cl)nc3Cc3ccc(/C=C/C4CCCCC4)cc3)cc2)S(=O)(=O)N1] | 5-{4-[2-[4-(2-Cyclohexyl-vinyl)-benzyl]-4-(2,4-dichloro-phenyl)-imidazol-1-yl]-phenyl} 1,2,5]thiadiazolidin-3-one-1,1-dioxide |
| 182 | 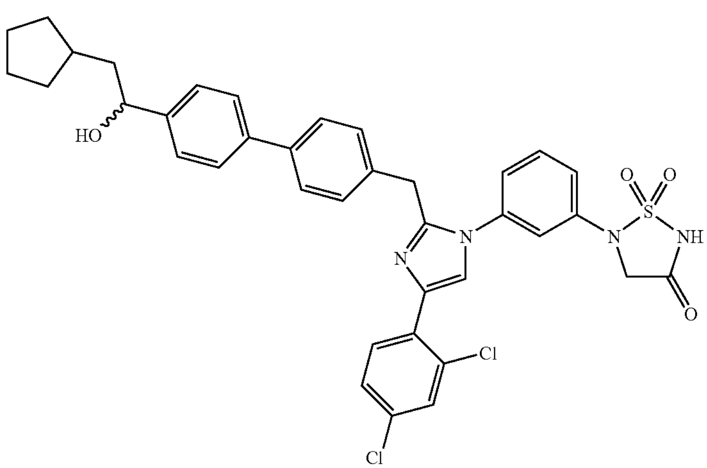 [SMILES: O=C1CN(c2cccc(-n3cc(-c4ccc(Cl)cc4Cl)nc3Cc3ccc(-c4ccc(C(O)CC5CCCC5)cc4)cc3)c2)S(=O)(=O)N1] | 5-{3-[2-[4'-(2-Cyclopentyl-1-hydroxy-ethyl)-biphenyl-4-ylmethyl]-4-(2,4-dichloro-phenyl)-imidazol-1-yl]-phenyl}-1,2,5-thiadiazolidin-3-one-1,1-dioxide |

TABLE 1-continued

| Ex. | Structure | Name |
|---|---|---|
| 183 | 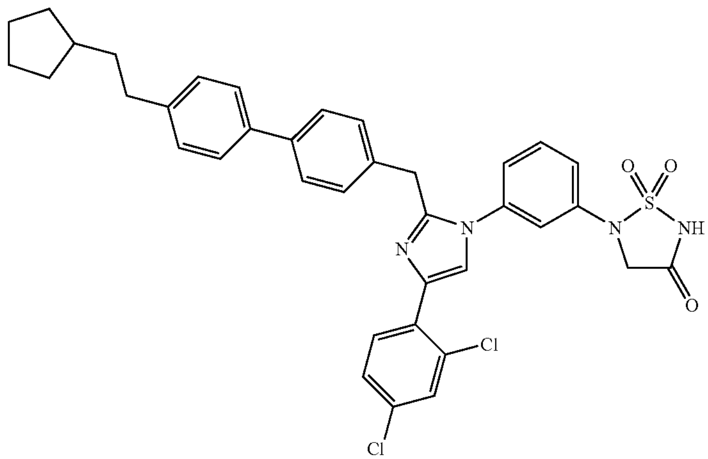 [SMILES: O=C1CN(c2cccc(-n3cc(-c4ccc(Cl)cc4Cl)nc3Cc3ccc(-c4ccc(CCC5CCCC5)cc4)cc3)c2)S(=O)(=O)N1] | 5-{3-[2-[4'-(2-Cyclopentyl-ethyl)-biphenyl-4-ylmethyl]-4-(2,4-dichloro-phenyl)-imidazol-1-yl]-phenyl}-1,2,5-thiadiazolidin-3-one-1,1-dioxide |
| 184 | 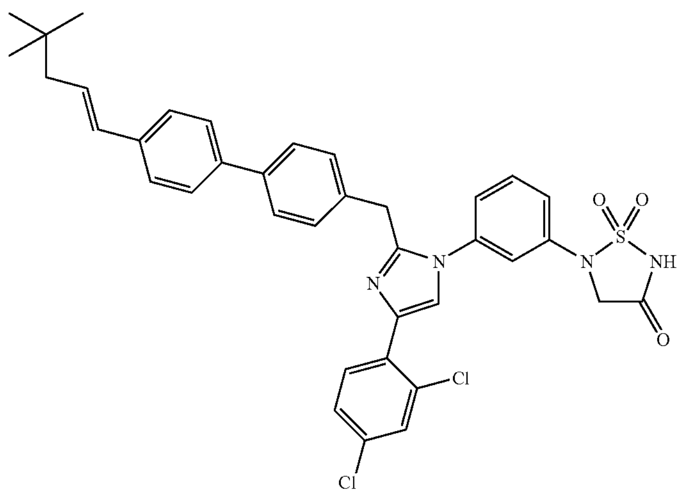 [SMILES: CC(C)(C)C/C=C/c1ccc(-c2ccc(Cc3nc(-c4ccc(Cl)cc4Cl)cn3-c3cccc(N4CC(=O)NS4(=O)=O)c3)cc2)cc1] | 5-(3-{4-(2,4-Dichloro-phenyl)-2-[4'-(4,4-dimethyl-pent-1-enyl)-biphenyl-4-ylmethyl]-imidazol-1-yl}-phenyl)-1,2,5-thiadiazolidin-3-one-1,1-dioxide |
| 185 | 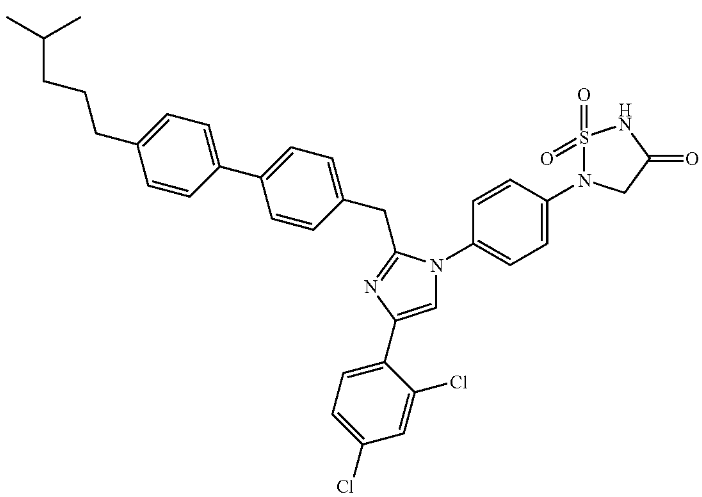 [SMILES: CC(C)CCCc1ccc(-c2ccc(Cc3nc(-c4ccc(Cl)cc4Cl)cn3-c3ccc(N4CC(=O)NS4(=O)=O)cc3)cc2)cc1] | 5-(4-{4-(2,4-Dichloro-phenyl)-2-[4'-(4-methyl-pentyl)-biphenyl-4-ylmethyl]-imidazol-1-yl}-phenyl)-1,2,5-thiadiazolidin-3-one-1,1-dioxide |

TABLE 1-continued

| Ex. | Structure | Name |
|---|---|---|
| 186 | 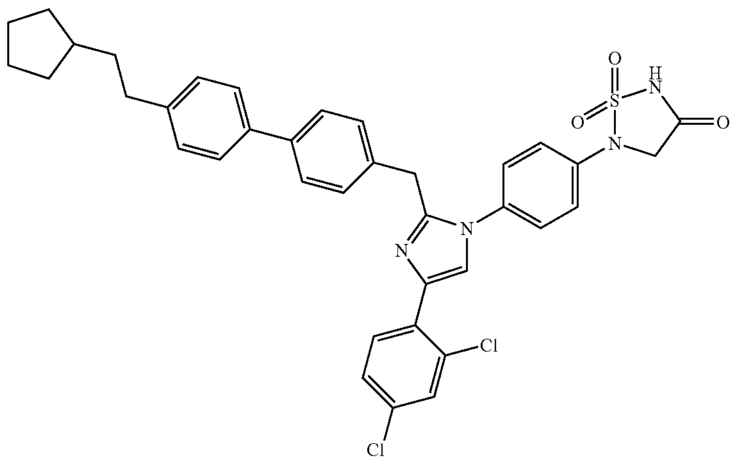 [SMILES: O=C1CN(c2ccc(-n3cc(-c4ccc(Cl)cc4Cl)nc3Cc3ccc(-c4ccc(CCC5CCCC5)cc4)cc3)cc2)S(=O)(=O)N1] | 5-{4-[2-[4'-(2-Cyclopentyl-ethyl)-biphenyl-4-ylmethyl]-4-(2,4-dichloro-phenyl)-imidazol-1-yl]-phenyl}-1,2,5-thiadiazolidin-3-one-1,1-dioxide |
| 187 | 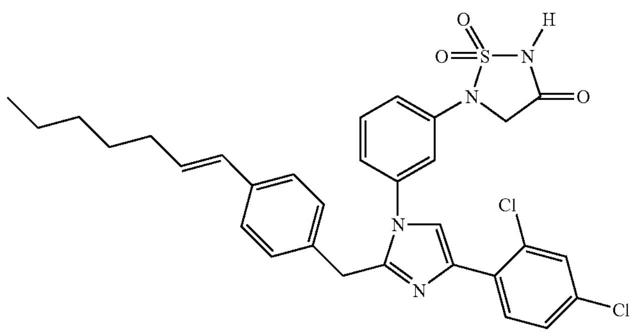 [SMILES: CCCCC/C=C/c1ccc(Cc2nc(-c3ccc(Cl)cc3Cl)cn2-c2cccc(N3CC(=O)NS3(=O)=O)c2)cc1] | 5-{3-[4-(2,4-Dichloro-phenyl)-2-(4-hept-1-enyl-benzyl)-imidazol-1-yl]-phenyl}-1,2,5-thiadiazolidine-3-one-1,1-dioxide |
| 188 | 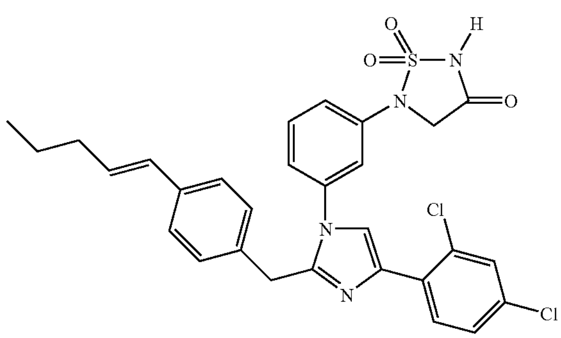 [SMILES: CCC/C=C/c1ccc(Cc2nc(-c3ccc(Cl)cc3Cl)cn2-c2cccc(N3CC(=O)NS3(=O)=O)c2)cc1] | 5-{3-[4-(2,4-Dichloro-phenyl)-2-(4-pent-1-enyl-benzyl)-imidazol-1-yl]-phenyl}-1,2,5-thiadiazolidine-3-one-1,1-dioxide |
| 189 | 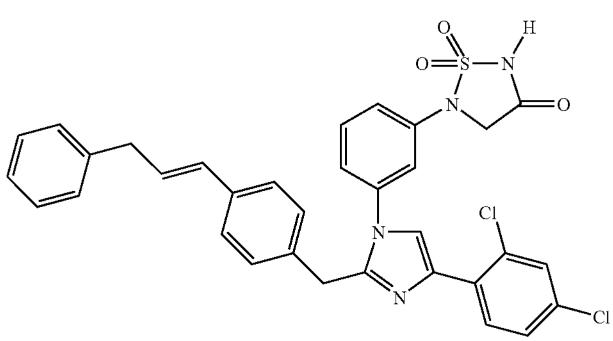 [SMILES: O=C1CN(c2cccc(-n3cc(-c4ccc(Cl)cc4Cl)nc3Cc3ccc(/C=C/Cc4ccccc4)cc3)c2)S(=O)(=O)N1] | 5-(3-{4-(2,4-Dichloro-phenyl)-2-[4-(3-phenyl-propenyl)-benzyl]-imidazol-1-yl}-phenyl)-1,2,5-thiadiazolidine-3-one-1,1-dioxide |

TABLE 1-continued

| Ex. | Structure | Name |
|---|---|---|
| 190 | 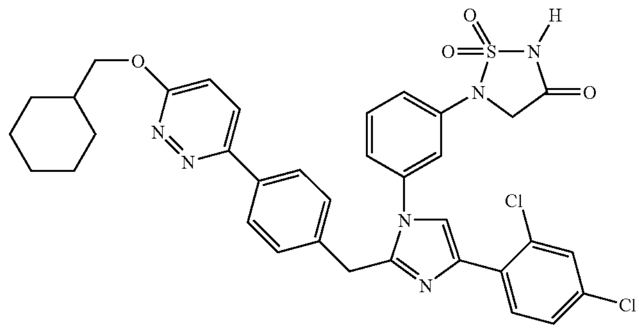 [SMILES: O=C1CN(c2cccc(-n3cc(-c4ccc(Cl)cc4Cl)nc3Cc3ccc(-c4ccc(OCC5CCCCC5)nn4)cc3)c2)S(=O)(=O)N1] | 5-{3-[2-[4-(6-Cyclohexylmethoxy-pyridazin-3-yl)-benzyl]-4-(2,4-dichloro-phenyl)-imidazol-1-yl]-phenyl}-1,2,5-thiadiazolidine-3-one-1,1-dioxide |
| 191 | 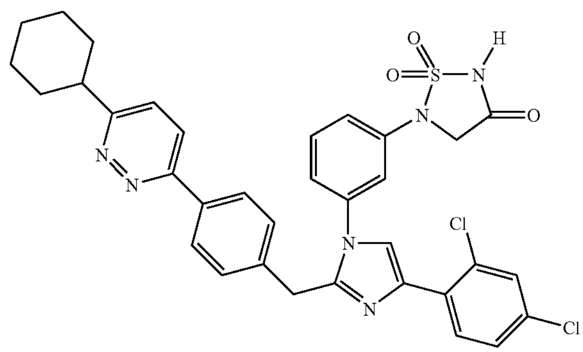 [SMILES: O=C1CN(c2cccc(-n3cc(-c4ccc(Cl)cc4Cl)nc3Cc3ccc(-c4ccc(C5CCCCC5)nn4)cc3)c2)S(=O)(=O)N1] | 5-{3-[2-[4-(6-Cyclohexyl-pyridazin-3-yl)-benzyl]-4-(2,4-dichloro-phenyl)-imidazol-1-yl]-phenyl}-1,2,5-thiadiazolidine-3-one-1,1-dioxide |
| 192 | 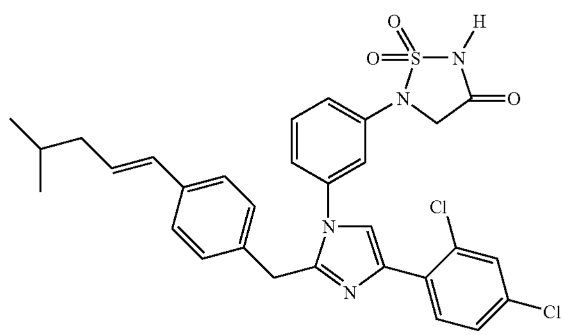 [SMILES: CC(C)C/C=C/c1ccc(Cc2nc(-c3ccc(Cl)cc3Cl)cn2-c2cccc(N3CC(=O)NS3(=O)=O)c2)cc1] | 5-(3-{4-(2,4-Dichloro-phenyl)-2-[4-(4-methyl-pent-1-enyl)-benzyl]-imidazol-1-yl}-phenyl)-1,2,5-thiadiazolidine-3-one-1,1-dioxide |
| 193 | 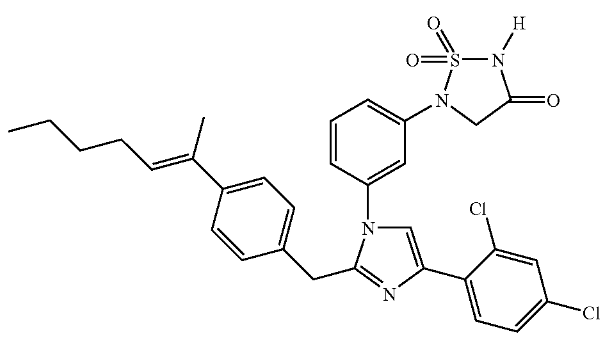 [SMILES: CCCC/C=C(\C)c1ccc(Cc2nc(-c3ccc(Cl)cc3Cl)cn2-c2cccc(N3CC(=O)NS3(=O)=O)c2)cc1] | 5-(3-{4-(2,4-Dichloro-phenyl)-2-[4-(1-methyl-hex-1-enyl)-benzyl]-imidazol-1-yl}-phenyl)-1,2,5-thiadiazolidine-3-one-1,1-dioxide |

TABLE 1-continued

| Ex. | Structure | Name |
|---|---|---|
| 194 | 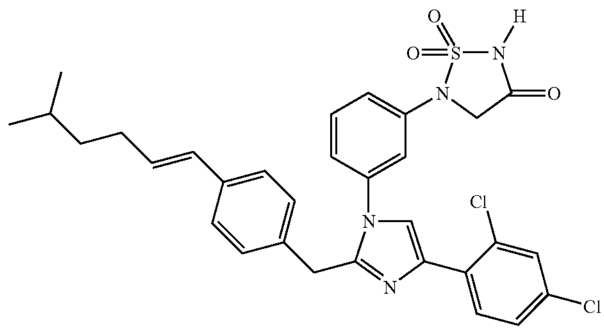 [SMILES: CC(C)CC/C=C/c1ccc(Cc2nc(-c3ccc(Cl)cc3Cl)cn2-c2cccc(N3CC(=O)NS3(=O)=O)c2)cc1] | 5-(3-{4-(2,4-Dichloro-phenyl)-2-[4-(5-methyl-hex-1-enyl)-benzyl]-imidazol-1-yl}-phenyl)-1,2,5-thiadiazolidine-3-one-1,1-dioxide |
| 195 | 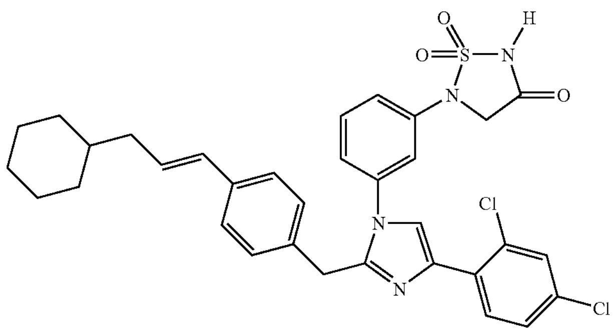 [SMILES: O=C1CN(c2cccc(-n3cc(-c4ccc(Cl)cc4Cl)nc3Cc3ccc(/C=C/CC4CCCCC4)cc3)c2)S(=O)(=O)N1] | 5-{3-[2-[4-(3-Cyclohexyl-propenyl)-benzyl]-4-(2,4-dichloro-phenyl)-imidazol-1-yl]-phenyl}-1,2,5-thiadiazolidine-3-one-1,1-dioxide |

Incomplete valences for heteroatoms such as oxygen and nitrogen in the chemical structures listed in Table 1 are assumed to be completed by hydrogen.

In another aspect, the present invention comprises a pharmaceutical composition comprising the compound of Formula (I-IV) and a pharmaceutically acceptable carrier, excipient, diluent, or a mixture thereof.

As used herein, the term "lower" refers to a group having between one and six carbons.

As used herein, the term "alkyl" refers to a straight or branched chain hydrocarbon having from one to ten carbon atoms, optionally substituted and multiple degrees of substitution being allowed. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted and multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted and multiple degrees of substitution being allowed. Examples of "alkenyl" as used herein include, but are not limited to, 3,3-dimethyl-but-1-enyl, 4-hex-1-enyl, and the like.

As used herein, the term "alkenylene" refers to a straight or branched chain divalent hydrocarbon radical having from two to ten carbon atoms and one or more carbon-carbon double bonds, optionally substituted and multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted and multiple degrees of substitution being allowed. Examples of "alkynyl" as used herein include, but are not limited to, 4-hex-1ynyl, 3,3-dimethyl-but-1ynyl, and the like.

As used herein, the term "alkynylene" refers to a straight or branched chain divalent hydrocarbon radical having from two to ten carbon atoms and one or more carbon-carbon triple bonds, optionally substituted and multiple degrees of substitution being allowed. Examples of "alkynylene" as used herein include, but are not limited to, ethyne-1,2-diyl, propyne-1,3-diyl, and the like.

As used herein, "cycloalkyl" refers to an alicyclic hydrocarbon group and optionally possessing one or more degrees of unsaturation, having from three to twelve carbon atoms, optionally substituted and multiple degrees of substitution being allowed. Examples of "cycloalkyl" as used herein include, but are not limited to, cyclopropyl, cyclobutyl, cyclopentyl, cyclohexyl, cycloheptyl, cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents and multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, cyclooctyl-1,5-diyl, and the like.

As used herein, the term "heterocyclic" or the term "heterocyclyl" refers to a non-aromatic three to twelve-membered heterocyclic ring optionally possessing one or more degrees of unsaturation, containing one or more heteroatomic substitutions selected from S, SO, $SO_2$, O, or N, optionally substituted and multiple degrees of substitution being allowed. Such a ring may be optionally fused to one or more of another "heterocyclic" ring(s) or cycloalkyl ring(s).

Examples of "heterocyclyl" include, but are not limited to, tetrahydrofuran, tetrahydropyran, 1,4-dioxane, 1,3-dioxane, piperidine, pyrrolidine, morpholine, piperazine, and the like.

As used herein, the term "heterocyclylene" refers to a non-aromatic three to twelve-membered heterocyclic ring diradical optionally having one or more degrees of unsaturation containing one or more heteroatoms selected from S, SO, $SO_2$, O, or N, optionally substituted and multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to benzene ring fused to one to three benzene rings, optionally substituted and multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one to three optionally substituted benzene rings, optionally substituted and multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted and multiple degrees of substitution being allowed. For polycyclic aromatic ring systems, one or more of the rings may contain one or more heteroatoms. Examples of "heteroaryl" used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted and multiple degrees of substitution being allowed. For polycyclic aromatic ring system diradicals, one or more of the rings may contain one or more heteroatoms. Examples of "heteroarylene" used herein include, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfinyl" refers to the group $R_aS(O)$—, where $R_a$ is alkyl.

As used herein, the term "alkenylsulfinyl" refers to the group $R_aS(O)$—, where $R_a$ is alkenyl.

As used herein, the term "alkynylsulfinyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylatic administration to a patient. The phrase "one or more substituents", as used herein, refers to a number of substituents that equals from on to the maximum number of substituents possible based on the number of available bonding sites, provided that the above conditions of stability and chemical feasibility are met.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —SO$_2$NH$_2$.

As used herein, the term "carbamoyl" shall refer to the substituent —C(O)NH$_2$.

As used herein, the term "sulfanyl" shall refer to the substituent —S—.

As used herein, the term "sulfinyl" shall refer to the substituent —S(O)—.

As used herein, the term "sulfonyl" shall refer to the substituent —S(O)$_2$—.

As used herein, the term "haloalkyl" refers to a straight or branched chain hydrocarbon having from one to ten carbon atoms, substituted with at least one halogen atom and optionally substituted at the remaining positions with a halogen atom. A haloalkyl group may be substituted with one or more types of halogen atoms. Examples of "haloalkyl" as used herein include, but are not limited to, a trifluoromethyl group, a 2,2,2-trifluoroethyl group, and the like.

As used herein, the term "perhaloalkyl" refers to a straight or branched chain hydrocarbon having from one to ten carbon atoms, where each position for substitution is substituted with a halogen atom. A perhaloalkyl group may be substituted with one or more types of halogen atoms. Examples of "perhaloalkyl" as used herein include, but are not limited to, a trifluoromethyl group and a 1,1-dichloro-2,2,2-trifluoroethyl group, and the like.

The compounds can be prepared according to the following reaction Schemes (in which variables are as defined before or are defined) using readily available starting materials, and reagents. In these reactions, it is also possible to make use of variants which are themselves known to those of ordinary skill in this art, but are not mentioned in greater detail.

The present invention also provides a method for the synthesis of compounds useful as intermediates in the preparation of compounds of Formula (I-IV) along with methods for the preparation of compounds of Formula (I-IV). Unless otherwise specified, structural variables in the schemes below are as defined for Formula (I-IV). In Schemes 1-7, Ar$^a$ and Ar$^d$ may be a ring selected from the group consisting of: phenyl, indanyl, tetrahydronaphthyl, pyridazine, pyrimidine, pyrazine, pyridine, piperidine, 4,5-diaza-indanyl, 5,6,7,8-tetrahydro-cinnoline, and 1-H-pyridin-2-one, 5,6,7,8-tetrahydro-cinnoline, wherein Ar$^a$ and Ar$^d$ are optionally substituted with R$^b$. In an embodiment, Ar$^1$ and Ar$^d$ form a biphenyl group where Ar$^d$ is unsubstituted and Ar$^a$ is substituted 1-3 times with R$^b$. In Schemes 1-7, L$^a$ is a linker group including, but not limited to, $C_{1-10}$ alkylene and a direct bond. In an embodiment, L$^a$ may be —CH$_2$—. For simplicity of the figures, in schemes other than Scheme 1, a phenyl group substituted with the group —R$^{1-5}$ is used to refer the a phenyl group having groups R$^1$, R$^2$, R$^3$, R$^4$, and R$^5$.

Compounds of formula (1) may be prepared according to Scheme 1. In one embodiment, a bromo or iodo aryl compound (2) can be subjected to palladium catalyzed coupling (Syn. Commu. 1981, 11, 513-574) with an optionally substituted boronic acid Ar$^d$—B(OH)$_2$. Typical conditions used to carry out the coupling reaction include the use of a boronic acid or ester as the coupling partner, a palladium catalyst (2 to 20 mole %) such as Pd(PPh$_3$)$_4$ or [1,1-bis(diphenylphosphino)-ferrocene]dichloro-palladium (II) and base such as potassium carbonate, sodium carbonate, barium hydroxide, potassium phosphate or triethyl amine in a suitable solvent such as aqueous dimethoxyethane, THF, acetone, DMF or toluene at temperatures ranging from 25° C. to 125° C.

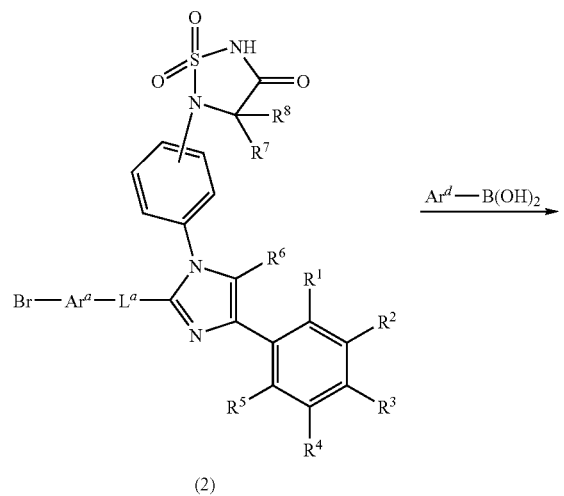

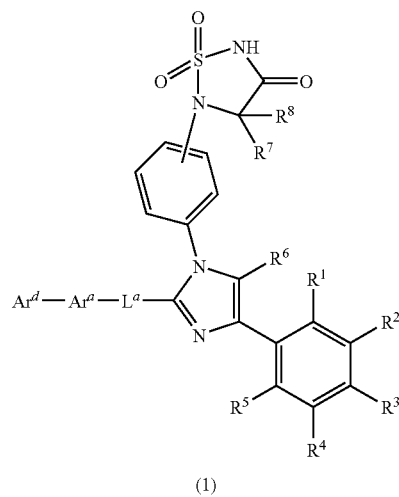

In the place of boronic acids of the formula Ar$^d$—B(OH)$_2$, one may use 1-alkenyl boronic acids of the formula R$^f$—CH=CH—B(OH)$_2$ to prepare compounds of formula (3) in Scheme 2. Alternately, a 9-BBN derived alkenyl borane may be employed to synthesize similar compounds.

Scheme 2

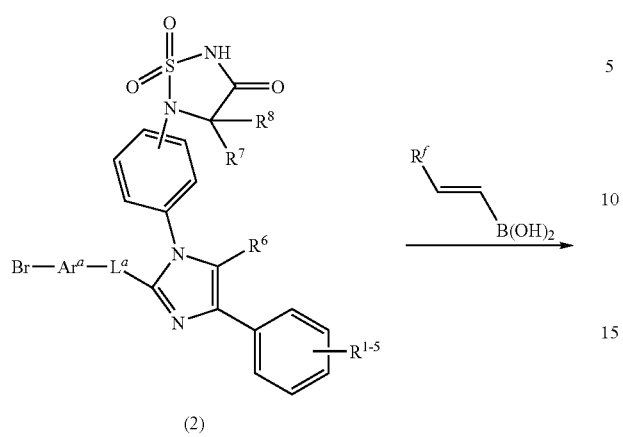

(2)

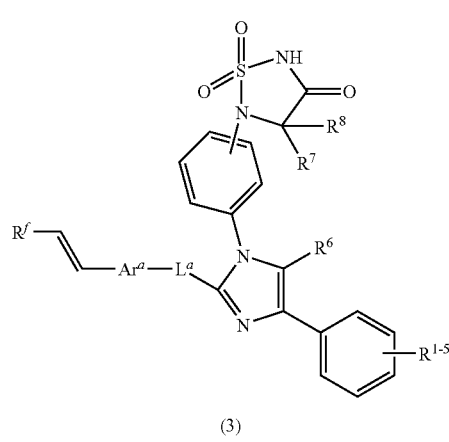

(3)

In another embodiment, under Sonogashihara reaction conditions, aryl bromides of formula (2) may be coupled with acetylenes to prepare compounds of formula (4) shown in Scheme 3.

Scheme 3

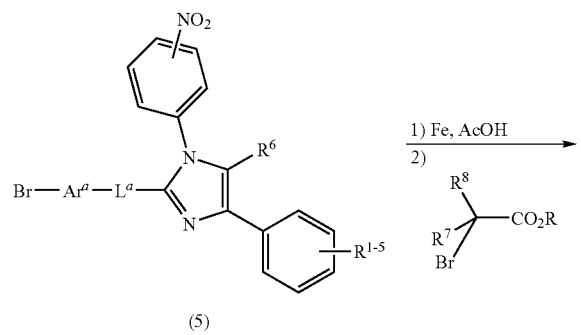

(2)

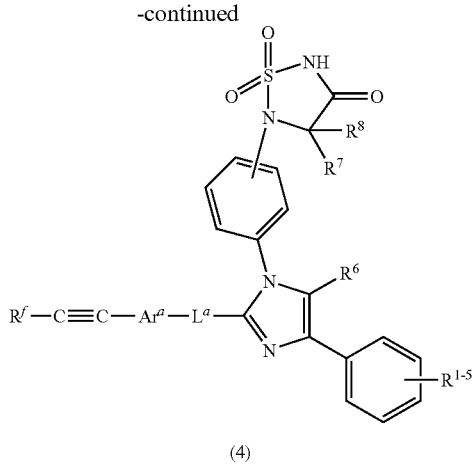

(4)

Construction of isothiazolidinonedioxide ring in the compound of formula (2) is outlined in Scheme 4. The nitro group of an aryl nitro compound (5) may be reduced to an aniline using iron-acetic acid or under a variety of other well-known reagent systems. Resulting anilines are converted to α-substituted glycine ester derivatives (6) by alkylating the amines with an α-bromoacetate derivative. The glycine ester derivatives (6) are then treated with chlorosulfonyl isocyanate followed by t-butanol to form a sulfamoyl chloride. Treatment of sulfamoyl carbamate with trifluoroacetic acid followed by sodium hydroxide provides bromo aryl compound (2).

Scheme 4

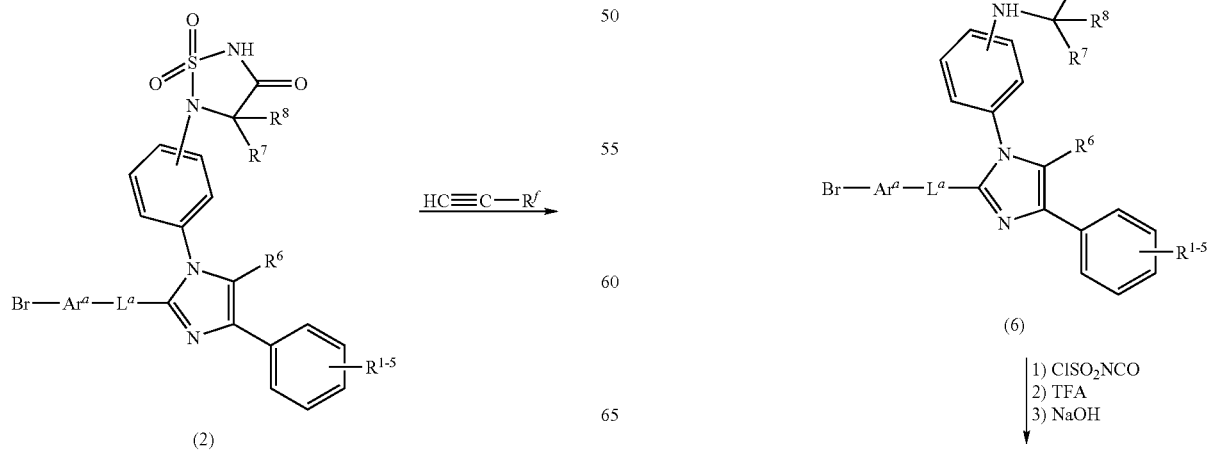

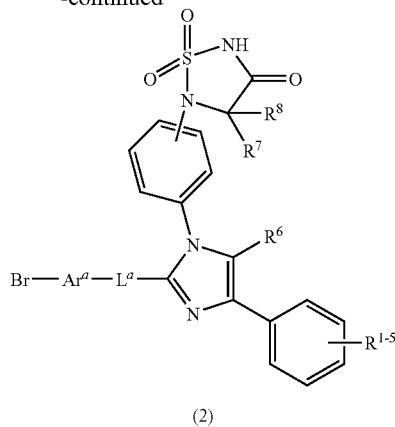

(2)

In another scenario to circumvent chemoselectivity issues, glycine ester derivatives (6) may be converted into a compound of formula (1) via Suzuki coupling using boronic acid $Ar^d$—$B(OH)_2$ followed by isothiazolidinonedioxide ring construction as described above (Scheme 5).

Scheme 5

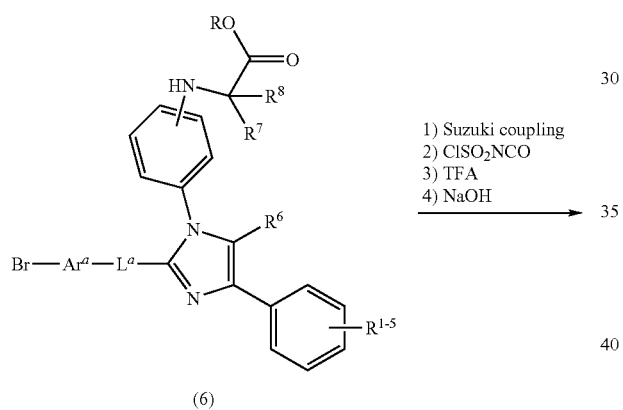

1) Suzuki coupling
2) ClSO₂NCO
3) TFA
4) NaOH

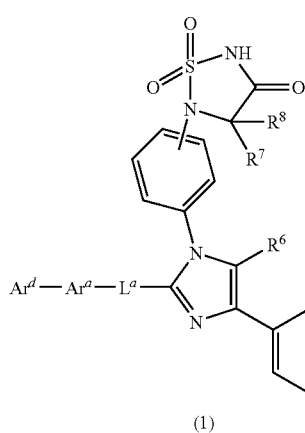

(1)

Aryl nitro compounds (5) may be accessed via aromatic nucleophilic substitution of appropriate halo-nitrobenzene or via Ullman type reaction on imidazoles of formula (7).

Scheme 6

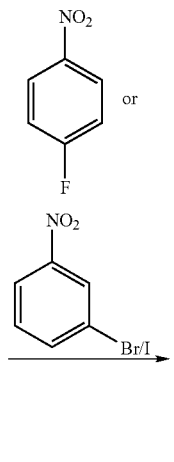

(7)

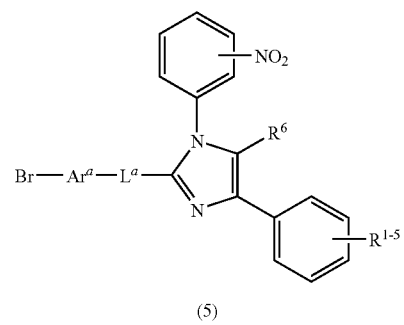

(5)

Imidazoles of formula (7) may be prepared according to Scheme 7. A carboxylic acid (8) may be reacted with an aryl acyl bromide (9) in the presence of base such as DIEA, triethylamine, or DBU, in a polar solvent such as THF or DMF to afford intermediate keto-ester (10), which can be treated with ammonium acetate in acetic acid at temperatures ranging from 60-120° C., which leads to a mixture of oxazole and imidazole (7) (Strzybny, P. P. E., van Es, T.; Backeberg, O. G., J. Org. Chem. 1963, 25, 1151). The ratio of oxazole and imidazole (7) may vary depending on the substitution and reaction conditions. The oxazole and imidazole (7) may be separated through silica gel column. Alternatively other conditions may also be employed for cyclization of keto-ester (10), such as $BF_3/Et_2O$, methanolic ammonia, at temperatures ranging from room temperature to 120° C.

Scheme 7

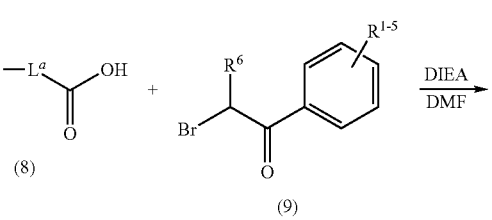

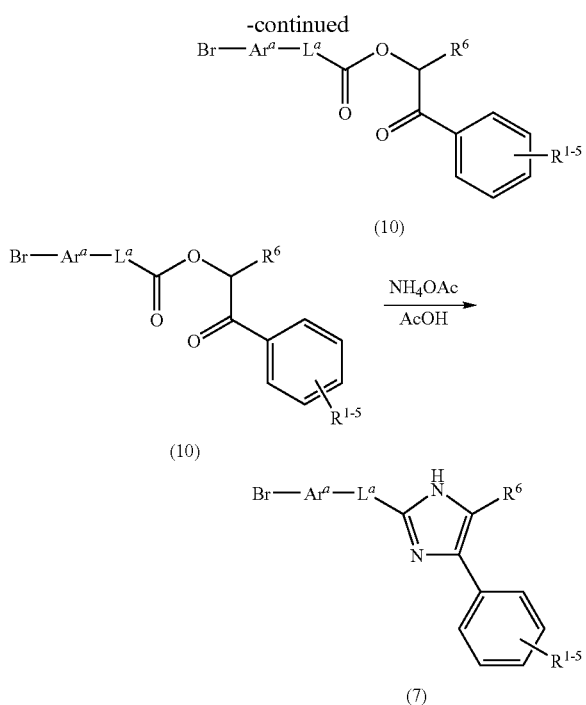

Imidazoles of formula (1) may also be prepared according to Scheme 8. A tertiary amide (11) may be cyclized in a polar solvent such as THF or DMF and ammonium acetate in acetic acid at temperatures ranging from 60-120° C., which leads to an imidazole (1).

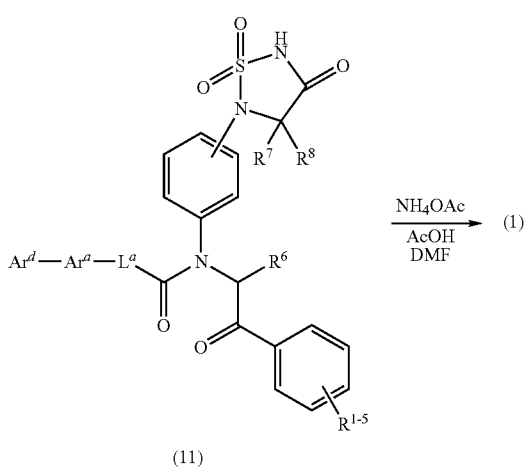

Embodiments of the present invention demonstrate utility in inhibiting protein tyrosine phosphatase PTP 1B. The compounds of the present invention set forth in the present examples were found to inhibit protein tyrosine phosphatase PTP1B with inhibitory potencies (IC50's) of less than about 10 μM.

In general, embodiments of the present invention useful for pharmaceutical applications may have inhibitory potencies (IC50's) for a protein of interest of below about 100 μM. In an embodiment, embodiments of the present invention useful for pharmaceutical applications may have inhibitory potencies (IC50's) for a protein of interest of below about 50 μM. For particular applications, lower inhibitory potencies are useful. Thus, in another embodiment, compounds of the present invention may inhibit protein tyrosine phosphatase PTP1B with inhibitory potencies (IC50's) in a range of about 0.001 μM to about 10 μM. In another embodiment, compounds of the present invention may inhibit protein tyrosine phosphatase PTP1B with inhibitory potencies (IC50's) of about 0.001 μM to about 3 μM.

Embodiments of the compounds of the present invention demonstrate utility as inhibitors of protein tyrosine phosphatases (PTPases). Embodiments of the invention described herein are additionally directed to pharmaceutical compositions and methods of inhibiting PTPase activity in a mammal, which methods comprise administering, to a mammal in need of inhibition of PTPase activity, a therapeutically defined amount of a compound of Formula (I-IV), defined above, as a single or polymorphic crystalline form or forms, an amorphous form, a single enantiomer, a racemic mixture, a single stereoisomer, a mixture of stereoisomers, a single diastereoisomer, a mixture of diastereoisomers, an isotopically enriched form, a solvate, a pharmaceutically acceptable salt, a solvate, a prodrug, a biohydrolyzable ester, or a biohydrolyzable amide thereof.

As used herein the terms "pharmaceutically acceptable carrier", "pharmaceutically acceptable diluent", and pharmaceutically acceptable excipient" means the carrier, diluent or excipient must be compatible with the other ingredients of the formulation and not deleterious to the recipient thereof.

As used herein the term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

Thus, the present invention provides a method of inhibiting a PTPase, comprising the step of administering to a subject in need thereof a therapeutically effective amount of a compound of the present invention. The invention further provides a pharmaceutical composition comprising a pharmaceutically acceptable carrier and a therapeutically effective amount of a compound of the present invention sufficient to inhibit a PTPase. A PTPase-inhibiting amount can be an amount that reduces or inhibits a PTPase activity in the subject.

The compound of Formula (I-IV) may comprise a single or polymorphic crystalline form or forms, an amorphous form, a single enantiomer, a racemic mixture, a single stereoisomer, a mixture of stereoisomers, a single diastereoisomer, a mixture of diastereoisomers, an isotopically enriched form, a solvate, a pharmaceutically acceptable salt, a solvate, a prodrug, a biohydrolyzable ester, or a biohydrolyzable amide thereof.

Additionally provided is a pharmaceutical composition comprising a pharmaceutically acceptable carrier and a therapeutically effective amount of a compound of Formula (I-IV) of the present invention sufficient to treat glucose intolerance.

Further, the present invention provides a pharmaceutical composition comprising a pharmaceutically acceptable carrier and a therapeutically effective amount of a compound of Formula (I-IV) of the present invention sufficient to treat Type I diabetes.

Further, the present invention provides a pharmaceutical composition comprising a pharmaceutically acceptable carrier and a therapeutically effective amount of a compound of Formula (I-IV) of the present invention sufficient to treat Type II diabetes.

Further, the present invention provides a pharmaceutical composition comprising a pharmaceutically acceptable carrier and a therapeutically effective amount of a compound of Formula (I-IV) of the present invention sufficient to treat immune dysfunction. In an embodiment, the immune dysfunction is AIDS. In another embodiment, the immune dysfunction is an allergic disease. In another embodiment, the immune dysfunction is an inflammatory disease. In another embodiment, the immune dysfunction is an autoimmune disease. In another embodiment, the immune dysfunction is an autoimmune disease selected from the group consisting of psoriasis.

Further, the present invention provides a pharmaceutical composition comprising a pharmaceutically acceptable carrier and a therapeutically effective amount of a compound of Formula (I-IV) of the present invention sufficient to treat obesity.

Further, the present invention provides a pharmaceutical composition comprising a pharmaceutically acceptable carrier and a therapeutically effective amount of a compound of Formula (I-IV) of the present invention sufficient to treat cancer.

Further, the present invention provides a pharmaceutical composition comprising a pharmaceutically acceptable carrier and a therapeutically effective amount of a compound of Formula (I-IV) of the present invention sufficient to treat an infectious disease.

Further, the present invention provides a pharmaceutical composition comprising a pharmaceutically acceptable carrier and a therapeutically effective amount of a compound of Formula (I-IV) of the present invention sufficient to treat a disease involving the modulated synthesis of growth hormone.

Further, the present invention provides a pharmaceutical composition comprising a pharmaceutically acceptable carrier and a therapeutically effective amount of a compound of Formula (I-IV) of the present invention sufficient to treat a disease that involves at least in part the modulated synthesis of growth factors or cytokines that affect the production of growth hormone.

Further, the present invention provides a pharmaceutical composition comprising a pharmaceutically acceptable carrier and a therapeutically effective amount of a compound of Formula (I-IV) of the present invention sufficient to treat Alzheimer's disease.

The compounds of the present invention can be administered to subjects in need of inhibition of PTPase activity. Such subjects can include, for example, horses, cows, sheep, pigs, mice, dogs, cats, primates such as chimpanzees, gorillas, rhesus monkeys, and, humans. In an embodiment, a subject is a human in need of inhibition of PTPase activity.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention. Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

As used herein, the term "other pharmaceutically acceptable counter ions" refers to a non-toxic counter ions such as, but not limited to, ammonium, morpholinium, sodium, potassium, barium, calcium, and the like, and which may be installed by reacting the acidic hydrogen of a thiadiazolidine derivative with the appropriate organic or inorganic base.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug thereof, and one or more pharmaceutically acceptable carriers, excipients, or diluents.

The compounds of the present invention may selectively act as inhibitors of one PTPase in preference to one or more other PTPases, and therefore may possess advantage in the treatment of one or more PTPase-mediated disease in preference to others.

In a further aspect, the present invention may provide a method comprising administering to a human a compound of Formula (I-IV). In one embodiment, the present invention comprises method for the inhibition of PTPases. Thus, an embodiment of the present invention provides a method for treating a disease state mediated at least in part by a PTPase enzyme, comprising administering to a subject in need thereof a compound of the present invention. In alternate embodiments, the disease treated using a method of the present invention comprises glucose intolerance including Type I diabetes and Type II diabetes, immune dysfunction including AIDS, allergic diseases, inflammatory diseases, and autoimmunity such as psoriasis, infectious diseases, obesity, cancer, diseases involving the modulated synthesis of growth hormone or the modulated synthesis of growth factors or cytokines which affect the production of growth hormone, or Alzheimer's disease. In an embodiment, a therapeutically effective amount may be administered. In another embodiment a therapeutically effective amount may be administered. In another embodiment, at least one compound of Formula (I-IV) is utilized, either alone or in combination with one or more known therapeutic agents. In a further embodiment, the present invention provides method of prevention and/or treatment of PTPase-mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of Formula (I-IV).

In this method, factors which may influence what constitutes an effective amount include, but are not limited to, the size and weight of the subject, the biodegradability of the therapeutic agent, the activity of the therapeutic agent, as well as its bioavailability. As used herein, the phrase "a subject in need thereof" includes mammalian subjects, such as humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

The following is a non-exhaustive listing of adjuvants and additional therapeutic agents which may be utilized in combination with the PTPase inhibitors of the present invention:

Pharmacologic Classifications of Anticancer Agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins Pharmacologic Classifications of Treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic Classifications of Treatment for Diabetes Mellitus
1. Sulfonylureas: Tolbutamide, Tolazamide, Glyburide, Glipizide
2. Biguanides: Metformin
3. Miscellaneous oral agents: Agents designed to reduce the absorption of glucose from the intestine (for example Acarbose), PPAR agonists such as Troglitazone, pioglitazone, and rosiglitazone), DPP-IV inhibitors, Glucokinase activators
4. Insulin, insulin mimetics, insulin secretagogues (for example glibenclamide, glipizide), insulin sensitizers
5. GLP-1, GLP-1 mimetics Pharmacologic Classifications of Treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid Pharmacologic Classifications of Treatment for Hyperlipidemia
1. HMG CoA reductase inhibitors Inhibitor: Mevinolin
2. Bile acid sequestrants such as cholestyramine
3. fibrates Additional therapeutic agents which may be utilized in combination with the PTPase inhibitors of the present invention include:
1) Agents designed to treat the complications of prolonged hyperglycaemia;
2) Anti-dyslipidaemia agents such as, HMG-CoA reductase inhibitors (statins, eg pravastatin); PPARa agonists (fibrates, eg gemfibrozil); cholesterol absorption inhibitors (plant stanols, synthetic inhibitors); bile acid absorption inhibitors (IBATi) and nicotinic acid and analogues (niacin and slow release formulations);
3) Antihypertensive agents such as, (β blockers (eg atenolol, inderal); ACE inhibitors (eg lisinopril); Calcium antagonists (eg. nifedipine); Angiotensin receptor antagonists (eg candesartan), a antagonists and diuretic agents (eg. furosemide, benzthiazide);
4) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
5) Anti-inflammatory agents, such as non-steroidal anti-inflammatory drugs (eg. aspirin) and steroidal anti-inflammatory agents (eg. cortisone).

Antiobesity agents or appetite regulating agents may also be used in combination with the compounds of the present invention. Examples of anti-obesity agents or appetite regulating agents that may be used in combination with the compounds of the present invention include but are not limited to:
1. a NPY receptor antagonist,
2. a Melanocyte-Concentrating Hormone (MCH) antagonist,
3. a GHSR antagonist,
4. a CRH antagonist,
5. a beta 3 adrenergic agonist,
6. a lipase inhibitor (orlistat),
7. a serotonin (and dopamine) reuptake inhibitor (sibutramine, topiramate or axokine),
8. a thyroid receptor beta drug and/or
9. an anorectic agent (dexamphetamine, amphetamine, phentermine, phenylpropanolamine or mazindol),
10. a $CB_1$ antagonist (rimonabant).

The beta 3 adrenergic agonists which may be employed in combination with a compound of the present invention include known beta 3 agonists, such as those disclosed in U.S. Pat. Nos. 5,541,204, 5,770,615, 5,491,134, 5,776,983 and 5,488,064.

Examples of lipase inhibitors which may be employed in combination with compounds of the present invention include orlistat or ATL-962 (Alizyme).

The serotonin (and dopamine) reuptake inhibitor which may be employed in combination with a compound of the present invention include sibutramine, topiramate (Johnson & Johnson) or axokine (Regeneron).

Examples of thyroid receptor beta compounds which may be employed in combination with a compound of the present invention include thyroid receptor ligands, such as those disclosed in WO97/21993 (U. Cal SF), WO99/00353 (KaroBio) and GB98/284425 (KaroBio).

The anorectic agent which may be employed in combination with a compound of the present invention include dexamphetamine, phentermine, phenylpropanolamine or mazindol.

An example of a $CB_1$ antagonist which may be employed in combination with a compound of the present invention include rimonabant.

In a further embodiment, the present invention provides a method of treating diseases mediated at least in part by a PTPase enzyme (i.e., PTPase mediated diseases), the method comprising administering to a subject in need thereof, a therapeutically effective amount of a compound of Formula (I-IV) in combination with a therapeutic agent. Examples of combination therapeutic agents may include, but are not limited to, alkylating agents, antimetabolites, plant alkaloids, antibiotics, hormones, biologic response modifiers, analgesics, NSAIDs, DMARDs, glucocorticoids, sulfonylureas, biguanides, acarbose, PPAR agonists, DPP-IV inhibitors, GK activators, insulin, insulin mimetics, insulin secretagogues, insulin sensitizers, GLP-1, GLP-1 mimetics, cholinesterase inhibitors, antipsychotics, antidepressants, anticonvulsants, HMG CoA reductase inhibitors, cholestyramine, or fibrates.

Generally speaking, a compound of Formula (I-IV) may be administered at a dosage level of from about 0.003 to 500 mg/kg of the body weight of the subject being treated. In an embodiment, a compound of Formula (I-IV) may be administered at a dosage range between about 0.003 and 200 mg/kg of body weight per day. In an embodiment, a compound of Formula (I-IV) may be administered at a dosage range between about 0.1 to 100 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I-IV) with an appropriate and convenient amount of carrier material which may vary from about 5 to 95 percent of the total composition. Dosage unit forms may generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The general procedures used in the methods of the present invention are described below.

General Experimental

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted. $^1$H NMR data was obtained on a Varian 400 MHz spectrometer.

General Procedure A: Imidazole Formation

To a mixture of a carboxylic acid (1 eq) and an aromatic acyl bromide (2 eq) in anhydrous DMF (0.1-0.5 M) was added DIEA (3 eq). The reaction mixture was stirred at room temperature under nitrogen for 6 to 8 hours. After that, it was poured into water, acidified with 10% citric acid and extracted with ethyl acetate. The organic extract was washed with water and brine, and dried over $Na_2SO_4$. After evaporation of the solvent, the pale-brown residue was recrystallized from EtOAc-Hexanes, dried and used directly in the next step.

The intermediate obtained above was dissolved in glacial acetic acid (0.1-0.5 M), and ammonium acetate (20 eq) was added. The mixture was then heated at 120° C. under nitrogen for 8 to 10 hours. At completion, it was poured into water, neutralized with saturated sodium bicarbonate and extracted with ethyl acetate. The organic extract was washed with water and brine, and dried over $Na_2SO_4$. After removal of the solvent in vacuo, the residue was purified by flash column chromatography to afford the desired product.

General Procedure B: Arylation of Imidazole Nitrogen Atom Using Aryl Fluoride/Aryl Bromide To a solution of imidazole compound (1 eq) in anhydrous DMF (0.1-0.5 M), the appropriate activated aryl fluoride or aryl bromide (1.5 eq) was added followed by $Cs_2CO_3$ (3 eq). The reaction mixture was then heated at 120° C. under nitrogen for 2 hours. At completion, the reaction mixture was diluted with water/EtOAc and the layers separated. The aqueous layer was re-extracted with EtOAc and the organic layers combined, washed with water and brine. The organic phase was then dried over $Na_2SO_4$, filtered, and the filtrate was concentrated and purified by silica gel chromatography to afford the aryl imidazole derivative.

General Procedure C: Preparation of 1,2,5-Thiadiazolidine-3-One-1,1-Dioxide Derivatives To a suspension of aryl nitro compound (1 eq) in HOAc (0.1-0.5 M), iron powder (~325 mesh, 8 eq) was added and the mixture was then heated at 80° C. under nitrogen for 5-10 minutes. The reaction mixture was then diluted with water/EtOAc and the leftover iron powder was filtered and washed with EtOAc. The combined organic layer was washed with water, saturated $NaHCO_3$ and brine. The organic layer was then dried over $Na_2SO_4$, filtered, and the filtrate was concentrated and purified by silica gel chromatography to afford the aniline derivative.

Alkylation of aniline: Method I) To a suspension of aniline compound (1 eq) in anhydrous DMF (0.1-0.5 M) at room temperature was added 1.2 eq of α-bromo ester followed by 2.5 eq of DIEA. The reaction mixture was then stirred at room temperature under nitrogen for 18 hours. The reaction mixture was then diluted with water/EtOAc and the layers separated. The aqueous layer was re-extracted with EtOAc and the organic layers were combined and washed with water and brine. The organic phase was then dried over $Na_2SO_4$, filtered, and the filtrate was concentrated and purified by silica gel chromatography to afford the α-anilino-ester derivative. Method II) To a suspension of aniline compound (1 eq) in anhydrous DMF (0.1-0.5 M) at room temperature was added 2 eq of α-bromo ester followed by 5 eq of anhydrous potassium tert-butoxide. The reaction mixture was then stirred at 100° C. under nitrogen for 18 hours. The reaction mixture was then diluted with water/EtOAc and the layers separated. The aqueous layer was re-extracted with EtOAc and the organic layers were combined and washed with water and brine. The organic phase was then dried over $Na_2SO_4$, filtered, and the filtrate was concentrated and purified by silica gel chromatography to afford the α-anilino-ester derivative.

Formation of 1,2,5-thiadiazolidine-3-one-1,1-dioxide: To a solution of chlorosulfonyl isocyanate (1.5 eq) in anhydrous 1,2-dichloroethane (0.1-0.5 M) at 0° C. was added 1.5 eq of tert-butanol as a solution in anhydrous 1,2-dichloroethane (0.5 M). The mixture was allowed to warm to room temperature while stirring and was then cooled to 0° C. again. A suspension of aniline-ester from the above (1.0 eq) in 1,2-dichloroethane (0.3-0.5 M) and 2.5 eq DIEA was cooled to 0° C. and the chlorosulfonyl isocyanate-tert-butanol mixture was added dropwise while stirring. The mixture was stirred at room temperature for 1 hour, then diluted with water/$CH_2Cl_2$ and the layers separated. The organic layers were combined and washed with water and brine. The organic phase was then dried over $Na_2SO_4$, filtered, and the filtrate was concentrated and purified by silica gel chromatography to afford the aniline N-Boc-sulfamide derivative (Boc refers to tert-butyloxycarbonyl group).

The Boc-protected sulfamide was stirred in dichloromethane/trifluoroacetic acid for 30 minutes. The solvent was removed and the residue was triturated several times with ether to afford the deprotected sulfamide.

To a suspension of the deprotected sulfamide compound in ethanol (0.1-0.5 M) was added 5.0 eq of NaOH as a 2 M solution in water. The mixture was stirred at room temperature for 5-7 minutes, then diluted with 2% citric acid/EtOAc and the layers separated. The organic layer was washed with water and brine. The organic layer was then dried over Na$_2$SO$_4$, filtered, and the filtrate was concentrated and purified by silica gel chromatography to afford the 1,2,5-thiadiazolidine-3-one-1,1-dioxide derivative.

General Procedure D: Reduction of Aryl Nitro Group

To a suspension of aryl nitro compound (1 eq) in HOAc (0.1-0.5 M), iron powder (−325 mesh, 8 eq) was added and the mixture was then heated at 80° C. under nitrogen for 5-10 minutes. The reaction mixture was then diluted with water/EtOAc and the leftover iron powder was filtered and washed with EtOAc. The combined organic layer was washed with water, saturated NaHCO$_3$ and brine. The organic layer was then dried over Na$_2$SO$_4$, filtered, and the filtrate was concentrated and purified by silica gel chromatography to afford the aniline derivative.

General Procedure E: Alkylation of Aniline

Method I) To a suspension of aniline derivative (1 eq) in anhydrous DMF (0.1-0.5 M) at room temperature was added 1.2 eq of α-bromo ester followed by 2.5 eq of DIEA. The reaction mixture was then stirred at room temperature under nitrogen for 18 hours. The reaction mixture was then diluted with water/EtOAc and the layers separated. The aqueous layer was re-extracted with EtOAc and the organic layers were combined and washed with water and brine. The organic phase was then dried over Na$_2$SO$_4$, filtered, and the filtrate was concentrated and purified by silica gel chromatography to afford the α-anilino-ester derivative.

Method II) To a suspension of aniline derivative (1 eq) in anhydrous DMF (0.1-0.5 M) at room temperature was added 2 eq of α-bromo ester followed by 5 eq of anhydrous potassium tert-butoxide. The reaction mixture was then stirred at 100° C. under nitrogen for 18 hours. The reaction mixture was then diluted with water/EtOAc and the layers separated. The aqueous layer was re-extracted with EtOAc and the organic layers were combined and washed with water and brine. The organic phase was then dried over Na$_2$SO$_4$, filtered, and the filtrate was concentrated and purified by silica gel chromatography to afford the α-anilino-ester derivative.

General Procedure F: Formation of 1,2,5-thiadiazolidine-3-one-1,1-dioxide

To a solution of chlorosulfonyl isocyanate (1.5 eq) in anhydrous 1,2-dichloroethane (0.1-0.5 M) at 0° C. was added 1.5 eq of tert-butanol as a solution in anhydrous 1,2-dichloroethane (0.5 M). The mixture was allowed to warm to room temperature while stirring and was then cooled to 0° C. again. A suspension of aniline-ester from general procedure E (1.0 eq) in 1,2-dichloroethane (0.3-0.5 M) and 2.5 eq DIEA was cooled to 0° C. and the chlorosulfonyl isocyanate-tert-butanol mixture was added drop-wise while stirring. The mixture was stirred at room temperature for 1 hour, then diluted with water/CH$_2$Cl$_2$ and the layers separated. The organic layers were combined and washed with water and brine. The organic phase was then dried over Na$_2$SO$_4$, filtered, and the filtrate was concentrated and purified by silica gel chromatography to afford the aniline N-Boc sulfamide derivative.

The Boc protected sulfamide was stirred in dichloromethane/trifluoroacetic acid for 30 minutes. The solvent was removed and the residue was triturated several times with ether to afford the deprotected sulfamide.

To a suspension of the deprotected sulfamide derivative in ethanol (0.1-0.5 M) was added 5.0 eq of NaOH as a 2 M solution in water. The mixture was stirred at room temperature for 5-7 minutes, then diluted with 2% citric acid/EtOAc and the layers separated. The organic layer was washed with water and brine. The organic layer was then dried over Na$_2$SO$_4$, filtered, and the filtrate was concentrated and purified by silica gel chromatography to afford the 1,2,5-thiadiazolidine-3-one-1,1-dioxide.

General Procedure G: Suzuki Coupling

To a solution of the bromo-compound (1 eq) in a 2:1 mixture of toluene and ethanol (0.1-0.5 M) was added the appropriate boronic acid (2 eq) and a catalytic amount of tetrakis(triphenylphosphine)palladium(0) (0.1 eq), followed by 2 M sodium carbonate solution in water (30 eq). The reaction mixture was stirred at 90° C. under nitrogen for 6 hours. After cooling, the reaction mixture was diluted with water and extracted with ethyl acetate. The organic extract was washed with water and brine, and dried over Na$_2$SO$_4$. After removal of the solvent in vacuo, the residue was purified by flash column chromatography to afford the desired compound.

General Procedure H: Alkylation of Phenolic Oxygen Atom of Hydroxyphenylboronic Acid To a solution of hydroxyphenylboronic acid (1 eq) in anhydrous DMF (0.1-0.5 M) was added an alkyl bromide or mesylate (2 eq) followed by freshly ground K$_2$CO$_3$ (4 eq) and the reaction mixture was heated at 100° C. under nitrogen for 6 hours. The mixture was then diluted with water/EtOAc and the layers separated. The aqueous layer was further extracted with EtOAc, and the organic layers combined and dried over Na$_2$SO$_4$. The solvent was removed in vacuo and the residue was purified by silica gel chromatography to yield the desired product.

General Procedure I: Alkylation of Sulfur Atom of Mercaptophenylboronic Acid

To a solution of mercaptophenylboronic acid (1 eq) in anhydrous DMF (0.1-0.5 M) was added an alkyl bromide (2 eq) followed by DIEA (4 eq) and the reaction mixture was stirred at room temperature under nitrogen overnight. The mixture was then diluted with water/EtOAc and the layers separated. The aqueous layer was further extracted with EtOAc, and the organic layers combined and dried over Na$_2$SO$_4$. The solvent was removed in vacuo and the residue was purified by silica gel chromatography to yield the desired product.

General Procedure J: Alkylation of Amino-Phenylboronic Acid

To a solution of amino-phenylboronic acid (1 eq) in anhydrous DMF (0.1-0.5 M) was added an alkyl/aryl bromide followed by freshly ground K$_2$CO$_3$ (4 eq) and the reaction mixture was stirred under nitrogen at room temperature for 16 hours. The mixture was then diluted with water/EtOAc and the layers separated. The aqueous layer was further extracted with EtOAc, and the organic layers combined and dried over Na$_2$SO$_4$. The solvent was removed in vacuo and the residue was purified by silica gel chromatography to yield the desired product.

General Procedure K: Alkylation of Aniline, Phenol or Thiol

To solution of a phenol, aniline or thiol (1 eq) in anhydrous DMF (0.1-0.5 M) was added an alkyl halide (2 eq) followed by freshly ground Cs$_2$CO$_3$ (4 eq). The reaction mixture was heated at 100° C. under nitrogen for 2 hours. The mixture was then diluted with water/EtOAc and the layers separated. The aqueous layer was further extracted with EtOAc, and the organic layers combined and dried over Na$_2$SO$_4$. The solvent was removed in vacuo and the residue was purified by silica gel chromatography to yield the desired product.

General Procedure L: Alkylation of Aniline, Phenol or Imidazole and Heteroarylation of Alcohol, Thiol or Amine To a solution of a phenol, alcohol, aniline or imidazole (1 eq) in anhydrous DMF (0.1-0.5M) was added sodium hydride (2 eq). The mixture was stirred at room temperature for 20 min and a solution of alkyl halide or heteroaryl halide in DMF (1-3 eq) was added. Stirring continued for 3 hour, then the mixture was diluted with water/EtOAc and neutralized with 10% aqueous citric acid. The organic layer was washed with brine, dried over $Na_2SO_4$, and evaporated in vacuo. The residue was purified by silica gel chromatography to provide the desired product.

General Procedure M: Preparation of 1-(3-Aminophenyl) Imidazole

To a mixture of 3-aminoacetanilide (1 eq) and an aromatic acyl bromide (2 eq) in anhydrous DMF (0.1-0.5 M) was added $NaHCO_3$ (5 eq). The reaction mixture was stirred at room temperature under nitrogen for 3 hours. At completion, the reaction mixture was diluted with water/EtOAc and the layers separated. The aqueous layer was extracted with EtOAc and the organic layers combined and washed with water and brine. The organic solution was then dried over $Na_2SO_4$, filtered, and the filtrate was concentrated and the residue was dried and used directly in the next step.

The aniline derivative obtained above was dissolved in dry DMF (0.1-0.5 M) and eq of $NaHCO_3$ was added. While stirring under nitrogen on ice, a solution of p-bromophenylacetyl chloride (1.1 eq) in benzene was added dropwise. The mixture was then stirred for 1 hour and allowed to warm to room temperature. The reaction mixture was diluted with water/EtOAc and the layers separated. The aqueous layer was extracted with EtOAc and the organic layers combined and washed with water and brine. The organic solution was then dried over $Na_2SO_4$, filtered, and the filtrate was concentrated and the residue was dried and used directly in the next step.

The tertiary anilide obtained above was dissolved in glacial acetic acid (0.1-0.5 M) and ammonium acetate (10 eq) was added. The mixture was then heated at 110° C. under nitrogen for 8 hours. At completion, the mixture was poured into water, neutralized with saturated sodium bicarbonate and extracted with ethyl acetate. The organic extract was washed with water and brine and dried over $Na_2SO_4$. After removal of the solvent in vacuo, the residue was purified by silica gel column chromatography to afford the desired imidazole N-(3-acetamido) phenyl derivative.

The intermediate obtained above was dissolved in a 6:1 v/v mixture of 4M HCl/dioxane and water (0.1-0.5 M) and heated at 70° C. for 3 hours. The mixture was then poured into water, neutralized with saturated sodium bicarbonate and extracted with ethyl acetate. The organic extract was washed with water and brine and dried over $Na_2SO_4$. After removal of the solvent in vacuo, the residue was dried and used without further purification.

General Procedure N: Preparation of Tertiary Anilide

The aniline derivative obtained above was dissolved in dry DMF (0.1-0.5 M) and 5 eq of $NaHCO_3$ was added. While stirring under nitrogen on ice, a solution of p-bromophenyl acetyl chloride (1.1 eq) in benzene was added dropwise. The mixture was then stirred for 1 hour and allowed to warm to room temperature. The reaction mixture was diluted with water/EtOAc and the layers separated. The aqueous layer was extracted with EtOAc and the organic layers combined and washed with water and brine. The organic solution was then dried over $Na_2SO_4$, filtered, and the filtrate was concentrated and the residue was dried and used directly in the next step.

General Procedure O: Preparation of Imidazole

The tertiary anilide obtained above was dissolved in glacial acetic acid (0.1-0.5 M) and ammonium acetate (10 eq) was added. The mixture was then heated at 110° C. under nitrogen for 8 hours. At completion, the mixture was poured into water, neutralized with saturated sodium bicarbonate and extracted with ethyl acetate. The organic extract was washed with water and brine and dried over $Na_2SO_4$. After removal of the solvent in vacuo, the residue was purified by silica gel column chromatography to afford the desired 1-(3-acetamido)phenylimidazole derivative.

General Procedure P: Hydrolysis of Ester

The ester (1 eq) was suspended in a mixture of MeOH: $THF:H_2O$ (1:1:1; 0.1-0.2 M). LiOH (20 eq) was added and the mixture stirred at 100° C. for 0.5 hours. The solution was acidified with 10% citric acid solution, and extracted with ethyl acetate. The organic extracts were combined, washed with brine, dried over $Na_2SO_4$, and the solvent removed in vacuo. The residue was purified by silica gel chromatography to yield the desired acid.

General Procedure Q: Hydrogenation of Phenyl Group

To 1 equivalent of the desired substituted phenyl compound suspension in methanol (0.1-0.5 M) was added a catalytic amount of platinum (IV) oxide (wet). After degassing and introducing of nitrogen and degassing again, hydrogen was introduced (~50 psi). The reaction mixture was stirred at room temperature for 3 to 4 days (hydrogen was recharged to maintain 40~50 psi pressure). The reaction mixture was then filtered through celite, the celite cake was washed three times with ethyl acetate, and the filtrates combined. The solvent was then removed in vacuo, and the residue was purified by silica gel chromatography to afford the desired compound.

General Procedure R: Ullmann Coupling

To a solution of oxygen- or nitrogen-containing nucleophile (1 eq) in anhydrous NMP (0.1-0.5 M), the appropriate aryl bromide or iodide (1.5 eq) was added followed by CuCl (0.2 eq), 2,2,6,6-tetramethyl-3,5-heptanedione (0.2 eq) and $Cs_2CO_3$ (3 eq). The reaction mixture was then heated at 120° C. under nitrogen for 6 to 8 hours. At completion, the reaction mixture was diluted with water/EtOAc and the layers separated. The aqueous layer was re-extracted with EtOAc and the organic layers combined, washed with water and brine. The organic phase was then dried over $Na_2SO_4$, filtered, and the filtrate was concentrated and purified by silica gel chromatography to afford the desired product (diary) ether or substituted aniline derivative).

General Procedure S: Oxidation of Sulfide Using Peracetic Acid

To a solution of thioether compound (1 eq) in 1:1 DCM/ HOAc (0.1-0.5 M) was added peracetic acid (32 wt. % solution in acetic acid, 10 eq) at 0° C. and the solution was stirred at the same temperature for half an hour. At completion, the reaction mixture was diluted with water/EtOAc. The combined organic layer was washed with water, saturated $NaHCO_3$ and brine. The organic phase was then dried over $Na_2SO_4$, filtered, and concentrated. The residue was triturated several times with hexanes to afford the desired sulfone derivative.

General Procedure T: Oxidation of Sulfide Using Hydrogen Peroxide

To a solution or suspension of thioether compound (1 eq) in methanol (0.1-0.5 M) was added hydrogen peroxide (50% solution in water, 10 eq) at 0° C. and the reaction mixture was stirred at room temperature for an hour. At completion, the reaction mixture was diluted with water/EtOAc. The combined organic layer was washed with water and brine. The organic phase was then dried over $Na_2SO_4$, filtered, and concentrated. The residue was triturated several times with hexanes to afford the desired sulfoxide derivative.

General Procedure U: Coupling of Aniline or Amine with Sulfonyl Chloride, Sulfonic Anhydride or Chloroformate To a suspension of amine compound (1 eq) in anhydrous DCM (0.1-0.5 M) at 0° C. was added DIEA (1.2 eq) followed by the appropriate sulfonyl chloride, sulfonic anhydride, or chloroformate (1.2 eq, diluted in anhydrous DCM). The reaction mixture was then warmed up and stirred at room temperature under nitrogen for 3 to 4 hours. At completion, the reaction mixture was diluted with water/EtOAc and the layers separated. The aqueous layer was re-extracted with EtOAc and the organic layers combined, washed with 10% citric acid, water and brine. The organic phase was then dried over $Na_2SO_4$, filtered, and the filtrate was concentrated and purified by silica gel chromatography to afford the sulfonamide or the carbamate derivative.

General Procedure V: Removal of the T-Butyl Carbamate Group

The boc-protected compound was stirred in 4N HCl/dioxane for 1 hour. The solvent removed, and the product triturated several times with ether to afford the desired compound.

General Procedure W: Silyl Group Deprotection

To a solution of O— or N— silyl compound (1 eq) in THF (0.1-0.5 M) was added 5 eq of tetrabutylammonium fluoride as a solution in THF. The mixture was stirred at 65° C. for 1-3 hours, then was evaporated to a small volume and taken up in water/EtOAc. Layers were separated and the aqueous layer was further extracted with EtOAc. The combined organic extracts were washed with brine, dried over $Na_2SO_4$, and evaporated in vacuo. The residue was purified by silica gel column chromatography to give the desired product.

General Procedure X: Reductive Amination

To a solution of amine (1 eq) in 1,2-dichloroethane (0.1-0.5 M) was added an aldehyde (1.2 eq) and a catalytic amount of acetic acid. The mixture was stirred at room temperature for 30 minutes under nitrogen, then sodium triacetoxyborohydride (3 eq) was added and the mixture was allowed to stir for 12-16 hours at room temperature. The mixture was then diluted with water/EtOAc and layers were separated. The aqueous layer was extracted additionally with EtOAc and the combined organic extracts were washed with water, brine, dried over $Na_2SO_4$ and evaporated in vacuo. The residue was purified by silica gel column chromatography to provide the desired product.

General Procedure Y: Preparation of Boronic Acid

To a suspension of m- or p-bromobenzaldehyde in THF (0.1-0.5 M) was added drop-wise alkylmagnesium bromide or chloride in ether or THF (1.1 eq) while stirring on ice. The mixture was allowed to warm to room temperature and stirred for 30 minutes, then poured into saturated $NH_4Cl$/EtOAc and the layers separated. The aqueous layer was extracted with EtOAc and the organic layers combined and washed with water and brine. The organic solution was then dried over $Na_2SO_4$, filtered, and the filtrate was concentrated and the residue was dried and used directly in the next step.

The Grignard product obtained above was dissolved in trifluoroacetic acid (0.1-0.5 M) under nitrogen and cooled in an ice-salt bath maintained at −10° C. Triethylsilane (4 eq) was added to the solution slowly in order to maintain the bath at −10° C. The solution was then allowed to warm to room temperature and stirred for 3 hours. At completion, the mixture was poured into water and extracted with dichloromethane. The organic extract was washed with saturated aqueous $NaHCO_3$ and brine and dried over $Na_2SO_4$. After removal of the solvent in vacuo, the residue was purified by silica gel column chromatography to afford the desired m- or p-bromophenylalkane product.

A solution of m- or p-bromophenylalkane in dry THF (0.1-0.5 M) was stirred under nitrogen in a dry ice-acetone bath, and sec-butyllithium in cyclohexane (2 eq) was added drop-wise, all on dry ice-acetone bath. The mixture was stirred 10 minutes, then triisopropyl borate (3 eq) was added drop-wise. The mixture was stirred an additional 30 minutes, then poured into excess 2M HCl and stirred 20 minutes at room temperature. Then EtOAc was added and layers were separated. The aqueous layer was extracted with EtOAc and the organic layers combined and washed with water and brine. The organic solution was then dried over $Na_2SO_4$, filtered, and the filtrate was concentrated. The residue was re-crystallized from EtOAc/hexanes, dried, and used in boronic acid coupling reactions.

General Procedure Z: Grignard Reaction

To a suspension of m- or p-bromobenzaldehyde in THF (0.1-0.5 M) was added drop-wise alkylmagnesium bromide or chloride in ether or THF (1.1 eq) while stirring on ice. The mixture was allowed to warm to room temperature and stirred for 30 minutes, then poured into saturated $NH_4Cl$/EtOAc and the layers separated. The aqueous layer was extracted with EtOAc and the organic layers combined and washed with water and brine. The organic solution was then dried over $Na_2SO_4$, filtered, and the filtrate was concentrated and the residue was dried and used directly in the next step.

General Procedure AA: Reduction of Benzyl Alcohol

The alcohol obtained from general procedure Z was dissolved in trifluoroacetic acid (0.1-0.5 M) under nitrogen and cooled in an ice-salt bath maintained at −10° C. Triethylsilane (4 eq) was added to the solution slowly in order to maintain the bath at −10° C. The solution was then allowed to warm to room temperature and stirred for 3 hours. At completion, the mixture was poured into water and extracted with dichloromethane. The organic extract was washed with saturated aqueous $NaHCO_3$ and brine and dried over $Na_2SO_4$. After removal of the solvent in vacuo, the residue was purified by silica gel column chromatography to afford the desired m- or p-bromophenylalkane product.

General Procedure AB: Preparation of N-alkyl 5-chloro-isothiazole-sulfones:

Dithio-acid (1.0 eq) was dissolved in thionyl chloride (0.1-0.5 M) and the mixture was heated at 80-100° C. for 3 to 6 hours. At completion, the excess thionyl chloride was removed under pressure and compound was dried under vacuum and resulted white solid was used directly in the next step.

Tert-butylamine (1.0 eq) was dissolved in dry DMF (0.1-0.5 M) and 5 eq of $NaHCO_3$ was added. While stirring under nitrogen on ice, a solution of aryl/alky acetyl chloride (1.1 eq) in benzene was added drop wise. The mixture was then stirred for one hour and allowed to warm to room temperature. The reaction mixture was diluted with water/EtOAc and the layers separated. The aqueous layer was extracted with EtOAc and the organic layers combined and washed with water and brine. The organic solution was then dried over $Na_2SO_4$, filtered, and the filtrate was concentrated and the residue was dried and used directly in the next step.

A solution of di-amide (1.0 eq) was dissolved in anhydrous dichloromethane (0.1-0.5M) and was treated with sulfuryl chloride (1.1 eq) drop-wise at 0° C. and stirred at 25° C. for 3 to 6 hours. At completion, the reaction mixture was cooled to 0° C., quenched with water and stirred for 10 to 30 min. The organic layer was separated and aqueous layer was re-extracted with dichloromethane. The combined organic layers were dried with $MgSO_4$, filtered and concentrated to a light brown oil. The crude oil was purified by flash column chromatography (100% hexane to 40% ethyl acetate/hexane to 100% ethyl acetate) to yield off white solid.

To a solution of isothiazole compound (1 eq) in 1:1 DCM/HOAc (0.1-0.5 M) was added peracetic acid (32 wt. % solution in acetic acid, 10 eq) at 0° C. and the solution was stirred at the same temperature for 2 to 6 hours. At completion, the reaction mixture was diluted with water/EtOAc. The combined organic layer was washed with water, saturated NaHCO₃ and brine. The organic phase was then dried over Na₂SO₄, filtered, and concentrated. The residue was triturated several times with hexanes to afford the desired isothiazole-sulfone derivative.

General Procedure AC: Pd(II)-Catalyzed Coupling Reactions

A solution of aryl boronic acid (1.0 eq) in anhydrous dioxane (0.1-0.5 M) was added potassium carbonate (5-10 eq), aryl halide (1.1 eq) and Pd Cl₂ (dppf) (2.5 eq) under nitrogen atmosphere. The reaction mixture was degassed by the freeze-thaw method thrice and was heated at 80° C. for 24 to 48 hours. At completion the reaction mixture was cooled to 25° C., poured into water and extracted with dichloromethane. The combined organic layers were washed with brine, dried with MgSO₄ and concentrated in vacuo. The crude residue was purified by flash chromatography to yield light red solid.

General Procedure AD: Preparation of Boronic Acid Pinacol Cyclic Ester

To a solution of substituted aryl bromide (1 eq) in anhydrous DMF (0.1-0.5 M) was added bis(pinacolato)diboron (3 eq), [1,1'-bis(diphenylphosphino)ferrocene]-dichloro-palladium(II) (0.1 eq), and cesium carbonate (5 eq). The colored heterogeneous reaction mixture was stirred at 100° C. for 4-6 hours under nitrogen. At completion, the resulting slurry was filtered through celite, washed with ethyl acetate. The combined organic layers was washed with water and brine, dried over Na₂SO₄ and evaporated in vacuo. The residue was purified by silica gel column chromatography to provide the desired arylboronic acid-pinacol ester.

General Procedure AE: Preparation of 3- or 4-(Alkenyl)Phenylboronic Acid

To a suspension of m- or p-bromobenzaldehyde in THF (0.1-0.5 M) was added drop-wise alkylmagnesium bromide or chloride in ether or THF (1.1 eq) while stirring on ice. The mixture was allowed to warm to room temperature and stirred for 30 minutes, then poured into saturated NH₄Cl/EtOAc and the layers separated. The aqueous layer was extracted with EtOAc and the organic layers combined and washed with water and brine. The organic solution was then dried over Na₂SO₄, filtered, and the filtrate was concentrated and the residue was dried and used directly in the next step.

The Grignard product from step above was dissolved in dry dichloromethane (0.1-0.5 M) and N,N-diisopropylethylamine (5 eq) was added. The mixture was cooled on an ice bath and methanesulfonyl chloride (2 eq) was added dropwise. The mixture was allowed to warm to room temperature and stirred for 18 hours. At completion, the mixture was poured into water and extracted with dichloromethane. The organic extract was washed with water and brine and dried over Na₂SO₄. After removal of the solvent in vacuo, the residue was purified by silica gel column chromatography to afford the desired m- or p-bromophenylalkene product.

A solution of m- or p-bromophenylalkene in dry THF (0.1-0.5 M) was stirred under nitrogen in a dry ice-acetone bath, and s-butyllithium in cyclohexane (2 eq) was added dropwise. The mixture was stirred 10 minutes, then triisopropyl borate (3 eq) was added dropwise. The mixture was stirred an additional 30 minutes, then poured into excess 2M HCl and stirred 20 minutes. Then EtOAc was added and layers were separated. The aqueous layer was extracted with EtOAc and the organic layers combined and washed with water and brine. The organic solution was then dried over Na₂SO₄, filtered, and the filtrate was concentrated. The residue was recrystallized from EtOAc/hexanes, dried, and used in boronic acid coupling reactions.

General Procedure AF: Sonogashira Coupling

To a solution of the bromo-compound (1 eq) in anhydrous DMF (0.1-0.5 M) was added the appropriate terminal alkyne compound (2 eq) and a catalytic amount of tetrakis(triphenylphosphine)palladium(0) (0.2 eq), followed by copper(I) iodide (0.2 eq) and DIEA (5 eq). The reaction mixture was stirred at 120° C. under nitrogen for 6 hours. After cooling, the reaction mixture was diluted with water and extracted with ethyl acetate. The organic extract was washed with water and brine, and dried over Na₂SO₄. After removal of the solvent in vacuo, the residue was purified by flash column chromatography to afford the desired compound.

General Procedure AG: Removal of Tertiary-Butyl Group

A solution of N-tert-butyl compound (1.0 eq) in TFA (0.1M-0.5M) was treated with triisopropylsilane (0.05 M). The reaction mixture was heated at 70° C. for 24 to 48 hours. At completion, the mixture was cooled to 25° C. and concentrated in vacuo and co-evaporated with toluene. The crude residue was purified by column chromatography to yield off white solid.

General Procedure AH: Dealkylation

To 1 equivalent of the n-alkyl phenolic ether in DCM at −78° C. was added 10 equivalents of BBr₃. The solution was warmed to room temperature over 30 minutes, and the reaction mixture quenched with MeOH. The reaction mixture was then diluted with water/EtOAc and the layers separated. The aqueous layer was further extracted with EtOAc, and the organic layers combined, washed with water and brine, and dried over Na₂SO₄. The solvent was removed in vacuo and the residue subjected to silica gel chromatography to yield the final product.

Example 1

4-Bromophenylacetic acid (107.5 g, 0.5 mol) was treated according to general procedure A using 2,4-dichlorophenacyl bromide to give 2-(4-bromo-benzyl)-4-(2,4-dichloro-phenyl)-1H-imidazole.

LCMS: m/z 383 (M+H)⁺; ¹H NMR (CD₃OD, 400 MHz): δ 4.14 (s, 2H), 7.51 (d, 2H), 7.69 (d, 2H), 7.71 (m, 2H), 8.02 (m, 1H), 8.05 (s, 1H) ppm.

2-(4-Bromo-benzyl)-4-(2,4-dichloro-phenyl)-1H-imidazole (38.2 g, 0.1 mol) was treated as described in general procedure B using 1-fluoro-4-nitrobenzene to give 2-(4-bromo-benzyl)-1-(4-nitro-phenyl)-4-(2,4-dichloro-phenyl)-1H-imidazole.

LCMS: m/z 504 (M+H)⁺.

2-(4-Bromo-benzyl)-1-(4-nitro-phenyl)-4-(2,4-dichloro-phenyl)-1H-imidazole (30.2 g, 60 mmol) was treated as described in general procedure C to give 5-{4-[2-(4-bromo-benzyl)-4-(2,4-dichloro-phenyl)-imidazol-1-yl]-phenyl}-1,2,5-thiadiazolidine-3-one-1,1-dioxide.

LCMS: m/z 593 (M+H)⁺; ¹H NMR (DMSO-d₆, 400 MHz): δ 4.05 (s, 2H), 4.07 (s, 2H), 7.15 (d, 2H), 7.27 (d, 2H), 7.47 (dd, 1H), 7.51 (d, 2H), 7.53 (d, 2H), 7.64 (d, 1H), 7.89 (s, 1H), 8.19 (d, 1H) ppm.

5-{4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-tert-butylphenylboronic acid (36 mg, 0.2 mmol) to give 5-{4-[2-(4'-tert-butyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 645 (M+H)⁺; ¹H NMR (DMSO-d₆, 400 MHz): δ 1.30 (s, 9H), 4.06 (s, 2H), 4.08 (s, 2H), 7.15 (d, 2H), 7.19 (d,

2H), 7.36 (d, 2H), 7.45 (d, 2H), 7.49 (dd, 1H), 7.52 (d, 2H), 7.54 (d, 2H), 7.64 (d, 1H), 7.90 (s, 1H), 8.20 (d, 1H) ppm.

Example 2

5-{-4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-cyclopentylphenylboronic acid (38 mg, 0.2 mmol) to give 5-{-4-[2-(4'-cyclopentyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 657 (M+H)$^+$; $^1$H NMR (DMSO-d$_6$, 400 MHz): δ 1.22-1.81 (m, 8H), 2.52 (m, 1H), 4.05 (s, 2H), 4.07 (s, 2H), 7.15 (d, 2H), 7.18 (d, 2H), 7.27 (d, 2H), 7.37 (d, 2H), 7.48 (dd, 1H), 7.51 (d, 2H), 7.53 (d, 2H), 7.64 (d, 1H), 7.89 (s, 1H), 8.19 (d, 1H) ppm.

Example 3

5-{-4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 3-propoxyphenylboronic acid (36 mg, 0.2 mmol) to give 5-{-4-[4-(2,4-dichloro-phenyl)-2-(3'-propoxy-biphenyl-4-ylmethyl)-imidazol-1-yl]-phenyl}-1,2,5-thiadiazolidine-3-one-1,1-dioxide.

LCMS: m/z 647 (M+H)$^+$; $^1$H NMR (DMSO-d$_6$, 400 MHz): δ 0.99 (t, 3H), 1.73 (m, 2H), 3.99 (t, 2H), 4.05 (s, 2H), 4.08 (s, 2H), 7.16 (d, 2H), 7.18-7.25 (m, 4H), 7.28 (d, 2H), 7.48 (dd, 1H), 7.51 (d, 2H), 7.53 (d, 2H), 7.63 (d, 1H), 7.88 (s, 1H), 8.18 (d, 1H) ppm.

Example 4

5-{-4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-propoxyphenylboronic acid (36 mg, 0.2 mmol) to give 5-{-4-[4-(2,4-dichloro-phenyl)-2-(4'-propoxy-biphenyl-4-ylmethyl)-imidazol-1-yl]-phenyl}-1,2,5-thiadiazolidine-3-one-1,1-dioxide.

LCMS: m/z 647 (M+H)$^+$; $^1$H NMR (DMSO-d$_6$, 400 MHz): δ 1.01 (t, 3H), 1.74 (m, 2H), 4.00 (t, 2H), 4.05 (s, 2H), 4.08 (s, 2H), 7.15 (d, 2H), 7.18 (d, 2H), 7.20 (d, 2H), 7.27 (d, 2H), 7.48 (dd, 1H), 7.51 (d, 2H), 7.53 (d, 2H), 7.63 (d, 1H), 7.88 (s, 1H), 8.18 (d, 1H) ppm.

Example 5

5-{-4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 3-(cyclopentylmethoxy)phenylboronic acid (44 mg, 0.2 mmol, prepared according to general procedure H) to give 5-{-4-[2-(3'-cyclopentylmethoxy-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 687 (M+H)$^+$; $^1$H NMR (DMSO-d$_6$, 400 MHz): δ 1.32-2.16 (m, 9H), 3.82 (d, 2H), 4.05 (s, 2H), 4.07 (s, 2H), 7.15 (d, 2H), 7.18-7.24 (m, 4H), 7.35 (d, 2H), 7.48 (dd, 1H), 7.51 (d, 2H), 7.53 (d, 2H), 7.64 (d, 1H), 7.89 (s, 1H), 8.19 (d, 1H) ppm.

Example 6

5-{-4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 3-(3,3-dimethyl-butoxy)phenylboronic acid (45 mg, 0.2 mmol, prepared according to general procedure H) to give 5-(4-{4-(2,4-dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide.

LCMS: m/z 689 (M+H)$^+$; $^1$H NMR (DMSO-d$_6$, 400 MHz): δ 1.00 (s, 9H), 1.70 (t, 2H), 4.05 (s, 2H), 4.07 (t, 2H), 4.08 (s, 2H), 7.15 (d, 2H), 7.18-7.24 (m, 4H), 7.33 (d, 2H), 7.38 (d, 2H), 7.47 (dd, 1H), 7.55 (d, 2H), 7.64 (d, 1H), 7.89 (s, 1H), 8.18 (d, 1H) ppm.

Example 7

5-{-4-[2-(4-Bromo-benzyl)-4-(2,4-dichloro-phenyl)-imidazol-1-yl]-phenyl}-1,2,5-thiadiazolidine-3-one-1,1-dioxide (119 mg, 0.2 mmol) was treated as described in general procedure R using 4-phenylpiperidine (162 mg, 1 mmol) to give 5-(4-{4-(2,4-dichloro-phenyl)-2-[4-(4-phenyl-piperidin-1-yl)-benzyl]-imidazol-1-yl}-phenyl)-1,2,5-thiadiazolidine-3-one-1,1-dioxide.

LCMS: m/z 672 (M+H)$^+$; $^1$H NMR (DMSO-d$_6$, 400 MHz): δ 1.62-1.79 (m, 4H), 2.56 (m, 1H), 3.21-3.34 (m, 4H), 4.05 (s, 2H), 4.08 (s, 2H), 7.15 (d, 2H), 7.18-7.34 (m, 7H), 7.38 (d, 2H), 7.47 (dd, 1H), 7.55 (d, 2H), 7.64 (d, 1H), 7.89 (s, 1H), 8.18 (d, 1H) ppm.

Example 8

5-{-4-[2-(4-Bromo-benzyl)-4-(2,4-dichloro-phenyl)-imidazol-1-yl]-phenyl}-1,2,5-thiadiazolidine-3-one-1,1-dioxide (119 mg, 0.2 mmol) was treated as described in general procedure G using 3-methoxycarbonylphenylboronic acid (108 mg, 0.6 mmol) to give 4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-3-carboxylic acid methyl ester.

LCMS: m/z 647 (M+H)$^+$; $^1$H NMR (DMSO-d$_6$, 400 MHz): δ 3.79 (s, 3H), 4.06 (s, 2H), 4.09 (s, 2H), 7.15 (d, 2H), 7.18-7.24 (m, 4H), 7.33 (d, 2H), 7.38 (d, 2H), 7.47 (dd, 1H), 7.55 (d, 2H), 7.64 (d, 1H), 7.89 (s, 1H), 8.18 (d, 1H) ppm.

Example 9

4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-3-carboxylic acid methyl ester (33 mg, 0.05 mmol) was treated as described in general procedure P to give 4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-3-carboxylic acid.

LCMS: m/z 633 (M+H)$^+$; $^1$H NMR (DMSO-d$_6$, 400 MHz): δ 4.06 (s, 2H), 4.09 (s, 2H), 7.16 (d, 2H), 7.19-7.26 (m, 4H), 7.33 (d, 2H), 7.38 (d, 2H), 7.47 (dd, 1H), 7.55 (d, 2H), 7.64 (d, 1H), 7.90 (s, 1H), 8.19 (d, 1H) ppm.

Example 10

5-{-4-[2-(4-Bromo-benzyl)-4-(2,4-dichloro-phenyl)-imidazol-1-yl]-phenyl}-1,2,5-thiadiazolidine-3-one-1,1-dioxide (592 mg, 1 mmol) was treated as described in general procedure G using 2-chloro-5-pyridine-boronic acid (315 mg, 2 mmol) to give 5-{-4-[2-[4-(6-chloro-pyridin-3-yl)-benzyl]-4-(2,4-dichloro-phenyl)-imidazol-1-yl]-phenyl}-1,2,5-thiadiazolidine-3-one-1,1-dioxide.

LCMS: m/z 624 (M+H)$^+$; $^1$H NMR (DMSO-d$_6$, 400 MHz): δ 4.06 (s, 2H), 4.09 (s, 2H), 7.15 (d, 2H), 7.18-7.34 (m, 4H), 7.38 (d, 2H), 7.47 (dd, 1H), 7.55 (d, 2H), 7.64 (d, 1H), 7.89 (s, 1H), 8.18 (d, 1H), 8.37 (d, 1H) ppm.

Example 11

5-{4-[2-[4-(6-Chloro-pyridin-3-yl)-benzyl]-4-(2,4-dichloro-phenyl)-imidazol-1-yl]-phenyl}-1,2,5-thiadiazolidine-3-one-1,1-dioxide (63 mg, 0.1 mmol) was treated as described in general procedure L using cyclohexanol (20 mg, 0.2 mmol) to give 5-{4-[2-[4-(6-cyclohexyloxy-pyridin-3-yl)-benzyl]-4-(2,4-dichloro-phenyl)-imidazol-1-yl]-phenyl}-1,2,5-thiadiazolidine-3-one-1,1-dioxide.

LCMS: m/z 688 (M+H)$^+$; $^1$H NMR (DMSO-d$_6$, 400 MHz): δ 1.34-2.16 (m, 10H), 4.06 (s, 2H), 4.09 (s, 2H), 4.23 (m, 1H), 7.15 (d, 2H), 7.18-7.34 (m, 4H), 7.38 (d, 2H), 7.47 (dd, 1H), 7.55 (d, 2H), 7.64 (d, 1H), 7.89 (s, 1H), 8.18 (d, 1H), 8.28 (d, 1H) ppm.

Example 12

5-{4-[2-[4-(6-Chloro-pyridin-3-yl)-benzyl]-4-(2,4-dichloro-phenyl)-imidazol-1-yl]-phenyl}-1,2,5-thiadiazolidine-3-one-1,1-dioxide (63 mg, 0.1 mmol) was treated as described in general procedure L using piperidine (17 mg, 0.2 mmol) to give 5-(4-{4-(2,4-dichloro-phenyl)-2-[4-(3,4,5,6-tetrahydro-2H-[1,2']bipyridinyl-5'-yl)-benzyl]-imidazol-1-yl}-phenyl)-1,2,5-thiadiazolidine-3-one-1,1-dioxide.

LCMS: m/z 673 (M+H)$^+$; $^1$H NMR (DMSO-d$_6$, 400 MHz): δ 1.62-1.78 (m, 6H), 3.19-3.31 (m, 4H), 4.05 (s, 2H), 4.07 (s, 2H), 7.15 (d, 2H), 7.18-7.34 (m, 4H), 7.38 (d, 2H), 7.47 (dd, 1H), 7.55 (d, 2H), 7.64 (d, 1H), 7.89 (s, 1H), 8.18 (d, 1H), 8.25 (d, 1H) ppm.

Example 13

2-(4-Bromo-benzyl)-4-(2,4-dichloro-phenyl)-1H-imidazole (382 mg, 1 mmol) was treated as described in general procedure B using 5-fluoro-2-nitrotoluene (310 mg, 2 mmol) to give 2-(4-bromo-benzyl)-4-(2,4-dichloro-phenyl)-1-(3-methyl-4-nitro-phenyl)-1H-imidazole.

LCMS: m/z 518 (M+H)$^+$.

2-(4-Bromo-benzyl)-4-(2,4-dichloro-phenyl)-1-(3-methyl-4-nitro-phenyl)-1H-imidazole (310 mg, 0.6 mmol) was treated as described in general procedure C to give 5-{-4-[2-(4-bromo-benzyl)-4-(2,4-dichloro-phenyl)-imidazol-1-yl]-2-methyl-phenyl}-1,2,5-thiadiazolidine-3-one-1,1-dioxide.

LCMS: m/z 607 (M+H)$^+$; $^1$H NMR (DMSO-d$_6$, 400 MHz): δ 2.34 (s, 3H), 4.05 (s, 2H), 4.07 (s, 2H), 7.15 (d, 2H), 7.27-7.51 (m, 4H), 7.53 (d, 2H), 7.64 (d, 1H), 7.89 (s, 1H), 8.18 (d, 1H) ppm.

5-{-4-[2-(4-Bromo-benzyl)-4-(2,4-dichloro-phenyl)-imidazol-1-yl]-2-methyl-phenyl}-1,2,5-thiadiazolidine-3-one-1,1-dioxide (61 mg, 0.1 mmol) was treated as described in general procedure G using 4-cyclohexylphenylboronic acid (41 mg, 0.2 mmol) to give 5-{4-[2-(4'-cyclohexyl-biphenyl-4-ylmethyl)-4-(2,4-dichloro-phenyl)-imidazol-1-yl]-2-methyl-phenyl}-1,2,5-thiadiazolidine-3-one-1,1-dioxide.

LCMS: m/z 685 (M+H)$^+$; $^1$H NMR (DMSO-d$_6$, 400 MHz): δ 1.13-1.40 (m, 5H), 1.65-1.78 (m, 5H), 2.34 (s, 3H), 2.52 (m, 1H), 4.05 (s, 2H), 4.08 (s, 2H), 7.15 (d, 2H), 7.18-7.27 (m, 4H), 7.44-7.48 (m, 4H), 7.55 (d, 2H), 7.64 (d, 1H), 7.89 (s, 1H), 8.18 (d, 1H) ppm.

Example 14

5-{-4-[2-(4-Bromo-benzyl)-4-(2,4-difluoro-phenyl)-imidazol-1-yl]-phenyl}-1,2,5-thiadiazolidine-3-one-1,1-dioxide (prepared according to general procedures A, B and C subsequently) (56 mg, 0.1 mmol) was treated as described in general procedure G using 4-cyclohexylphenylboronic acid (41 mg, 0.2 mmol) to give 5-{4-[2-(4'-cyclohexyl-biphenyl-4-ylmethyl)-4-(2,4-difluoro-phenyl)-imidazol-1-yl]-phenyl}-1,2,5-thiadiazolidine-3-one-1,1-dioxide.

LCMS: m/z 639 (M+H)$^+$; $^1$H NMR (DMSO-d$_6$, 400 MHz): δ 1.22-1.44 (m, 5H), 1.69-1.81 (m, 5H), 2.52 (m, 1H), 4.05 (s, 2H), 4.07 (s, 2H), 7.13-7.16 (m, 5H), 7.27 (d, 2H), 7.37 (d, 2H), 7.41 (m, 1H), 7.51-7.55 (m, 5H), 8.12 (m, 1H) ppm.

By analogous methods to those used to prepare Example 14, the following compounds were synthesized:

| Ex. | Name | LC/MS (m/z) |
| --- | --- | --- |
| 15 | 5-{4-[2-(4'-Cyclohexyl-biphenyl-4-ylmethyl)-4-(2,4-difluoro-phenyl)-imidazol-1-yl]-2-methyl-phenyl}-1,2,5-thiadiazolidine-3-one-1,1-dioxide | 653 (M + H)$^+$ |
| 16 | 5-{4-[4-(4-Chloro-phenyl)-2-(4'-cyclohexyl-biphenyl-4-ylmethyl)-imidazol-1-yl]-phenyl}-1,2,5-thiadiazolidine-3-one-1,1-dioxide | 637 (M + H)$^+$ |
| 17 | 5-{4-[4-(2-Chloro-phenyl)-2-(4'-cyclohexyl-biphenyl-4-ylmethyl)-imidazol-1-yl]-phenyl}-1,2,5-thiadiazolidine-3-one-1,1-dioxide | 637 (M + H)$^+$ |
| 18 | 5-{4-[2-(4'-Cyclohexyl-biphenyl-4-ylmethyl)-4-(2,6-dichloro-phenyl)-imidazol-1-yl]-phenyl}-1,2,5-thiadiazolidine-3-one-1,1-dioxide | 671 (M + H)$^+$ |
| 19 | 5-{4-[2-(4'-Cyclohexyl-biphenyl-4-ylmethyl)-4-(2,4,6-trichloro-phenyl)-imidazol-1-yl]-phenyl}-1,2,5-thiadiazolidine-3-one-1,1-dioxide | 705 (M + H)$^+$ |
| 20 | 5-{4-[4-(2-Chloro-4-fluoro-phenyl)-2-(4'-cyclohexyl-biphenyl-4-ylmethyl)-imidazol-1-yl]-phenyl}-1,2,5-thiadiazolidine-3-one-1,1-dioxide | 655 (M + H)$^+$ |

Example 21

5-{-4-[2-(4-Bromo-benzyl)-4-(2,4-dichloro-phenyl)-imidazol-1-yl]-phenyl}-1,2,5-thiadiazolidine-3-one-1,1-dioxide (592 mg, 1 mmol) was treated as described in general procedure G using 4-aminophenylboronic acid (274 mg, 2 mmol) to give 5-{-4-[2-(4'-amino-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 604 (M+H)$^+$.

5-{4-[2-(4'-Amino-biphenyl-4-ylmethyl)-4-(2,4-dichloro-phenyl)-imidazol-1-yl]-phenyl}-1,2,5-thiadiazolidine-3-one-1,1-dioxide (61 mg, 0.1 mmol) was treated subsequently according to general procedure K using 3-(bromomethyl)-5-methylisoxazole (27 mg, 0.15 mmol) and general procedure U using isopropyl chloroformate (1M solution in toluene) (0.2 mL, 0.2 mmol) to give (4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-(5-methyl-isoxazol-3-ylmethyl)-carbamic acid isopropyl ester.

LCMS: m/z 785 (M+H)+; $^1$H NMR (DMSO-$d_6$, 400 MHz): δ 1.25 (d, 6H), 2.33 (s, 3H), 4.06 (s, 2H), 4.08 (s, 2H), 4.65 (s, 2H), 4.93 (m, 1H), 7.05-7.18 (m, 5H), 7.27 (d, 2H), 7.37 (d, 2H), 7.43-7.54 (m, 5H), 7.64 (d, 1H), 7.88 (s, 1H), 8.18 (d, 1H) ppm.

Example 22

5-{4-[2-(4'-Amino-biphenyl-4-ylmethyl)-4-(2,4-dichloro-phenyl)-imidazol-1-yl]-phenyl}-1,2,5-thiadiazolidine-3-one-1,1-dioxide (61 mg, 0.1 mmol) was treated subsequently according to general procedure K using 1-bromo-2-methylpropane (21 mg, 0.15 mmol) and general procedure U using isopropyl chloroformate (1M solution in toluene) (0.2 mL, 0.2 mmol) to give (4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-isobutyl-carbamic acid isopropyl ester.

LCMS: m/z 746 (M+H)+; $^1$H NMR (DMSO-$d_6$, 400 MHz): δ 0.87 (d, 6H), 1.24 (d, 6H), 1.66 (m, 1H), 3.51 (d, 2H), 4.06 (s, 2H), 4.08 (s, 2H), 4.93 (m, 1H), 7.16 (d, 2H), 7.18 (d, 2H), 7.27 (d, 2H), 7.37 (d, 2H), 7.47 (dd, 1H), 7.51 (d, 2H), 7.53 (d, 2H), 7.64 (d, 1H), 7.88 (s, 1H), 8.18 (d, 1H) ppm.

Example 23

3-[2-(4-Bromo-benzyl)-4-(2,4-dichloro-phenyl)-imidazol-1-yl]-phenylamine (prepared as described in general procedure M) (28.4 g, 60 mmol) was treated as described in general procedures E to F to give 5-{3-[2-(4-bromo-benzyl)-4-(2,4-dichloro-phenyl)-imidazol-1-yl]-phenyl}-1,2,5-thiadiazolidine-3-one-1,1-dioxide.

LCMS: m/z 593 (M+H)+; $^1$H NMR (DMSO-$d_6$, 400 MHz): δ 4.05 (s, 2H), 4.07 (s, 2H), 7.15 (d, 2H), 7.27 (d, 2H), 7.47-7.53 (m, 5H), 7.64 (d, 1H), 7.89 (s, 1H), 8.19 (d, 1H) ppm.

5-{3-[2-(4-Bromo-benzyl)-4-(2,4-dichloro-phenyl)-imidazol-1-yl]-phenyl}-1,2,5-thiadiazolidine-3-one-1,1-dioxide (592 mg, 1 mmol) was treated as described in general procedure G using 4-cyclohexylphenylboronic acid (408 mg, 2 mmol) to give 5-{3-[2-(4'-cyclohexyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 671 (M+H)+; $^1$H NMR (DMSO-$d_6$, 400 MHz): δ 1.22-1.43 (m, 5H), 1.69-1.81 (m, 5H), 2.52 (m, 1H), 4.05 (s, 2H), 4.07 (s, 2H), 7.15 (d, 2H), 7.18 (d, 2H), 7.27 (d, 2H), 7.37 (d, 2H), 7.46-7.54 (m, 5H), 7.64 (d, 1H), 7.89 (s, 1H), 8.19 (d, 1H) ppm.

The title compound can also be prepared using the following procedure starting from 3-nitroaniline. Methyl bromoacetate (6.77 mL, 73.5 mmol) was added to a mixture of 3-nitroaniline (9.21 g, 66.7 mmol), NaHCO$_3$ (14 g, 167 mol) and dimethylformamide (75 mL). The mixture was stirred at 70-75° C. for 3 hr and then cooled to room temperature. Water (600 mL) was added to the reaction mixture and the product was collected by filtration and washed 3 times with 50 mL portions of water. The yellow product, (3-nitrophenylamino)-acetic acid methyl ester was dried under reduced pressure to afford 12.4 g (88%).

Chlorosulfonyl isocyanate (8.68 mL, 100 mmol) was added dropwise to a solution of t-butyl alcohol (9.61 mL, 100 mmol) in dichloromethane (48.2 mL) at 0° C. The mixture was allowed to warm to room temperature and stirred for 30 min. 37.5 mL of this solution was then added dropwise to a mixture of (3-nitrophenylamino)-acetic acid methyl ester (10.5 g, 50 mmol), diisopropylethylamine (26 mL, 150 mol) and dichloromethane (50 mL) at 0° C. After the addition the mixture was allowed to warm to room temperature and washed with water (2×500 mL). The extract was dried (MgSO$_4$) and filtered. This extract containing Boc-protected sulfamide was diluted to a total volume of 300 mL by the addition of dichloromethane. Trifluoroacetic acid (75 mL) was added to the solution at 0° C. and the solution was stirred for 3 hr or until no starting material remained by TLC. The solution was washed with water (3×500 mL) and the product was precipitated by the addition of hexanes and collected by filtration. The product was washed with 5% dichloromethane in hexanes (50 mL) and dried under reduced pressure to afford 10.5 g of product.

A solution of NaOH (2 M, 2.0 equivalents) was added to a suspension of the Boc deprotected material (10.5 g, 36.3 mmol) in ethanol (75 mL) at 0° C. with rapid stirring until a thick precipitate formed (2 min). The mixture was acidified to pH of 5.0 by adding 6.0 M hydrochloric acid. The product, 1,1-dioxo-5-(3-nitrophenyl)-[1,2,5]thiadiazolidin-3-one was collected by filtration and washed with diethyl ether (50 mL). The product was dried under reduced pressure to afford the cyclized product (8.5 g, 91%).

A solution of nitro compound (8.5 g) in methanol (40 mL) was treated with 1.7 g of 10% Pd/C catalyst under hydrogen atmosphere for 18 h. The catalyst was removed by filtration. The solution was concentrated and 5-(3-amino-phenyl)-1,1-dioxo-[1,2,5]thiadiazolidin-3-one was crystallized out by addition of dichloromethane, collected by filtration and dried to provide 6.9 g of product (92% yield).

To a solution of 5-(3-amino-phenyl)-1,1-dioxo-[1,2,5]thiadiazolidin-3-one (5 g, 22 mmol) in 37.5 mL of 9:1 v/v acetonitrile-water was added NaHCO$_3$ (4.62 g, 55 mmol). The mixture was stirred at 25° C. while 2-bromo-1-(2,4-dichloro-phenyl)-ethanone (7.1 g, 26.4 mmol) was added. The mixture was stirred for 12-16 hours at 35° C. The mixture was cooled on an ice bath to further precipitate the product, which was then collected by filtration. The filtrate was concentrated under reduced pressure and a second crop of crude product was collected. The combined crude product was washed once with 25 mL water and dried, then washed once with 10 mL methyl tert-butyl ether and dried, to provide 6.36 g (70% yield) of 5-{3-[2-(2,4-dichloro-phenyl)-2-oxo-ethylamino]-phenyl}-1,1-dioxo-[1,2,5]thiadiazolidin-3-one.

To a mixture of phenacyl amine (9.4 g, 23 mmol), and NaHCO$_3$ (5.04 g, 60 mmol) in dichloromethane (30 mL) was added slowly a dichloromethane (10 mL) solution of (4'-cyclohexylbiphenyl)acetyl chloride (34 mmol), which was prepared by the reaction of oxalyl chloride with (4'-cyclohexyl-biphenyl-4-yl)-acetic acid (10 g, 34 mmol) which in turn was prepared from (4-cyclohexylphenyl)boronic acid and 4-bromophenylacetic acid via Suzuki coupling. The mixture was allowed to stir at 25° C. for 9 hours. The mixture was then diluted with tetrahydrofuran, washed with dilute brine, dried over sodium sulfate, and evaporated. The product, 2-(4'-cyclohexyl-biphenyl-4-yl)-N-[2-(2,4-dichloro-phenyl)-2-oxo-ethyl]-N-[3-(1,1,4-trioxo-[1,2,5]thiadiazolidin-2-yl)- phenyl]-acetamide, was purified by column chromatography on silica gel using 1-8% methanol in dichloromethane.

To a solution of ammonium acetate (223 mg, 2.9 mmol) in acetic acid (0.5 mL), was added the above tertiary amide (200 mg. 0.29 mmol) in dimethylformamide (0.5 mL) and the mixture was then stirred at 90° C. for 18 hours, after which it was diluted with tetrahydrofuran and washed 5 times with dilute brine, dried over sodium sulfate, and evaporated to dryness. The crude solid material was washed extensively with methanol to provide 140 mg of pure title product.

Example 24

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-tert-butylphenylboronic acid (36 mg, 0.2 mmol) to give 5-{3-[2-(4'-tert-butyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 645 (M+H)$^+$; $^1$H NMR (DMSO-d$_6$, 400 MHz): δ 1.30 (s, 9H), 4.06 (s, 2H), 4.08 (s, 2H), 7.15 (d, 2H), 7.19 (d, 2H), 7.29 (d, 2H), 7.38 (d, 2H), 7.46-7.54 (m, 5H), 7.64 (d, 1H), 7.90 (s, 1H), 8.19 (d, 1H) ppm.

Example 25

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 3-(3,3-dimethyl-butoxy)phenylboronic acid (45 mg, 0.2 mmol, prepared according to general procedure H) to give 5-(3-{4-(2,4-dichloro-phenyl)-2-[3'-(3,3-dimethyl-butoxy)-biphenyl-4-ylmethyl-imidazol-1-yl}-phenyl)-1,2,5-thiadiazolidine-3-one-1,1-dioxide.

LCMS: m/z 689 (M+H)$^+$; $^1$H NMR (DMSO-d$_6$, 400 MHz): δ 0.97 (s, 9H), 1.67 (t, 2H), 4.05 (s, 2H), 4.07 (t, 2H), 4.08 (s, 2H), 7.05-7.12 (m, 4H), 7.29 (d, 2H), 7.38 (d, 2H), 7.46-7.54 (m, 5H), 7.64 (d, 1H), 7.90 (s, 1H), 8.19 (d, 1H) ppm.

By analogous methods to those used to prepare Example 25, the following compounds were synthesized:

| Ex. | Name | LC/MS (m/z) |
|---|---|---|
| 26 | 5-{3-[4-(2,4-Dichloro-phenyl)-2-(3'-methanesulfonyl-biphenyl-4-ylmethyl)-imidazol-1-yl]-phenyl}-1,2,5-thiadiazolidine-3-one-1,1-dioxide | 667 (M + H)$^+$ |
| 27 | 5-{3-[2-(3'-Cyclohexanesulfonyl-biphenyl-4-ylmethyl)-4-(2,4-dichloro-phenyl)-imidazol-1-yl]-phenyl}-1,2,5-thiadiazolidine-3-one-1,1-dioxide | 735 (M + H)$^+$ |
| 28 | 5-{3-[2-(4'-Cyclohexanesulfonyl-biphenyl-4-ylmethyl)-4-(2,4-dichloro-phenyl)-imidazol-1-yl]-phenyl}-1,2,5-thiadiazolidine-3-one-1,1-dioxide | 735 (M + H)$^+$ |
| 29 | 5-{3-[4-(2,4-Dichloro-phenyl)-2-(3'-propoxy-biphenyl-4-ylmethyl)-imidazol-1-yl]-phenyl}-1,2,5-thiadiazolidine-3-one-1,1-dioxide | 647 (M + H)+ |
| 30 | 5-{3-[2-(3'-Butoxy-biphenyl-4-ylmethyl)-4-(2,4-dichloro-phenyl)-imidazol-1-yl]-phenyl}-1,2,5-thiadiazolidine-3-one-1,1-dioxide | 661 (M + H)$^+$ |
| 31 | 5-(3-{4-(2,4-Dichloro-phenyl)-2-[3'-(4,4,4-trifluoro-butoxy)-biphenyl-4-ylmethyl-imidazol-1-yl}-phenyl)-1,2,5-thiadiazolidine-3-one-1,1-dioxide | 715 (M + H)+ |
| 32 | 5-{3-[4-(2,4-Dichloro-phenyl)-2-(3'-ethoxy-biphenyl-4-ylmethyl)-imidazol-1-yl]-phenyl}-1,2,5-thiadiazolidine-3-one-1,1-dioxide | 633 (M + H)$^+$ |
| 33 | 5-{3-[2-(3'-Cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide | 701 (M + H)$^+$ |
| 34 | 5-(3-{4-(2,4-Dichloro-phenyl)-2-[3'-(3-methyl-butoxy)-biphenyl-4-ylmethyl-imidazol-1-yl}-phenyl)-1,2,5-thiadiazolidine-3-one-1,1-dioxide | 675 (M + H)$^+$ |
| 35 | 5-{3-[2-(3'-Cyclopentylmethoxy-biphenyl-4-ylmethyl)-4-(2,4-dichloro-phenyl)-imidazol-1-yl]-phenyl}-1,2,5-thiadiazolidine-3-one-1,1-dioxide | 687 (M + H)$^+$ |
| 36 | 5-{3-[2-(3'-Cyclohexyloxy-biphenyl-4-ylmethyl)-4-(2,4-dichloro-phenyl)-imidazol-1-yl]-phenyl}-1,2,5-thiadiazolidine-3-one-1,1-dioxide | 687 (M + H)$^+$ |
| 37 | 5-(3-{4-(2,4-Dichloro-phenyl)-2-[3'-(2,2-dimethyl-propoxy)-biphenyl-4-ylmethyl-imidazol-1-yl}-phenyl)-1,2,5-thiadiazolidine-3-one-1,1-dioxide | 675 (M + H)$^+$ |
| 38 | 5-{3-[2-(3'-tert-Butoxy-biphenyl-4-ylmethyl)-4-(2,4-dichloro-phenyl)-imidazol-1-yl]-phenyl}-1,2,5-thiadiazolidine-3-one-1,1-dioxide | 661 (M + H)$^+$ |
| 39 | 5-{3-[2-[3'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide | 715 (M + H)$^+$ |
| 40 | 5-{3-[2-[3'-(2-Cyclopentyl-ethoxy)-biphenyl-4-ylmethyl]-4-(2,4-dichloro-phenyl)-imidazol-1-yl]-phenyl}-1,2,5-thiadiazolidine-3-one-1,1-dioxide | 701 (M + H)$^+$ |
| 41 | 5-{3-[4-(2,4-Dichloro-phenyl)-2-(3'-phenethyloxy-biphenyl-4-ylmethyl)-imidazol-1-yl]-phenyl}-1,2,5-thiadiazolidine-3-one-1,1-dioxide | 709 (M + H)$^+$ |
| 42 | 5-(3-{4-(2,4-Dichloro-phenyl)-2-[3'-(4,4-dimethyl-pentyl)-biphenyl-4-ylmethyl-imidazol-1-yl}-phenyl)-1,2,5-thiadiazolidine-3-one-1,1-dioxide | 687 (M + H)$^+$ |

-continued

| Ex. | Name | LC/MS (m/z) |
|---|---|---|
| 43 | 5-{3-[2-[3'-(2-Cyclohexyl-ethyl)-biphenyl-4-ylmethyl]-4-(2,4-dichloro-phenyl)-imidazol-1-yl]-phenyl}-1,2,5-thiadiazolidine-3-one-1,1-dioxide | 699 (M + H)+ |
| 44 | 5-(3-{4-(2,4-Dichloro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide | 705 (M + H)+ |

Example 45

5-(3-{4-(2,4-Dichloro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide (14 mg, 0.02 mmol) was treated as described in general procedure S to give 5-(3-{4-(2,4-dichloro-phenyl)-2-[3'-(3,3-dimethyl-butane-1-sulfonyl)-biphenyl-4-ylmethyl]-imidazol-1-yl}-phenyl)-1,2,5-thiadiazolidine-3-one-1,1-dioxide.

LCMS: m/z 737 (M+H)+; $^1$H NMR (DMSO-$d_6$, 400 MHz): δ 0.89 (s, 9H), 1.46 (m, 2H), 3.27 (m, 2H), 4.06 (s, 2H), 4.09 (s, 2H), 7.18 (d, 2H), 7.21 (d, 2H), 7.29-7.41 (m, 4H), 7.49-7.58 (m, 5H), 7.63 (d, 1H), 7.88 (s, 1H), 8.18 (d, 1H) ppm.

Example 46

5-(3-{4-(2,4-Dichloro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide (14 mg, 0.02 mmol) was treated as described in general procedure T to give 5-(3-{4-(2,4-dichloro-phenyl)-2-[3'-(3,3-dimethyl-butane-1-sulfinyl)-biphenyl-4-ylmethyl]-imidazol-1-yl}-phenyl)-1,2,5-thiadiazolidine-3-one-1,1-dioxide.

LCMS: m/z 721 (M+H)+; $^1$H NMR (DMSO-$d_6$, 400 MHz): δ 0.86 (s, 9H), 1.45 (m, 2H), 2.98 (m, 2H), 4.05 (s, 2H), 4.08 (s, 2H), 7.18 (d, 2H), 7.21 (d, 2H), 7.26-7.38 (m, 4H), 7.47-7.56 (m, 5H), 7.63 (d, 1H), 7.88 (s, 1H), 8.18 (d, 1H) ppm.

Example 47

5-{3-[2-(4-Bromo-benzyl)-4-(2,4-dichloro-phenyl)-imidazol-1-yl]-phenyl}-1,2,5-thiadiazolidine-3-one-1,1-dioxide (119 mg, 0.2 mmol) was treated as described in general procedure G using 3-(cyclohexylmethylsulfanyl)phenylboronic acid (100 mg, 0.4 mmol, prepared according to general procedure I) to give 5-{3-[2-(3'-cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 717 (M+H)+; $^1$H NMR (DMSO-$d_6$, 400 MHz): δ 0.97-1.23 (m, 6H), 1.48 (m, 1H), 1.58-1.87 (m, 4H), 2.88 (d, 2H), 4.05 (s, 2H), 4.08 (s, 2H), 7.12-7.18 (m, 4H), 7.33-7.38 (m, 4H), 7.46-7.58 (m, 5H), 7.63 (d, 1H), 7.88 (s, 1H), 8.18 (d, 1H) ppm.

Example 48

5-{3-[2-(3'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide (15 mg, 0.02 mmol) was treated as described in general procedure S to give 5-{3-[2-(3'-cyclohexylmethylsulfonyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 749 (M+H)+; $^1$H NMR (DMSO-$d_6$, 400 MHz): δ 1.00-1.24 (m, 6H), 1.53 (m, 1H), 1.59-1.89 (m, 4H), 3.20 (d, 2H), 4.05 (s, 2H), 4.08 (s, 2H), 7.18 (d, 2H), 7.21 (d, 2H), 7.29-7.41 (m, 4H), 7.46-7.58 (m, 5H), 7.63 (d, 1H), 7.88 (s, 1H), 8.18 (d, 1H) ppm.

Example 49

5-{3-[2-(3'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide (15 mg, 0.02 mmol) was treated as described in general procedure T to give 5-{3-[2-(3'-cyclohexylmethylsulfinyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 733 (M+H)+; $^1$H NMR (CD$_3$OD, 400 MHz): δ 1.00-1.86 (m, 11H), 3.03 (m, 2H), 4.05 (s, 2H), 4.08 (s, 2H), 7.18 (d, 2H), 7.21 (d, 2H), 7.27-7.39 (m, 4H), 7.46-7.58 (m, 5H), 7.63 (d, 1H), 7.88 (s, 1H), 8.18 (d, 1H) ppm.

Example 50

5-{3-[2-(4-Bromo-benzyl)-4-(2,4-dichloro-phenyl)-imidazol-1-yl]-phenyl}-1,2,5-thiadiazolidine-3-one-1,1-dioxide (119 mg, 0.2 mmol) was treated as described in general procedure G using 3-(cyclohexylmethylsulfanyl)phenylboronic acid (106 mg, 0.4 mmol, prepared according to general procedure I) to give 5-{3-[2-(3'-(2-cyclohexyl-ethylsulfanyl)-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 731 (M+H)+; $^1$H NMR (DMSO-$d_6$, 400 MHz): δ 0.85-1.72 (m, 13H), 3.03 (t, 2H), 4.05 (s, 2H), 4.08 (s, 2H), 7.17-7.26 (m, 4H), 7.34-7.42 (m, 4H), 7.47-7.58 (m, 5H), 7.64 (d, 1H), 7.89 (s, 1H), 8.19 (d, 1H) ppm.

Example 51

5-{3-[2-(3'-(2-Cyclohexyl-ethylsulfanyl)-biphenyl-4-ylmethyl)-4-(2,4-dichloro-phenyl)-imidazol-1-yl]-phenyl}-1,2,5-thiadiazolidine-3-one-1,1-dioxide (15 mg, 0.02 mmol) was treated as described in general procedure S to give 5-{3-[2-(3'-(2-cyclohexyl-ethanesulfonyl)-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 763 (M+H)+; $^1$H NMR (DMSO-$d_6$, 400 MHz): δ 0.85-1.72 (m, 13H), 3.33 (m, 2H), 4.05 (s, 2H), 4.08 (s, 2H), 7.22-7.29 (m, 4H), 7.37-7.47 (m, 4H), 7.51-7.59 (m, 5H), 7.64 (d, 1H), 7.89 (s, 1H), 8.19 (d, 1H) ppm.

Example 52

5-{3-[2-(3'-(2-Cyclohexyl-ethylsulfanyl)-biphenyl-4-ylmethyl)-4-(2,4-dichloro-phenyl)-imidazol-1-yl]-phenyl}-1,2,5-thiadiazolidine-3-one-1,1-dioxide (15 mg, 0.02 mmol) was treated as described in general procedure T to give 5-{3-[2-(3'-(2-cyclohexyl-ethanesulfinyl)-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 747 (M+H)⁺; ¹H NMR (CD₃OD, 400 MHz): δ 0.85-1.72 (m, 13H), 3.07 (m, 2H), 4.05 (s, 2H), 4.08 (s, 2H), 7.21-7.28 (m, 4H), 7.37-7.44 (m, 4H), 7.49-7.58 (m, 5H), 7.64 (d, 1H), 7.88 (s, 1H), 8.18 (d, 1H) ppm.

Example 53

5-{3-[2-(4-Bromo-benzyl)-4-(2,4-dichloro-phenyl)-imidazol-1-yl]-phenyl}-1,2,5-thiadiazolidine-3-one-1,1-dioxide (119 mg, 0.2 mmol) was treated as described in general procedure G using 3-(phenethylsulfanyl)phenylboronic acid (104 mg, 0.4 mmol, prepared according to general procedure I) to give 5-{3-[4-(2,4-dichloro-phenyl)-2-(3'-phenethylsulfanyl-biphenyl-4-ylmethyl)-imidazol-1-yl]-phenyl}-1,2,5-thiadiazolidine-3-one-1,1-dioxide.

LCMS: m/z 725 (M+H)⁺; ¹H NMR (DMSO-d₆, 400 MHz): δ 2.89 (t, 2H), 3.30 (t, 2H), 4.07 (s, 2H), 4.09 (s, 2H), 7.18-7.22 (m, 5H), 7.25-7.32 (m, 6H), 7.37-7.49 (m, 4H), 7.53 (m, 1H), 7.57 (d, 2H), 7.64 (d, 1H), 7.90 (s, 1H), 8.20 (d, 1H) ppm.

Example 54

5-{3-[2-(4-Bromo-benzyl)-4-(2,4-difluoro-phenyl)-imidazol-1-yl]-phenyl}-1,2,5-thiadiazolidine-3-one-1,1-dioxide (prepared according to general procedures A, J and C stepwise) (112 mg, 0.2 mmol) was treated as described in general procedure G using 3-(3,3-dimethyl-butylsulfanyl)phenylboronic acid (96 mg, 0.4 mmol, prepared according to general procedure I) to give 5-(3-{4-(2,4-difluoro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide.

LCMS: m/z 673 (M+H)⁺; ¹H NMR (DMSO-d₆, 400 MHz): δ 0.91 (s, 9H), 1.49 (m, 2H), 2.96 (m, 2H), 4.05 (s, 2H), 4.07 (s, 2H), 7.12-7.18 (m, 4H), 7.27-7.36 (m, 5H), 7.53-7.59 (m, 5H), 7.95-8.11 (m, 2H) ppm.

Example 55

5-(3-{4-(2,4-Difluoro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide (14 mg, 0.02 mmol) was treated as described in general procedure S to give 5-(3-{4-(2,4-difluoro-phenyl)-2-[3'-(3,3-dimethyl-butane-1-sulfonyl)-biphenyl-4-ylmethyl]-imidazol-1-yl}-phenyl)-1,2,5-thiadiazolidine-3-one-1,1-dioxide.

LCMS: m/z 705 (M+H)⁺; ¹H NMR (CD₃OD, 400 MHz): δ 0.90 (s, 9H), 1.48 (m, 2H), 3.25 (m, 2H), 4.05 (s, 2H), 4.07 (s, 2H), 7.14-7.21 (m, 4H), 7.28-7.39 (m, 5H), 7.53-7.59 (m, 5H), 7.95-8.11 (m, 2H) ppm.

Example 56

5-(3-{4-(2,4-Difluoro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide (14 mg, 0.02 mmol) was treated as described in general procedure T to give 5-(3-{4-(2,4-difluoro-phenyl)-2-[3'-(3,3-dimethyl-butane-1-sulfinyl)-biphenyl-4-ylmethyl]-imidazol-1-yl}-phenyl)-1,2,5-thiadiazolidine-3-one-1,1-dioxide.

LCMS: m/z 689 (M+H)⁺; ¹H NMR (DMSO-d₆, 400 MHz): δ 0.91 (s, 9H), 1.48 (m, 2H), 2.98 (m, 2H), 4.05 (s, 2H), 4.08 (s, 2H), 7.13-7.21 (m, 4H), 7.27-7.39 (m, 5H), 7.53-7.59 (m, 5H), 7.95-8.11 (m, 2H) ppm.

Example 57

5-{3-[2-(4-Bromo-benzyl)-4-(2,4-difluoro-phenyl)-imidazol-1-yl]-phenyl}-1,2,5-thiadiazolidine-3-one-1,1-dioxide (prepared according to general procedures A, R and C stepwise) (56 mg, 0.1 mmol) was treated as described in general procedure G using 4-cyclohexylphenylboronic acid (41 mg, 0.2 mmol) to give 5-{3-[2-(4'-cyclohexyl-biphenyl-4-ylmethyl)-4-(2,4-difluoro-phenyl)-imidazol-1-yl]-phenyl}-1,2,5-thiadiazolidine-3-one-1,1-dioxide.

LCMS: m/z 639 (M+H)⁺; ¹H NMR (DMSO-d₆, 400 MHz): δ 1.22-1.44 (m, 5H), 1.69-1.81 (m, 5H), 2.52 (m, 1H), 4.05 (s, 2H), 4.07 (s, 2H), 7.13-7.16 (m, 5H), 7.27 (d, 2H), 7.37 (d, 2H), 7.41 (m, 1H), 7.51-7.55 (m, 5H), 8.12 (m, 1H) ppm.

By analogous methods to those used to prepare Example 57, the following compounds were synthesized:

| Ex. | Name | LC/MS (m/z) |
| --- | --- | --- |
| 58 | 5-{5-[2-(4'-Cyclohexyl-biphenyl-4-ylmethyl)-4-(2,4-difluoro-phenyl)-imidazol-1-yl]-2-methyl-phenyl}-1,2,5-thiadiazolidine-3-one-1,1-dioxide | 653 (M + H)⁺ |
| 59 | 5-{5-[2-(4'-Cyclohexyl-biphenyl-4-ylmethyl)-4-(2,4-dichloro-phenyl)-imidazol-1-yl]-2-methyl-phenyl}-1,2,5-thiadiazolidine-3-one-1,1-dioxide | 685 (M + H)⁺ |
| 60 | 5-{5-[2-(4'-Cyclohexyl-biphenyl-4-ylmethyl)-4-(2,4-dichloro-phenyl)-imidazol-1-yl]-2-methoxy-phenyl}-1,2,5-thiadiazolidine-3-one-1,1-dioxide | 701 (M + H)⁺ |
| 61 | 5-{3-[2-(4'-Cyclohexyl-biphenyl-4-ylmethyl)-4-(2,6-dichloro-phenyl)-imidazol-1-yl]-phenyl}-1,2,5-thiadiazolidine-3-one-1,1-dioxide | 671 (M + H)⁺ |
| 62 | 5-{3-[2-(4'-Cyclohexyl-biphenyl-4-ylmethyl)-4-(2,4,6-trichloro-phenyl)-imidazol-1-yl]-phenyl}-1,2,5-thiadiazolidine-3-one-1,1-dioxide | 705 (M + H)⁺ |
| 63 | 5-(3-{4-(2,6-Dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide | 689 (M + H)⁺ |
| 64 | 5-{3-[2-(3'-Cyclohexylmethoxy-biphenyl-4-ylmethyl)-4-(2,6-dichloro-phenyl)-imidazol-1-yl]-phenyl}-1,2,5-thiadiazolidine-3-one-1,1-dioxide | 701 (M + H)⁺ |
| 65 | 5-(3-{4-(2,4-Difluoro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide | 657 (M + H)+ |

Example 66

4-Iodophenylacetic acid (26.2 g, 0.1 mol) was treated according to general procedure A using 2,4-dichlorophenacyl bromide to give 4-(2,4-dichloro-phenyl)-2-(4-iodo-benzyl)-1H-imidazole.

LCMS: m/z 429 (M+H)$^+$.

4-(2,4-Dichloro-phenyl)-2-(4-iodo-benzyl)-1H-imidazole (12.9 g, 30 mmol) was treated as described in general procedures B and C stepwise to give 5-{-4-[4-(2,4-dichloro-phenyl)-2-(4-iodo-benzyl)-imidazol-1-yl]-phenyl}-1,2,5-thiadiazolidine-3-one-1,1-dioxide.

LCMS: m/z 639 (M+H)$^+$.

5-{-4-[4-(2,4-Dichloro-phenyl)-2-(4-iodo-benzyl)-imidazol-1-yl]-phenyl}-1,2,5-thiadiazolidine-3-one-1,1-dioxide (3.2 g, 5 mmol) was treated as described in general procedure G using 4-bromophenylboronic acid (2.0 g, 10 mmol) to give 5-{-4-[2-(4'-bromo-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 669 (M+H)$^+$; $^1$H NMR (DMSO-d$_6$, 400 MHz): δ 4.05 (s, 2H), 4.07 (s, 2H), 7.15 (d, 2H), 7.19 (d, 2H), 7.36 (d, 2H), 7.45 (d, 2H), 7.49 (dd, 1H), 7.52 (d, 2H), 7.54 (d, 2H), 7.64 (d, 1H), 7.89 (s, 1H), 8.19 (d, 1H) ppm.

5-{4-[2-(4'-Bromo-biphenyl-4-ylmethyl)-4-(2,4-dichloro-phenyl)-imidazol-1-yl]-phenyl}-1,2,5-thiadiazolidine-3-one-1,1-dioxide (268 mg, 0.4 mmol) was treated as described in general procedure R using excess piperazine (346 mg, 4 mmol) to give the desired compound 5-{-4-[4-(2,4-dichloro-phenyl)-2-(4'-piperazin-1-yl-biphenyl-4-ylmethyl)-imidazol-1-yl]-phenyl}-1,2,5-thiadiazolidine-3-one-1,1-dioxide.

LCMS: m/z 673 (M+H)$^+$; $^1$H NMR (DMSO-d$_6$, 400 MHz): δ 3.01 (m, 4H), 3.31 (m, 4H), 4.05 (s, 2H), 4.08 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 67

5-{4-[2-(4'-Bromo-biphenyl-4-ylmethyl)-4-(2,4-dichloro-phenyl)-imidazol-1-yl]-phenyl}1,2,5-thiadiazolidine-3-one-1,1-dioxide (67 mg, 0.1 mmol) was treated as described in general procedure R using excess 1-methylpiperazine (100 mg, 1 mmol) to give 5-(4-{4-(2,4-dichloro-phenyl)-2-[4'-(4-methyl-piperazin-1-yl)-biphenyl-4-ylmethyl]-imidazol-1-yl}-phenyl)-1,2,5-thiadiazolidine-3-one-1,1-dioxide.

LCMS: m/z 687 (M+H)$^+$; $^1$H NMR (DMSO-d$_6$, 400 MHz): δ 2.43 (s, 3H), 3.12 (m, 4H), 3.34 (m, 4H), 4.05 (s, 2H), 4.08 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 68

5-{4-[2-(4'-Bromo-biphenyl-4-ylmethyl)-4-(2,4-dichloro-phenyl)-imidazol-1-yl]-phenyl}1,2,5-thiadiazolidine-3-one-1,1-dioxide (134 mg, 0.2 mmol) was treated as described in general procedure R using excess piperazin-2-one (200 mg, 2 mmol) to give 4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-piperazin-2-one.

LCMS: m/z 687 (M+H)$^+$; $^1$H NMR (DMSO-d$_6$, 400 MHz): δ 3.22-3.34 (m, 4H), 4.01 (s, 2H), 4.05 (s, 2H), 4.08 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 69

5-{4-[4-(2,4-Dichloro-phenyl)-2-(4'-piperazin-1-yl-biphenyl-4-ylmethyl)-imidazol-1-yl]-phenyl}-1,2,5-thiadiazolidine-3-one-1,1-dioxide (20 mg, 0.03 mmol) was treated as described in general procedure U using neopentyl chloroformate (9 mg, 0.06 mmol) to give 4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-piperazine-1-carboxylic acid 2,2-dimethyl-propyl ester.

LCMS: m/z 787 (M+H)$^+$; $^1$H NMR (CD$_3$OD, 400 MHz): δ 1.06 (s, 9H), 3.17-3.36 (m, 8H), 4.02 (s, 2H), 4.06 (s, 2H), 4.08 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.20 (d, 1H) ppm.

Example 70

5-{4-[2-(4'-Bromo-biphenyl-4-ylmethyl)-4-(2,4-dichloro-phenyl)-imidazol-1-yl]-phenyl}-1,2,5-thiadiazolidine-3-one-1,1-dioxide (268 mg, 0.4 mmol) was treated as described in general procedure L using 2-(trimethylsilyl)ethoxymethyl chloride (142 µL, 0.8 mmol) to give 5-{-4-[2-(4'-bromo-biphenyl-4-ylmethyl)-4-(2,4-dichloro-phenyl)-imidazol-1-yl]-phenyl}-2-(2-trimethylsilanyl-ethoxymethyl)-1,2,5-thiadiazolidine-3-one-1,1-dioxide.

LCMS: m/z 799 (M+H)$^+$.

5-{4-[2-(4'-Bromo-biphenyl-4-ylmethyl)-4-(2,4-dichloro-phenyl)-imidazol-1-yl]-phenyl}-2-(2-trimethylsilanyl-ethoxymethyl)-1,2,5-thiadiazolidine-3-one-1,1-dioxide (240 mg, 0.3 mmol) was treated as described in general procedure R using excess piperazin-2-one (301 mg, 3 mmol) to give 4-[4'-(4-(2,4-dichloro-phenyl)-1-{4-[1,1,4-trioxo-5-(2-trimethylsilanyl-ethoxymethyl)-[1,2,5]thiadiazolidin-2-yl]-phenyl}-1H-imidazol-2-ylmethyl)-biphenyl-4-yl]-piperazin-2-one.

LCMS: m/z 817 (M+H)$^+$.

4-[4'-(4-(2,4-Dichloro-phenyl)-1-{4-[1,1,4-trioxo-5-(2-trimethylsilanyl-ethoxymethyl)-[1,2,5]thiadiazolidin-2-yl]-phenyl}-1H-imidazol-2-ylmethyl)-biphenyl-4-yl]-piperazin-2-one (17 mg, 0.02 mmol) was treated as described in general procedure L (using iodomethane) and general procedure W stepwise to give the desired compound 4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-1-methyl-piperazin-2-one.

LCMS: m/z 701 (M+H)$^+$; $^1$H NMR (CD$_3$OD, 400 MHz): δ 2.94 (s, 3H), 3.28-3.36 (m, 4H), 4.01 (s, 2H), 4.08 (s, 2H), 4.16 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 71

4-[4'-(4-(2,4-Dichloro-phenyl)-1-{4-[1,1,4-trioxo-5-(2-trimethylsilanyl-ethoxymethyl)-[1,2,5]thiadiazolidin-2-yl]-phenyl}-1H-imidazol-2-ylmethyl)-biphenyl-4-yl]-piperazin-2-one (17 mg, 0.02 mmol) was treated as described in general procedure L (using iodoethane) and general procedure W stepwise to give 4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-1-ethyl-piperazin-2-one.

LCMS: m/z 715 (M+H)$^+$; $^1$H NMR (CD$_3$OD, 400 MHz): δ 1.09 (t, 3H), 3.28-3.36 (m, 4H), 3.57 (q, 2H), 4.01 (s, 2H), 4.08 (s, 2H), 4.16 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 72

4-[4'-(4-(2,4-Dichloro-phenyl)-1-{4-[1,1,4-trioxo-5-(2-trimethylsilanyl-ethoxymethyl)-[1,2,5]thiadiazolidin-2-yl]- phenyl}-1H-imidazol-2-ylmethyl)-biphenyl-4-yl]-piperazin-2-one (17 mg, 0.02 mmol) was treated as described in general procedure L (using 2-iodopropane) and general procedure W stepwise to give 4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-1-isopropyl-piperazin-2-one.

LCMS: m/z 729 (M+H)$^+$; $^1$H NMR (CD$_3$OD, 400 MHz): δ 1.06 (d, 6H), 3.28-3.36 (m, 4H), 3.71 (m, 1H), 4.01 (s, 2H), 4.08 (s, 2H), 4.15 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 73

4-[4'-(4-(2,4-Dichloro-phenyl)-1-{-4-[1,1,4-trioxo-5-(2-trimethylsilanyl-ethoxymethyl)-[1,2,5]thiadiazolidin-2-yl]-phenyl}-1H-imidazol-2-ylmethyl)-biphenyl-4-yl]-piperazin-2-one (17 mg, 0.02 mmol) was treated as described in general procedure L [using iodocyclohexane (13 mg, 0.06 mmol)] and general procedure W stepwise to give 1-cyclohexyl-4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-piperazin-2-one.

LCMS: m/z 769 (M+H)$^+$; $^1$H NMR (CD$_3$OD, 400 MHz): δ 1.42-1.71 (m, 10H), 3.28-3.36 (m, 4H), 4.01 (s, 2H), 4.07 (s, 2H), 4.09 (m, 1H), 4.17 (s, 2H), 6.94 (d, 2H), 7.19 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 74

5-{-4-[2-(4-Bromo-benzyl)-4-(2,4-dichloro-phenyl)-imidazol-1-yl]-phenyl}-1,2,5-thiadiazolidine-3-one-1,1-dioxide (592 mg, 1 mmol) was treated as described in general procedure L using 2-(trimethylsilyl)ethoxymethyl chloride (354 µL, 2 mmol) to give 5-{4-[2-(4-bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 723 (M+H)$^+$.

5-{-4-[2-(4-Bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (361 mg, 0.5 mmol) was treated as described in general procedure G using 4-aminophenylboronic acid (137 mg, 1 mmol) to give 5-{-4-[2-(4'-amino-biphenyl-4-ylmethyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 734 (M+H)$^+$.

5-{4-[2-(4'-Amino-biphenyl-4-ylmethyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (74 mg, 0.1 mmol) was treated as described in general procedure U using 5-bromovaleryl chloride (40 mg, 0.2 mmol) to give the intermediate 5-bromo-pentanoic acid [4'-(4-(2,4-dichloro-phenyl)-1-{-4-[1,1,4-trioxo-5-(2-trimethylsilanyl-ethoxymethyl)-[1,2,5]thiadiazolidin-2-yl]-phenyl}-1H-imidazol-2-ylmethyl)-biphenyl-4-yl]-amide, which was treated with 1,8-diazabicyclo[5,4,0]undec-7-ene (46 mg, 0.3 mmol) at 0° C. in 1 mL anhydrous DMF (stirring at room temperature under nitrogen over night), followed by regular ethyl acetate/water workup and silica gel column chromatography to give 1-[4'-(4-(2,4-dichloro-phenyl)-1-{-4-[1,1,4-trioxo-5-(2-trimethylsilanyl-ethoxymethyl)-[1,2,5]thia-diazolidin-2-yl]-phenyl}-1H-imidazol-2-ylmethyl)-biphenyl-4-yl]-piperidin-2-one, which was finally treated as described in general procedure W to give the desired compound 1-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-piperidin-2-one.

LCMS: m/z 686 (M+H)$^+$; $^1$H NMR (CD$_3$OD, 400 MHz): δ 1.84 (m, 4H), 2.43 (m, 2H), 3.39 (m, 2H), 4.08 (s, 2H), 4.16 (s, 2H), 7.21 (d, 2H), 7.29 (d, 2H), 7.36 (d, 2H), 7.45-7.52 (m, 5H), 7.56 (d, 2H), 7.64 (d, 1H), 7.89 (s, 1H), 8.18 (d, 1H) ppm.

Example 75

2-(4-Bromo-benzyl)-1-(4-nitro-phenyl)-4-(2,4-dichloro-phenyl)-1H-imidazole (5.0 g, 10 mmol) was treated as described in general procedure G using 3-chloro-4-pyridine-boronic acid (3.2 g, 20 mmol) to give 2-chloro-4-{-4-[4-(2,4-dichloro-phenyl)-1-(4-nitro-phenyl)-1H-imidazol-2-ylmethyl]-phenyl}-pyridine.

LCMS: m/z 535 (M+H)$^+$.

2-Chloro-4-{4-[4-(2,4-dichloro-phenyl)-1-(4-nitro-phenyl)-1H-imidazol-2-ylmethyl]-phenyl}-pyridine (1.6 g, 3 mmol) was refluxed with 6M NaOH in 1/1 water/ethanol (10 mL, 60 mmol) for 2 to 4 hours, followed by regular ethyl acetate/water workup and silica gel column chromatography to give the intermediate 4-{4-[4-(2,4-dichloro-phenyl)-1-(4-nitro-phenyl)-1H-imidazol-2-ylmethyl]-phenyl}-1H-pyridin-2-one, which was then treated as described in general procedure L [using iodocyclohexane (0.78 mL, 6 mmol)] to give 1-cyclohexyl-4-{4-[4-(2,4-dichloro-phenyl)-1-(4-nitro-phenyl)-1H-imidazol-2-ylmethyl]-phenyl}-1H-pyridin-2-one.

LCMS: m/z 599 (M+H)$^+$.

1-Cyclohexyl-4-{-4-[4-(2,4-dichloro-phenyl)-1-(4-nitro-phenyl)-1H-imidazol-2-ylmethyl]-phenyl}-1H-pyridin-2-one (300 mg, 0.5 mmol) was treated as described in general procedure C to give the desired compound 1-cyclohexyl-4-(4-{4-(2,4-dichloro-phenyl)-1-[4-(1,1,4-trioxo-[1,2,5]thiadiazolidin-2-yl)-phenyl]-1H-imidazol-2-ylmethyl}-phenyl)-1H-pyridin-2-one.

LCMS: m/z 688 (M+H)$^+$; $^1$H NMR (DMSO-d$_6$, 400 MHz): δ 1.66-1.84 (m, 6H), 2.33-2.46 (m, 4H), 4.05 (s, 2H), 4.08 (s, 2H), 4.23 (m, 1H), 7.11-7.36 (m, 5H), 7.45-7.52 (m, 4H), 7.56 (d, 2H), 7.64 (d, 1H), 7.89 (s, 1H), 8.18 (d, 1H), 8.28 (d, 1H) ppm.

Example 76

5-{-4-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-(3-ethyl-cyclobutyl)phenylboronic acid (41 mg, 0.2 mmol, prepared according to general procedure Y using 3-(4-bromophenyl)cyclobutan-1-one in stead of bromobenzaldehyde) to give 5-(4-{4-(2,4-dichloro-phenyl)-2-[4'-(3-ethyl-cyclobutyl)-biphenyl-4-ylmethyl]-imidazol-1-yl}-phenyl)-1,2,5-thiadiazolidine-3-one-1,1-dioxide.

LCMS: m/z 671 (M+H)$^+$; $^1$H NMR (DMSO-d$_6$, 400 MHz): δ 0.94 (t, 3H), 1.32-1.81 (m, 7H), 2.52 (m, 1H), 4.05 (s, 2H), 4.07 (s, 2H), 7.15 (d, 2H), 7.18 (d, 2H), 7.27 (d, 2H), 7.37 (d, 2H), 7.48 (dd, 1H), 7.51 (d, 2H), 7.53 (d, 2H), 7.64 (d, 1H), 7.89 (s, 1H), 8.19 (d, 1H) ppm.

Example 77

2-(4-Bromo-benzyl)-1-(4-nitro-phenyl)-4-(2,4-dichloro-phenyl)-1H-imidazole (503 mg, 1 mmol) was treated as described in general procedures E and F using methyl 2-bromopropionate (335 µL, 3 mmol) to give 5-{-4-[2-(4-bromobenzyl)-4-(2,4-dichloro-phenyl)-imidazol-1-yl]-phenyl}-4-methyl-1,2,5-thiadiazolidine-3-one-1,1-dioxide.

LCMS: m/z 607 (M+H)$^+$; $^1$H NMR (DMSO-d$_6$, 400 MHz): δ 1.09 (d, 3H), 4.05 (s, 2H), 4.10 (m, 1H), 7.15 (d, 2H), 7.27 (d, 2H), 7.47 (dd, 1H), 7.51 (d, 2H), 7.53 (d, 2H), 7.64 (d, 1H), 7.89 (s, 1H), 8.19 (d, 1H) ppm.

5-{-4-[2-(4-Bromo-benzyl)-4-(2,4-dichloro-phenyl)-imidazol-1-yl]-phenyl}-4-methyl-1,2,5-thiadiazolidine-3-one-1,1-dioxide (61 mg, 0.1 mmol) was treated as described in general procedure G using 4-tert-butylphenylboronic acid (36 mg, 0.2 mmol) to give 5-{4-[2-(4'-tert-butyl-biphenyl-4-ylmethyl)-4-(2,4-dichloro-phenyl)-imidazol-1-yl]-phenyl}-4-methyl-1,2,5-thiadiazolidine-3-one-1,1-dioxide.

LCMS: m/z 659 (M+H)$^+$; $^1$H NMR (DMSO-d$_6$, 400 MHz): δ 1.09 (d, 3H), 1.30 (s, 9H), 4.06 (s, 2H), 4.10 (m, 1H), 7.15 (d, 2H), 7.19 (d, 2H), 7.36 (d, 2H), 7.45 (d, 2H), 7.49 (dd, 1H), 7.52 (d, 2H), 7.54 (d, 2H), 7.64 (d, 1H), 7.90 (s, 1H), 8.20 (d, 1H) ppm.

By analogous methods to those used to prepare Example 77, the following compounds were synthesized:

| Ex. | Name | LC/MS (m/z) |
| --- | --- | --- |
| 78 | 5-{4-[2-(4'-tert-Butyl-biphenyl-4-ylmethyl)-4-(2,4-dichloro-phenyl)-imidazol-1-yl]-phenyl}-4-ethyl-1,2,5-thiadiazolidine-3-one-1,1-dioxide | 673 (M + H)$^+$ |
| 79 | 5-{4-[2-(4'-tert-Butyl-biphenyl-4-ylmethyl)-4-(2,4-dichloro-phenyl)-imidazol-1-yl]-phenyl}-4,4-dimethyl-1,2,5-thiadiazolidine-3-one-1,1-dioxide | 673 (M + H)$^+$ |
| 80 | 1-{4-[2-(4'-tert-Butyl-biphenyl-4-ylmethyl)-4-(2,4-dichloro-phenyl)-imidazol-1-yl]-phenyl}-2,2-dioxo-thia-1,3-diaza-spiro[4.5]decan-4-one | 713 (M + H)$^+$ |

Example 81

5-{-4-[2-(4-Bromo-benzyl)-4-(2,4-difluoro-phenyl)-imidazol-1-yl]-phenyl}-1,2,5-thiadiazolidine-3-one-1,1-dioxide (prepared according to general procedures A, B and C subsequently) (56 mg, 0.1 mmol) was treated as described in general procedure G using 4-tert-butylphenylboronic acid (36 mg, 0.2 mmol) to give 5-{-4-[2-(4'-tert-butyl-biphenyl-4-ylmethyl)-4-(2,4-difluoro-phenyl)-imidazol-1-yl]-phenyl}-1,2,5-thiadiazolidine-3-one-1,1-dioxide.

LCMS: m/z 613 (M+H)$^+$; $^1$H NMR (DMSO-d$_6$, 400 MHz): δ 1.31 (s, 9H), 4.05 (s, 2H), 4.07 (s, 2H), 7.13-7.16 (m, 5H), 7.27 (d, 2H), 7.37 (d, 2H), 7.41 (m, 1H), 7.51-7.55 (m, 5H), 8.12 (m, 1H) ppm.

Example 82

2-(4-Bromo-benzyl)-4-(2,4-dichloro-phenyl)-1H-imidazole (3.8 g, 10 mmol) was treated as described in general procedure G using 4-tert-butylphenylboronic acid (3.6 g, 20 mmol) to give 2-(4'-tert-butyl-biphenyl-4-ylmethyl)-4-(2,4-dichloro-phenyl)-1H-imidazole, which was treated as described in general procedure R using 1,4-diiodobenzene (13.2 g, 40 mmol) to give 2-(4'-tert-butyl-biphenyl-4-ylmethyl)-4-(2,4-dichloro-phenyl)-1-(4-iodo-phenyl)-1H-imidazole.

LCMS: m/z 637 (M+H)$^+$.

2-(4'-tert-Butyl-biphenyl-4-ylmethyl)-4-(2,4-dichloro-phenyl)-1-(4-iodo-phenyl)-1H-imidazole (191 mg, 0.3 mmol) was treated as described in general procedure R using D-2-aminobutyric acid (310 mg, 3 mmol) to give (R)-2-{-4-[2-(4'-tert-butyl-biphenyl-4-ylmethyl)-4-(2,4-dichloro-phenyl)-imidazol-1-yl]-phenylamino}-butyric acid, which was then treated as described in general procedure F to give (4R)-5-{-4-[2-(4'-tert-butyl-biphenyl-4-ylmethyl)-4-(2,4-dichloro-phenyl)-imidazol-1-yl]-phenyl}-4-ethyl-1,2,5-thiadiazolidine-3-one-1,1-dioxide.

LCMS: m/z 673 (M+H)$^+$; $^1$H NMR (DMSO-d$_6$, 400 MHz): δ 1.03 (t, 3H), 1.30 (s, 9H), 1.45 (m, 2H), 4.06 (s, 2H), 4.10 (t, 1H), 7.15 (d, 2H), 7.19 (d, 2H), 7.36 (d, 2H), 7.45 (d, 2H), 7.49 (dd, 1H), 7.52 (d, 2H), 7.54 (d, 2H), 7.64 (d, 1H), 7.88 (s, 1H), 8.19 (d, 1H) ppm.

Example 83

2-(4'-tert-Butyl-biphenyl-4-ylmethyl)-4-(2,4-dichloro-phenyl)-1-(4-iodo-phenyl)-1H-imidazole (191 mg, 0.3 mmol) was treated as described in general procedure R using L-2-aminobutyric acid (310 mg, 3 mmol) to give (S)-2-{-4-[2-(4'-tert-butyl-biphenyl-4-ylmethyl)-4-(2,4-dichloro-phenyl)-imidazol-1-yl]-phenylamino}-butyric acid, which was then treated as described in general procedure F to give (4S)-5-{-4-[2-(4'-tert-butyl-biphenyl-4-ylmethyl)-4-(2,4-dichloro-phenyl)-imidazol-1-yl]-phenyl}-4-ethyl-1,2,5-thiadiazolidine-3-one-1,1-dioxide.

LCMS: m/z 673 (M+H)$^+$; $^1$H NMR (DMSO-d$_6$, 400 MHz): δ 1.04 (t, 3H), 1.31 (s, 9H), 1.45 (m, 2H), 4.06 (s, 2H), 4.10 (t, 1H), 7.15 (d, 2H), 7.19 (d, 2H), 7.36 (d, 2H), 7.45 (d, 2H), 7.49 (dd, 1H), 7.52 (d, 2H), 7.54 (d, 2H), 7.64 (d, 1H), 7.89 (s, 1H), 8.20 (d, 1H) ppm.

Example 84

2-(4'-tert-Butyl-biphenyl-4-ylmethyl)-4-(2,4-dichloro-phenyl)-1-(4-iodo-phenyl)-1H-imidazole (191 mg, 0.3 mmol) was treated as described in general procedure R using L-norvaline (352 mg, 3 mmol) to give (S)-2-{-4-[2-(4'-tert-butyl-biphenyl-4-ylmethyl)-4-(2,4-dichloro-phenyl)-imidazol-1-yl]-phenylamino}-pentanoic acid, which was then treated as described in general procedure F to give (4S)-5-{-4-[2-(4'-tert-butyl-biphenyl-4-ylmethyl)-4-(2,4-dichloro-phenyl)-imidazol-1-yl]-phenyl}-4-propyl-1,2,5-thiadiazolidine-3-one-1,1-dioxide.

LCMS: m/z 687 (M+H)$^+$; $^1$H NMR (DMSO-d$_6$, 400 MHz): δ 0.99 (t, 3H), 1.31 (s, 9H), 1.39-1.46 (m, 4H), 4.06 (s, 2H), 4.10 (t, 1H), 7.15 (d, 2H), 7.19 (d, 2H), 7.36 (d, 2H), 7.45 (d, 2H), 7.49 (dd, 1H), 7.52 (d, 2H), 7.54 (d, 2H), 7.64 (d, 1H), 7.89 (s, 1H), 8.19 (d, 1H) ppm.

Example 85

4-Iodophenylacetic acid (26.2 g, 0.1 mol) was treated according to general procedure A using 2,4-dichlorophenacyl bromide to give 4-(2,4-dichloro-phenyl)-2-(4-iodo-benzyl)-1H-imidazole.

LCMS: m/z 429 (M+H)$^+$.

4-(2,4-Dichloro-phenyl)-2-(4-iodo-benzyl)-1H-imidazole (12.9 g, 30 mmol) was treated as described in general procedures R and C stepwise to give 5-{3-[4-(2,4-dichloro-phenyl)-2-(4-iodo-benzyl)-imidazol-1-yl]-phenyl}-1,2,5-thiadiazolidine-3-one-1,1-dioxide.

LCMS: m/z 639 (M+H)$^+$.

5-{3-[4-(2,4-Dichloro-phenyl)-2-(4-iodo-benzyl)-imidazol-1-yl]-phenyl}-1,2,5-thiadiazolidine-3-one-1,1-dioxide (3.2 g, 5 mmol) was treated as described in general procedure G using 4-bromophenylboronic acid (2.0 g, 10 mmol) to give 5-{3-[2-(4'-bromo-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 669 (M+H)$^+$; $^1$H NMR (DMSO-d$_6$, 400 MHz): δ 4.05 (s, 2H), 4.07 (s, 2H), 7.15 (d, 2H), 7.19 (d, 2H), 7.36-7.49 (m, 5H), 7.52 (d, 2H), 7.54 (d, 2H), 7.64 (d, 1H), 7.89 (s, 1H), 8.19 (d, 1H) ppm.

5-{3-[2-(4'-Bromo-biphenyl-4-ylmethyl)-4-(2,4-dichloro-phenyl)-imidazol-1-yl]-phenyl}-1,2,5-thiadiazolidine-3-one-1,1-dioxide (134 mg, 0.2 mmol) was treated as described in general procedure R using excess (S)-3-phenyl-pyrrolidine (147 mg, 1 mmol) to give the desired compound 5-(3-{4-(2,4-dichloro-phenyl)-2-{4'-[(3S)-3-phenyl-pyrrolidin-1-yl]-biphenyl-4-ylmethyl}-imidazol-1-yl}-phenyl)-1,2,5-thiadiazolidine-3-one-1,1-dioxide.

LCMS: m/z 734 (M+H)$^+$; $^1$H NMR (DMSO-d$_6$, 400 MHz): δ 1.87-2.35 (m, 2H), 3.00-3.60 (m, 5H), 4.07 (s, 2H), 4.10 (s, 2H), 6.94 (d, 2H), 7.19 (d, 2H), 7.27 (m, 1H), 7.32-7.46 (m, 9H), 7.55-7.76 (m, 5H), 7.89 (s, 1H), 8.18 (d, 1H) ppm.

By analogous methods to those used to prepare Example 85, the following compounds were synthesized:

| Ex. | Name | LC/MS (m/z) |
|---|---|---|
| 86 | 5-(3-{4-(2,4-Dichloro-phenyl)-2-{4'-[(3R)-3-phenyl-pyrrolidin-1-yl]-biphenyl-4-ylmethyl}-imidazol-1-yl}-phenyl)-1,2,5-thiadiazolidine-3-one-1,1-dioxide | 734 (M + H)$^+$ |
| 87 | 5-{3-[2-{4'-[(3S)-3-Cyclohexyl-pyrrolidin-1-yl]-biphenyl-4-ylmethyl}-4-(2,4-dichloro-phenyl)-imidazol-1-yl]-phenyl}-1,2,5-thiadiazolidine-3-one-1,1-dioxide | 740 (M + H)$^+$ |
| 88 | 5-{3-[2-{4'-[(3R)-3-Cyclohexyl-pyrrolidin-1-yl]-biphenyl-4-ylmethyl}-4-(2,4-dichloro-phenyl)-imidazol-1-yl]-phenyl}-1,2,5-thiadiazolidine-3-one-1,1-dioxide | 740 (M + H)$^+$ |
| 89 | 5-{3-[2-{3'-[(3S)-3-Cyclohexyl-pyrrolidin-1-yl]-biphenyl-4-ylmethyl}-4-(2,4-dichloro-phenyl)-imidazol-1-yl]-phenyl}-1,2,5-thiadiazolidine-3-one-1,1-dioxide | 740 (M + H)$^+$ |

Example 90

2-(4-Bromo-phenyl)-4-(2,4-dichloro-phenyl)-5-(4-nitro-phenyl)-1H-imidazole (prepared according to general procedure A) (979 mg, 2 mmol) was treated as described in general procedure G using 4-tert-butylphenylboronic acid (712 mg, 4 mmol) to give 2-(4'-tert-butyl-biphenyl-4-yl)-4-(2,4-dichloro-phenyl)-5-(4-nitro-phenyl)-1H-imidazole, which was treated as described in general procedure L using 2-(trimethylsilyl)ethoxymethyl chloride (0.7 mL, 4 mmol) to give 2-(4'-tert-butyl-biphenyl-4-yl)-4-(2,4-dichloro-phenyl)-5-(4-nitro-phenyl)-1-(2-trimethylsilanyl-ethoxymethyl)-1H-imidazole.

LCMS: m/z 672 (M+H)$^+$.

2-(4'-tert-Butyl-biphenyl-4-yl)-4-(2,4-dichloro-phenyl)-5-(4-nitro-phenyl)-1-(2-trimethylsilanyl-ethoxymethyl)-1H-imidazole (336 mg, 0.5 mmol) was treated as described in general procedure C [using methyl bromoacetate (95 μL, 1 mmol)] to give 5-{4-[2-(4'-tert-butyl-biphenyl-4-yl)-5-(2,4-dichloro-phenyl)-3-(2-trimethylsilanyl-ethoxymethyl)-3H-imidazol-4-yl]-phenyl}-1,2,5-thiadiazolidine-3-one-1,1-dioxide, which was then treated according to general procedure W to give 5-{4-[2-(4'-tert-butyl-biphenyl-4-yl)-5-(2,4-dichloro-phenyl)-3H-imidazol-4-yl]-phenyl}-1,2,5-thiadiazolidine-3-one-1,1-dioxide.

LCMS: m/z 631 (M+H)$^+$; $^1$H NMR (DMSO-d$_6$, 400 MHz): δ 1.30 (s, 9H), 4.09 (s, 2H), 7.15 (d, 2H), 7.19 (d, 2H), 7.36 (d, 2H), 7.45 (d, 2H), 7.49 (dd, 1H), 7.52-7.64 (m, 4H), 7.90 (s, 1H), 8.20 (d, 1H) ppm.

Example 91

2-(4-Bromo-benzyl)-4-(2,4-dichloro-phenyl)-5-(4-nitro-phenyl)-1H-imidazole (prepared according to general procedure A) (1.0 g, 2 mmol) was treated as described in general procedure G using 4-tert-butylphenylboronic acid (712 mg, 4 mmol) to give 2-(4'-tert-butyl-biphenyl-4-ylmethyl)-4-(2,4-dichloro-phenyl)-5-(4-nitro-phenyl)-1H-imidazole, which was treated as described in general procedure L using 2-(trimethylsilyl)ethoxymethyl chloride (0.7 mL, 4 mmol) to give 2-(4'-tert-butyl-biphenyl-4-ylmethyl)-4-(2,4-dichloro-phenyl)-5-(4-nitro-phenyl)-1-(2-trimethylsilanyl-ethoxymethyl)-1H-imidazole.

LCMS: m/z 686 (M+H)$^+$.

2-(4'-tert-Butyl-biphenyl-4-yl)-4-(2,4-dichloro-phenyl)-5-(4-nitro-phenyl)-1-(2-trimethylsilanyl-ethoxymethyl)-1H-imidazole (343 mg, 0.5 mmol) was treated as described in general procedure C [using methyl bromoacetate (95 μL, 1 mmol)] to give 5-{4-[2-(4'-tert-butyl-biphenyl-4-ylmethyl)-5-(2,4-dichloro-phenyl)-3-(2-trimethylsilanyl-ethoxymethyl)-3H-imidazol-4-yl]-phenyl}-1,2,5-thiadiazolidine-3-one-1,1-dioxide, which was then treated according to general procedure W to give 5-{4-[2-(4'-tert-butyl-biphenyl-4-ylmethyl)-5-(2,4-dichloro-phenyl)-3H-imidazol-4-yl]-phenyl}-1,2,5-thiadiazolidine-3-one-1,1-dioxide.

LCMS: m/z 645 (M+H)$^+$; $^1$H NMR (DMSO-d$_6$, 400 MHz): δ 1.29 (s, 9H), 4.06 (s, 2H), 4.09 (s, 2H), 7.15 (d, 2H), 7.19 (d, 2H), 7.36 (d, 2H), 7.45 (d, 2H), 7.49 (dd, 1H), 7.52-7.64 (m, 4H), 7.89 (s, 1H), 8.19 (d, 1H) ppm.

Example 92

2-(4-Bromo-benzyl)-4-(2,4-dichloro-phenyl)-1H-imidazole (382 mg, 1 mmol) was treated as described in general procedure K using 4-nitrobenzyl bromide (432 mg, 2 mmol) to give 2-(4-bromo-benzyl)-4-(2,4-dichloro-phenyl)-1-(4-nitro-benzyl)-1H-imidazole.

LCMS: m/z 518 (M+H)$^+$.

2-(4-Bromo-benzyl)-4-(2,4-dichloro-phenyl)-1-(4-nitro-benzyl)-1H-imidazole (310 mg, 0.6 mmol) was treated as described in general procedure C to give 5-{4-[2-(4-bromobenzyl)-4-(2,4-dichloro-phenyl)-imidazol-1-ylmethyl]-phenyl}-1,2,5-thiadiazolidine-3-one-1,1-dioxide.

LCMS: m/z 607 (M+H)+.

5-{-4-[2-(4-Bromo-benzyl)-4-(2,4-dichloro-phenyl)-imidazol-1-ylmethyl]-phenyl}-1,2,5-thiadiazolidine-3-one-1,1-dioxide (61 mg, 0.1 mmol) was treated as described in general procedure G using 4-cyclohexylphenylboronic acid (41 mg, 0.2 mmol) to give 5-{-4-[2-(4'-cyclohexyl-biphenyl-4-ylmethyl)-4-(2,4-dichloro-phenyl)-imidazol-1-ylmethyl]-phenyl}-1,2,5-thiadiazolidine-3-one-1,1-dioxide.

LCMS: m/z 685 (M+H)+; $^1$H NMR (DMSO-$d_6$, 400 MHz): δ 1.13-1.40 (m, 5H), 1.65-1.78 (m, 5H), 2.52 (m, 1H), 4.05 (s, 2H), 4.08 (s, 2H), 5.35 (s, 2H), 7.15 (d, 2H), 7.20 (d, 2H), 7.32 (d, 2H), 7.41 (d, 2H), 7.47 (d, 2H), 7.51-7.58 (m, 3H), 7.64 (d, 1H), 7.89 (s, 1H), 8.18 (d, 1H) ppm.

Example 93

4-Nitro-benzoic acid (1.7 g, 10 mmol) was treated as described in general procedure A to give 4-(2,4-dichloro-phenyl)-2-(4-nitro-phenyl)-1H-imidazole, which was the treated as described in general procedure K using 4-bromobenzyl bromide (3.8 g, 15 mmol) to give 1-(4-bromo-benzyl)-4-(2,4-dichloro-phenyl)-2-(4-nitro-phenyl)-1H-imidazole.

LCMS: m/z 504 (M+H)+.

1-(4-Bromo-benzyl)-4-(2,4-dichloro-phenyl)-2-(4-nitro-phenyl)-1H-imidazole (503 mg, 1 mmol) was treated as described in general procedure C to give 5-{-4-[1-(4-bromo-benzyl)-4-(2,4-dichloro-phenyl)-1H-imidazol-2-yl]-phenyl}-1,2,5-thiadiazolidine-3-one-1,1-dioxide.

LCMS: m/z 593 (M+H)+.

5-{-4-[1-(4-Bromo-benzyl)-4-(2,4-dichloro-phenyl)-1H-imidazol-2-yl]-phenyl}-1,2,5-thiadiazolidine-3-one-1,1-dioxide (59 mg, 0.1 mmol) was treated as described in general procedure G using 4-cyclohexylphenylboronic acid (41 mg, 0.2 mmol) to give 5-{4-[1-(4'-cyclohexyl-biphenyl-4-ylmethyl)-4-(2,4-dichloro-phenyl)-1H-imidazol-2-yl]-phenyl}-1,2,5-thiadiazolidine-3-one-1,1-dioxide.

LCMS: m/z 671 (M+H)+; $^1$H NMR (DMSO-$d_6$, 400 MHz): δ 1.13-1.40 (m, 5H), 1.65-1.78 (m, 5H), 2.52 (m, 1H), 4.08 (s, 2H), 5.35 (s, 2H), 7.15 (d, 2H), 7.20 (d, 2H), 7.32 (d, 2H), 7.41 (d, 2H), 7.47 (d, 2H), 7.51-7.58 (m, 3H), 7.64 (d, 1H), 7.89 (s, 1H), 8.18 (d, 1H) ppm.

Example 94

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 3-hydroxyphenylboronic acid (28 mg, 0.2 mmol) to give 5-{4-[4-(2,4-dichloro-phenyl)-2-(3'-hydroxybiphenyl-4-ylmethyl)-imidazol-1-yl]-phenyl}-1,2,5-thiadiazolidine-3-one-1,1-dioxide.

LCMS: m/z 605 (M+H)+; $^1$H NMR (DMSO-$d_6$, 400 MHz): δ 4.05 (s, 2H), 4.08 (s, 2H), 6.93-7.22 (m, 5H), 7.32 (d, 2H), 7.38 (d, 2H), 7.46 (d, 2H), 7.51 (d, 2H), 7.64 (d, 1H), 7.90 (s, 1H), 8.20 (d, 1H) ppm.

Example 95

5-{-4-[2-(4-Bromo-benzyl)-4-(2,4-dichloro-phenyl)-imidazol-1-yl]-phenyl}-1,2,5-thiadiazolidine-3-one-1,1-dioxide (592 mg, 1 mmol) was treated as described in general procedure L using 2-(trimethylsilyl)ethoxymethyl chloride (354 μL, 2 mmol) to give 5-{4-[2-(4-bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was then treated according to general procedure AD to give 5-(4-{4-(2,4-dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one.

LCMS: m/z 769 (M+H)+.

5-(4-{4-(2,4-Dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one (154 mg, 0.2 mmol) was treated as described in general procedure G using 2,5-dibromopyridine (95 mg, 0.4 mmol) to give 5-{-4-[2-[4-(5-bromo-pyridin-2-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was again treated as described in general procedure G using cyclohexen-1-ylboronic acid (51 mg, 0.4 mmol) to give 5-{-4-[2-[4-(5-cyclohex-1-enyl-pyridin-2-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 800 (M+H)+.

5-{4-[2-[4-(5-Cyclohex-1-enyl-pyridin-2-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (40 mg, 0.05 mmol) was dissolved in 1 mL dry acetic acid, iron powder (−325 mesh, 56 mg, 1 mmol) was added and the mixture was then heated at 100° C. under nitrogen for 2 days. At completion, the reaction mixture was then diluted with water/EtOAc and the leftover iron powder was filtered and washed with EtOAc. The combined organic layer was washed with water, saturated NaHCO$_3$ and brine. The organic layer was then dried over Na$_2$SO$_4$, filtered, and the filtrate was concentrated and purified by silica gel chromatography to afford 5-{4-[2-[4-(5-cyclohexyl-pyridin-2-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 802 (M+H)+.

5-{-4-[2-[4-(5-Cyclohexyl-pyridin-2-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (16 mg, 0.02 mmol) was treated as described in general procedure W using tetrabutylammonium fluoride (26 mg, 0.1 mmol) to give 5-{-4-[2-[4-(5-cyclohexyl-pyridin-2-yl)-benzyl]-4-(2,4-dichloro-phenyl)-imidazol-1-yl]-phenyl}-1,2,5-thiadiazolidine-3-one-1,1-dioxide.

LCMS: m/z 672 (M+H)+; $^1$H NMR (CD$_3$OD, 400 MHz): δ 1.22-1.43 (m, 5H), 1.69-1.81 (m, 5H), 2.52 (m, 1H), 4.08 (s, 2H), 4.10 (s, 2H), 7.15-7.27 (m, 5H), 7.37 (d, 2H), 7.46-7.54 (m, 5H), 7.64 (d, 1H), 7.89 (s, 1H), 8.19 (d, 1H) ppm.

Example 96

5-{3-[2-(4-Bromo-benzyl)-4-(2,4-dichloro-phenyl)-imidazol-1-yl]-phenyl}-1,2,5-thiadiazolidine-3-one-1,1-dioxide (1.19 g, 2 mmol) was treated as described in general procedure L using 2-(trimethylsilyl)ethoxymethyl chloride (708 μL, 4 mmol) to give 5-{3-[2-(4-bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was then treated according to general procedure AD to give 5-(3-{4-(2,4-dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one.

LCMS: m/z 769 (M+H)+.

5-(3-{4-(2,4-Dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one (385 mg, 0.5 mmol) was treated as described in general procedure G using 3,6-dichloropyridazine (149 mg, 1 mmol) to give 5-{3-[2-[4-(6-chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 756 (M+H)$^+$.

5-{3-[2-[4-(6-Chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (38 mg, 0.05 mmol) was treated as described in general procedure L using 2-cyclohexyl ethanol (35 µL, 0.25 mmol) to give 5-{3-[2-{-4-[6-(2-cyclohexyl-ethoxy)-pyridazin-3-yl]-benzyl}-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 847 (M+H)$^+$.

5-{3-[2-{-4-[6-(2-Cyclohexyl-ethoxy)-pyridazin-3-yl]-benzyl}-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (17 mg, 0.02 mmol) was treated as described in general procedure W using tetrabutylammonium fluoride (26 mg, 0.1 mmol) to give 5-{3-[2-{-4-[6-(2-cyclohexyl-ethoxy)-pyridazin-3-yl]-benzyl}-4-(2,4-dichloro-phenyl)-imidazol-1-yl]-phenyl}-1,2,5-thiadiazolidine-3-one-1,1-dioxide.

LCMS: m/z 717 (M+H)$^+$; $^1$H NMR (CD$_3$OD, 400 MHz): δ 0.97-1.43 (m, 5H), 1.65 (m, 2H), 1.69-1.81 (m, 6H), 4.05 (t, 2H), 4.08 (s, 2H), 4.10 (s, 2H), 7.15-7.27 (m, 5H), 7.37 (d, 2H), 7.46-7.54 (m, 4H), 7.64 (d, 1H), 7.89 (s, 1H), 8.19 (d, 1H) ppm.

Example 97

5-{3-[2-[4-(6-Chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (76 mg, 0.1 mmol) was dissolved in 1 mL dry ethanol. Thiourea (76 mg, 1 mmol) was added and the mixture was refluxed under nitrogen over night. At completion, the reaction mixture was then diluted with water/EtOAc. The combined organic layer was washed with water, and brine, dried over Na$_2$SO$_4$, filtered, and the filtrate was concentrated to give 5-(3-{4-(2,4-dichloro-phenyl)-2-[4-(6-mercapto-pyridazin-3-yl)-benzyl]-imidazol-1-yl}-phenyl)-1,1-dioxo-2-(2-trimethylsilanyl-ethoxymethyl)-[1,2,5]thiadiazolidin-3-one, which was then treated as described in general procedure K using 1-bromo-2-cyclohexylethane (79 µL, 0.5 mmol) to give 5-{3-[2-{-4-[6-(2-cyclohexyl-ethylsulfanyl)-pyridazin-3-yl]-benzyl}-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 863 (M+H)$^+$.

5-{3-[2-{-4-[6-(2-Cyclohexyl-ethylsulfanyl)-pyridazin-3-yl]-benzyl}-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (17 mg, 0.02 mmol) was treated as described in general procedure W using tetrabutylammonium fluoride (26 mg, 0.1 mmol) to give 5-{3-[2-{-4-[6-(2-cyclohexyl-ethylsulfanyl)-pyridazin-3-yl]-benzyl}-4-(2,4-dichloro-phenyl)-imidazol-1-yl]-phenyl}-1,2,5-thiadiazolidine-3-one-1,1-dioxide.

LCMS: m/z 733 (M+H)$^+$; $^1$H NMR (CD$_3$OD, 400 MHz): δ 0.97-1.41 (m, 5H), 1.48 (m, 2H), 1.69-1.81 (m, 6H), 3.03 (t, 2H), 4.08 (s, 2H), 4.10 (s, 2H), 7.15-7.27 (m, 5H), 7.37 (d, 2H), 7.46-7.54 (m, 4H), 7.64 (d, 1H), 7.89 (s, 1H), 8.19 (d, 1H) ppm.

Example 98

4-Bromophenylacetic acid (10.7 g, 50 mmol) was treated according to general procedure A using 2,4-dichlorophenacyl bromide to give 2-(4-bromo-benzyl)-4-(2,4-dichloro-phenyl)-1H-imidazole. 2-(4-Bromo-benzyl)-4-(2,4-dichloro-phenyl)-1H-imidazole (3.8 g, 10 m mol) was reacted with 4-nitro benzylbromide (2.5 g, 12 mmol) as described in general procedure B to give 2-(4-bromobenzyl)-4-(2,4-dichloro-phenyl)-1-(4-nitro-benzyl)-1H-imidazole.

2-(4-Bromo-benzyl)-4-(2,4-dichloro-phenyl)-1-(4-nitro-benzyl)-1H-imidazole (2.6 g, mmol) was reduced to amine and was reacted with methyl bromoacetate following general procedures D & E to give {-4-[2-(4-bromo-benzyl)-4-(2,4-dichloro-phenyl)-imidazol-1-ylmethyl]-phenylamino}-acetic acid methyl ester.

{-4-[2-(4-Bromo-benzyl)-4-(2,4-dichloro-phenyl)-imidazol-1-ylmethyl]-phenylamino}-acetic acid methyl ester (1.4 g, 2.5 mmol) was coupled with 4-sec-butyl phenyl-boronic acid (600 mg, 3.3 mmol) following general procedure G to give {4-[2-(4'-sec-butyl-biphenyl-4-ylmethyl)-4-(2,4-dichloro-phenyl)-imidazol-1-ylmethyl]-phenylamino}-acetic acid methyl ester.

5-{-4-[2-(4'-sec-Butyl-biphenyl-4-ylmethyl)-4-(2,4-dichloro-phenyl)-imidazol-1-ylmethyl]-phenyl}-1,2,5-thiadiazolidine-3-one-1,1-dioxide was prepared from {-4-[2-(4'-sec-butyl-biphenyl-4-ylmethyl)-4-(2,4-dichloro-phenyl)-imidazol-1-ylmethyl]-phenylamino}-acetic acid methyl ester (275 mg, 0.4 mmol) following general procedure F.

LCMS: m/z 659 (M+H)$^+$

Example 99

4-Bromophenylacetic acid (107.5 g, 0.5 mol) was treated according to general procedure A using 2,4-dichlorophenacyl bromide to give 2-(4-bromo-benzyl)-4-(2,4-dichloro-phenyl)-1H-imidazole. 2-(4-Bromo-benzyl)-4-(2,4-dichloro-phenyl)-1H-imidazole (38.2 g, 0.1 mol) was treated as described in general procedure B using 1-fluoro-4-nitrobenzene to give 2-(4-bromo-benzyl)-1-(4-nitro-phenyl)-4-(2,4-dichloro-phenyl)-1H-imidazole.

4-(2,4-Dichloro-phenyl)-1-(4-nitro-phenyl)-2-(4-bromo-benzyl)-1H-imidazole (5.0 g, 10 mmol) was reduced to amine and was reacted with methyl bromoacetate following general procedures D & E to give {-4-[2-(4-bromo-benzyl)-4-(2,4-dichloro-phenyl)-imidazol-1-yl]-phenylamino}-acetic acid methyl ester.

{-4-[2-(4-Bromo-benzyl)-4-(2,4-dichloro-phenyl)-imidazol-1-yl]-phenylamino}-acetic acid methyl ester (1.8 g, 3.3 mmol) was coupled with 4-sec butyl-phenyl boronic acid (750 mg, 4.0 mmol) according to general procedure G to give {-4-[2-(4'-sec-butyl-biphenyl-4-ylmethyl)-4-(2,4-dichloro-phenyl)-imidazol-1-yl]-phenylamino}-acetic acid methyl ester.

{-4-[2-(4'-sec-Butyl-biphenyl-4-ylmethyl)-4-(2,4-dichloro-phenyl)-imidazol-1-yl]-phenylamino}-acetic acid methyl ester (300 mg, 0.5 mmol) was treated following general procedure F to give 5-{4-[2-(4'-sec-butyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 645 (M+H)$^+$; $^1$H NMR (DMSO-d$_6$, 400 MHz): 0.89 (t, 3H), 1.18-1.20 (m, 2H), 1.22 (m, 1H), 3.99 (t, 2H), 4.04 (s, 2H), 4.07 (s, 2H), 7.14 (d, 2H), 7.16 (d, 2H), 7.24 (d,

2H), 7.35 (d, 2H), 7.46 (dd, 1H), 7.51 (d, 2H), 7.53 (d, 2H), 7.63 (d, 1H), 7.79 (s, 1H), 7.89 (d, 1H), 8.20 (d, 1H) ppm.

Example 100

{4-[2-(4-Bromo-benzyl)-4-(2,4-dichloro-phenyl)-imidazol-1-yl]-phenylamino}-acetic acid methyl ester (1.5 g, 2.7 mmol) was coupled with 4-cyclohexyl phenyl-boronic acid (700 m g, 3.4 mmol) according to general procedure G to give {4-[2-(4'-cyclohexyl-biphenyl-4-ylmethyl)-4-(2,4-dichloro-phenyl)-imidazol-1-yl]-phenylamino}acetic acid methyl ester.

{-4-[2-(4'-Cyclohexyl-biphenyl-4-ylmethyl)-4-(2,4-dichloro-phenyl)-imidazol-1-yl]-phenylamino}-acetic acid methyl ester (312 mg, 0.5 mmol) was treated following general procedure F to give 5-{-4-[2-(4'-cyclohexyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 671 (M+H)$^+$; $^1$HNMR (DMSO-$d_6$, 400 MHz): δ 1.35-43 (m, 5H), 1.78-1.84 (m, 5H), 4.04 (s, 2H), 4.07 (d, 2H), 7.14 (d, 2H), 7.18 (d, 2H), 7.28 (d, 2H), 7.37 (d, 2H), 7.46 (d, 2H), 7.48 (d, 2H), 7.50-7.53 (m, 2H), 7.63 (d, 1H), 7.89 (s, 1H), 8.19 (d, 1H) ppm.

By analogous methods to those used to prepare Example 100, the following compounds were synthesized:

| Ex. | Name | LC/MS (m/z) |
|---|---|---|
| 101 | 5-{4-[4-(2,4-Dichloro-phenyl)-2-(4'-isobutyl-biphenyl-4-ylmethyl)-imidazol-1-yl]-phenyl}-1,2,5-thiadiazolidine-3-one-1,1-dioxide | 645 (M + H)$^+$ |
| 102 | 5-{4-[4-(2,4-Dichloro-phenyl)-2-(4'-morpholin-4-yl-biphenyl-4-ylmethyl)-imidazol-1-yl]-phenyl}-1,2,5-thiadiazolidine-3-one-1,1-dioxide | 674 (M + H)$^+$ |
| 103 | 5-{4-[2-(4'-Butyl-biphenyl-4-ylmethyl)-4-(2,4-dichloro-phenyl)-imidazol-1-yl]-phenyl}-1,2,5-thiadiazolidine-3-one-1,1-dioxide | 645 (M + H)$^+$ |
| 104 | 5-{4-[4-(2,4-Dichloro-phenyl)-2-(4'-piperidin-1-yl-biphenyl-4-ylmethyl)-imidazol-1-yl]-phenyl}-1,2,5-thiadiazolidine-3-one-1,1-dioxide | 672 (M + H)$^+$ |
| 105 | 5-{4-[4-(2,4-Dichloro-phenyl)-2-(4'-isopropyl-biphenyl-4-ylmethyl)-imidazol-1-yl]-phenyl}-1,2,5-thiadiazolidine-3-one-1,1-dioxide | 631 (M + H)$^+$ |
| 106 | 5-{4-[2-(3'-Nitro-4'-isobutyl-biphenyl-4-ylmethyl)-4-(2,4-dichloro-phenyl)-imidazol-1-yl]-phenyl}-1,2,5-thiadiazolidine-3-one-1,1-dioxide | 690 (M + H)$^+$ |

Example 107

5-{-4-[2-(3'-Nitro-4'-Iso-Butyl-biphenyl-4-ylmethyl)-4-(2,4-dichloro-phenyl)-imidazol-1-yl]-phenyl}-[1,2,5]thiadiazolidin-3-one-1,1-dioxide (70 mg, 0.10 mmol) was reduced to 5-{-4-[2-(3'-amino-4'-isobutyl-biphenyl-4-ylmethyl)-4-(2,4-dichloro-phenyl)-imidazol-1-yl]-phenyl}-1,2,5-thiadiazolidine-3-one-1,1-dioxide according to general procedure D.

LCMS: m/z 660 (M+H)$^+$.

Example 108

5-{-4-[2-(3'-Amino-4'-isobutyl-biphenyl-4-ylmethyl)-4-(2,4-dichloro-phenyl)-imidazol-1-yl]-phenyl}-[1,2,5]thiadiazolidin-3-one-1,1-dioxide (22 mg, 0.03 mmol) was reacted with acetaldehyde (1.7 mg, 0.03 mmol) according to general procedure X to give 5-{4-[4-(2,4-dichloro-phenyl)-2-(3'-diethylamino-4'-isobutyl-biphenyl-4-ylmethyl)-imidazol-1-yl]-phenyl}-1,2,5-thiadiazolidine-3-one-1,1-dioxide.

LCMS: m/z 716 (M+H)$^+$.

Example 109

4-Bromophenylacetic acid (10.7 g, 50 mmol) was treated according to general procedure A using 4-(2-Bromo-acetyl)-benzoic acid methyl ester to give 4-[2-(4-bromo-benzyl)-1H-imidazol-4-yl]-benzoic acid methyl ester.

4-[2-(4-Bromo-benzyl)-1H-imidazol-4-yl]-benzoic acid methyl ester (12.3 g, 33 mmol) was treated as described in general procedure B using 1-fluoro-4-nitrobenzene to give 4-[2-(4-bromo-benzyl)-1-(4-Nitro-phenyl)-1H-imidazol-4-yl]-benzoic acid methyl ester.

4-[2-(4-Bromo-benzyl)-1-(4-Nitro-phenyl)-1H-imidazol-4-yl]-benzoic acid methyl ester (9.8 g, 20 mmol) was reduced to amine and was reacted with methyl bromoacetate following general procedures D & E to give 4-{2-(4-Bromo-benzyl)-1-[4-(methoxycarbonylmethyl-amino)-phenyl]-1H-imidazol-4-yl}-benzoic acid methyl ester.

4-{2-(4-Bromo-benzyl)-1-[4-(methoxycarbonylmethyl-amino)-phenyl]-1H-imidazol-4-yl}-benzoic acid methyl ester (2.7 g, 5 mmol) was coupled with 4-cyclohexyl-phenyl-boronic acid (1.25 g, 6.0 mmol) according to general procedure G to give 4-{2-(4'-cyclohexyl-biphenyl-4-ylmethyl)-1-[4-(methoxycarbonylmethyl-amino)-phenyl]-1H-imidazol-4-yl}-benzoic acid methyl ester.

4-{2-(4'-Cyclohexyl-biphenyl-4-ylmethyl)-1-[4-(methoxycarbonylmethyl-amino)-phenyl]-1H-imidazol-4-yl}-benzoic acid methyl ester (1.0 g, 1.6 mmol) was treated following general procedure F to give 4-{2-(4'-cyclohexyl-biphenyl-4-ylmethyl)-1-[4-(1,1,4-trioxo-1-[1,2,5]thiadiazolidin-2-yl)-phenyl]-1H-imidazol-4-yl}-benzoic acid methyl ester.

LCMS: m/z 660 (M+H)$^+$; $^1$H NMR (DMSO-$d_6$, 400 MHz): δ 1.19-1.38 (m, 5H), 1.66-1.89 (m, 5H), 2.39 (m, 1H), 3.59 (s, 3H), 4.04 (s, 2H), 4.09 (s, 2H), 7.17 (d, 2H), 7.19 (d, 2H), 7.28 (d, 2H), 7.36-7.42 (m, 4H), 7.44-7.57 (m, 4H), 7.66 (d, 1H), 7.87 (s, 1H), 8.18 (d, 1H) ppm.

Example 110

4-{2-(4'-Cyclohexyl-biphenyl-4-ylmethyl)-1-[4-(1,1,4-trioxo-1-[1,2,5]thiadiazolidin-2-yl)-phenyl]-1H-imidazol-4-yl}-benzoic acid methyl ester (220 mg, 0.33 mmol) was hydrolyzed following general procedure P to give 4-{2-(4'-cyclohexyl-biphenyl-4-ylmethyl)-1-[4-(1,1,4-trioxo-1-[1,2,5]thiadiazolidin-2-yl)-phenyl]-1H-imidazol-4-yl}-benzoic acid.

LCMS: m/z 646 (M+H)+; 1H NMR (DMSO-d6, 400 MHz): δ 1.22-1.43 (m, 5H), 1.69-1.81 (m, 5H), 2.52 (m, 1H), 4.05 (s, 2H), 4.07 (s, 2H), 7.15 (d, 2H), 7.18 (d, 2H), 7.26 (d, 2H), 7.34-7.42 (m, 4H), 7.46-7.54 (m, 5H), 7.64 (d, 1H), 7.89 (s, 1H), 8.19 (d, 1H) ppm.

Example 111

{4-[2-(4-Bromo-benzyl)-4-(2,4-dichloro-phenyl)-imidazol-1-yl]-phenylamino}-acetic acid methyl ester (1.8 g, 3.3 mmol) was coupled with 4-propionyl-phenyl boronic acid (712 m g, 4.0 mmol) according to general procedure G to give {4-[4-(2,4-dichloro-phenyl)-2-(4'-propionyl-biphenyl-4-ylmethyl)-imidazol-1-yl]-phenylamino}-acetic acid methyl ester.

{-4-[4-(2,4-Dichloro-phenyl)-2-(4'-propionyl-biphenyl-4-ylmethyl)-imidazol-1-yl]-phenylamino}-aceticacid methyl ester (299 mg, 0.5 mmol) was treated following general procedure F to give 5-{-4-[4-(2,4-dichloro-phenyl)-2-(4'-propionyl-biphenyl-4-ylmethyl)-imidazol-1-yl]-phenyl}-1,2,5-thiadiazolidine-3-one-1,1-dioxide.

LCMS: m/z 645 (M+H)+.

Example 112

{4-[2-(4-Bromo-benzyl)-4-(2,4-dichloro-phenyl)-imidazol-1-yl]-phenylamino}-acetic acid methyl ester (1.8 g, 3.3 mmol) was coupled with 4-n-pentylbenzene boronic acid (769 m g, 4.0 mmol) according to general procedure G to give {4-[4-(2,4-dichloro-phenyl)-2-(4'-pentyl-biphenyl-4-ylmethyl)-imidazol-1-yl]-phenylamino}-acetic acid methyl ester.

{-4-[4-(2,4-Dichloro-phenyl)-2-(4'-pentyl-biphenyl-4-ylmethyl)-imidazol-1-yl]-phenylamino}-acetic acid methyl ester (310 mg, 0.5 mmol) was treated following general procedure F to give 5-{-4-[4-(2,4-dichloro-phenyl)-2-(4'-pentyl-biphenyl-4-ylmethyl)-imidazol-1-yl]-phenyl}-1,2,5-thiadiazolidine-3-one-1,1-dioxide.

LCMS: m/z 659 (M+H)+; 1H NMR (DMSO-d6, 400 MHz): δ 0.98 (t, 3H), 1.29 (m, 2H), 1.41 (m, 2H), 1.83 (m, 2H), 4.02 (t, 2H), 4.05 (s, 2H), 4.08 (s, 2H), 7.05-7.12 (m, 4H), 7.29 (d, 2H), 7.38 (d, 2H), 7.46-7.54 (m, 5H), 7.64 (d, 1H), 7.89 (s, 1H), 8.19 (d, 1H) ppm.

Example 113

4-Bromophenylacetic acid (10.7 g, 50 mmol) was treated according to general procedure A using 4-trifluoromethylphenacyl bromide to give 2-(4-bromo-benzyl)-4-(4-trifluoromethyl-phenyl)-1H-imidazole.

2-(4-Bromo-benzyl)-4-(4-trifluoromethyl-phenyl)-1H-imidazole (9.6 g, 25 mmol) was treated as described in general procedure B using 1-fluoro-4-nitrobenzene to give 2-(4-bromo-benzyl)-1-(4-Nitro-phenyl)-4-(4-trifluoromethyl-phenyl)-1H-imidazole.

2-(4-Bromo-benzyl)-1-(4-Nitro-phenyl)-4-(4-trifluoromethyl-phenyl)-1H-imidazole (2.5 g, 5 mmol) was reduced to amine and was reacted with methyl bromoacetate following general procedures D & E to give {-4-[2-(4-bromo-benzyl)-4-(4-trifluoromethyl-phenyl)-imidazol-1-yl]-phenylamino}-acetic acid methyl ester.

{-4-[2-(4-Bromo-benzyl)-4-(4-trifluoromethyl-phenyl)-imidazol-1-yl]-phenylamino}-acetic acid methyl ester (1.3 g, 2.4 m mol) was coupled with 4-cyclohexyl-phenylboronic acid (615 mg, 3.0 mmol) according to general procedure G to give {4-[2-(4'-cyclohexyl-biphenyl-4-ylmethyl)-4-(4-trifluoromethyl-phenyl)-imidazol-1-yl]phenylamino}-acetic acid methyl ester.

{-4-[2-(4'-Cyclohexyl-biphenyl-4-ylmethyl)-4-(4-trifluoromethyl-phenyl)-imidazol-1-yl]phenylamino}-acetic acid methyl ester (312 mg, 0.5 mmol) was treated following general procedure F to give 5-{-4-[2-(4'-cyclohexyl-biphenyl-4-ylmethyl)-4-(4-trifluoromethyl-phenyl)-imidazol-1-yl]-phenyl}-1,2,5-thiadiazolidine-3-one-1,1-dioxide.

LCMS: m/z 670 (M+H)+.

Example 114

{4-[2-(4-Bromo-benzyl)-4-(2,4-dichloro-phenyl)-imidazol-1-yl]-phenylamino}-acetic acid methyl ester (1.8 g, 3.3 mmol) was coupled with 4-n-propyl-phenyl boronic acid (659 m g, 4.0 mmol) according to general procedure G to give {4-[4-(2,4-dichloro-phenyl)-2-(4'-propyl-biphenyl-4-ylmethyl)-imidazol-1-yl]-phenylamino}-acetic acid methyl ester.

{-4-[4-(2,4-Dichloro-phenyl)-2-(4'-propyl-biphenyl-4-ylmethyl)-imidazol-1-yl]-phenylamino}-acetic acid methyl ester (295 mg, 0.5 mmol) was treated following general procedure F to give 5-{-4-[4-(2,4-dichloro-phenyl)-2-(4'-propyl-biphenyl-4-ylmethyl)-imidazol-1-yl]-phenyl}-1,2,5-thiadiazolidine-3-one-1,1-dioxide.

LCMS: m/z 631 (M+H)+; 1H NMR (DMSO-d6, 400 MHz): δ 0.99 (t, 3H), 1.41 (m, 2H), 4.02 (t, 2H), 4.04 (s, 2H), 4.07 (s, 2H), 7.02-7.15 (m, 4H), 7.27 (d, 2H), 7.39 (d, 2H), 7.42-7.54 (m, 5H), 7.66 (d, 1H), 7.87 (s, 1H), 8.19 (d, 1H) ppm.

Example 115

4-Bromophenylacetic acid (10.7 g, 50 mmol) was treated according to general procedure A using 2-bromo-1-(4-methylsulfonyl-phenyl)-1-ethanone to give 2-(4-bromo-benzyl)-4-(4-methanesulfonyl-phenyl)-1H-imidazole.

2-(4-Bromo-benzyl)-4-(4-methanesulfonyl-phenyl)-1H-imidazole (9.8 g, 25 mmol) was treated as described in general procedure B using 1-fluoro-4-nitrobenzene to give 2-(4-Bromo-benzyl)-1-(4-nitro-phenyl)-4-(4-methanesulfonyl-phenyl)-1H-imidazole.

2-(4-Bromo-benzyl)-1-(4-nitro-phenyl)-4-(4-methanesulfonyl-phenyl)-1H-imidazole (2.6 g, 5 mmol) was reduced to amine and was reacted with methyl bromoacetate following general procedures D & E to give {-4-[2-(4-bromo-benzyl)-4-(4-methanesulfonyl-phenyl)-imidazol-1-yl]-phenylamino}-acetic acid methyl ester.

{-4-[2-(4-Bromo-benzyl)-4-(4-methanesulfonyl-phenyl)-imidazol-1-yl]-phenyl-amino}-acetic acid methyl ester (1.4 g, 2.5 mmol) was coupled with 4-cyclohexyl-phenyl boronic acid (615 mg, 3.0 mmol) according to general procedure G to give {4-[2-(4'-cyclohexyl-biphenyl-4-ylmethyl)-4-(4-methanesulfonyl-phenyl)-imidazol-1-yl]-phenylamino}-acetic acid methyl ester.

{-4-[2-(4'-Cyclohexyl-biphenyl-4-ylmethyl)-4-(4-methanesulfonyl-phenyl)-imidazol-1-yl]-phenylamino}-acetic acid methyl ester (317 mg, 0.5 mmol) was treated following general procedure F to give 5-{-4-[2-(4'-cyclohexyl-biphenyl-4-ylmethyl)-4-(4-methanesulfonyl-phenyl)-imidazol-1-yl]-phenyl}-1,2,5-thiadiazolidine-3-one-1,1-dioxide.

LCMS: m/z 680 (M+H)+; 1H NMR (DMSO-d6, 400 MHz): δ 1.17-1.42 (m, 5H), 1.68-1.80 (m, 5H), 2.39 (m, 1H), 3.21 (s, 3H), 4.10 (s, 2H), 4.49 (s, 2H), 7.11 (d, 2H), 7.13 (d, 2H), 7.26 (d, 2H), 7.46 (d, 2H), 7.48-7.7.52 (m, 5H), 7.74 (d, 2H), 7.89 (s, 1H), 8.09 (d, 1H) ppm.

Example 116

5-{-4-[4-(2,4-Dichloro-phenyl)-2-(4'-propionyl-biphenyl-4-ylmethyl)-imidazol-1-yl]-phenyl}-[1,2,5]thiadiazolidin-3-one-1,1-dioxide (66 mg, 0.1 mmol) was reacted with ethyl magnesium bromide (40 mg, 0.3 mmol) following general procedure Z and resulted tertiary alcohol was reduced according to general procedure AA to give 5-(4-{4-(2,4-dichloro-phenyl)-2-[4'-(1-ethyl-propyl)-biphenyl-4-ylmethyl]-imidazol-1-yl}-phenyl)-1,2,5-thiadiazolidine-3-one-1,1-dioxide.

LCMS: m/z 687 (M+H)$^+$; $^1$H NMR (DMSO-d$_6$, 400 MHz): δ 0.98-1.11 (m, 3H), 1.13-1.21 (m, 3H), 1.28 (t, 1H), 3.87 (m, 2H), 3.99 (m, 2H), 4.04 (s, 2H), 4.09 (s, 2H), 7.11-7.21 (m, 4H), 7.27 (d, 2H), 7.35 (d, 2H), 7.38 (d, 2H), 7.46-7.54 (m, 3H), 7.63 (d, 1H), 7.89 (s, 1H), 8.18 (d, 1H) ppm.

Example 117

5-{-4-[2-(3'-Amino-4'-isobutyl-biphenyl-4-ylmethyl)-4-(2,4-dichloro-phenyl)-imidazol-1-yl]-phenyl}-[1,2,5]thiadiazolidin-3-one-1,1-dioxide (22 mg, 0.03 mmol) was reacted with isopropyl chloroformate (5 mg, 0.04 mmol) according to general procedure U to give (4'-{4-(2,4-dichloro-phenyl)-1-[4-(1,1,4-trioxo-1-[1,2,5]thiadiazolidin-2-yl)-phenyl]-1H-imidazol-2-ylmethyl}-4-isobutyl-biphenyl-3-yl)-carbamic acid isopropyl ester.

LCMS: m/z 746 (M+H)$^+$

Example 118

5-{-4-[2-(3'-Amino-4'-isobutyl-biphenyl-4-ylmethyl)-4-(2,4-dichloro-phenyl)-imidazol-1-yl]-phenyl}-[1,2,5]thiadiazolidin-3-one-1,1-dioxide (22 mg, 0.03 mmol) was reacted with butyraldehyde (2.2 mg, 0.03 mmol) according to general procedure X to give 5-{4-[2-(3'-butylamino-4'-isobutyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 716 (M+H)$^+$.

Example 119

2-(4-Bromo-benzyl)-4-(2,4-dichloro-phenyl)-1H-imidazole (3.9 g, 10 mmol) was treated as described in general procedure B using 1-iodo-3-nitrobenzene to give 2-(4-bromo-benzyl)-1-(3-nitro-phenyl)-4-(2,4-dichloro-phenyl)-1H-imidazole.

2-(4-Bromo-benzyl)-4-(2,4-dichloro-phenyl)-1-(3-nitrophenyl-phenyl)-1H-imidazole (1.3 g, 2.5 mmol) was reduced to amine and was reacted with methyl bromo acetate following general procedures D & E to give {3-[2-(4-bromo-benzyl)-4-(2,4-dichloro-phenyl)-imidazol-1-yl]-phenylamino}-acetic acid methyl ester.

{3-[2-(4-Bromo-benzyl)-4-(2,4-dichloro-phenyl)-imidazol-1-yl]-phenylamino}-acetic acid methyl ester (55 mg, 0.1 mmol) was coupled with 4-n-butyl-phenylboronic acid (36 mg, 0.2 mmol) according to general procedure G to give {3-[2-(4'-butyl-biphenyl-4-ylmethyl)-4-(2,4-dichloro-phenyl)-imidazol-1-yl]-phenylamino}-acetic acid methyl ester.

{3-[2-(4'-Butyl-biphenyl-4-ylmethyl)-4-(2,4-dichloro-phenyl)-imidazol-1-yl]-phenylamino}-acetic acid methyl ester (30 mg, 0.05 mmol) was treated following general procedure F to give 5-{3-[2-(4'-butyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 645 (M+H)$^+$; $^1$H NMR (DMSO-d$_6$, 400 MHz): δ 0.98 (t, 3H), 1.19 (m, 2H), 1.34 (m, 2H), 2.67 (t, 2H), 4.04 (s, 2H), 4.09 (s, 2H), 7.11-7.18 (m, 4H), 7.26 (d, 2H), 7.37 (d, 2H), 7.45-7.53 (m, 5H), 7.61 (d, 1H), 7.88 (s, 1H), 8.19 (d, 1H) ppm.

Example 120

3-[2-(4-Bromo-benzyl)-4-(2,4-dichloro-phenyl)-imidazol-1-yl]-phenylamino}-acetic acid methyl ester (55 mg, 0.1 mmol) was coupled with 4-iso-butyl-phenylboronic acid (36 m g, 0.2 mmol) according to general procedure G to give {3-[2-(4'-isobutyl-biphenyl-4-ylmethyl)-4-(2,4-dichloro-phenyl)-imidazol-1-yl]-phenylamino}-acetic acid methyl ester.

{3-[2-(4'-Iso-Butyl-biphenyl-4-ylmethyl)-4-(2,4-dichloro-phenyl)-imidazol-1-yl]-phenylamino}-acetic acid methyl ester (20 mg, 0.033 mmol) was treated following general procedure F to give 5-{3-[4-(2,4-dichloro-phenyl)-2-(4'-isobutyl-biphenyl-4-ylmethyl)-imidazol-1-yl]-phenyl}-1,2,5-thiadiazolidine-3-one-1,1-dioxide.

LCMS: m/z 645 (M+H)$^+$; $^1$H NMR (DMSO-d$_6$, 400 MHz): 1.11-1.23 (m, 6H), 2.95 (t, 1H), 3.29 (m, 2H), 4.04 (s, 2H), 4.09 (s, 2H), 7.09-7.17 (m, 3H), 7.27 (d, 2H), 7.36 (d, 2H), 7.47 (d, 2H), 7.42-7.54 (m, 4H), 7.65 (d, 1H), 7.87 (s, 1H), 8.19 (d, 1H) ppm.

By analogous methods to those used to prepare Example 120, the following compounds were synthesized:

| Ex. | Name | LC/MS (m/z) |
|-----|------|-------------|
| 121 | 5-{3-[4-(2,4-Dichloro-phenyl)-2-(4'-piperidin-1-yl-biphenyl-4-ylmethyl)-imidazol-1-yl]-phenyl}-1,2,5-thiadiazolidine-3-one-1,1-dioxide | 672 (M + H)$^+$ |
| 122 | 5-{3-[2-(3'-Nitro-4'-isobutyl-biphenyl-4-ylmethyl)-4-(2,4-dichloro-phenyl)-imidazol-1-yl]-phenyl}-1,2,5-thiadiazolidine-3-one-1,1-dioxide | 690 (M + H)$^+$ |

Example 123

5-{3-[2-(3'-amino-4'-isobutyl-biphenyl-4-ylmethyl)-4-(2,4-dichloro-phenyl)-imidazol-1-yl]-phenyl}-1,2,5-thiadiazolidine-3-one-1,1-dioxide was prepared according to general procedure D from the compound of Example 122.

LCMS: m/z 660 (M+H)$^+$.

Example 124

(4'-{4-(2,4-Dichloro-phenyl)-1-[3-(1,1,4-trioxo-1-[1,2,5]thiadiazolidin-2-yl)-phenyl]-1H-imidazol-2-ylmethyl}-4-isobutyl-biphenyl-3-yl)-carbamic acid methyl ester was prepared according to general procedure U from the compound of Example 123.

By analogous methods to those used to prepare Example 120, the following compounds were synthesized:

| Ex. | Name | LC/MS (m/z) |
|-----|------|-------------|
| 125 | 5-{3-[4-(2,4-Dichloro-phenyl)-2-(2'-fluoro-5'-propoxy-biphenyl-4-ylmethyl)-imidazol-1-yl]-phenyl}-1,2,5-thiadiazolidine-3-one-1,1-dioxide | 665 (M + H)+ |
| 126 | 5-{3-[2-(2'-Butoxy-biphenyl-4-ylmethyl)-4-(2,4-dichloro-phenyl)-imidazol-1-yl]-phenyl}-1,2,5-thiadiazolidine-3-one-1,1-dioxide | 661 (M + H)+ |
| 127 | 5-(3-{4-(2,4-Dichloro-phenyl)-2-[4'-(3,3-dimethyl-butoxy)-biphenyl-4-ylmethyl]-imidazol-1-yl}-phenyl)-1,2,5-thiadiazolidine-3-one-1,1-dioxide | 689 (M + H)+ |
| 128 | 5-{3-[4-(2,4-Dichloro-phenyl)-2-(4'-isobutoxy-biphenyl-4-ylmethyl)-imidazol-1-yl]-phenyl}-1,2,5-thiadiazolidine-3-one-1,1-dioxide | 689 (M + H)+ |
| 129 | 5-{3-[2-(4'-Cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide | 701 (M + H)+ |
| 130 | 5-(3-{4-(2,4-Dichloro-phenyl)-2-[4'-(3,3-dimethyl-butylsulfanyl)-biphenyl-4-ylmethyl]-imidazol-1-yl}-phenyl)-1,2,5-thiadiazolidine-3-one-1,1-dioxide | 705 (M + H)+ |

Example 131

3-[2-(4-Bromo-benzyl)-4-(2,4-dichloro-phenyl)-imidazol-1-yl]-phenylamino}-acetic acid methyl ester (55 mg, 0.1 mmol) was treated as described in general procedure G using 4-(cyclohexylmethylsulfanyl)-phenylboronic acid (50 mg, 0.2 mmol, prepared according to general procedure I) to give {3-[2-(4'-cyclohexylmethylsulfanyl-biphenyl-4-ylmethyl)-4-(2,4-dichloro-phenyl)-imidazol-1-yl]-phenylamino}-aceticacid methyl ester.

{3-[2-(4'-Cyclohexylmethylsulfanyl-biphenyl-4-ylmethyl)-4-(2,4-dichloro-phenyl)-imidazol-1-yl]-phenylamino}-aceticacid methyl ester (23 mg, 0.033 mmol) was treated following general procedure F to give 5-{3-[2-(4'-cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 717 (M+H)+; $^1$H NMR (DMSO-$d_6$, 400 MHz): δ 0.99-1.21 (m, 6H), 1.47 (m, 1H), 1.57-1.88 (m, 4H), 2.87 (d, 2H), 4.04 (s, 2H), 4.09 (s, 2H), 7.11-7.17 (m, 4H), 7.31-7.38 (m, 4H), 7.42-7.58 (m, 5H), 7.63 (d, 1H), 7.87 (s, 1H), 8.19 (d, 1H) ppm.

Example 132

5-{3-[2-(4'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide (7.2 mg, 0.01 mmol) was treated as described in general procedure S to give 5-{3-[2-(4'-cyclohexylmethanesulfonyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 749 (M+H)+; $^1$H NMR (DMSO-$d_6$, 400 MHz): δ 1.00-1.25 (m, 6H), 1.52 (m, 1H), 1.58-1.87 (m, 4H), 3.21 (d, 2H), 4.04 (s, 2H), 4.09 (s, 2H), 7.17 (d, 2H), 7.21 (d, 2H), 7.27-7.41 (m, 4H), 7.44-7.58 (m, 5H), 7.64 (d, 1H), 7.87 (s, 1H), 8.19 (d, 1H) ppm.

Example 133

3-[2-(4-Bromo-benzyl)-4-(2,4-dichloro-phenyl)-imidazol-1-yl]-phenylamino}-acetic acid methyl ester (55 mg, 0.1 mmol) was treated as described in general procedure G using-3-(2-cyclohexyl-ethoxy)-phenylboronic acid (50 mg, 0.2 mmol, prepared according to general procedure H) to give {3-[2-[4'-(2-cyclohexyl-ethoxy)-biphenyl-4-ylmethyl]-4-(2,4-dichloro-phenyl)-imidazol-1-yl]-phenylamino}-acetic acid methyl ester.

{3-[2-[4'-(2-Cyclohexyl-ethoxy)-biphenyl-4-ylmethyl]-4-(2,4-dichloro-phenyl)-imidazol-1-yl]-phenylamino}-acetic acid methyl ester (22 mg, 0.03 mmol) was treated following general procedure F to give 5-{3-[2-[4'-(2-cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide.

LCMS: m/z 715 (M+H)+; $^1$H NMR (DMSO-$d_6$, 400 MHz): δ 0.86-0.88 (m, 2H), 1.14-1.21 (m, 4H), 1.45 (m, 1H), 1.49-1.71 (m, 6H), 4.01 (m, 4H), 4.12 (s, 2H), 6.87 (dd, 1H), 7.13-7.19 (m, 5H), 7.31 (d, 2H), 7.37 (d, 2H), 7.46-7.57 (m, 3H), 7.65 (d, 1H), 7.87 (s, 1H), 8.19 (d, 1H) ppm.

Example 134

5-{3-[2-(4'-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-(cyclohexylmethylamino)-phenylboronic acid (47 mg, 0.2 mmol, prepared according to general procedure J) to give 5-{3-[2-[4'-(cyclohexylmethyl-amino)-biphenyl-4-ylmethyl]-4-(2,4-dichloro-phenyl)-imidazol-1-yl]-phenyl}-1,2,5-thiadiazolidine-3-one-1,1-dioxide.

LCMS: m/z 700 (M+H)+; $^1$H NMR (DMSO-$d_6$, 400 MHz): δ 0.90-0.93 (m, 2H), 1.18-1.25 (m, 5H), 1.67-1.80 (m, 4H), 2.84 (d, 2H), 4.01 (s, 2H), 4.07 (s, 2H), 6.57 (d, 2H), 6.91 (dd, 1H), 6.93-7.09 (m, 2H), 7.23 (d, 2H), 7.25 (d, 2H), 7.32-7.49 (m, 3H), 7.64 (d, 2H), 7.92 (s, 1H), 8.18 (d, 1H) ppm.

Example 135

5-{3-[2-(4'-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-amino-phenylboronic acid (28 mg, 0.2 mmol) to give 5-{3-[2-(4'-amino-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 604 (M+H)+.

Example 136

5-{3-[2-(4'-Amino-biphenyl-4-ylmethyl)-4-(2,4-dichloro-phenyl)-imidazol-1-yl]-phenyl}-[1,2,5]thiadiazolidin-3-one-1,1-dioxide (7 mg, 0.01 mmol) was reacted with 1-bromo-3-3-dimethyl butane (3.3 mg, 0.02 mmol) following general procedure E to give-5-{3-[2-{4'-[bis-(3,3-dimethyl-butyl)-amino]-biphenyl-4-ylmethyl}-4-(2,4-dichloro-phenyl)-imidazol-1-yl]-phenyl}-1,2,5-thiadiazolidine-3-one-1,1-dioxide.

LCMS: m/z 772 (M+H)$^+$

Example 137

3-[2-(4-Bromo-benzyl)-4-(2,4-dichloro-phenyl)-imidazol-1-yl]-phenylamino}-acetic acid methyl ester (55 mg, 0.1 mmol) was coupled with 4-morpholino-phenyl boronic acid (40 m g, 0.2 mmol) according to general procedure G to give {3-[4-(2,4-dichloro-phenyl)-2-(4'-morpholin-4-yl-biphenyl-4-ylmethyl)-imidazol-1-yl]-phenylamino}-acetic acid methylester.

{3-[4-(2,4-Dichloro-phenyl)-2-(4'-morpholin-4-yl-biphenyl-4-ylmethyl)-imidazol-1-yl]-phenylamino}-acetic acid methyl ester (20 mg, 0.03 mmol) was treated following general procedure F to give 5-{3-[4-(2,4-dichloro-phenyl)-2-(4'-morpholin-4-yl-biphenyl-4-ylmethyl)-imidazol-1-yl]-phenyl}-1,2,5-thiadiazolidine-3-one-1,1-dioxide.

LCMS: m/z 674 (M+H)$^+$; $^1$H NMR (DMSO-d$_6$, 400 MHz): δ 0.83-1.05 (m, 2H), 1.10-1.20 (m, 2H), 3.12-3.14 (m, 2H), 3.72-3.74 (m, 2H), 4.01 (s, 2H), 4.10 (s, 2H), 6.98 (d, 2H), 7.01 (d, 2H), 7.12 (d, 2H), 7.20 (d, 2H), 7.42-7.50 (m, 3H), 7.64 (d, 1H), 7.86 (s, 1H), 7.92 (d, 2H), 8.18 (d, 1H) ppm.

Example 138

3-[2-(4-Bromo-benzyl)-4-(2,4-dichloro-phenyl)-imidazol-1-yl]-phenylamino}-acetic acid methyl ester (55 mg, 0.1 mmol) was treated as described in general procedure G using 4-(2-cyclohexylethylsulfanyl)-phenylboronic acid (52 mg, 0.2 mmol, prepared according to general procedure I) to give {3-[2-[4'-(2-cyclohexyl-ethylsulfanyl)-biphenyl-4-ylmethyl]-4-(2,4-dichloro-phenyl)-imidazol-1-yl]-phenylamino}-acetic acid methyl ester.

{3-[2-[4'-(2-Cyclohexyl-ethylsulfanyl)-biphenyl-4-ylmethyl]-4-(2,4-dichloro-phenyl)-imidazol-1-yl]-phenylamino}-acetic acid methyl ester (23 mg, 0.033 mmol) was treated following general procedure F to give 5-{3-[2-[4'-(2-cyclohexyl-ethylsulfanyl)-biphenyl-4-ylmethyl]-4-(2,4-dichloro-phenyl)-imidazol-1-yl]-phenyl}-1,2,5-thiadiazolidine-3-one-1,1-dioxide.

LCMS: m/z 731 (M+H)$^+$; $^1$H NMR (DMSO-d$_6$, 400 MHz): δ 0.86-0.89 (m, 2H), 1.14-1.21 (m, 6H), 1.45 (m, 1H), 1.47-1.80 (m, 4H), 2.97 (m, 2H), 4.01 (s, 2H), 4.12 (s, 2H), 7.02 (d, 2H), 7.04 (d, 2H), 7.16 (d, 2H), 7.33 (d, 2H), 7.42-7.57 (m, 5H), 7.64 (d, 1H), 7.78 (s, 1H), 8.17 (d, 1H) ppm.

Example 139

5-{3-[2-[4'-(Cyclohexylmethyl-amino)-biphenyl-4-ylmethyl]-4-(2,4-dichloro-phenyl)-imidazol-1-yl]-phenyl}-[1,2,5]thiadiazolidin-3-one-1,1-dioxide (7 mg, 0.01 mmol) was reacted with acetaldehyde (2 mg, 0.04 mmol) following general procedure X to give 5-{3-[2-[4'-(cyclohexylmethyl-ethyl-amino)-biphenyl-4-ylmethyl]-4-(2,4-dichloro-phenyl)-imidazol-1-yl]-phenyl}-1,2,5-thiadiazolidine-3-one-1,1-dioxide.

LCMS: m/z 728 (M+H)$^+$.

Example 140

2-tert-Butyl-5-chloro-isothiazolin-3-one-1,1-dioxide [(2.3 g, 10 mmol)-prepared following general procedure AB) was coupled with 3-boc-amino-phenylboronic acid (3.0 g, 12 mmol) according to general procedure AC to give [3-(2-tert-butyl-1,1,3-trioxo-2,3-dihydro-1H-isothiazol-5-yl)-phenyl]-carbamic acid tert-butylester.

[3-(2-tert-Butyl-1,1,3-trioxo-2,3-dihydro-1H-isothiazol-5-yl)-phenyl]-carbamic acid tert-butylester (77 mg, 0.20 mmol) was treated with 1,4-dioxane-HCl following general procedure V to give 5-(3-Amino-phenyl)-2-tert-butyl-isothiazol-3-one-1,1-dioxide.

LCMS: m/z 280 (M+H)$^+$; $^1$H NMR (CDCl$_3$, 400 MHz): δ 1.68 (s, 9H), 6.66 (s, 1H), 7.32 (d, 2H), 7.34 (d, 2H), 7.39 (dd, 1H), 7.79 (s, 1H) ppm.

5-(3-Amino-phenyl)-2-tert-butyl-isothiazol-3-one-1,1-dioxide (70 mg, 0.25 mmol) was treated with 2-bromo-2,4-dichloro-acetophenone (70 g, 0.26 mmol) following general procedure N to give 2-tert-butyl-5-{3-[2-(2,4-dichloro-phenyl)-2-oxo-ethylamino]-phenyl}-isothiazol-3-one-1,1-dioxide.

LCMS: m/z 467 (M+H)$^+$; $^1$H NMR (CDCl$_3$, 400 MHz): δ 1.69 (s, 9H), 4.57 (s, 2H), 6.62 (s, 1H), 6.78 (d, 1H), 6.87 (s, 1H), 7.03 (d, 1H), 7.33 (dd, 1H), 7.37 (d, 1H), 7.52 (s, 1H), 7.64 (d, 1H) ppm.

2-tert-Butyl-5-{3-[2-(2,4-dichloro-phenyl)-2-oxo-ethylamino]-phenyl}-isothiazol-3-one-1,1-dioxide (47 mg, 0.10 mmol) was reacted with 4-bromo-phenacetyl chloride (25 mg, 0.10 mmol) according to general procedure N to give 2-(4-bromo-phenyl)-N-[3-(2-tert-butyl-1,1,3-trioxo-2,3-dihydro-1H-isothiazol-5-yl)-phenyl]-N-[2-(2,4-dichloro-phenyl)-2-oxo-ethyl]-acetamide.

LCMS: m/z 664 (M+H)$^+$; $^1$H NMR (CDCl$_3$, 400 MHz): δ 1.68 (s, 9H), 3.62 (s, 2H), 3.70 (s, 2H), 6.66 (s, 1H), 7.16 (d, 2H), 7.22 (d, 2H), 7.40 (d, 2H), 7.41-7.48 (m, 2H), 7.53 (d, 2H), 7.98 (s, 1H) ppm.

2-(4-Bromo-phenyl)-N-[3-(2-tert-butyl-1,1,3-trioxo-2,3-dihydro-isothiazol-5-yl)-phenyl]-N-[2-(2,4-dichloro-phenyl)-2-oxo-ethyl]-acetamide-1,1-dioxide (23 mg, 0.03 mmol) was treated as described in general procedure O to give 5-{3-[2-(4-bromo-benzyl)-4-(2,4-dichloro-phenyl)-imidazol-1-yl]-phenyl}-2-tert-butyl-isothiazol-3-one-1,1-dioxide.

LCMS: m/z 645 (M+H)$^+$; $^1$H NMR (DMSO-d$_6$, 400 MHz): δ 1.59 (s, 9H), 3.66 (s, 2H), 7.14 (s, 1H), 7.28 (d, 2H), 7.47-7.53 (m, 5H), 7.73 (d, 2H), 8.06 (s, 1H), 10.4 (s. 1H) ppm.

5-{3-[2-(4-Bromo-benzyl)-4-(2,4-dichloro-phenyl)-imidazol-1-yl]-phenyl}-2-tert-butyl-isothiazol-3-one-1,1-dioxide (7 mg, 0.01 mmol) was treated as described in general procedure G using 4-(cyclohexylmethoxy)-phenylboronic acid (5 mg, 0.02 mmol, prepared according to general procedure H) to give 2-tert-Butyl-5-{3-[2-(4'-cyclohexylmethoxy-biphenyl-4-ylmethyl)-4-(2,4-dichloro-phenyl)-imidazol-1-yl]-phenyl}-isothiazol-3-one-1,1-dioxide.

LCMS: m/z 754 (M+H)$^+$; $^1$H NMR (CDCl$_3$, 400 MHz): δ 0.89-1.07 (m, 2H), 1.25-1.32 (m, 5H), 1.64 (s, 9H), 1.69-1.90 (m, 6H), 3.77 (s, 2H), 3.79 (s, 2H), 6.59 (s, 1H), 6.70 (s, 1H), 6.93 (d, 2H), 7.08 (d, 1H), 7.10 (d, 2H), 7.36-7.47 (m, 5H), 7.70 (d, 2H), 7.78 (d, 1H) ppm.

Example 141

2-(4-Bromo-benzyl)-4-(2,4-dichlorophenyl)-1H-imidazole (3.27 g, 8.6 mmol) was treated as described in general procedure B using 4-fluoronitrobenzene to provide 2-(4-bromo-benzyl)-4-(2,4-dichloro-phenyl)-1-(4-nitro-phenyl)-1H-imidazole, which was treated with 4-hydroxyphenyl boronic acid according to general procedure G to provide 4'-[4-(2,4-dichloro-phenyl)-1-(4-nitro-phenyl)-1H-imidazol-2-ylmethyl]-biphenyl-4-ol (996 mg, 22% for two steps). To a solution of the phenol in THF (0.5 M) was added N-boc-4-hydroxypiperidine (2 eq) and triphenylphosphine (2 eq) under nitrogen, then while sonicating this mixture diisopropyl azodicarboxylate (2 eq) was added. After sonicating 1 hour the reaction mixture was evaporated in vacuo and the reside was purified by silica gel column chromatography to afford 4-{4'-[4-(2,4-dichloro-phenyl)-1-(4-nitro-phenyl)-1H-imidazol-2-ylmethyl]-biphenyl-4-yloxy}-piperidine-1-carboxylic acid tert-butyl ester.

The boc-protected alkyl aryl ether product (911 mg, 1.3 mmol) was deprotected according to general procedure V and the neopentyl carbamate group was introduced according to general procedure U to provide 4-{4'-[4-(2,4-dichloro-phenyl)-1-(4-nitro-phenyl)-1H-imidazol-2-ylmethyl]-biphenyl-4-yloxy}-piperidine-1-carboxylic acid 2,2-dimethyl-propyl ester. The resulting nitro compound was reduced, alkylated and cyclized according to general procedure C to provide 4-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yloxy)-piperidine-1-carboxylic acid 2,2-dimethyl-propyl ester.

LCMS: m/z 802 (M+H)$^+$; $^1$H NMR (acetone-d$_6$, 400 MHz): δ 0.95 (s, 9H), 1.28 (m, 2H), 1.66 (m, 2H), 1.97 (m, 2H), 3.37 (m, 2H), 3.78 (m, 4H), 4.02 (s, 1H), 4.32 (s, 1H), 4.60 (m, 1H), 6.97-7.04 (m, 2H), 7.14 (m, 2H), 7.21, (m, 2H), 7.28 (m, 2H), 7.38-7.45 (m, 3H), 7.47-7.54 (m, 3H), 7.83 (s, 1H), 8.35 (d, 1H) ppm.

Example 142

5-{-4-[2-(4-bromo-benzyl)-4-(2,4-dichloro-phenyl)-imidazol-1-yl]-phenyl}-1,2,5-thiadiazolidine-3-one-1,1-dioxide (100 mg, 0.17 mmol) was treated as described in general procedure G using 3-isopropylphenyl boronic acid to provide 5-{4-[4-(2,4-dichloro-phenyl)-2-(3'-isopropyl-biphenyl-4-ylmethyl)-imidazol-1-yl]-phenyl}-1,2,5-thiadiazolidine-3-one-1,1-dioxide.

LCMS: m/z 631 (M+H)$^+$.

Example 143

5-{-4-[2-(4-bromo-benzyl)-4-(2,4-dichloro-phenyl)-imidazol-1-yl]-phenyl}-1,2,5-thiadiazolidine-3-one-1,1-dioxide (100 mg, 0.17 mmol) was treated as described in general procedure G using 4-trifluoromethylphenylboronic acid to provide 5-{4-[4-(2,4-dichloro-phenyl)-2-(4'-trifluoromethyl-biphenyl-4-ylmethyl)-imidazol-1-yl]-phenyl}-1,2,5-thiadiazolidine-3-one-1,1-dioxide.

LCMS: m/z 657 (M+H)$^+$.

Example 144

5-{-4-[2-(4-bromo-benzyl)-4-(2,4-dichloro-phenyl)-imidazol-1-yl]-phenyl}-1,2,5-thiadiazolidine-3-one-1,1-dioxide (143 mg, 0.24 mmol) was stirred in DMF (0.1-0.5 M) with 1.1 eq of N-chlorosuccinimide under nitrogen at room temperature for 12 hours. The mixture was poured into water and extracted with ethyl acetate. The organic extract was washed with water, saturated aqueous NaHCO$_3$ and brine and dried over Na$_2$SO$_4$. After removal of the solvent in vacuo, the residue was dried and used directly in the next step.

The crude chlorinated compound was treated as described in general procedure G using 4-cyclohexylphenyl boronic acid to provide 5-{2-chloro-4-[2-(4'-cyclohexyl-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 705 (M+H)$^+$.

Example 145

2-(4'-Cyclohexyl-biphenyl-4-ylmethyl)-4-(2,4-dichloro-phenyl)-1H-imidazole (250 mg, 0.54 mmol) was treated according to general procedure B using 2-fluoro-5-nitrotoluene to provide 2-(4'-cyclohexyl-biphenyl-4-ylmethyl)-4-(2,4-dichloro-phenyl)-1-(2-methyl-4-nitro-phenyl)-1H-imidazole, which was collected without purification. Treatment of the nitro compound as described in general procedure C provided 5-{4-[2-(4'-cyclohexyl-biphenyl-4-ylmethyl)-4-(2,4-dichloro-phenyl)-imidazol-1-yl]-3-methyl-phenyl}-1,2,5-thiadiazolidine-3-one-1,1-dioxide.

LCMS: m/z 685 (M+H)$^+$.

By analogous methods to those used to prepare Example 145, the following compounds were synthesized:

| Ex. | Name | LC/MS (m/z) |
| --- | --- | --- |
| 146 | 5-{3-Chloro-4-[2-(4'-cyclohexyl-biphenyl-4-ylmethyl)-4-(2,4-dichloro-phenyl)-imidazol-1-yl]-phenyl}-1,2,5-thiadiazolidine-3-one-1,1-dioxide | 705 (M + H)$^+$ |
| 147 | 5-{4-[2-(4'-Cyclohexyl-biphenyl-4-ylmethyl)-4-(2,4-dichloro-phenyl)-imidazol-1-yl]-3-trifluoromethyl-phenyl}-1,2,5-thiadiazolidine-3-one-1,1-dioxide | 739 (M + H)$^+$ |
| 148 | 5-{4-[2-(4'-Cyclohexyl-biphenyl-4-ylmethyl)-4-(2,4-dichloro-phenyl)-imidazol-1-yl]-3-fluoro-phenyl}-1,2,5-thiadiazolidine-3-one-1,1-dioxide | 689 (M + H)$^+$ |

Example 149

5-{-4-[2-(4-bromo-benzyl)-4-(2,4-dichloro-phenyl)-imidazol-1-yl]-phenyl}-1,2,5-thiadiazolidine-3-one-1,1-dioxide (200 mg, 0.34 mmol) was treated as described in general procedure G using 4-(2-ethoxycarbonyl-vinyl)phenyl boronic acid to provide 3-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-acrylic acid ethyl ester.

LCMS: m/z 687 (M+H)$^+$; $^1$H NMR (DMSO-d$_6$, 400 MHz): δ 1.27 (t, 3H), 4.05 (s, 2H), 4.10 (s, 2H), 4.19 (q, 2H), 6.67 (d, 1H), 7.15-7.22 (m, 4H), 7.37 (m, 2H), 7.45-7.53 (m, 2H), 7.59-7.72 (m, 5H), 7.79 (m, 2H), 7.90 (s, 1H), 8.19 (d, 1H) ppm.

Example 150

5-{4-[2-(4-bromo-benzyl)-4-(2,4-dichloro-phenyl)-imidazol-1-yl]-phenyl}-1,2,5-thiadiazolidine-3-one-1,1-dioxide (300 mg, 0.51 mmol) was treated as described in general procedure G using 4-(2-ethoxycarbonyl-ethyl)phenyl boronic acid to provide 3-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-propionic acid ethyl ester.

LCMS: m/z 689 (M+H)$^+$; $^1$H NMR (DMSO-$d_6$, 400 MHz): δ 1.16 (t, 3H), 2.63 (t, 2H), 2.87 (t, 2H), 4.01-4.12 (m, 6H), 7.13-7.21 (m, 4H), 7.29 (m, 2H), 7.37 (m, 2H), 7.48 (m, 1H), 7.51-7.57 (m, 4H), 7.65 (m, 1H), 7.90 (s, 1H), 8.19 (d, 1H) ppm.

Example 151

(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-acrylic acid ethyl ester (36 mg, 52 μmol) was treated as described in general procedure P to provide 3-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-acrylic acid.

LCMS: m/z 659 (M+H)$^+$; $^1$H NMR (DMSO-$d_6$, 400 MHz): δ 4.05 (s, 2H), 4.10 (s, 2H), 6.57 (d, 1H), 7.14-7.22 (m, 4H), 7.38 (m, 2H), 7.48 (m, 1H), 7.58-7.66 (m, 4H), 7.70 (m, 2H), 7.76 (m, 2H), 7.90 (s, 1H), 8.19 (d, 1H) ppm.

Example 152

3-(4'-{4-(2,4-Dichloro-phenyl)-1-[4-(1,1,4-trioxo-[1,2,5]thiadiazolidin-2-yl)-phenyl]-1H-imidazol-2-ylmethyl}-biphenyl-4-yl)-propionic acid ethyl ester (54 mg, 78 μmol) was treated as described in general procedure P to provide 3-(4'-{4-(2,4-dichloro-phenyl)-1-[4-(1,1,4-trioxo-[1,2,5]thiadiazolidin-2-yl)-phenyl]-1H-imidazol-2-ylmethyl}-biphenyl-4-yl)-propionic acid.

LCMS: m/z 661 (M+H)$^+$; $^1$H NMR (DMSO-$d_6$, 400 MHz): δ 2.56 (t, 2H), 2.84 (t, 2H), 4.07 (s, 2H), 4.12 (s, 2H), 7.14-7.22 (m, 4H), 7.29 (m, 2H), 7.40 (m, 2H), 7.49-7.57 (m, 5H), 7.69 (m, 1H), 7.96 (s, 1H), 8.13 (d, 1H) ppm.

Example 153

4'-[4-(2,4-Dichloro-phenyl)-1H-imidazol-2-ylmethyl]-biphenyl-4-carboxylic acid ethyl ester (500 mg, 1.1 mmol) was treated as described in general procedure Z using 2 equivalents of propylmagnesium chloride. The crude Grignard product was subjected directly to reduction according to general procedure AA, after which the reduction product was alkylated with 4-fluoronitrobenzene according to general procedure B. The crude nitro compound was treated as described in general procedure C to provide 5-(4-{4-(2,4-dichloro-phenyl)-2-[4'-(1-propyl-butyl)-biphenyl-4-ylmethyl]-imidazol-1-yl}-phenyl)-1,2,5-thiadiazolidine-3-one-1,1-dioxide.

LCMS: m/z 687 (M+H)$^+$; $^1$H NMR (DMSO-$d_6$, 400 MHz): δ 0.82 (t, 6H), 1.05-1.20 (m, 4H), 1.48-1.61 (m, 4H), 2.55 (m, 1H), 3.91 (s, 2H), 4.05 (s, 2H), 7.12-7.20 (m, 4H), 7.23 (m, 2H), 7.36 (m, 2H), 7.47 (dd, 1H), 7.55 (m, 4H), 7.64 (d, 1H), 7.90 (s, 1H), 8.20 (d, 1H) ppm.

Example 154

2-(4-Bromo-benzyl)-4-(2,4-dichloro-phenyl)-1H-imidazole (1 g, 2.6 mmol) was treated with (3-iodo-phenyl)-carbamic acid tert-butyl ester following general procedure R to provide {3-[2-(4-bromo-benzyl)-4-(2,4-dichloro-phenyl)-imidazol-1-yl]-phenyl}-carbamic acid tert-butyl ester. The bromophenyl product (370 mg, 0.64 mmol) was treated as described in general procedure G using 4-ethoxycarbonylphenyl boronic acid to provide 4'-[1-(3-tert-butoxycarbonylamino-phenyl)-4-(2,4-dichloro-phenyl)-1H-imidazol-2-ylmethyl]-biphenyl-4-carboxylic acid ethyl ester.

The benzoate ester obtained above (153 mg, 0.24 mmol) was treated to general procedure Z using 2 eq of 3,3-dimethylbutylmagnesium chloride, followed by reduction of the Grignard product according to general procedure AA to provide [3-(4-(2,4-dichloro-phenyl)-2-{4'4-[1-(3,3-dimethyl-butyl)-4,4-dimethyl-pentyl]-biphenyl-4-ylmethyl}-imidazol-1-yl)-phenyl]-carbamic acid tert-butyl ester. After removal of the Boc group according to general procedure V, the resulting aniline compound was treated according to general procedures E and F successively to provide 5-[3-(4-(2,4-dichloro-phenyl)-2-{4'-[1-(3,3-dimethyl-butyl)-4,4-dimethyl-pentyl]-biphenyl-4-yl methyl}-imidazol-1-yl)-phenyl]-1,2,5-thiadiazolidine-3-one-1,1-dioxide.

LCMS: m/z 771 (M+H)$^+$.

Example 155

4-Bromobenzaldehyde (1 g, 5.4 mmol) was converted to 4-(4,4-dimethyl-pentyl)phenyl boronic acid according to general procedure Y using 3,3-dimethylbutylmagnesium chloride (1 eq).

3-[2-(4-Bromo-benzyl)-4-(2,4-dichloro-phenyl)-imidazol-1-yl]-phenylamine was prepared from 3-aminoacetanilide according to general procedure M, then alkylated with methyl bromoacetate according to general procedure E to produce crude {3-[2-(4-bromo-benzyl)-4-(2,4-dichloro-phenyl)-imidazol-1-yl]-phenylamino}-acetic acid methyl ester. The bromo compound (44 mg, 80 μmol) was coupled with 4-(4,4-dimethyl-pentyl)phenyl boronic acid as described in general procedure G to provide (3-{4-(2,4-dichloro-phenyl)-2-[4'-(4,4-dimethyl-pentyl)-biphenyl-4-ylmethyl]-imidazol-1-yl}-phenylamino)-acetic acid methyl ester. The product was then treated according to general procedure F to provide 5-(3-{4-(2,4-dichloro-phenyl)-2-[4'-(4,4-dimethyl-pentyl)-biphenyl-4-ylmethyl]-imidazol-1-yl}-phenyl)-1,2,5-thiadiazolidine-3-one-1,1-dioxide.

LCMS: m/z 687 (M+H)$^+$; $^1$H NMR (DMSO-$d_6$, 400 MHz): δ 0.76 (s, 9H), 1.10-1.20 (m, 2H), 1.48 (m, 2H), 2.47 (t, 2H), 4.03 (s, 2H), 4.22 (s, 2H), 6.71 (m, 1H), 7.04-7.16 (m, 5H), 7.20 (m, 2H), 7.29 (dd, 1H), 7.31-7.40 (m, 5H), 7.79 (s, 1H), 8.23 (d, 1H) ppm.

By analogous methods to those used to prepare Example 155, the following compounds were synthesized:

| Ex. | Name | LC/MS (m/z) |
|---|---|---|
| 156 | 5-{3-[2-[4'-(2-Cyclohexyl-ethyl)-biphenyl-4-ylmethyl]-4-(2,4-dichloro-phenyl)-imidazol-1-yl]-phenyl}-1,2,5-thiadiazolidine-3-one-1,1-dioxide | 699 (M + H)$^+$ |

| Ex. | Name | LC/MS (m/z) |
|---|---|---|
| 157 | 5-(3-{4-(2,4-Dichloro-phenyl)-2-[4'-(3,3-dimethyl-butyl)-biphenyl-4-ylmethyl]-imidazol-1-yl}-phenyl)-1,2,5-thiadiazolidine-3-one-1,1-dioxide | 673 $(M + H)^+$ |
| 158 | 5-{3-[2-(4'-Cyclohexylmethyl-biphenyl-4-ylmethyl)-4-(2,4-dichloro-phenyl)-imidazol-1-yl]-phenyl}-1,2,5-thiadiazolidine-3-one-1,1-dioxide | 685 $(M + H)^+$ |
| 159 | 5-(3-{4-(2,4-Dichloro-phenyl)-2-[4'-(4-methyl-pentyl)-biphenyl-4-ylmethyl]-imidazol-1-yl}-phenyl)-1,2,5-thiadiazolidine-3-one-1,1-dioxide | 673 $(M + H)^+$ |

Example 160

4-Bromobenzaldehyde (6.5 g, 35 mmol) was converted to 4-(2-cyclohexylvinyl)phenyl boronic acid according to general procedure AE using cyclohexylmethylmagnesium bromide.

3-[2-(4-Bromo-benzyl)-4-(2,4-dichloro-phenyl)-imidazol-1-yl]-phenylamine was prepared from 3-aminoacetanilide according to general procedure M, then alkylated with methyl bromoacetate according to general procedure E to produce crude {3-[2-(4-bromo-benzyl)-4-(2,4-dichloro-phenyl)-imidazol-1-yl]-phenylamino}-acetic acid methyl ester. The bromo compound (500 mg, 0.91 mmol) was coupled with 4-(2-cyclohexylvinyl)phenyl boronic acid as described in general procedure G to provide {3-[2-[4'-(2-cyclohexyl-vinyl)-biphenyl-4-ylmethyl]-4-(2,4-dichloro-phenyl)-imidazol-1-yl]-phenylamino}-acetic acid methyl ester. The product was then treated according to general procedure F to provide 5-{3-[2-[4'-(2-cyclohexyl-vinyl)-biphenyl-4-ylmethyl]-4-(2,4-dichloro-phenyl)-imidazol-1-yl]-phenyl}-1,2,5-thiadiazolidine-3-one-1,1-dioxide.

LCMS: m/z 697 $(M+H)^+$; $^1$H NMR (DMSO-$d_6$, 400 MHz): δ 1.12-1.36 (m, 5H), 1.65 (m, 2H), 1.75 (m, 3H), 2.14 (m, 1H), 4.00 (s, 2H), 4.13 (s, 2H), 6.29 (dd, 1H), 6.39 (d, 1H), 6.94 (m, 1H), 7.05 (m, 1H), 7.18 (m, 2H), 7.26 (m, 1H), 7.41-7.46 (m, 3H), 7.49 (dd, 1H), 7.51-7.58 (m, 4H), 7.65 (d, 1H), 7.94 (s, 1H), 8.19 (d, 1H) ppm.

Example 161

4-Bromophenylacetic acid (2.2 g, 10 mmol) was treated according to general procedures A and B to give 2-(4-bromo-benzyl)-1-(4-nitro-phenyl)-4-(2,4-dichloro-phenyl)-1H-imidazole, which was then treated as described in general procedure C to give 5-{4-[2-(4-bromo-benzyl)-4-(2,4-dichloro-phenyl)-imidazol-1-yl]-phenyl}-1,2,5-thiadiazolidine-3-one-1,1-dioxide.

LCMS: m/z 593 $(M+H)^+$; $^1$H NMR (DMSO-$d_6$, 400 MHz): δ 4.05 (s, 2H), 4.07 (s, 2H), 7.15 (d, 2H), 7.27 (d, 2H), 7.47 (dd, 1H), 7.51 (d, 2H), 7.53 (d, 2H), 7.64 (d, 1H), 7.89 (s, 1H), 8.19 (d, 1H) ppm.

Example 162

4-Bromophenylacetic acid (2.2 g, 10 mmol) was treated according to general procedures A and B to give 2-(4-bromo-benzyl)-1-(4-nitro-phenyl)-4-(2,6-dichloro-phenyl)-1H-imidazole, which was then treated as described in general procedure C to give 5-{4-[2-(4-bromo-benzyl)-4-(2,6-dichloro-phenyl)-imidazol-1-yl]-phenyl}-1,2,5-thiadiazolidine-3-one-1,1-dioxide.

LCMS: m/z 593 $(M+H)^+$; $^1$H NMR (DMSO-$d_6$, 400 MHz): δ 4.05 (s, 2H), 4.07 (s, 2H), 7.15 (d, 2H), 7.27 (d, 2H), 7.44-7.52 (m, 5H), 7.63 (d, 1H), 7.88 (s, 1H), 8.18 (d, 1H) ppm.

Example 163

2-(4-Bromo-benzyl)-1-(3-nitro-phenyl)-4-(2,4-dichloro-phenyl)-1H-imidazole (prepared from 4-bromophenylacetic acid according to general procedures A and R) (503 mg, 1 mmol) was treated as described in general procedure C to give 5-{3-[2-(4-bromo-benzyl)-4-(2,4-dichloro-phenyl)-imidazol-1-yl]-phenyl}-1,2,5-thiadiazolidine-3-one-1,1-dioxide.

LCMS: m/z 593 $(M+H)^+$; $^1$H NMR (DMSO-$d_6$, 400 MHz): δ 4.05 (s, 2H), 4.07 (s, 2H), 7.15 (d, 2H), 7.29-7.50 (m, 5H), 7.53 (d, 2H), 7.64 (d, 1H), 7.89 (s, 1H), 8.19 (d, 1H) ppm.

Example 164

2-(4-Bromo-benzyl)-1-(4-nitro-phenyl)-4-(2,4-difluoro-phenyl)-1H-imidazole (prepared from 4-bromophenylacetic acid according to general procedures A and B) (470 mg, 1 mmol) was treated as described in general procedure C to give 5-{4-[2-(4-bromo-benzyl)-4-(2,4-difluoro-phenyl)-imidazol-1-yl]-phenyl}-1,2,5-thiadiazolidine-3-one-1,1-dioxide.

LCMS: m/z 560 $(M+H)^+$; $^1$H NMR (DMSO-$d_6$, 400 MHz): δ 4.05 (s, 2H), 4.07 (s, 2H), 7.12-7.19 (m, 5H), 7.47 (m, 1H), 7.51-7.56 (m, 5H), 8.12 (m, 1H) ppm.

Example 165

2-(4-Bromo-benzyl)-4-(2,4-dichloro-phenyl)-1-(4-methyl-3-nitro-phenyl)-1H-imidazole (prepared from 4-bromophenylacetic acid according to general procedures A and R) (517 mg, 1 mmol) was treated as described in general procedure C to give 5-{5-[2-(4-bromo-benzyl)-4-(2,4-dichloro-phenyl)-imidazol-1-yl]-2-methyl-phenyl}-1,2,5-thiadiazolidine-3-one-1,1-dioxide.

LCMS: m/z 607 $(M+H)^+$; $^1$H NMR (DMSO-$d_6$, 400 MHz): δ 2.30 (s, 3H), 4.05 (s, 2H), 4.07 (s, 2H), 7.27-7.43 (m, 4H), 7.51 (d, 2H), 7.53 (d, 2H), 7.64 (d, 1H), 7.89 (s, 1H), 8.19 (d, 1H) ppm.

Example 166

2-(4-Bromo-benzyl)-4-(2,4-difluoro-phenyl)-1-(4-methyl-3-nitro-phenyl)-1H-imidazole (prepared from 4-bromophenylacetic acid according to general procedures A and R) (484 mg, 1 mmol) was treated as described in general procedure C to give 5-{5-[2-(4-bromo-benzyl)-4-(2,4-difluoro-phenyl)-imidazol-1-yl]-2-methyl-phenyl}-1,2,5-thiadiazolidine-3-one-1,1-dioxide.

LCMS: m/z 574 $(M+H)^+$; $^1$H NMR (DMSO-$d_6$, 400 MHz): δ 2.29 (s, 3H), 4.05 (s, 2H), 4.07 (s, 2H), 7.12-7.19 (m, 4H), 7.47 (m, 1H), 7.51-7.56 (m, 5H), 8.12 (m, 1H) ppm.

Example 167

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-phenoxyphenylboronic acid (43 mg, 0.2 mmol) to give 5-{3-[4-(2,4-dichloro-phenyl)-2-(4'-phenoxy-biphenyl-4-ylmethyl)-imidazol-1-yl]-phenyl}-1,2,5-thiadiazolidine-3-one-1,1-dioxide.

LCMS: m/z 681 (M+H)$^+$; $^1$H NMR (DMSO-d$_6$, 400 MHz): δ 4.05 (s, 2H), 4.08 (s, 2H), 7.05 (d, 2H), 7.07 (d, 2H), 7.14-7.19 (m, 5H), 7.36-7.43 (m, 4H), 7.47 (m, 1H), 7.53 (d, 2H), 7.64-7.66 (m, 3H), 7.90 (s, 1H), 8.20 (d, 1H) ppm.

By analogous methods to those used to prepare Example 167, the following compounds were synthesized:

| Ex. | Name | LC/MS (m/z) |
|---|---|---|
| 168 | 5-{3-[4-(2,4-Dichloro-phenyl)-2-(4-hex-1-enyl-benzyl)-imidazol-1-yl]-phenyl}-1,2,5-thiadiazolidine-3-one-1,1-dioxide | 595 (M + H)$^+$ |
| 169 | 5-(3-{4-(2,4-Dichloro-phenyl)-2-[4-(3,3-dimethyl-but-1-enyl)-benzyl]-imidazol-1-yl}-phenyl)-1,2,5-thiadiazolidine-3-one-1,1-dioxide | 595 (M + H)$^+$ |
| 170 | 5-{3-[2-[4-(2-Cyclohexyl-vinyl)-benzyl]-4-(2,4-dichloro-phenyl)-imidazol-1-yl]-phenyl}-1,2,5-thiadiazolidine-3-one-1,1-dioxide | 595 (M + H)$^+$ |
| 171 | 5-{4-[2-[3'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide | 715 (M + H)$^+$ |

Example 172

5-{-4-[2-(4-Bromo-benzyl)-4-(2,4-dichloro-phenyl)-imidazol-1-yl]-phenyl}-1,2,5-thiadiazolidine-3-one-1,1-dioxide (1.19 g, 2 mmol) was treated as described in general procedure L using 2-(trimethylsilyl)ethoxymethyl chloride (708 μL, 4 mmol) to give 5-{4-[2-(4-bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was then treated according to general procedure AD to give 5-(4-{4-(2,4-dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one.

LCMS: m/z 769 (M+H)$^+$.

5-(4-{4-(2,4-Dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one (385 mg, 0.5 mmol) was treated as described in general procedure G using 3,6-dichloropyridazine (149 mg, 1 mmol) to give 5-{4-[2-[4-(6-chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 756 (M+H)$^+$.

5-{4-[2-[4-(6-Chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (38 mg, 0.05 mmol) was treated as described in general procedure L using 2-cyclohexyl ethanol (35 μL, 0.25 mmol) to give 5-{-4-[2-{-4-[6-(2-cyclohexyl-ethoxy)-pyridazin-3-yl]-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 847 (M+H)$^+$.

5-{4-[2-{4-[6-(2-Cyclohexyl-ethoxy)-pyridazin-3-yl]-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (17 mg, 0.02 mmol) was treated as described in general procedure W using tetrabutylammonium fluoride (26 mg, 0.1 mmol) to give 5-{-4-[2-{-4-[6-(2-cyclohexyl-ethoxy)-pyridazin-3-yl]-benzyl}-4-(2,4-dichloro-phenyl)-imidazol-1-yl]-phenyl}-1,2,5-thiadiazolidine-3-one-1,1-dioxide.

LCMS: m/z 717 (M+H)$^+$; $^1$H NMR (CD$_3$OD, 400 MHz): δ 0.97-1.43 (m, 5H), 1.65 (m, 2H), 1.69-1.81 (m, 6H), 4.05 (t, 2H), 4.08 (s, 2H), 4.10 (s, 2H), 7.17 (d, 2H), 7.21 (d, 2H), 7.37 (d, 2H), 7.46-7.54 (m, 5H), 7.64 (d, 1H), 7.89 (s, 1H), 8.19 (d, 1H) ppm.

Example 173

5-{3-[2-(4-Bromo-benzyl)-4-(2,4-dichloro-phenyl)-imidazol-1-yl]-phenyl}-1,2,5-thiadiazolidine-3-one-1,1-dioxide (1.19 g, 2 mmol) was treated as described in general procedure L using 2-(trimethylsilyl)ethoxymethyl chloride (708 μL, 4 mmol) to give 5-{3-[2-(4-bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was then treated according to general procedure AD to give 5-(3-{4-(2,4-dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one.

LCMS: m/z 769 (M+H)$^+$.

5-(3-{4-(2,4-Dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one (385 mg, 0.5 mmol) was treated as described in general procedure G using 3,6-dichloropyridazine (149 mg, 1 mmol) to give 5-{3-[2-[4-(6-chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 756 (M+H)$^+$.

5-{3-[2-[4-(6-Chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (38 mg, 0.05 mmol) was treated as described in general procedure G using 1-cyclohexen-1-yl-boronic acid (13 mg, 0.1 mmol) to give 5-{3-[2-[4-(6-cyclohex-1-enyl-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 801 (M+H)$^+$.

5-{3-[2-[4-(6-Cyclohex-1-enyl-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (16 mg, 0.02 mmol) was treated as described in general procedure W using tetrabutylammonium fluoride (26 mg, 0.1 mmol) to give 5-{3-[2-[4-(6-cyclohex-1-enyl-pyridazin-3- yl)-benzyl]-4-(2,4-dichloro-phenyl)-imidazol-1-yl]-phenyl}-1,2,5-thiadiazolidine-3-one-1,1-dioxide.

LCMS: m/z 671 (M+H)+; $^1$H NMR (CD$_3$OD, 400 MHz): δ 1.56 (m, 4H), 2.15 (m, 4H), 4.06 (s, 2H), 4.09 (s, 2H), 6.41 (m, 1H), 7.15-7.27 (m, 5H), 7.37 (d, 2H), 7.46-7.54 (m, 4H), 7.64 (d, 1H), 7.89 (s, 1H), 8.19 (d, 1H) ppm.

Example 174

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using trans-1-octen-1-ylboronic acid (47 mg, 0.3 mmol) to give 5-{3-[4-(2,4-dichloro-phenyl)-2-(4-oct-1-enyl-benzyl)-imidazol-1-yl]-phenyl}-1,2,5-thiadiazolidine-3-one-1,1-dioxide.

LCMS: m/z 623 (M+H)+; $^1$H NMR (DMSO-d$_6$, 400 MHz): δ 0.86 (t, 3H), 1.27 (m, 6H), 1.41 (m, 2H), 2.16 (m, 2H), 4.02 (s, 2H), 4.05 (s, 2H), 6.22 (m, 1H), 6.32 (d, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) ppm.

Example 175

5-{-4-[2-(4-Bromo-benzyl)-4-(2,4-dichloro-phenyl)-imidazol-1-yl]-phenyl}-1,2,5-thiadiazolidine-3-one-1,1-dioxide (119 mg, 0.2 mmol) was treated as described in general procedure AF using 1-hexyne (46 μL, 0.4 mmol) to give 5-{-4-[4-(2,4-dichloro-phenyl)-2-(4-hex-1-ynyl-benzyl)-imidazol-1-yl]-phenyl}-1,2,5-thiadiazolidine-3-one-1,1-dioxide.

LCMS: m/z 593 (M+H)+; $^1$H NMR (DMSO-d$_6$, 400 MHz): δ 0.90 (t, 3H), 1.41 (m, 2H), 1.50 (m, 2H), 2.39 (t, 2H), 4.02 (s, 2H), 4.04 (s, 2H), 7.04 (d, 2H), 7.16 (d, 2H), 7.24 (d, 2H), 7.32 (d, 2H), 7.47 (dd, 1H), 7.64 (d, 1H), 7.89 (s, 1H), 8.18 (d, 1H) ppm.

Example 176

2-tert-Butyl-5-{3-[2-(4'-cyclohexylmethoxy-biphenyl-4-ylmethyl)-4-(2,4-dichloro-phenyl)-imidazol-1-yl]-phenyl}-isothiazol-3-one-1,1-dioxide (4 mg, 0.005 mmol) was treated with TFA following general procedure to give 5-{3-[2-(4'-cyclohexylmethoxy-biphenyl-4-ylmethyl)-4-(2,4-dichloro-phenyl)-imidazol-1-yl]-phenyl}-isothiazol-3-one-1,1-dioxide.

LCMS: m/z 698 (M+H)+; $^1$H NMR (CDCl$_3$, 400 MHz): δ 0.89-1.07 (m, 2H), 1.25-1.32 (m, 5H), 1.69-1.90 (m, 6H), 3.77 (s, 2H), 3.79 (s, 2H), 6.59 (s, 1H), 6.70 (s, 1H), 6.93 (d, 2H), 7.08 (d, 1H), 7.10 (d, 2H), 7.36-7.47 (m, 5H), 7.70 (d, 2H), 7.78 (d, 1H) ppm.

Example 177

4-[2-(4-Bromo-benzyl)-4-(2,4-dichloro-phenyl)-imidazol-1-yl]-phenylamino}-acetic acid methyl ester (55 mg, 0.1 mmol) was treated as described in general procedure G using 4-(cyclohexylmethoxy)phenylboronic acid (47 mg, 0.2 mmol, prepared according to general procedure H) to give {-4-[2-(4'-cyclohexylmethoxy-biphenyl-4-ylmethyl)-4-(2,4-dichloro-phenyl)-imidazol-1-yl]-phenylamino}-acetic acid methyl ester.

{4-[2-(4'-Cyclohexylmethoxy-biphenyl-4-ylmethyl)-4-(2,4-dichloro-phenyl)-imidazol-1-yl]-phenylamino}-acetic acid methyl ester (22 mg, 0.033 mmol) was treated following general procedure F to give 5-{-4-[2-(4'-cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide.

LCMS: m/z 701 (M+H)+; $^1$H NMR (DMSO-d$_6$, 400 MHz): δ 1.01-1.27 (m, 5H), 1.69-1.82 (m, 6H), 3.79 (d, 2H), 4.07 (s, 2H), 4.10 (s, 2H), 6.96 (d, 2H), 7.12 (d, 2H), 7.18 (d, 2H), 7.38 (d, 2H), 7.49-7.55 (m, 5H), 7.69 (d, 1H), 7.96 (s, 1H), 8.11 (d, 1H) ppm.

Example 178

4-[2-(4-Bromo-benzyl)-4-(2,4-dichloro-phenyl)-imidazol-1-yl]-phenylamino}-acetic acid methyl ester (55 mg, 0.1 mmol) was treated as described in general procedure G using 4-(3,3-dimethyl-butoxy)phenylboronic acid (45 mg, 0.2 mmol, prepared according to general procedure H) to give (4-{4-(2,4-dichloro-phenyl)-2-[4'-(3,3-dimethyl-butoxy)-biphenyl-4-ylmethyl]-imidazol-1-yl}-phenylamino)-acetic acid methyl ester.

(4-{4-(2,4-Dichloro-phenyl)-2-[4'-(3,3-dimethyl-butoxy)-biphenyl-4-ylmethyl]-imidazol-1-yl}-phenylamino)-acetic acid methyl ester (22 mg, 0.033 mmol) was treated following general procedure F to give 5-(4-{4-(2,4-dichloro-phenyl)-2-[4'-(3,3-dimethyl-butoxy)-biphenyl-4-ylmethyl]-imidazol-1-yl}-phenyl)-1,2,5-thiadiazolidine-3-one-1,1-dioxide.

LCMS: m/z 689 (M+H)+; $^1$H NMR (DMSO-d$_6$, 400 MHz): δ 0.96 (s, 9H), 1.64 (t, 2H), 4.02 (t, 2H), 4.04 (s, 2H), 4.06 (s, 2H), 6.97 (d, 2H), 7.12-7.18 (m, 4H), 7.35 (d, 2H), 7.48-7.55 (m, 5H), 7.63 (d, 1H), 7.89 (s, 1H), 8.18 (d, 1H) ppm.

Example 179

4-[2-(4-Bromo-benzyl)-4-(2,4-dichloro-phenyl)-imidazol-1-yl]-phenylamino}-acetic acid methyl ester (55 mg, 0.1 mmol) was treated as described in general procedure G using 3-(2-cyclohexyl-ethoxy)-phenylboronic acid (50 mg, 0.2 mmol, prepared according to general procedure H) to give {4-[2-[4'-(2-cyclohexyl-ethoxy)-biphenyl-4-ylmethyl]-4-(2,4-dichloro-phenyl)-imidazol-1-yl]-phenylamino}-acetic acid methyl ester.

{4-[2-[4'-(2-Cyclohexyl-ethoxy)-biphenyl-4-ylmethyl]-4-(2,4-dichloro-phenyl)-imidazol-1-yl]-phenylamino}-acetic acid methyl ester (22 mg, 0.03 mmol) was treated following general procedure F to give 5-{-4-[2-[4'-(2-cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide.

LCMS: m/z 715 (M+H)+; $^1$H NMR (DMSO-d$_6$, 400 MHz): δ 0.93-0.96 (m, 2H), 1.14-1.23 (m, 5H), 1.59-1.75 (m, 6H), 4.00 (m, 2H), 4.02 (s, 2H), 4.06 (s, 2H), 6.96 (d, 2H), 7.12-7.18 (m, 4H), 7.35 (d, 2H), 7.46-7.55 (m, 5H), 7.63 (d, 1H), 7.89 (s, 1H), 8.20 (d, 1H) ppm.

Example 180

6-methoxy-2-naphthylacetic acid (1.0 g, 4 mmol) was treated according to general procedure A using 2,4-dichlorophenacyl bromide to give 4-(2,4-dichloro-phenyl)-2-(6-methoxy-naphthalen-2-ylmethyl)-1H-imidazole.

LCMS: m/z 383 (M+H)+, $^1$H NMR (CD$_3$OD, 400 MHz): δ 3.67 (s, 3H), 4.10 (s, 2H), 7.21 (d, 2H), 7.37 (d, 2H), 7.42-7.51 (m, 2H), 7.57-7.69 (m, 3H), 8.05 (s, 1H) ppm 4-(2,4-Dichloro-phenyl)-2-(6-methoxy-naphthalen-2-ylmethyl)-1H-imidazole (383 mg, 1 mmol) was treated as described in general procedure B using 1-fluoro-4-nitrobenzene to give 4-(2,4-dichloro-phenyl)-1-(4-nitro-phenyl)-2-(6-methoxy-naphthalen-2-ylmethyl)-1H-imidazole.

4-(2,4-Dichloro-phenyl)-1-(4-nitro-phenyl)-2-(6-methoxy-naphthalen-2-ylmethyl)-1H-imidazole (252 mg, 0.5 mmol) was reduced to amine and was reacted with methyl bromoacetate following general procedures D & E to give {4-[4-(2,4-dichloro-phenyl)-2-(6-methoxy-naphthalen-2-ylmethyl)-imidazol-1-yl]-phenylamino}-acetic acid methyl ester.

{-4-[4-(2,4-Dichloro-phenyl)-2-(6-methoxy-naphthalen-2-ylmethyl)-imidazol-1-yl]-phenylamino}-acetic acid methyl ester (137 mg, 0.25 mmol) was de-alkylated with BBr$_3$ following general procedure AH and resulted phenol was alkylated with bromomethyl-cyclohexane following general procedure H to give {4-[2-(6-cyclohexylmethoxy-naphthalen-2-ylmethyl)-4-(2,4-dichloro-phenyl)-imidazol-1-yl]-phenylamino}-acetic acid methyl ester.

{-4-[2-(6-Cyclohexylmethoxy-naphthalen-2-ylmethyl)-4-(2,4-dichloro-phenyl)-imidazol-1-yl]-phenylamino}-acetic acid methyl ester (60 mg, 0.09 mmol) was treated as described in general procedure F to give 5-{-4-[2-(6-cyclohexylmethoxy-naphthalen-2-ylmethyl)-4-(2,4-dichloro-phenyl)-imidazol-1-yl]-phenyl}1,2,5]-thiadiazolidin-3-one-1,1-dioxide.

LCMS: m/z 675 (M+H)$^+$; $^1$H NMR (DMSO-d$_6$, 400 MHz): δ 1.0-1.25 (m, 5H), 1.70-1.88 (m, 6H), 3.77 (d, 2H), 4.03 (s, 2H), 4.10 (s, 2H), 6.91 (dd, 1H), 6.97 (d, 2H), 7.04 (s, 1H), 7.15 (d, 2H), 7.27 (d, 2H), 7.41-7.51 (m, 3H), 7.55 (d, 1H), 7.67 (s, 1H), 8.19 (d, 1H) ppm.

Example 181

{4-[2-(4-Bromo-benzyl)-4-(2,4-dichloro-phenyl)-imidazol-1-yl]-phenylamino}-acetic acid methyl ester (137 mg, 0.25 mmol) was coupled with 2-cyclohexylvinylboronic acid (59 mg, 0.38 mmol) according to general procedure G to give {-4-[2-[4-(2-cyclohexyl-vinyl)-benzyl]-4-(2,4-dichloro-phenyl)-imidazol-1-yl]-phenylamino}-acetic acid methyl ester.

{-4-[2-[4-(2-Cyclohexyl-vinyl)-benzyl]-4-(2,4-dichloro-phenyl)-imidazol-1-yl]-phenylamino}-acetic acid methyl ester (60 mg, 1 mmol) was treated following general procedure F to give 5-{-4-[2-[4-(2-cyclohexyl-vinyl)-benzyl]-4-(2,4-dichloro-phenyl)-imidazol-1-yl]-phenyl}-1,2,5]-thiadiazolidin-3-one-1,1-dioxide.

LCMS: m/z 621 (M+H)$^+$; $^1$H NMR (DMSO-d$_6$, 400 MHz): δ 0.84-0.86 (m, 2H), 1.11-1.29 (m, 5H), 1.69-1.89 (m, 5H), 4.01 (s, 2H), 4.04 (s, 2H), 6.19 (dd, 1H), 6.26 (d, 1H), 6.98 (d, 2H), 7.14 (d, 2H), 7.24 (d, 2H), 7.31 (d, 2H), 7.45 (d, 1H), 7.48 (d, 2H), 7.63 (s, 1H), 8.17 (d, 1H) ppm.

Example 182

4-(4,4,5,5-Tetramethyl-[1,3,2]dioxaborolan-2-yl)-benzaldehyde (3.48 g, 15 mmol) was converted to 2-cyclopentyl-1-[4-(4,4,5,5-tetramethyl-[1,3,2]dioxaborolan-2-yl)-phenyl]-ethanol according to general procedure Z using cyclopentylmethylmagnesium bromide.

3-[2-(4-Bromo-benzyl)-4-(2,4-dichloro-phenyl)-imidazol-1-yl]-phenylamine was prepared from 3-aminoacetanilide according to general procedure M, then the aniline was converted to 5-{3-[2-(4-bromo-benzyl)-4-(2,4-dichloro-phenyl)-imidazol-1-yl]-phenyl}-1,2,5-thiadiazolidin-3-one-1,1-dioxide as described in general procedures E and F. The bromo-thiadiazolidinone (100 mg, 0.17 mmol) was coupled with 2-cyclopentyl-1-[4-(4,4,5,5-tetramethyl-[1,3,2]dioxaborolan-2-yl)-phenyl]-ethanol according to general procedure G to provide 5-{3-[2-[4'-(2-cyclopentyl-1-hydroxy-ethyl)-biphenyl-4-ylmethyl]-4-(2,4-dichloro-phenyl)-imidazol-1-yl]-phenyl}-1,2,5-thiadiazolidin-3-one-1,1-dioxide.

LCMS: m/z 701 (M+H)$^+$; $^1$H NMR (DMSO-d$_6$, 400 MHz): δ 1.06-1.16 (m, 2H), 1.40-1.50 (m, 2H), 1.51-1.60 (m, 3H), 1.65-1.84 (m, 4H), 4.00 (s, 2H), 4.13 (s, 2H), 4.53 (m, 1H), 5.10 (d, 1H), 6.94 (m, 1H), 7.05 (m, 1H), 7.18 (m, 2H), 7.26 (m, 1H), 7.36 (m, 2H), 7.47 (t, 1H), 7.49 (dd, 1H), 7.52 (m, 2H), 7.56 (m, 2H), 7.65 (d, 1H), 7.94 (s, 1H), 8.19 (d, 1H) ppm.

Example 183

5-{3-[2-[4'-(2-Cyclopentyl-1-hydroxy-ethyl)-biphenyl-4-ylmethyl]-4-(2,4-dichloro-phenyl)-imidazol-1-yl]-phenyl}-1,2,5-thiadiazolidin-3-one-1,1-dioxide (45 mg, 64 μmol) was reduced according to general procedure AA to provide 5-{3-[2-[4'-(2-cyclopentyl-ethyl)-biphenyl-4-ylmethyl]-4-(2,4-dichloro-phenyl)-imidazol-1-yl]-phenyl}-1,2,5-thiadiazolidin-3-one-1,1-dioxide.

LCMS: m/z 685 (M+H)$^+$; $^1$H NMR (CD$_3$OD, 400 MHz): δ 1.08-1.20 (m, 2H), 1.47-1.57 (m, 2H), 1.58-1.68 (m, 4H), 1.75-1.86 (m, 3H), 2.64 (t, 2H), 4.17 (s, 2H), 4.21 (s, 2H), 6.83 (m, 1H), 7.07 (m, 2H), 7.15 (m, 1H), 7.21 (m, 2H), 7.28 (m, 1H), 7.34-7.48 (m, 7H), 7.73 (s, 1H), 8.01 (d, 1H) ppm.

Example 184

4-Bromobenzaldehyde (4.26 g, 23 mmol) was converted to 4'-(4,4-dimethyl-pent-1-enyl)phenyl boronic acid according to general procedure AE using 3,3-dimethylbutylmagnesium chloride.

3-[2-(4-Bromo-benzyl)-4-(2,4-dichloro-phenyl)-imidazol-1-yl]-phenylamine was prepared from 3-aminoacetanilide according to general procedure M, then the aniline was converted to 5-{3-[2-(4-bromo-benzyl)-4-(2,4-dichloro-phenyl)-imidazol-1-yl]-phenyl}-1,1-dioxo-1,2,5-thiadiazolidin-3-one-1,1-dioxide as described in general procedures E and F. The bromo-thiadiazolidinone (50 mg, 84 μmol) was coupled with 4'-(4,4-dimethyl-pent-1-enyl)phenyl boronic acid according to general procedure G to provide 5-(3-{4-(2,4-dichloro-phenyl)-2-[4'-(4,4-dimethyl-pent-1-enyl)-biphenyl-4-ylmethyl]-imidazol-1-yl}-phenyl)-1,2,5-thiadiazolidin-3-one-1,1-dioxide.

LCMS: m/z 685 (M+H)$^+$.

Example 185

4-Bromobenzaldehyde was converted to 4-(4-methylpentyl)phenyl boronic acid according to general procedure Y using 3-methylbutylmagnesium bromide (1 eq). The crude boronic acid was used below without purification.

{-4-[2-(4-Bromo-benzyl)-4-(2,4-dichloro-phenyl)-imidazol-1-yl]-phenylamino}-acetic acid methyl ester (500 mg, 0.91 mmol) was coupled with 4-(4-methylpentyl)phenyl boronic acid according to general procedure G to give (4-{4-(2,4-dichloro-phenyl)-2-[4'-(4-methyl-pentyl)-biphenyl-4-ylmethyl]-imidazol-1-yl}-phenylamino)-acetic acid methyl ester.

(4-{4-(2,4-Dichloro-phenyl)-2-[4'-(4-methyl-pentyl)-biphenyl-4-ylmethyl]-imidazol-1-yl}-phenylamino)-acetic acid methyl ester (356 mg, 0.57 mmol) was treated following general procedure F to give 5-(4-{4-(2,4-dichloro-phenyl)-2-[4'-(4-methyl-pentyl)-biphenyl-4-ylmethyl]-imidazol-1-yl}-phenyl)-1,2,5-thiadiazolidin-3-one-1,1-dioxide.

LCMS: m/z 673 (M+H)$^+$; $^1$H NMR (DMSO-d$_6$, 400 MHz): δ 0.86 (d, 6H), 1.20 (m, 2H), 1.50-1.63 (m, 3H), 2.58 (t, 2H), 4.07 (s, 2H), 4.09 (s, 2H), 7.14-7.21 (m, 4H), 7.25 (m, 2H), 7.37 (m, 2H), 7.48 (dd, 1H), 7.51-7.56 (m, 4H), 7.64 (d, 1H), 7.90 (s, 1H), 8.20 (d, 1H) ppm.

Example 186

4-(4,4,5,5-Tetramethyl-[1,3,2]dioxaborolan-2-yl)-benzaldehyde (3.48 g, 15 mmol) was converted to 2-cyclopentyl-1-[4-(4,4,5,5-tetramethyl-[1,3,2]dioxaborolan-2-yl)-phenyl]-ethanol according to general procedure Z using cyclopentylmethylmagnesium bromide.

{-4-[2-(4-Bromo-benzyl)-4-(2,4-dichloro-phenyl)-imidazol-1-yl]-phenylamino}-acetic acid methyl ester (433 mg, 0.79 mmol) was coupled with 2-cyclopentyl-1-[4-(4,4,5,5-tetramethyl-[1,3,2]dioxaborolan-2-yl)phenyl]-ethanol according to general procedure G to give {-4-[2-[4'-(2-cyclopentyl-1-hydroxy-ethyl)-biphenyl-4-ylmethyl]-4-(2,4-dichloro-phenyl)-imidazol-1-yl]-phenylamino}-acetic acid methyl ester. The product benzyl alcohol was reduced according to general procedure AA and the reduced product was treated following general procedure F to give 5-{-4-[2-[4'-(2-cyclopentyl-ethyl)-biphenyl-4-ylmethyl]-4-(2,4-dichloro-phenyl)-imidazol-1-yl]-phenyl}-1,2,5-thiadiazolidin-3-one-1,1-dioxide.

LCMS: m/z 685 (M+H)$^+$; $^1$H NMR (CD$_3$OD, 400 MHz): δ 1.10-1.22 (m, 2H), 1.45-1.69 (m, 6H), 1.75-1.87 (m, 3H), 2.65 (t, 2H), 4.11 (s, 2H), 4.30 (s, 2H), 7.09 (m, 2H), 7.19-7.27 (m, 6H), 7.37 (dd, 1H), 7.44-7.49 (m, 5H), 7.69 (s, 1H), 8.02 (d, 1H) ppm.

Example 187

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using trans-1-heptenylboronic acid (43 mg, 0.3 mmol) to give 5-{3-[4-(2,4-dichloro-phenyl)-2-(4-hept-1-enyl-benzyl)-imidazol-1-yl]-phenyl}-1,2,5-thiadiazolidine-3-one-1,1-dioxide.

LCMS: m/z 609 (M+H)$^+$; $^1$H NMR (DMSO-d$_6$, 400 MHz): δ 0.86 (t, 3H), 1.29 (m, 4H), 1.42 (m, 2H), 2.14 (m, 2H), 4.02 (s, 2H), 4.05 (s, 2H), 6.23 (m, 1H), 6.32 (d, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) ppm.

Example 188

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using trans-1-penten-1-ylboronic acid (34 mg, 0.3 mmol) to give 5-{3-[4-(2,4-dichloro-phenyl)-2-(4-pent-1-enyl-benzyl)-imidazol-1-yl]-phenyl}-1,2,5-thiadiazolidine-3-one-1,1-dioxide.

LCMS: m/z 581 (M+H)$^+$; $^1$H NMR (DMSO-d$_6$, 400 MHz): δ 0.90 (t, 3H), 1.43 (m, 2H), 2.13 (m, 2H), 4.02 (s, 2H), 4.05 (s, 2H), 6.22 (m, 1H), 6.32 (d, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) ppm.

Example 189

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using trans-3-phenyl-1-propen-1-ylboronic acid (49 mg, 0.3 mmol) to give 5-(3-{4-(2,4-dichloro-phenyl)-2-[4-(3-phenyl-propenyl)-benzyl]-imidazol-1-yl}-phenyl)-1,2,5-thiadiazolidine-3-one-1,1-dioxide.

LCMS: m/z 629 (M+H)$^+$; $^1$H NMR (DMSO-d$_6$, 400 MHz): δ 3.49 (d, 2H), 4.02 (s, 2H), 4.04 (s, 2H), 6.37 (m, 1H), 6.42 (d, 1H), 7.01 (d, 2H), 7.17 (m, 2H), 7.20-7.36 (m, 9H), 7.47 (dd, 1H), 7.63 (d, 1H), 7.87 (s, 1H), 8.18 (d, 1H) ppm.

Example 190

5-{3-[2-(4-Bromo-benzyl)-4-(2,4-dichloro-phenyl)-imidazol-1-yl]-phenyl}-1,2,5-thiadiazolidine-3-one-1,1-dioxide (1.19 g, 2 mmol) was treated as described in general procedure L using 2-(trimethylsilyl)ethoxymethyl chloride (708 μL, 4 mmol) to give 5-{3-[2-(4-bromo-benzyl)-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was then treated according to general procedure AD to give 5-(3-{4-(2,4-dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one.

LCMS: m/z 769 (M+H)$^+$.

5-(3-{4-(2,4-Dichloro-phenyl)-2-[4-(4,4,5,5-tetramethyl-[1,3,2]dioxaborolan-2-yl)-benzyl]-imidazol-1-yl}-phenyl)-1,1-dioxo-2-(2-trimethylsilanyl-ethoxymethyl)-[1,2,5]thiadiazolidin-3-one (385 mg, 0.5 mmol) was treated as described in general procedure G using 3,6-dichloropyridazine (149 mg, 1 mmol) to give 5-{3-[2-[4-(6-chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 756 (M+H)$^+$.

5-{3-[2-[4-(6-Chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (38 mg, 0.05 mmol) was treated as described in general procedure L using cyclohexanemethanol (31 μL, 0.25 mmol) to give 5-{3-[2-[4-(6-cyclohexylmethoxy-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 833 (M+H)$^+$.

5-{3-[2-[4-(6-Cyclohexylmethoxy-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (17 mg, 0.02 mmol) was treated as described in general procedure W using tetrabutylammonium fluoride (26 mg, 0.1 mmol) to give 5-{3-[2-[4-(6-cyclohexylmethoxy-pyridazin-3-yl)-benzyl]-4-(2,4-dichloro-phenyl)-imidazol-1-yl]-phenyl}-1,2,5-thiadiazolidine-3-one-1,1-dioxide.

LCMS: m/z 703 (M+H)$^+$; $^1$H NMR (CD$_3$OD, 400 MHz): δ 0.97-1.93 (m, 11H), 3.91 (d, 2H), 4.08 (s, 2H), 4.10 (s, 2H), 7.15-7.27 (m, 5H), 7.37 (d, 2H), 7.46-7.54 (m, 4H), 7.64 (d, 1H), 7.89 (s, 1H), 8.19 (d, 1H) ppm.

Example 191

5-{3-[2-[4-(6-Chloro-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (76 mg, 0.1 mmol) was treated as described in general procedure G using 1-cyclohexen-1-yl-boronic acid (51 mg, 0.4 mmol) to give 5-{3-[2-[4-(6-cyclohex-1-enyl-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one, which was then dissolved in 1 mL dry acetic acid, iron powder (−325 mesh, 112 mg, 2 mmol) was added and the mixture was then heated at 100° C. under nitrogen for 2 days. At completion, the reaction mixture was then diluted with water/EtOAc and the leftover iron powder was filtered and washed with EtOAc. The combined organic layer was washed with water, saturated NaHCO$_3$ and brine. The organic layer was then dried over Na$_2$SO$_4$, filtered, and the filtrate was concentrated and purified by silica gel chromatography to afford 5-{3-[2-[4-(6-cyclohexyl-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one.

LCMS: m/z 803 (M+H)$^+$.

5-{3-[2-[4-(6-Cyclohexyl-pyridazin-3-yl)-benzyl]-4-(2,4-dichloro-phenyl)-imidazol-1-yl]-phenyl}-1,1-dioxo-2-(2-trimethylsilanyl-ethoxymethyl)-[1,2,5]thiadiazolidin-3-one (16 mg, 0.02 mmol) was treated as described in general procedure W using tetrabutylammonium fluoride (26 mg, 0.1 mmol) to give 5-{3-[2-[4-(6-cyclohexyl-pyridazin-3-yl)-benzyl]-4-(2,4-dichloro-phenyl)-imidazol-1-yl]-phenyl}-1,2,5-thiadiazolidine-3-one-1,1-dioxide.

LCMS: m/z 673 (M+H)$^+$; $^1$H NMR (CD$_3$OD, 400 MHz): δ 1.14-1.77 (m, 10H), 2.53 (m, 1H), 4.06 (s, 2H), 4.09 (s, 2H), 7.15-7.27 (m, 5H), 7.37 (d, 2H), 7.46-7.54 (m, 4H), 7.64 (d, 1H), 7.89 (s, 1H), 8.18 (d, 1H) ppm.

Example 192

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 4-methyl-1-pentenylboronic acid (39 mg, 0.3 mmol) to give 5-(3-{4-(2,4-dichloro-phenyl)-2-[4-(4-methyl-pent-1-enyl)-benzyl]-imidazol-1-yl}-phenyl)-1,2,5-thiadiazolidine-3-one-1,1-dioxide.

LCMS: m/z 595 (M+H)$^+$; $^1$H NMR (DMSO-d$_6$, 400 MHz): δ 0.89 (d, 6H), 1.68 (m, 1H), 2.03 (q, 2H), 4.02 (s, 2H), 4.05 (s, 2H), 6.22 (m, 1H), 6.32 (d, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) Ppm.

Example 193

To a solution of 2-heptyne (129 µL, 1 mmol) in 2 mL dry THF at 0° C. was added 2 mL 0.5 M 9-BBN solution in THF. The resulting solution was stirred at room temperature under nitrogen for 4 hr. Then it was condensed under vacuum and used as boronic acid derivative according to general procedure G, reacting with 5-{3-[2-(4-bromo-benzyl)-4-(2,4-dichloro-phenyl)-imidazol-1-yl]-phenyl}-1,2,5-thiadiazolidine-3-one-1,1-dioxide (119 mg, 0.2 mmol) to give 5-(3-{4-(2,4-dichloro-phenyl)-2-[4-(1-methyl-hex-1-enyl)-benzyl]-imidazol-1-yl}-phenyl)-1,2,5-thiadiazolidine-3-one-1,1-dioxide.

LCMS: m/z 609 (M+H)$^+$; $^1$H NMR (DMSO-d$_6$, 400 MHz): δ 0.90 (t, 3H), 1.29-1.40 (m, 4H), 1.93 (d, 3H), 2.13 (m, 2H), 4.02 (s, 2H), 4.05 (s, 2H), 5.77 (m, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) ppm.

Example 194

5-{3-[2-(4-Bromo-benzyl)-4-(2,4-dichloro-phenyl)-imidazol-1-yl]-phenyl}-1,2,5-thiadiazolidine-3-one-1,1-dioxide (59 mg, 0.1 mmol) was treated as described in general procedure G using 5-methyl-1-hexenylboronic acid (43 mg, 0.3 mmol) to give 5-(3-{4-(2,4-dichloro-phenyl)-2-[4-(5-methyl-hex-1-enyl)-benzyl]-imidazol-1-yl}-phenyl)-1,2,5-thiadiazolidine-3-one-1,1-dioxide.

LCMS: m/z 609 (M+H)$^+$; $^1$H NMR (DMSO-d$_6$, 400 MHz): δ 0.89 (d, 6H), 1.31 (m, 2H), 1.53 (m, 1H), 2.16 (m, 2H), 4.02 (s, 2H), 4.05 (s, 2H), 6.22 (m, 1H), 6.33 (d, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) ppm.

Example 195

To a solution of 3-cyclohexyl-1-propyne (145 µL, 1 mmol) in 2 mL dry THF at 0° C. was added 2 mL 0.5 M 9-BBN solution in THF. The resulting solution was stirred at room temperature under nitrogen for 4 hr. Then it was condensed under vacuum and used as boronic acid derivative according to general procedure G, reacting with 5-{3-[2-(4-bromo-benzyl)-4-(2,4-dichloro-phenyl)-imidazol-1-yl]-phenyl}-1,2,5-thiadiazolidine-3-one-1,1-dioxide (119 mg, 0.2 mmol) to give 5-{3-[2-[4-(3-cyclohexyl-propenyl)-benzyl]-4-(2,4-dichloro-phenyl)-imidazol-1-yl]-phenyl}-1,2,5-thiadiazolidine-3-one-1,1-dioxide.

LCMS: m/z 635 (M+H)$^+$; $^1$H NMR (DMSO-d$_6$, 400 MHz): δ 0.87-1.71 (m, 11H), 2.05 (m, 2H), 4.02 (s, 2H), 4.05 (s, 2H), 6.21 (m, 1H), 6.30 (d, 1H), 7.01 (d, 2H), 7.17 (m, 2H), 7.25 (d, 2H), 7.36-7.48 (m, 3H), 7.64 (d, 1H), 7.88 (s, 1H), 8.18 (d, 1H) ppm.

Biological Assay

The following assay methods are utilized to identify compounds of formula I which are effective in inhibiting the activity of certain phosphatases, an example of which, as used herein, is PTP1B.

PTP1B ASSAY

The assay for PTP1B inhibition is based on the detection of the complex between Malachite Green dye and free phosphate, liberated from the phosphopeptide substrate by PTPase action. To each well of a flat-bottom assay plate is added 45 µL assay buffer [~50 mM Imidazole, pH 7.2, 100 mM NaCl, 5 mM DTT, and 1 mM EDTA] and 10 µL of peptide substrate (Tyrosine Phosphopeptide-1, END($_p$Y)INASL (SEQ ID NO: 1), 80 µM FAC, Promega Cat # V256A) to a total volume of 55 µL. Test compound (10 µL in up to 50% DMSO) is then added. The mixture is incubated for 5 min, at 25° C., and 10 µL of PTP-1B (Protein Tyrosine Phosphatase 1B (PTP-1B); FAC 0.8 nM; BIOMOL-SE332) is then added. The mixture is incubated for 30 min at 25° C. Subsequently, 25 µL of Malachite Green reagent (10% (w/v) Ammonium Molybdate in water, Sigma Cat # A-7302, 0.2% (w/v) Malachite Green in 4 N HCl, Aldrich Cat #21, 302-0) is then added. After incubation for 15 min at 27° C., the reaction endpoint is measured at 640 nM.

The Malachite Green reagent is prepared by mixing one volume of 10% Ammonium Molybdate with 3 volumes of 0.2% Malachite Green solution, stirring at room temperature for 30 min and then filtering and collecting the filtrate. The Malachite Green reagent is treated with 10 µL of 5% Tween 20 per 990 µL of dye solution before use.

Test compounds are typically examined at eight concentrations in the above assay. For this assay, the IC50 (µM) of the enzyme inhibition assay represents the concentration of compound at which 50% signal has been inhibited. The compounds of Formula I in Table I inhibit PTP-IB with an IC50 of less than 10 µM.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated for PTPase-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

What is claimed is:

1. A method of treating type I diabetes, type II diabetes, or glucose intolerance comprising administering to a human a compound of Formula II(d)

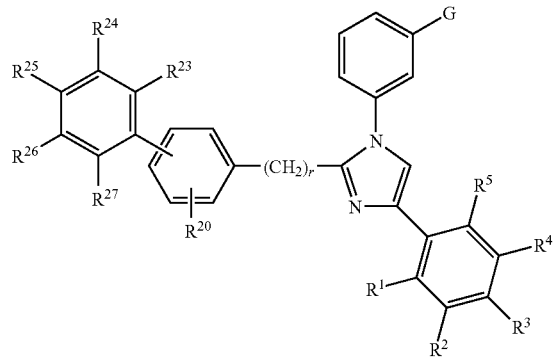

wherein
$R^1$, $R^2$, $R^3$, $R^4$, and $R^5$ are independently selected from the group consisting of hydrogen, fluoro, and chloro, wherein at least one of $R^1$, $R^2$, $R^3$, $R^4$, and $R^5$ is not hydrogen;

$R^{20}$ is hydrogen;

$R^{23}$, $R^{24}$, $R^{25}$, $R^{26}$, and $R^{27}$ are independently selected from the group consisting of: hydrogen, methyl, ethyl, propyl, butyl, pentyl, hexyl, 1-ethyl-propyl, 1-propyl-butyl, 3,3-dimethyl-butyl, 4-methyl-pentyl, 4,4-dimethyl-pentyl, 1-(3,3-dimethyl-butyl)-4,4-dimethyl-pentyl, isobutyl, isopropyl, sec-butyl, tert-butyl, trifluoromethyl, 4,4,4-trifluorobutoxy, methoxy, ethoxy, propoxy, butoxy, pentoxy, hexyloxy, isobutoxy, isopropoxy, tert-butoxy, 2-phenethoxy, 2,2-dimethylpropoxy, 3-methyl-butoxy, 3,3-dimethyl-butoxy, phenethyloxy, 2-cyclohexyl-ethanesulfonyl, 3,3-dimethyl-butane-1-sulfonyl, cyclohexanesulfonyl, cyclohexylmethylsulfonyl, 2-cyclohexyl-ethanesulfinyl, 3,3-dimethyl-butane-1-sulfinyl, cyclohexylmethylsulfinyl, 2-cyclohexyl-ethylsulfanyl, 3,3-dimethyl-butylsulfanyl, phenethylsulfanyl, cyclohexylmethylsulfanyl, cyclopentyl, cyclohexyl, cyclopentyloxy, cyclohexyloxy, cyclopentylmethyl, cyclohexylmethyl, 2-cyclopentylethyl, 2-cyclohexylethyl, cyclopentylmethoxy, cyclohexylmethoxy, 2-cyclopentylethoxy, 2-cyclohexylethoxy, 2-cyclohexyl-vinyl, 3-ethyl-cyclobutyl, chloro, fluoro, and phenyl, wherein at least one of $R^{23}$, $R^{24}$, $R^{25}$, $R^{26}$, and $R^{27}$ is not hydrogen;

G is

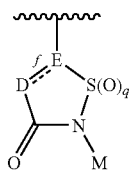

wherein q is 2, D is $C(R^7)(R^8)$, E is N, and side f is a single bond
wherein $R^7$ and $R^8$ are selected from the group consisting of: hydrogen and $C_{1-4}$ alkyl;
M is hydrogen;
r is 1,
or a pharmaceutically acceptable salt thereof.

2. The method of claim 1, wherein the compound has the formula:

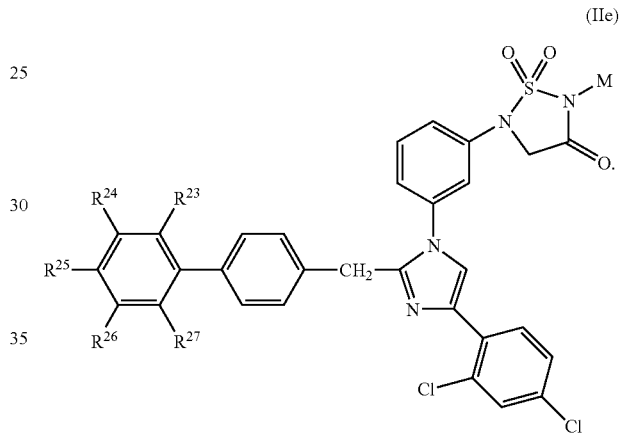

3. The method of claim 1, wherein the compound is 5-{3-[2-(4'-Cyclohexyl-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

4. The method of claim 1, wherein the compound is 5-{3-[2-(4'-Tert-butyl-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

5. The method of claim 1, wherein the compound is 5-(3-{-4-(2,4-Dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide or a pharmaceutically acceptable salt thereof.

6. The method of claim 1, wherein the compound is 5-{3-[2-(3'-Cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

7. The method of claim 1, wherein the compound is 5-{3-[2-[3'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide or a pharmaceutically acceptable salt thereof.

8. The method of claim 1, wherein the compound is 5-{3-[4-(2,4-Dichloro-phenyl)-2-(3'-phenethyloxy-biphenyl-4- ylmethyl)-imidazol-1-yl]-phenyl}-1,2,5-thiadiazolidine-3-one-1,1-dioxide or a pharmaceutically acceptable salt thereof.

9. The method of claim 1, wherein the compound is 5-(3-{4-(2,4-Dichloro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide or a pharmaceutically acceptable salt thereof.

10. The method of claim 1, wherein the compound is 5-(3-{4-(2,4-Dichloro-phenyl)-2-[3'-(3,3-dimethyl-butane-1-sulfonyl)-biphenyl-4-ylmethyl]-imidazol-1-yl}-phenyl)-1,2,5-thiadiazolidine-3-one-1,1-dioxide or a pharmaceutically acceptable salt thereof.

11. The method of claim 1, wherein the compound is 5-{3-[2-(3'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

12. The method of claim 1, wherein the compound is 5-{3-[2-(3'-Cyclohexylmethylsulfonyl-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

13. The method of claim 1, wherein the compound is 5-{3-[2-(3'-(2-Cyclohexyl-ethylsulfanyl)-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

14. The method of claim 1, wherein the compound is 5-{3-[2-(3'-(2-Cyclohexyl-ethanesulfonyl)-biphenyl-4-ylmethyl)-4-(2,4-dichloro-phenyl)-imidazol-1-yl]-phenyl}-1,2,5-thiadiazolidine-3-one-1,1-dioxide or a pharmaceutically acceptable salt thereof.

15. The method of claim 1, wherein the compound is selected from the group consisting of:
- 5-(3-{4-(2,4-Difluoro-phenyl)-2-[3'-(3,3-dimethyl-butylsulfanyl)-biphenyl-4-ylmethyl]-imidazol-1-yl}-phenyl)-1,2,5-thiadiazolidine-3-one-1,1-dioxide;
- 5-(3-{4-(2,4-Difluoro-phenyl)-2-[3'-(3,3-dimethyl-butane-1-sulfonyl)-biphenyl-4-ylmethyl]-imidazol-1-yl}-phenyl)-1,2,5-thiadiazolidine-3-one-1,1-dioxide;
- 5-{3-[2-(4'-Cyclohexyl-biphenyl-4-ylmethyl)-4-(2,6-dichloro-phenyl)-imidazol-1-yl]-phenyl}-1,2,5-thiadiazolidine-3-one-1,1-dioxide;
- 5-(3-{4-(2,6-Dichloro-phenyl)-2-[3'-(3,3-dimethyl-butoxy)-biphenyl-4-ylmethyl]-imidazol-1-yl}-phenyl)-1,2,5-thiadiazolidine-3-one-1,1-dioxide;
- 5-{3-[2-(3'-Cyclohexylmethoxy-biphenyl-4-ylmethyl)-4-(2,6-dichloro-phenyl)-imidazol-1-yl]-phenyl}-1,2,5-thiadiazolidine-3-one-1,1-dioxide;
- 5-(3-{4-(2,4-Dichloro-phenyl)-2-[4'-(3,3-dimethyl-butoxy)-biphenyl-4-ylmethyl]-imidazol-1-yl}-phenyl)-1,2,5-thiadiazolidine-3-one-1,1-dioxide;
- 5-{3-[2-(4'-Cyclohexylmethoxy-biphenyl-4-ylmethyl)-4-(2,4-dichloro-phenyl)-imidazol-1-yl]-phenyl}-1,2,5-thiadiazolidine-3-one-1,1-dioxide;
- 5-(3-{4-(2,4-Dichloro-phenyl)-2-[4'-(3,3-dimethyl-butylsulfanyl)-biphenyl-4-ylmethyl]-imidazol-1-yl}-phenyl)-1,2,5-thiadiazolidine-3-one-1,1-dioxide;
- 5-{3-[2-(4'-Cyclohexylmethylsulfanyl-biphenyl-4-ylmethyl)-4-(2,4-dichloro-phenyl)-imidazol-1-yl]-phenyl}-1,2,5-thiadiazolidine-3-one-1,1-dioxide;
- 5-{3-[2-(4'-Cyclohexylmethanesulfonyl-biphenyl-4-ylmethyl)-4-(2,4-dichloro-phenyl)-imidazol-1-yl]-phenyl}-1,2,5-thiadiazolidine-3-one-1,1-dioxide;
- 5-{3-[2-[4'-(2-Cyclohexyl-ethoxy)-biphenyl-4-ylmethyl]-4-(2,4-dichloro-phenyl)-imidazol-1-yl]-phenyl}-1,2,5-thiadiazolidine-3-one-1,1-dioxide;
- 5-{3-[2-[4'-(2-Cyclohexyl-ethyl)-biphenyl-4-ylmethyl]-4-(2,4-dichloro-phenyl)-imidazol-1-yl]-phenyl}-1,2,5-thiadiazolidine-3-one-1,1-dioxide; and
- 5-(3-{4-(2,4-Dichloro-phenyl)-2-[4'-(4,4-dimethyl-pent-1-enyl)-biphenyl-4-ylmethyl]-imidazol-1-yl}-phenyl)-1,2,5-thiadiazolidin-3-one-1,1-dioxide;

or a pharmaceutically acceptable salt thereof.

16. The method of claim 1, wherein the method is a method of treating type I diabetes.

17. The method of claim 1, wherein the method is a method of treating type II diabetes.

18. The method of claim 1, wherein the method is a method of treating glucose intolerance.

* * * * *